(12) United States Patent
Harrington et al.

(10) Patent No.: US 11,384,114 B2
(45) Date of Patent: Jul. 12, 2022

(54) POLYMORPHIC FORMS OF AN OXYSTEROL AND METHODS OF MAKING THEM

(71) Applicant: Warsaw Orthopedic, Inc., Warsaw, IN (US)

(72) Inventors: Roger E. Harrington, Collierville, TN (US); Jerbrena C. Jacobs, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/374,610

(22) Filed: Dec. 9, 2016

(65) Prior Publication Data
US 2018/0162900 A1     Jun. 14, 2018

(51) Int. Cl.
| | |
|---|---|
| *C07J 9/00* | (2006.01) |
| *C07J 17/00* | (2006.01) |
| *C07J 51/00* | (2006.01) |
| *C07J 7/00* | (2006.01) |

(52) U.S. Cl.
CPC ............... *C07J 9/00* (2013.01); *C07J 17/00* (2013.01); *C07B 2200/13* (2013.01); *C07J 7/002* (2013.01); *C07J 51/00* (2013.01)

(58) Field of Classification Search
CPC ....... A61K 31/575; A61K 45/06; A61P 19/08; A61P 19/10; A61P 29/00; A61P 9/10; C07J 17/00; C07J 51/00; C07J 7/002; C07J 9/00; C07B 2200/13
USPC ....................................................... 514/182
See application file for complete search history.

(56) References Cited

U.S. PATENT DOCUMENTS

| | | | |
|---|---|---|---|
| 4,877,864 A | 10/1989 | Wang et al. | |
| 5,683,459 A | 11/1997 | Brekke | |
| 5,899,939 A | 5/1999 | Boyce et al. | |
| 6,371,992 B1 | 4/2002 | Tanagho et al. | |
| 7,897,588 B2 | 3/2011 | Parhami | |

(Continued)

FOREIGN PATENT DOCUMENTS

| | | |
|---|---|---|
| CN | 108884123 A | 11/2018 |
| EP | 3333175 A2 | 6/2018 |

(Continued)

OTHER PUBLICATIONS

Tom Ellenberger( Biological Imaging by X-ray DiffractionBio5325, X-Crystallography Lectures, 2006).*

(Continued)

*Primary Examiner* — Sabiha N Qazi
(74) *Attorney, Agent, or Firm* — Sorell, Lenna & Schmidt, LLP; William D. Schmidt, Esq.

(57) ABSTRACT

Compositions and methods for preparing OXY133 polymorphs Form C to Form I are provided. The methods include subjecting a slurry of OXY133 to conditions sufficient to convert OXY133 to the OXY133 polymorph Form C, polymorph Form D, polymorph Form E, polymorph Form F, polymorph Form G, polymorph Form H, polymorph Form I or a mixture thereof. A polymorph of OXY133 is also provided and that polymorph can be polymorph Form C, polymorph Form D, polymorph Form E, polymorph Form F, polymorph Form G, polymorph Form H, polymorph Form I or a mixture thereof. Pharmaceutical compositions including OXY133 polymorphs are also provided.

2 Claims, 105 Drawing Sheets

(56) References Cited

U.S. PATENT DOCUMENTS

| | | | |
|---|---|---|---|
| 8,022,052 B2* | 9/2011 | Parhami | A61K 31/57 |
| | | | 514/170 |
| 8,268,008 B2 | 9/2012 | Betz et al. | |
| 8,475,824 B2 | 7/2013 | Mckay | |
| 8,586,070 B2 | 11/2013 | Briest | |
| 8,642,065 B2 | 2/2014 | Hans et al. | |
| 8,758,791 B2 | 6/2014 | McKay | |
| 8,877,221 B2 | 11/2014 | Mckay | |
| 8,900,617 B2 | 12/2014 | Mckay | |
| 9,271,821 B2 | 3/2016 | Roock et al. | |
| 9,611,288 B2* | 4/2017 | Harrington | C07J 9/00 |
| 9,679,244 B2* | 6/2017 | Ohno | G06F 17/18 |
| 9,717,742 B2* | 8/2017 | Parhami | A61K 31/575 |
| 9,878,070 B2 | 1/2018 | Reves et al. | |
| 9,987,290 B2* | 6/2018 | Harrington | A61K 31/575 |
| 10,201,635 B2* | 2/2019 | Reves | A61L 27/54 |
| 10,736,993 B2* | 8/2020 | Reves | A61K 38/1709 |
| 2003/0009235 A1 | 1/2003 | Manrique et al. | |
| 2006/0251735 A1 | 11/2006 | Parhami | |
| 2006/0270645 A1 | 11/2006 | Parhami | |
| 2007/0248575 A1 | 10/2007 | Connor et al. | |
| 2009/0202660 A1 | 8/2009 | Parhami | |
| 2009/0220562 A1 | 9/2009 | Parhami | |
| 2010/0034781 A1 | 2/2010 | Parhami et al. | |
| 2010/0112030 A1 | 5/2010 | Parhami et al. | |
| 2010/0119492 A1 | 5/2010 | Hans et al. | |
| 2011/0008297 A1 | 1/2011 | Parhami et al. | |
| 2011/0104230 A1 | 5/2011 | Mousa et al. | |
| 2011/0276147 A1 | 11/2011 | Cook et al. | |
| 2012/0107401 A1 | 5/2012 | Mckay | |
| 2012/0195952 A1 | 8/2012 | King | |
| 2012/0219599 A1 | 8/2012 | Moore et al. | |
| 2012/0265167 A1 | 10/2012 | Simonson et al. | |
| 2013/0244942 A1 | 9/2013 | Benedict et al. | |
| 2014/0170202 A1 | 6/2014 | Peters et al. | |
| 2014/0248372 A1 | 9/2014 | Boden et al. | |
| 2014/0335147 A1 | 11/2014 | Alexakis | |
| 2015/0118277 A1* | 4/2015 | Parhami | A61K 45/06 |
| | | | 424/423 |
| 2015/0140059 A1* | 5/2015 | Parhami | A61K 31/575 |
| | | | 424/423 |
| 2016/0159848 A1 | 6/2016 | Harrington et al. | |
| 2016/0159850 A1 | 6/2016 | Parhami et al. | |
| 2017/0007739 A1 | 1/2017 | Reves | |
| 2017/0022244 A1 | 1/2017 | Parhami et al. | |

FOREIGN PATENT DOCUMENTS

| | | |
|---|---|---|
| WO | 2005005453 A2 | 1/2005 |
| WO | 2008115469 A2 | 9/2008 |
| WO | 2009073186 A1 | 6/2009 |
| WO | 2012024581 A2 | 2/2012 |
| WO | 2012024584 A2 | 2/2012 |
| WO | 2013169399 A1 | 11/2013 |
| WO | 2014093836 A1 | 6/2014 |
| WO | 2014179756 A1 | 11/2014 |
| WO | 2015009991 A2 | 1/2015 |
| WO | 2015014872 A1 | 2/2015 |
| WO | 2015168636 A1 | 11/2015 |
| WO | 2016094421 A1 | 6/2016 |
| WO | 2017172615 A | 10/2017 |
| WO | 2017172615 A1 | 10/2017 |

OTHER PUBLICATIONS

Wayne Genck (Genck International, Nov. 8, 2010, Make The Most of Antisolvent Crystallization.A number of factors can affect solids' formation).*
Helming Tan et al. (Org. Process Res. Dev. 2008, 12, 1, 58-65, Publication Date:Dec. 15, 2007, , https://doi.org/10.1021/op700144e An Integrated High-Throughput Screening Approach for Purification of Solid Organic Compounds by Trituration and Crystallization in Solvents).*

Stappenbeck, Frank, et al. Novel oxysterols activate the Hedgehog pathway and induce osteogenesis. Bioorganic & Medicinal Chemistry Letters, vol. 22, pp. 5893-5897, 2012 Elsevier Ltd.
International Search Report and Written Opinion of the ISA/US dated Apr. 8, 2016 of PCT/US2015/064526 filed Dec. 8, 2015.
Nedelcu, et al. Oxysterol binding to the extracellular domain of Smoothened in Hedgehog Signaling. Nature Chemical Biology 9(9): 557-564 (2013) Supplementary information pp. 1-28, retrieved from internet Mar. 9, 2016 from URL: http://www.nature.com/nchembio/journal/v9/n9/extref/nchembio.1290-S1.pdf, entire document.
Haren, et al. Inhibition of cholesterol side-chain cleavage by intermediates of an alternative steroid biosynthetic pathway. FEBS Letters 232(2): 377-380; 1988. Retrieved on Mar. 9, 2016 from internet URL:http//onlinelibrary.wiley.com/doi/10.1016/0014-5793(88)80773-7/epdf>, entire document.
Pubchem, Compound Summary for SID 113493311, Create Date Mar. 11, 2011 retrieved from the internet Jan. 14, 2016 URL: https??pubchem.ncbi.nim.nih.gov/substance/113493311>, entire document.
International Search Report and Written Opinion of the ISA/KR dated Feb. 3, 2017 of PCT/US2016/058474 filed Oct. 24, 2016.
International Search Report and Written Opinion of the ISR/KR dated Oct. 17, 2018 of PCT/US2018/036578 filed Jun. 8, 2018.
Extended European Search Report dated Sep. 20, 2018 in European Application No. EP 18171483.3 for Oxysterol-Statin Compounds for Bone Growth, filed May 9, 2018.
Ruan, Feng, et al. Mechanisms of bone anabolism regulated by statins. Bioscience Reports, vol. 32, No. 6, Sep. 14, 2012, pp. 511-519.
Extended European Search Report dated Jul. 2, 2018 in European application EP No. 15868634.5 for Compounds and Methods Involving Sterols, filed Dec. 8, 2015.
Velgova, H., et al. On Steroids. CXXVI. Further compounds with antisclerotization effect on *Pyrrhocoris apterus* L. tarvae; Structure and activity correlations. Collection Symposium Series (XIIIth Symposium on Chemistry of Nucleic Acid Components Spindleruv Mlyn, Czech Republic, Sep. 3-9, 2; [Collection Symposium Series] XX, XX, vol. 34, Jan. 1, 1969, pp. 3354-3376.
Montgomery, Scott R., et al. A Novel Osteogenic Oxysterol Compound for Therapeutic Development to Promote Bone Growth: Activation of Hedgehog Signaling and Osteogenesis Through Smoothened Binding. Journal of Bone and Mineral Research, vol. 29, No. 8, Aug. 21, 2014, pp. 1872-1885.
Burger, Alain, et al. Acetylenic cholesteryl derivatives as irreversible inhibitors of ecdysone biosynthesis. Tetrahedron, vol. 44, No. 4, Jan. 1, 1988, pp. 1141-1152.
Litvinovskaya, R. P., et al. Synthesis of 5[alpha]-hydroxyecdysteroid analogs containing an isoxazole ring in the side chain. Russian Journal of Organic Chemistry, Nauka/Interperiodica, MO, vol. 40, No. 10, Oct. 1, 2004, pp. 1456-1461.
Extended European Search Report dated Oct. 9, 2018 in European application No. EP 18174762.7 for Moldable Formulations Containing an Oxysterol in an Acellular Tissue Matrix, filed May 29, 2018.
Extended European Search Report dated Sep. 12, 2018 in European application No. EP 18168537.1 for Oxysterol-Therapeutic Agent Derivative for Bone Healing, filed Apr. 20, 2018.
Extended European Search Report dated Jul. 29, 2019 in European application No. EP 18168537.1 for Oxysterol-Therapeutic Agent Derivative for Bone Healing, filed Apr. 20, 2018.
Chinese First Office Action dated Jun. 14, 2019 in Chinese Application No. 201580076053.4 for Compounds and Methods Involving Sterols, of Warsaw Orthopedic Inc., filed Dec. 8, 2015, English translation provided.
Petrow, Vladimir, et al. 20-Hydroxycholesterol. Journal of the Chemical Soc, Chemical Society, Letchworth, GB. Jan. 1, 1956, pp. 4675-4676.
Buser, Z., et al. Effect of Oxy133, an osteogenic oxysterol, on new bone formation in rat two-level posterolateral fusion model. Eur Spine J., (2017) 26:2763-2772, May 25, 2017.
Extended European Search Report issued by the European Patent Office and dated Oct. 29, 2019, issued in European Application No.

(56) References Cited

OTHER PUBLICATIONS

EP 17776389.3 for Polymorphic Forms of an Oxysterol and Methods of Making Them, filed on Mar. 27, 2017.
Office Action issued by the European Patent Office, dated Oct. 7, 2019, issued in European Patent Application No. 17200797.3 filed Nov. 9, 2017 for Polymorphic Forms of an Oxysterol and Methods of Making Them.
Singhal, D. et al., Drug polymorphism and dosage form design: a practical perspective, Advanced Drug Delivery Reviews, 2004, vol. 56, p. 33.
Caira M.R: "Crystalline Polymorphism of Organic Compounds", Design of Organic solids, Weber E et al. "ED", Springer, 1998.
Balbach S. et al., Pharmaceutical evaluation of early development candidates "The 100 mg approach", International Journal of Pharmaceutics, 2004, vol. 275, pp. 1-12.
Examination Report No. 1 dated Jul. 28, 2021 issued by the Australian IP Office in corresponding Australian Patent Application No. 2017241541 entitled Polymorphic forms of an oxysterol and methods of making them.
Office Action issued by the Chinese State IP Office dated Jun. 16, 2021 issued in corresponding Chinese Patent Application No. 201711293638.9 for Polymorphic Forms of an Oxysterol and Methods of Making Them.
Office Action issued by the European Patent Office, Communication pursuant to Article 94(3) EPC dated May 27, 2020, issued in European Application No. 17 200 797.3.

* cited by examiner

POLYMORPHIC FORMS OF AN OXYSTEROL AND METHODS OF MAKING THEM

CROSS-REFERENCE TO RELATED APPLICATION

This application is a continuation-in-part application of U.S. patent application Ser. No. 15/082,695 filed Mar. 28, 2016, entitled "POLYMORPHIC FORMS OF AN OXYSTEROL AND METHODS OF MAKING THEM," which is hereby incorporated by reference in its entirety.

BACKGROUND

Different biological substances are commonly employed to promote bone growth in medical applications including fracture healing and surgical management of bone disorders including spinal disorders. Spine fusion is often performed by orthopedic surgeons and neurosurgeons alike to address degenerative disc disease and arthritis affecting the lumbar and cervical spine. Historically, autogenous bone grafting, commonly taken from the iliac crest of the patient, has been used to augment fusion between vertebral levels.

One protein that is osteogenic and commonly used to promote spine fusion is recombinant human bone morphogenetic protein-2 (rhBMP-2). Its use has been approved by the US Food and Drug Administration (FDA) for single-level anterior lumbar interbody fusion. The use of rhBMP-2 has increased significantly and indications for its use have expanded to include posterior lumbar spinal fusion as well as cervical spinal fusion.

Oxysterols form a large family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some naturally occurring oxysterols have robust osteogenic properties and can be used to grow bone. The most potent osteogenic naturally occurring oxysterol, 20(S)-hydroxycholesterol, is both osteogenic and anti-adipogenic when applied to multipotent mesenchymal cells capable of differentiating into osteoblasts and adipocytes.

One such oxysterol is OXY133 or (3S,5S,6S,8R,9S,10R, 13S,14S,17S) 17-((S)-2-hydroxyoctan-2-yl)-10,13-dimethylhexadecahydro-1H-cyclopenta[a]phenanthrene-3,6-diol, which exhibits the following structures:

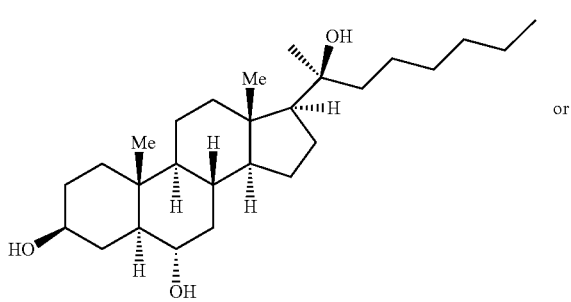

or

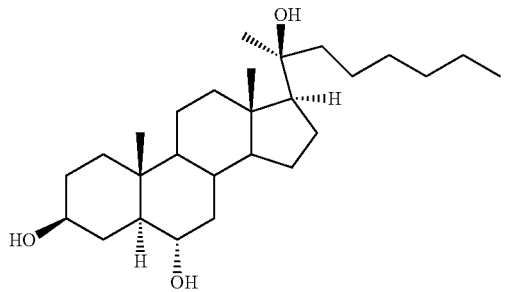

There is a need to develop different polymorphic forms of OXY133. There is also a need for providing a robust, reproducible and scalable process for the production of OXY133 monohydrate.

SUMMARY

In some embodiments, compositions and methods for preparing an OXY133 polymorph are provided. These compositions and methods include subjecting a slurry of OXY133 to conditions sufficient to convert OXY133 to OXY133 monohydrate or polymorph Form A. In some embodiments, the OXY133 monohydrate or OXY133 polymorph Form A produces an X-ray powder diffraction pattern (XRPD) comprising, consisting essentially of, or consisting of one or more of the following reflections: 16.4, 17.9 and 20.94±0.2 degree 2θ. In other embodiments, OXY133 polymorph Form A or OXY133 monohydrate further comprises, consists essentially of, or consists of one or more of the following reflections: 6.1, 12.3, 18.6±0.2 degree 2θ.

In various aspects, the conditions comprise dissolving a slurry of OXY133 in a solvent and precipitating the OXY133 polymorph by adding an anti-solvent at a temperature sufficient to precipitate the OXY133 polymorph. OXY133 useful for preparing the polymorphs described in this disclosure comprises at least one of (i) anhydrous OXY133 or OXY133 polymorph Form B; (ii) an OXY133 polymorph other than polymorph Form B; (iii) a hydrate of OXY133; or (iv) a solvate of OXY133.

In other embodiments, the conditions to convert OXY133 to an OXY133 polymorph comprise mixing OXY133 with: (i) an isopropanol solvent, and a water anti-solvent in a ratio from about 1:1 volume by volume (v/v) to about 1:2 v/v at a temperature from about 0° C. to about 20° C. to obtain OXY133 polymorph Form A or OXY133 monohydrate; (ii) a tetrahydrofuran solvent, and a water anti-solvent in a ratio of about 1:2 v/v at a temperature from about 10° C. to about 35° C. to obtain OXY133 polymorph Form A or OXY133 monohydrate; (iii) a tetrahydrofuran/acetone solvent, and a water anti-solvent at a temperature of about 35° C. to obtain OXY133 polymorph Form A or OXY133 monohydrate; or (iv) an acetone solvent, and a water anti-solvent in a ratio of about 1:1 v/v at a temperature of about 15° C. to about 25° C. to obtain OXY133 polymorph Form A or OXY133 monohydrate.

In other embodiments, OXY133 is prepared by reacting a diol having the formula:

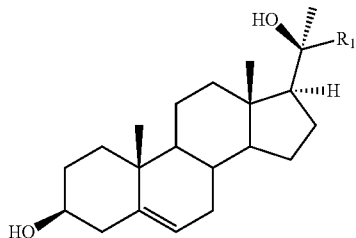

with borane, hydrogen peroxide and tetrahydrofuran to form an oxysterol or a pharmaceutically acceptable salt, hydrate or solvate thereof having the formula:

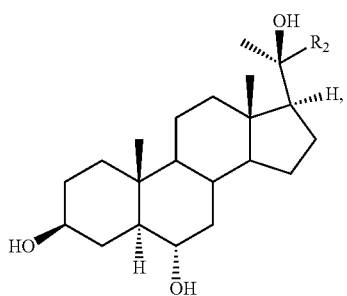

wherein $R_1$ and $R_2$ comprise a hexyl group and the diol comprises (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol (OXY133).

Other aspects of this disclosure are directed to providing a method for preparing OXY133 monohydrate or OXY133 polymorph Form A, the method comprises, consists essentially of, or consists of, slurrying OXY133 in a solvent system under conditions sufficient to convert OXY133 to an OXY133 monohydrate or polymorph Form A. In some aspects, the slurrying step comprises dissolving OXY133 in a solvent and precipitating the OXY133 monohydrate by adding an anti-solvent. In various embodiments, a solvent useful for dissolving OXY133 comprises, consists essentially of, or consists of, isopropanol, tetrahydrofuran, tetrahydrofuran/acetone or acetone and the anti-solvent comprises, consists essentially of, or consists of water. In some embodiments, the slurrying step occurs at a stirring temperature from about 0° C. to about 20° C. In other embodiments, OXY133 polymorph Form A is formed when the solvent is isopropanol, the anti-solvent is water in a ratio of 1:2 v/v at a temperature from about 0° C. to about 20° C.

In yet other embodiments, OXY133 polymorph Form A can be obtained when the solvent for dissolving the OXY133 slurry is tetrahydrofuran, the anti-solvent is water in a ratio of 1:2 v/v at a temperature from about 10° C. to about 35° C. In some aspects, the water content of OXY133 monohydrate comprises, consists essentially of, or consists of, a range from about 3.25% to about 4.1% by weight. In other aspects, OXY133 monohydrate obtained by the methods of this disclosure has a yield of from about 85% to about 94% by weight of OXY133. In other aspects, OXY133 monohydrate or OXY133 polymorph Form A obtained by the methods of this disclosure includes drying at about 20° C., which can be accomplished in a vacuum or a freeze dryer.

In other embodiments, this disclosure provides a method for isolating OXY133 monohydrate, the method comprising heating a mixture of anhydrous OXY133 with isopropanol at a temperature from about 25° C. to about 35° C., cooling the mixture to about 5° C., and precipitating OXY133 monohydrate from the cooled mixture by adding water to the mixture at a ratio of isopropanol to water of 1:2 v/v. In some aspects, the OXY133 monohydrate is dried at a temperature of about 20° C. The yield of OXY133 monohydrate obtained by methods described in this disclosure is from about 85% to about 94% by weight.

Other aspects of this disclosure provide a pharmaceutical composition which includes OXY133 polymorph Form A or OXY133 monohydrate. In some embodiments, the pharmaceutical composition includes OXY133 polymorph Form A or OXY133 monohydrate and pharmaceutically acceptable excipients.

In some embodiments, a solid form of OXY133 polymorph comprises polymorph Form C, polymorph Form D, polymorph Form E, polymorph Form F, polymorph Form G, polymorph Form H, polymorph Form I or a mixture thereof. These polymorphic forms may be in the form of a hydrate, including a monohydrate, dihydrate, hemihydrate, sesquihydrate, trihydrate, tetrahydrate or the like, as well as the corresponding solvated forms.

In certain embodiments, the OXY133 polymorph is polymorph Form C that produces an X-ray powder diffraction pattern comprising, consisting essentially of, or consisting of one or more of the following reflections: 13.2, 13.3 and 15.96±0.2 degree 2θ. In other embodiments, the X-ray powder diffraction pattern of polymorph Form C further comprises, consists essentially of, or consists of one or more of the following reflections: 11.8, 14.9 and 17.9±0.2 degree 2θ.

In some aspects, the OXY133 polymorph is polymorph Form D that produces an X-ray powder diffraction pattern comprising, consisting essentially of, or consisting of one or more of the following reflections: 15.3, 15.7 and 17.7±0.2 degree 2θ. In other aspects, the X-ray powder diffraction pattern of polymorph Form D further comprises, consists essentially of, or consists of one or more of the following reflections: 11.9, 13.2 and 18.0±0.2 degree 2θ.

In some aspects, the OXY133 polymorph is polymorph Form E that produces an X-ray powder diffraction pattern comprising, consisting essentially of, or consisting of one or more of the following reflections: 5.9, 10.2 and 14.96±0.2 degree 2θ. In other aspects, the X-ray powder diffraction pattern of polymorph Form E further comprises, consists essentially of, or consists of one or more of the following reflections: 11.79, 11.84 and 17.9±0.2 degree 2θ.

In some embodiments, the OXY133 polymorph is polymorph Form F that produces an X-ray powder diffraction pattern comprising, consisting essentially of, or consisting of one or more of the following reflections: 5.86, 13.38 and 20.01±0.2 degree 2θ. In other aspects, the X-ray powder diffraction pattern of polymorph Form F further comprises, consists essentially of, or consists of one or more of the following reflections: 11.85, 14.93 and 17.91±0.2 degree 2θ.

In some aspects, the OXY133 polymorph is polymorph Form G that produces an X-ray powder diffraction pattern comprising, consisting essentially of, or consisting of one or more of the following reflections: 15.0, 16.0 and 18.8±0.2 degree 2θ. In other aspects, the X-ray powder diffraction pattern of polymorph Form G further comprises, consists essentially of, or consists of one or more of the following reflections: 5.9, 11.9 and 17.96±0.2 degree 2θ.

In some embodiments, the OXY133 polymorph is polymorph Form H that produces an X-ray powder diffraction pattern comprising, consisting essentially of, or consisting of one or more of the following reflections: 7.87, 16.32 and 18.90±0.2 degree 2θ. In other aspects, the X-ray powder diffraction pattern of polymorph Form H further comprises, consists essentially of, or consists of one or more of the following reflections: 9.92, 15.00 and 16.72±0.2 degree 2θ.

In some aspects, the OXY133 polymorph is polymorph Form I that produces an X-ray powder diffraction pattern comprising, consisting essentially of, or consisting of one or more of the following reflections: 13.19, 13.42 and 14.98±0.2 degree 2θ. In other aspects, the X-ray powder diffraction pattern of polymorph Form I further comprises, consists essentially of, or consists of one or more of the following reflections: 5.91, 11.92 and 17.97±0.2 degree 2θ.

In various embodiments, a method for preparing an OXY133 polymorph is provided, the method comprising subjecting a slurry of OXY133 to conditions sufficient to convert OXY133 to the OXY133 polymorph, wherein the OXY133 polymorph comprises polymorph Form C, polymorph Form D, polymorph Form E, polymorph Form F, polymorph Form G, polymorph Form H, polymorph Form I or a mixture thereof. In certain embodiments, the conditions to convert to an OXY133 polymorph comprise, consists essentially of, or consist of mixing OXY133 with: (i) an acetone solvent, and a water anti-solvent in a ratio of about 1:1 v/v at a temperature of about 30° C. to about 60° C. to obtain OXY133 polymorph Form C; (ii) a methanol solvent, and a water anti-solvent in a ratio of about 1:1 v/v at a temperature of about 20° C. to about 70° C. to obtain OXY133 polymorph Form D; (iii) water at a temperature from about 20° C. to about 70° C. to obtain OXY133 polymorph Form E; (iv) an acetone solvent, and a water anti-solvent at a temperature from about 5° C. to about 15° C. to obtain OXY133 polymorph Form F; (v) an isopropanol solvent, and a water anti-solvent in a ratio of about 1:2 v/v at a temperature of about 40° C. to obtain OXY133 polymorph Form G; (vi) an isopropanol solvent, and a water anti-solvent in a ratio of about 1:2 at a temperature of about −10° C. to obtain OXY133 polymorph Form H; (vii) a methanol/acetone solvent, and a water anti-solvent at a temperature of about 20° C. to obtain OXY133 polymorph Form I; or (viii) acetone recrystallization at a temperature of about 20° C. to obtain OXY133 polymorph Form I.

In various embodiments, OXY133 is prepared by reacting a diol having the formula:

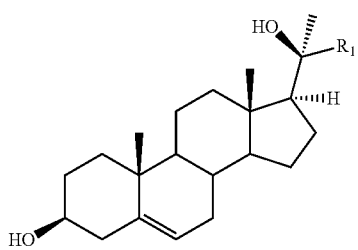

with borane, hydrogen peroxide and tetrahydrofuran to form an oxysterol or a pharmaceutically acceptable salt, hydrate or solvate thereof having the formula:

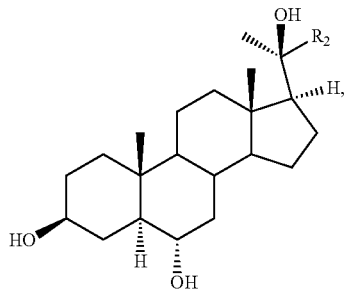

wherein $R_1$ and $R_2$ comprise a hexyl group and the diol comprises (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol (OXY133).

In certain embodiments, a pharmaceutical composition is provided comprising an OXY133 polymorph comprising polymorph Form C, polymorph Form D, polymorph Form E, polymorph Form F, polymorph Form G, polymorph Form H, polymorph Form I or a mixture thereof and a pharmaceutically acceptable excipient. In other embodiments, the OXY133 polymorph comprises, consists essentially of, or consists of (i) Form C that produces an X-ray powder diffraction pattern comprising one or more of the following reflections: 13.2, 13.3 and 15.96±0.2 degree 2θ; (ii) Form D that produces an X-ray powder diffraction pattern comprising one or more of the following reflections: 15.3, 15.7 and 17.7±0.2 degree 2θ; (iii) Form E that produces an X-ray powder diffraction pattern comprising one or more of the following reflections: 5.9, 10.2 and 14.96±0.2 degree 2θ; (iv) Form F that produces an X-ray powder diffraction pattern comprising one or more of the following reflections: 11.79, 11.84 and 17.9±0.2 degree 2θ; (v) Form G that produces an X-ray powder diffraction pattern comprising one or more of the following reflections: 15.0 16.0 and 18.8±0.2 degree 2θ; Form H that produces an X-ray powder diffraction pattern comprising one or more of the following reflections: 7.87, 16.32 and 18.90±0.2 degree 2θ; or (vi) Form I that produces an X-ray powder diffraction pattern comprising one or more of the following reflections: 13.19, 13.42 and 14.98±0.2 degree 2θ.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIGS. 6A, 6B, 6C, 6D, 6E, 6F, 6G, 6H, 6I, 6J, 6K, 6L, 6M, 6N, 6O, 6P, 6Q, 6R, 6S, 6T, 6U, 6V, 6W and 6X are XRPDs of OXY133 polymorph Form A;

FIG. 43 is an XRPD graph of OXY133 monohydrate batch FP-000477.

Figure 1:
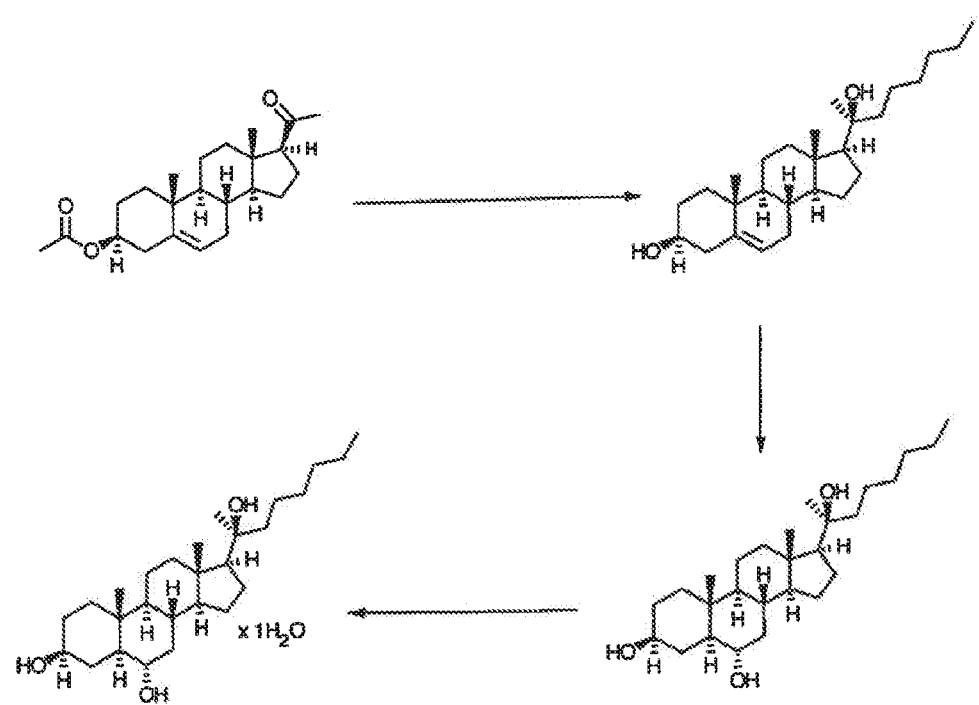
FIG. 1 illustrates a step-wise reaction for synthesizing OXY133 with starting reactants comprising pregnenolone acetate, as shown in one embodiment of this disclosure. The pregnenolone is reacted with an organometallic compound to produce a sterol or diol having two hydroxyl groups. The sterol or diol is then reacted with borane and hydrogen peroxide and purified to produce OXY133.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all sub ranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an alkanolamine" includes one, two, three or more alkanolamines.

The term "anti-solvent," as used herein, refers to a solvent in which a compound is substantially insoluble. An anti-solvent useful in this disclosure includes, but is not limited to, water.

The term "crystalline," as used herein, means having a regularly repeating arrangement of molecules or external face planes.

The term "crystalline composition," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, or desolvated solvates.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug". OXY133 is an example of a bioactive agent. Bioactive or pharmaceutical compositions are sometimes referred to herein as "pharmaceutical compositions" or "bioactive compositions" of the current disclosure. Sometimes the phrase "administration of OXY133" is used herein in the context of administration of this compound to a subject (e.g., contacting the subject with the compound, injecting the compound, administering the compound in a drug depot, etc.). It is to be understood that the compound for such a use can generally be in the form of a pharmaceutical composition or bioactive composition comprising the OXY133. It will be understood that unless otherwise specified a "drug" formulation may include more than one therapeutic agent, wherein exemplary combinations of therapeutic agents include a combination of two or more drugs. The term "drug" is also meant to refer to the "API" whether it is in a crude mixture or purified or isolated.

The term "biodegradable" includes compounds or components that will degrade over time by the action of enzymes, by hydrolytic action and/or by other similar mechanisms in the human body. In various embodiments, "biodegradable" includes components that can break down or degrade within the body to non-toxic components as cells (e.g., bone cells) infiltrate the components and allow repair of the defect. By "bioerodible" it is meant that the compounds or components will erode or degrade over time due, at least in part, to contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The term "alkyl" as used herein, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl" and/or "alkynyl" is used, as defined below. In some embodiments, the alkyl groups are (C1-C40) alkyl. In some embodiments, the alkyl groups are (C1-C6) alkyl.

The term "alkanyl" as used herein refers to a saturated branched, straight-chain or cyclic alkyl radical derived by the removal of one hydrogen atom from a single carbon atom of a parent alkane. Typical alkanyl groups include, but are not limited to, methanyl; ethenyl; propanyls such as propan-1-yl, propan-2-yl(isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are (C1-C40) alkanyl. In some embodiments, the alkanyl groups are (C1-C6) alkanyl.

The term "alkenyl" as used herein refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is (C2-C40) alkenyl. In some embodiments, the alkenyl group is (C2-C6) alkenyl.

The term "alkynyl" as used herein refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In some embodiments, the alkynyl group is (C2-C40) alkynyl. In some embodiments, the alkynyl group is (C2-C6) alkynyl.

The term "alkyldiyl" as used herein refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is (C1-C40) alkyldiyl. In some embodiments, the alkyldiyl group is (C1-C6) alkyldiyl. Also contemplated are saturated acyclic alkanyldiyl radicals in which the radical centers are at the terminal carbons, e.g., methandiyl (methano); ethan-1,2-diyl (ethano); propan-1,3-diyl(propano); butan-1,4-diyl(butano); and the like (also referred to as alkylenos, defined infra).

The term "alkyleno" as used herein refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is (C1-C40) alkyleno. In some embodiments, the alkyleno group is (C1-C6) alkyleno.

The terms "heteroalkyl," "heteroalkanyl," "heteroalkenyl," "heteroalkanyl," "heteroalkyldiyl" and "heteroalkyleno" as used herein refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR', =N—N=, —N=N—, —N(O)N—, —N=N—NR'—, —PH—, —P(O)2-, —O—P(O)2-, —SH2-, —S(O)2-, or the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

The term "aryl" as used herein refers to a monovalent aromatic hydrocarbon radical derived by the removal of one hydrogen atom from a single carbon atom of a parent aromatic ring system.

Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is (C5-C14) aryl or a (C5-C10) aryl. Some preferred aryls are phenyl and naphthyl.

The term "aryldiyl" as used herein refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryldiyl group is (C5-C14) aryldiyl or (C5-C10) aryldiyl. For example, some preferred aryldiyl groups are divalent radicals derived from benzene and naphthalene, especially phena-1,4-diyl, naphtha-2,6-diyl and naphtha-2,7-diyl.

The term "arydeno" as used herein refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

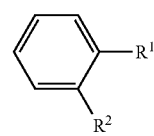

wherein $R^1$, when taken alone is hydrogen, or when taken together with $R^2$ is (C5-C14) aryleno; and $R^2$, when taken alone is hydrogen, or when taken together with $R^1$ is (C5-C14) aryleno.

When $R^1$ and $R^2$ are each hydrogen, the resultant compound is benzene. When $R^1$ taken together with $R^2$ is C6 aryleno (benzeno), the resultant compound is naphthalene. When $R^1$ taken together with $R^2$ is C10 aryleno (naphthaleno), the resultant compound is anthracene or phenanthrene. Typical aryleno groups include, but are not limited to, aceanthryleno, acenaphthyleno, acephenanthyleno, anthraceno, azuleno, benzeno (benzo), chryseno, coroneno, fluorantheno, fluoreno, hexaceno, hexapheno, hexyleno, as-indaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2]benzo), [1,2]naphthaleno, [2,3]naphthaleno, etc. Thus, in the above example, when $R^1$ taken together with $R^2$ is [2,3]naphthaleno, the resultant compound is anthracene. When $R^1$ taken together with $R^2$ is [1,2]naphthaleno, the resultant compound is phenanthrene. In one embodiment, the aryleno group is (C5-C14), or (C5-C10).

The term "arylaryl" as used herein refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. When the number of carbon atoms comprising an arylaryl group is specified, the numbers refer to the carbon atoms comprising each parent aromatic ring. For example, (C1-C14) arylaryl is an arylaryl group in which each aromatic ring comprises from 5 to 14 carbons, e.g., biphenyl, triphenyl, binaphthyl, phenylnaphthyl, etc. In some instances, each parent aromatic ring system of an arylaryl group is independently a (C5-C14) aromatic or a (C1-C10) aromatic. Some arylaryl groups in which all of the parent aromatic ring systems are identical include, e.g., biphenyl, triphenyl, binaphthyl, trinaphthyl, etc.

The term "biaryl" as used herein refers to an arylaryl radical having two identical parent aromatic systems joined directly together by a single bond. Typical biaryl groups include, but are not limited to, biphenyl, binaphthyl, bianthracyl, and the like. In some instances, the aromatic ring systems are (C5-C14) aromatic rings or (C5-C10) aromatic rings. In one embodiment, the biaryl group is biphenyl.

The term "arylalkyl" as used herein refers to an acyclic alkyl radical in which one of the hydrogen atoms bonded to a carbon atom, typically a terminal or sp2 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C6-C40) arylalkyl, e.g., the alkanyl, alkenyl or alkynyl moiety of the arylalkyl group is (C1-C26) and the aryl moiety is (C5-C14). In some embodiments, the arylalkyl group is (C6-C13), e.g., the alkanyl, alkenyl or alkynyl moiety of the arylalkyl group is (C1-C3) and the aryl moiety is (C5-C10).

The term "heteroaryl" as used herein refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl, or a 5-10 membered heteroaryl. Some heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryldiyl group is 5-14 membered heteroaryldiyl or a 5-10 membered heteroaryldiyl. Some heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryleno" as used herein refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

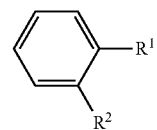

wherein $R^1$, when taken alone is hydrogen, or when taken together with $R^2$ is 5-14 membered heteroaryleno; and $R^2$, when taken alone is hydrogen, or when taken together with $R^1$ is 5-14 membered heteroaryleno.

When $R^1$ and $R^2$ are each hydrogen, the resultant compound is benzene. When $R_1$ taken together with $R^2$ is a 6-membered heteroaryleno pyridino, the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, furan, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, or the like. Where a specific connectivity is intended, the involved bridging atoms (of the heteroaryleno bridge) are denoted in brackets, e.g., [1,2] pyridino, [2,3]pyridino, [3,4]pyridino, etc. Thus, in the above example, when $R^1$ taken together with $R^2$ is [1,2] pyridino, the resultant compound is quinolizine. When $R^1$ taken together with $R_2$ is [2,3]pyridino, the resultant compound is quinoline. When $R^1$ taken together with $R^2$ is [3,4]pyridino, the resultant compound is isoquinoline. In some embodiments, the heteroaryleno group is 5-14 membered heteroaryleno or 5-10 membered heteroaryleno. Some heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyndmo, pyrrolo, quinazolino, quinolino, etc.

The term "heteroaryl-heteroaryl" as used herein refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridyl-purinyl, bipurinyl, etc. When the number of ring atoms is specified, the numbers refer to the number of atoms comprising each parent heteroaromatic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. In some embodiments, each parent heteroaromatic ring system is independently a 5-14 membered heteroaromatic, or a 5-10 membered heteroaromatic. Also, there are heteroaryl-heteroaryl groups in which all of the parent heteroaromatic ring systems are identical. Some heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "biheteroaryl" as used herein refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-14 membered heteroaromatic rings or 5-10 membered heteroaromatic rings. Some biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

The term "heteroarylalkyl" as used herein refers to an acyclic alkyl radical in which one of the hydrogen atoms bonded to a carbon atom, typically a terminal or sp2 carbon atom, is replaced with a heteroaryl radical. Where specific alkyl moieties are intended, the nomenclature heteroarylalkanyl, heteroarylakenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In some embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

The term "substituted" as used herein refers to a radical in which one or more hydrogen atoms are each independently replaced with the same or different substituent(s). Typical substituents include, but are not limited to, —X, —R, —O—, =O, —OR, —O—OR, —SR, —S—, =S, —NRR, =NR, perhalo (C1-C6) alkyl, —CX3, —CF3, —CN, —OCN, —SCN, —NCO, —NCS, —NO, —NO2, =N2, —N3, —S(O)2O—, —S(O)2OH, —S(O)2R, —C(O)R, —C(O)X, —C(S)R, —C(S)X, —C(O)OR, —C(O)O—, —C(S)OR, —C(O)SR, —C(S)SR, —C(O)NRR, —C(S)NRR and —C(NR)NRR, where each X is independently a halogen (e.g., —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

The term "solvate" as used herein refers to an aggregate that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be inorganic solvents such as for example water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent.

The term "pharmaceutically acceptable excipient," as used herein, includes any and all solvents, dispersion media, coatings, antibacterial and antifungal agents, isotonic and absorption delaying agents and the like. The use of such media and agents for pharmaceutical active substances is known in the art, such as in *Remington: The Science and Practice of Pharmacy, 20th ed.*; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

The term "solution," as used herein, refers to a mixture containing at least one solvent and at least one compound that is at least partially dissolved in the solvent.

The term "solvent," as used herein, means a substance, typically a liquid, that is capable of completely or partially dissolving another substance, typically a solid. Solvents useful in this disclosure include, but are not limited to, water, acetone, methanol, tetrahydrofuran (THF), isopropanol (IPA) or mixtures thereof.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol, sterol or diol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol, sterol or diol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol, sterol, or diol to assist in obtaining a controlled release depot effect, the oxysterol, sterol, or diol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The term "an OXY133 product" includes OXY133, as well as its polymorphs Forms A, B, C, D, E, F, G, H and I, and solvates or hydrates of OXY133, such as hydrates and those formed with organic solvents.

The term "impurity" is used herein to refer to an impurity of OXY133 or OXY133 monohydrate including diastereomer D1, diastereomer D2 or other OXY133 monohydrate impurity, for example $C_{27}H_{46}O_2$ diol used to synthesize OXY133 monohydrate or any combinations thereof.

A "therapeutically effective amount" or "effective amount" is such that when administered, the oxysterol (e.g., OXY133), sterol, diol, results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfiber particles, nanospheres, nanoparticles, coating, matrices, wafers, pills, pellets, emulsions, liposomes, micelles, gels, or other pharmaceutical delivery compositions or a combination thereof. Suitable materials for the depot are pharmaceutically acceptable biodegradable and/or any bioabsorbable materials that are FDA approved or GRAS materials. These materials can be polymeric or non-polymeric, as well as synthetic or naturally occurring, or a combination thereof.

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a bone cavity, or in close proximity (within about 0.1 cm, or within about 10 cm, for example) thereto. For example, the drug dose delivered locally from the drug depot may be, for example, 10%, 20%, 30%, 40%, 50%, 60%, 70%, 80%, 90%, 95%, 99%, 99.9% or 99.999% less than the oral dosage or injectable dose.

The term "mammal" refers to organisms from the taxonomy class "mammalian," including but not limited to humans, other primates such as chimpanzees, apes, orangutans and monkeys, rats, mice, cats, dogs, cows, horses, etc.

The oxysterol can be "osteogenic," where it can enhance or accelerate the ingrowth of new bone tissue by one or more mechanisms such as osteogenesis, osteoconduction and/or osteoinduction.

The term "slurry" or "re-slurry" refers to a crystallization technique wherein a product is dissolved in a solvent in which it has moderate to strong solubility. Subsequently, while stirring, an anti-solvent in which the product has poor solubility is slowly added until the product crystallizes out.

Compositions and methods for preparing OXY133 have been described in International Application No. PCT/2015/064526 filed on Dec. 8, 2015, the contents of which is incorporated herein by reference in its entirety.

New compositions and methods are provided to efficiently and safely make oxysterols including OXY133 and polymorphs of OXY133. Methods and compositions that can efficiently and safely generate OXY133, OXY133 polymorphs and that can be incorporated into pharmaceutical compositions including the same are also provided.

Any of the solid forms of OXY133 polymorphs described herein can be a component of a composition comprising OXY133. In some embodiments, these compositions comprise, consist essentially of, or consist of at least one of the solid forms of OXY133 polymorphs. In some embodiments, the composition can comprise only one polymorphic form of OXY133 form A, B, C, D, E, F, G, H, or form I. In other embodiments, the composition can comprise a plurality of polymorphic forms of OXY133 including forms A, B, C, D, E, F, G, H, and/or form I.

The section headings below should not be restricted and can be interchanged with other section headings.

Oxysterols

The present disclosure includes an osteogenic oxysterol (e.g., OXY133), sterol, or diol and its ability to promote osteogenic differentiation in vitro. OXY133 is a particularly effective osteogenic agent. In various applications, OXY133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of OXY133 is that it provides greater ease of synthesis and improved time to fusion when compared to other osteogenic oxysterols. OXY133 is a small molecule that can serve as an anabolic therapeutic agent for bone growth, as well as a useful agent for treatment of a variety of other conditions.

One aspect of the application disclosure is a compound, named OXY133, having the formula:

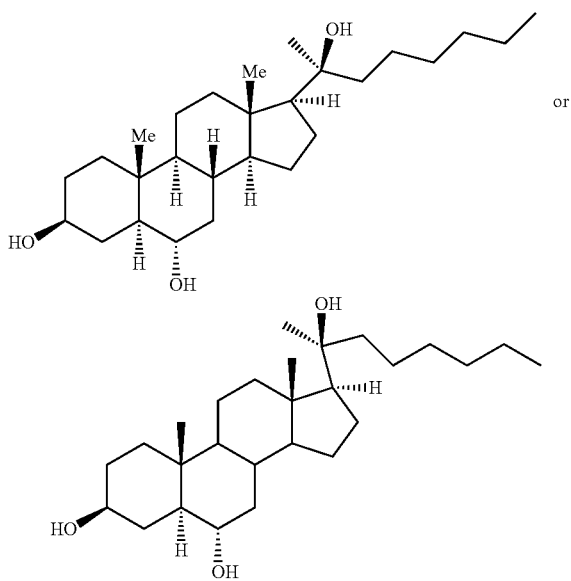

or a pharmaceutically acceptable salt, solvate or hydrate thereof. The OXY133 may be used as a bioactive or pharmaceutical composition comprising OXY133 or a pharmaceutically acceptable salt, solvate or hydrate thereof and a pharmaceutically acceptable carrier.

Another aspect of the disclosure is a method for inducing (stimulating, enhancing) a hedgehog (Hh) pathway mediated response, in a cell or tissue, comprising contacting the cell or tissue with a therapeutically effective amount of OXY133. The cell or tissue can be in vitro or in a subject, such as a mammal. The hedgehog (Hh) pathway mediated response involves the stimulation of osteoblastic differentiation, osteomorphogenesis, and/or osteoproliferation; the stimulation of hair growth and/or cartilage formation; the stimulation of neovasculogenesis, e.g. angiogenesis, thereby enhancing blood supply to ischemic tissues; or it is the inhibition of adipocyte differentiation, adipocyte morphogenesis, and/or adipocyte proliferation; or the stimulation of progenitor cells to undergo neurogenesis. The Hh mediated response can comprise the regeneration of any of a variety of types of tissues, for use in regenerative medicine. Another aspect of the disclosure is a method for treating a subject having a bone disorder, osteopenia, osteoporosis, or a bone fracture, comprising administering to the subject an effective amount of a bioactive composition or pharmaceutical composition comprising OXY133. The subject can be administered the bioactive composition or pharmaceutical composition at a therapeutically effective dose in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose in an effective dosage form at a selected interval to ameliorate the symptoms of osteoporosis. In some embodiments, a composition comprising OXY133 may include mesenchymal stem cells to induce osteoblastic differentiation of the cells at a targeted surgical area.

In various aspects, the OXY133 can be administered to a cell, tissue or organ by local administration. For example, the OXY133 can be applied locally with a cream or the like, or it can be injected or otherwise introduced directly into a cell, tissue or organ, or it can be introduced with a suitable medical device, such as a drug depot as discussed herein. In some embodiments, the OXY133 can be in an oral formulation, a topical patch, an intranasal or intrapulmonary formulation for inhalation.

In some embodiments, the dosage of OXY133, sterol, or diol is from approximately 10 pg/day to approximately 80 mg/day. Additional dosages of OXY133, sterol, or diol include from approximately 2.4 ng/day to approximately 50 mg/day; approximately 50 ng/day to approximately 2.5 mg/day; approximately 250 ng/day to approximately 250 mcg/day; approximately 250 ng/day to approximately 50 mcg/day; approximately 250 ng/day to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day.

In addition to the compound OXY133, sterol, or diol other embodiments of the disclosure encompass any and all individual stereoisomers at any of the stereocenters present in OXY133, including diastereomers, racemates, enantiomers, and other isomers of the compound. In embodiments of the disclosure, OXY133, sterol, oxysterol, diol may include all polymorphs, solvates or hydrates of the compound, such as hydrates and those formed with organic solvents.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts. Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

In various embodiments, OXY133, sterol, or diol includes one or more biological functions. That is, OXY133, sterol, or diol can induce a biological response when contacted with a mesenchymal stem cell or a bone marrow stromal cell. For example, OXY133, sterol, or diol may stimulate osteoblastic differentiation. In some embodiments, a bioactive composition including OXY133 sterol, or diol may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

Methods of Making Intermediary Diol

In some embodiments, the current disclosure provides a method for the preparation of an intermediary diol used in the production of OXY133, as shown below. The diol may be used to promote bone growth as well. Previous methods of synthesis for OXY133 production were inefficient and not suitable for scale up manufacturing. Some stereoisomers of OXY133 perform less optimally than others. The disclosed method is stereoselective and produces a high yield of the specific isomeric form of the diol shown below, which has been shown to produce an optimally effective isomeric form of OXY133.

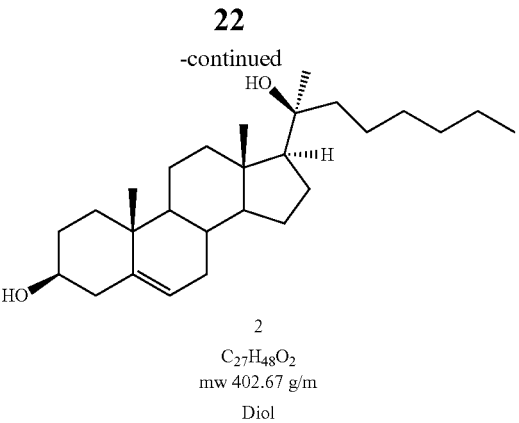

2
$C_{27}H_{48}O_2$
mw 402.67 g/m
Diol

In one embodiment, as shown above in Scheme 1, pregnenolone acetate (formula 1) may be alkylated by an organometallic reagent to synthesize the intermediary diol, shown above as formula 2. In some embodiments, pregnenolone acetate is reacted with a Grignard reagent to facilitate alkylation of the C20 position on the pregnenolone acetate molecule. In some embodiments, n-hexylmagnesium chloride is used as the organometallic reagent.

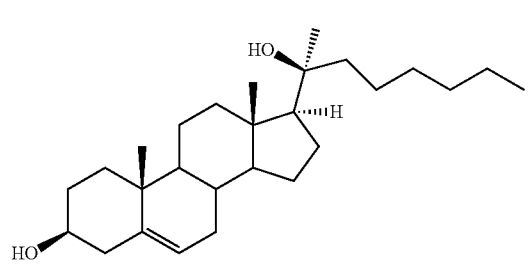

Disclosed are multiple embodiments of reactions to synthesize the intermediary diol. The diol synthesized has the IUPAC designation (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol. Generally, the method of synthesizing the diol includes reacting pregnenolone, pregnenolone acetate or a pregnenolone derivative with an organometallic reagent to facilitate alkylation of the C20 position, as shown below:

Scheme 1

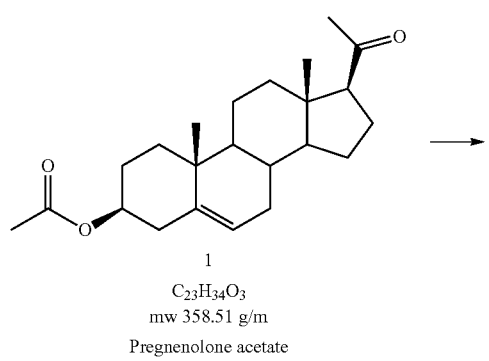

1
$C_{23}H_{34}O_3$
mw 358.51 g/m
Pregnenolone acetate

Scheme 2

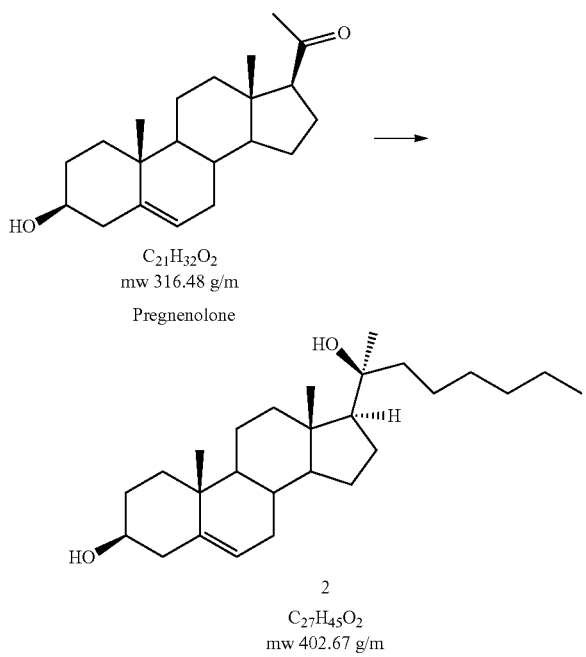

$C_{21}H_{32}O_2$
mw 316.48 g/m
Pregnenolone

2
$C_{27}H_{48}O_2$
mw 402.67 g/m

In some embodiments, as shown above as Scheme 2, pregnenolone is reacted with a Grignard reagent such as n-hexylmagnesium chloride to facilitate alkylation of the C20 position of the pregnenolone molecule to form the intermediary diol shown as formula 2.

The method of synthesizing the intermediary diol (formula 2) or (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol is stereoselective and produces a high yield of the diol. For example, in some embodiments, the yield of the desired stereoisomer of the diol is between about 60% and about 70%. In some embodiments, the yield of the desired stereoisomer of the diol is between about 50% and about 60%. However, it is contemplated that the percent yield may be higher or lower than these amounts. For example, the percent yield of formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the alkylation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, pregnenolone or pregnenolone acetate is used as a starting reactant. However, in other embodiments, derivatives of pregnenolone acetate may be used. For example, other specific examples of compounds which could be used in the present disclosure include: pregnenolone sulfate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3β-hydroxypregn-5-en-20-one sulfate, 3-hydroxy-19-norpregna-1,3,5(10)-trien-20-one, 3-hydroxy-19-norpregna-1,3,5(10),6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, 21-thiol esters of pregnenolone sulfate, pyridinium, imidazolium, 6-methylpregnenolone sulfate, 6,16α-dimethylpregnenolone sulfate, 3β-hydroxy-6-methylpregna-5,16-dien-20-one sulfate, 3β-hydroxy-6,16-dimethylpregna-5,16-dien-20-one sulfate, 3jβ-hydroxypregna-5,16-dien-20-one sulfate, diosgenin sulfate, 3β-hydroxyandrost-5-en-17β-carboxylic acid methyl ester sulfate, 3α hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol-3-methyl ether, 17-deoxyestrone, and 17β-hydroxyestra-1,3,5(10)-trien-3-yl carboxymethyl ether.

In some embodiments, the organometallic comprises n-hexylmagnesium chloride. However, in some embodiments, the alkylation reaction may be carried out with the use of an alkyllithium, such as, for example, n-hexyllithium. In various embodiments, the organometallic includes an alkyl halide. For example, the organometallic reagent may have the following formula:

R—Mg—X, where Mg comprises magnesium, X comprises chlorine, bromine, fluorine, iodine, or astatine and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a (C1-C20) alkyl or heteroalkyl, a (C$_2$-C$_{20}$) aryl or heteroaryl, a (C$_6$-C$_{26}$) arylalkyl or heteroalkyl and a (C$_5$-C$_{20}$) arylalkyl or heteroaryl-heteroalkyl, a (C$_4$-C$_{10}$) alkyldiyl or heteroalkyldiyl, or a (C$_4$-C$_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

Alternatively, the organometallic may comprise the formula:

R—Li, where Li comprises lithium and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a (C$_1$-C$_{20}$) alkyl or heteroalkyl, a (C$_2$-C$_{20}$) aryl or heteroaryl, a (C$_6$-C$_{26}$) arylalkyl or heteroalkyl and a (C5-C20) arylalkyl or heteroaryl-heteroalkyl, a (C4-C10) alkyldiyl or heteroalkyldiyl, or a (C4-C10) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

In some embodiments, the alkylation reaction is exothermic and the reaction vessel may be temperature controlled to maintain optimal reaction kinetics. In some embodiments, the exothermic reaction releases about 1000 BTU per pound of solution. Due to the strongly exothermic nature of the reaction, the Grignard reagent therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 15° C., 10° C., 5° C. or 1° C. In some embodiments, the reaction vessel is maintained at about 0° C. during the alkylation reaction to form the intermediary diol of formula 2.

In various embodiments, the diol of formula 2 is synthesized along with byproducts and can be purified. For example, the resulting diol of formula 2 may be a byproduct of a diastereomeric mixture. In various embodiments, the diol of formula 2 may be isolated and purified. That is, the diol of formula 2 can be isolated and purified to the desired purity, e.g., from about 95% to about 99.9% by filtration, centrifugation, distillation, which separates volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. The diol may be purified by contacting it with organic and/or inorganic solvents, for example, tetrahydrofuran, water, diethyl ether, dichloromethane, ethyl acetate, acetone, n,n-dimethylformamide, acetonitrile, dimethyl sulfoxide, ammonia, t-butanol, n-propanol, ethanol, methanol, acetic acid, or a combination thereof.

In various embodiments, the alkylation step and the purification step take place in the same reaction vessel.

In some embodiments, the diol is quenched with aqueous ammonium chloride or acetic acid to reduce the amount of anions present and neutralize the reaction and separated from the resulting organic layer. The separated residue is recovered by evaporation and purified by silica gel column chromatography.

The diol may be anhydrous or in the monohydrate form. However, in other embodiments the purified diol may be crystallized in other hydrous forms, such as, for example, a dihydrate, a hemihydrate, a sesquihydrate, a trihydrate, a tetrahydrate and the like, as well as the corresponding solvated forms. In other embodiments, the purified diol is crystallized as a co-crystal or a pharmaceutically acceptable salt.

Methods of Making OXY133

In some embodiments, the current disclosure provides a method for the preparation of an OXY133, as shown below. Previous methods of synthesis for OXY133 produce diastereomeric mixtures of OXY133 intermediates which require purification methods to separate. As discussed above to form the intermediary diol, the disclosed method is stereoselective and produces a high yield of the specific isomeric forms of OXY133. The formula of OXY133 is shown below.

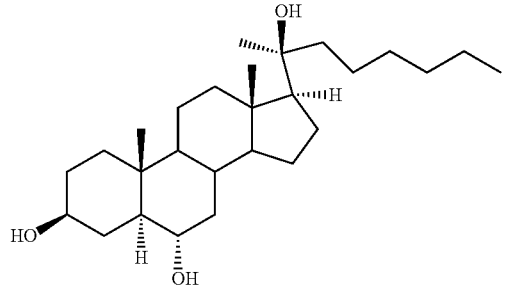 [SMILES: CCCCCC[C@](C)(O)[C@H]1CCC2C3C[C@H](O)[C@H]4C[C@@H](O)CC[C@]4(C)C3CC[C@@]21C]

Disclosed are multiple embodiments of reactions to synthesize OXY133. OXY133 has the IUPAC designation (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol. OXY133 has previously been synthesized through a complex process not suitable for scale-up as shown below:

Scheme 3

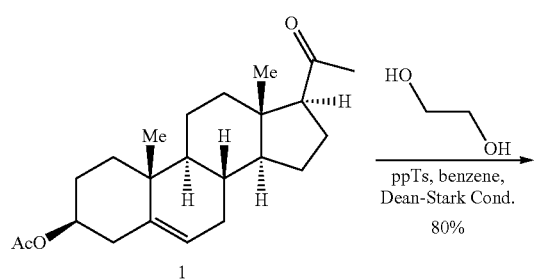

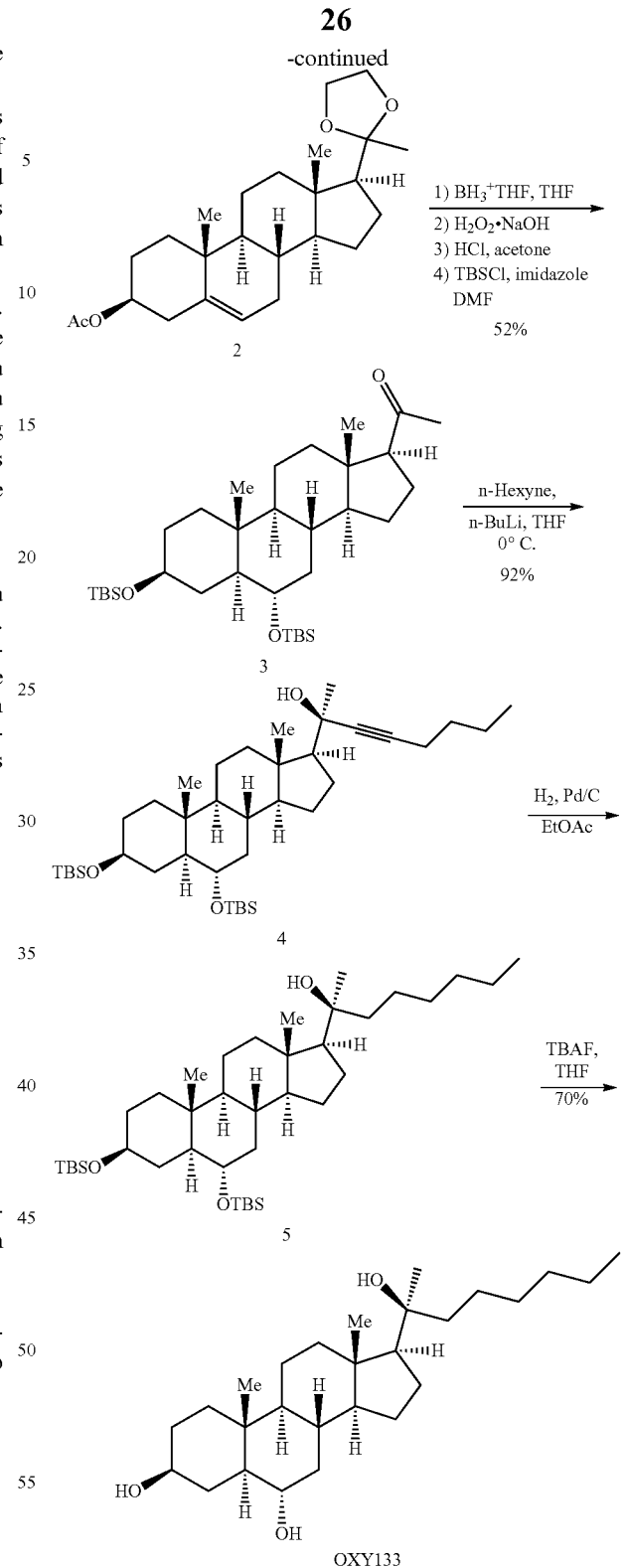

However, the reaction has difficulty being carried out in a single container. The reaction shown above involves more reagents to carry out reaction steps (e.g., blocking and deprotection groups and steps) which have an adverse environmental impact. Additionally, the known methods involve reagents that are expensive and often difficult to obtain. Further, the method shown in Scheme 3 gives relatively low yields, has more degradation products, impurities and creates many toxic byproducts.

Generally, the method of synthesizing OXY133 as disclosed herein includes reacting the diol synthesized as described herein with borane in the reaction shown below:

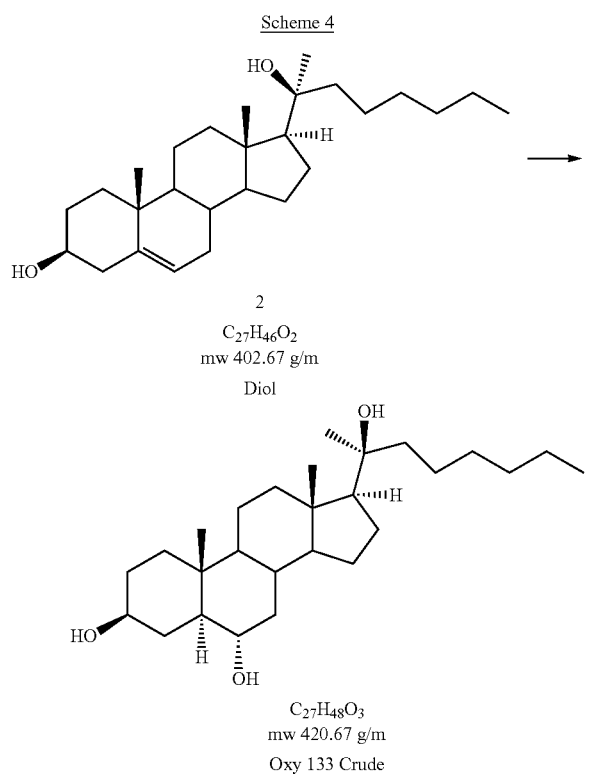

Scheme 4

2
$C_{27}H_{46}O_2$
mw 402.67 g/m
Diol $C_{27}H_{48}O_3$
mw 420.67 g/m
Oxy 133 Crude In some embodiments, crude and unpurified OXY133 is produced through a hydroboration and oxidation reaction of the intermediary diol having formula 2 in reaction Scheme 4. Borane compounds that can be used in the reaction include $BH_3$, $B_2H_6$, $BH_3S(CH_3)_2$ (BMS), borane adducts with phosphines and amines, e.g., borane triethylamine; monosubstituted boranes of the form $RBH_2$ where R=alkyl and halide, monoalkyl boranes (e.g., IpcBH2, monoisopinocampheylborane), monobromo- and monochloro-borane, complexes of monochloroborane and 1,4-dioxane, disubstituted boranes including bulky boranes, such as for example, dialkylborane compounds such as diethylborane, bis-3-methyl-2-butylborane (disiamylborane), 9-borabycyclo[3,3,1]nonane (9-BBN), disiamylborane (Sia2BH), dicyclohexylborane, Chx2BH, trialkylboranes, dialkylhalogenoboranes, dimesitylborane $(C_6H_2Me_3)_2BH$, alkenylboranes, pinacolborane, or catecholborane or a combination thereof.

Briefly, a hydroboration and oxidation reaction is a two-step reaction. The boron and hydrogen add across the double bond of an alkene to form a complex with the alkene. Thus the boration phase of the reaction is stereoselective and regioselective. The oxidation phase of the reaction involves basic aqueous hydrogen peroxide to furnish a hydroxyl substituent in place of the boron. See Vollhart, K P, Schore, N E, 2007, Organic Chemistry: Structure and Function, Fifth Ed., New York, N.Y., Custom Publishing Company. Thus, the intermediary diol having formula 2 is reacted with borane and hydrogen peroxide to form crude OXY133. In some embodiments, the step of forming crude OXY133 takes place in the same reaction vessel as the alkylation reaction. In other embodiments, the step of forming crude OXY133 takes place in a different reaction vessel as the alkylation reaction.

The hydroboration-oxidation step of the synthesis of OXY133, like the step of forming the intermediary diol, is stereoselective and produces a high yield. For example, in some embodiments, the percent yield of crude OXY133 may be higher or lower than these amounts. For example, the percent yield of formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the hydroboration-oxidation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, the hydroboration-oxidation reaction is exothermic and the reaction vessel can be temperature controlled to maintain optimal reaction kinetics. Specifically, the oxidation phase is extremely exothermic. Due to the strongly exothermic nature of the reaction, the hydrogen peroxide therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 10° C., 5° C., 1° C. or 0° C. In some embodiments, the reaction vessel is maintained at about −5° C. during the hydroboration-oxidation reaction.

In certain embodiments the diol can have a percent crystallinity of a salt, hydrate, solvate or crystalline form of diol to be at least 10%, at least 20%, at least 30%, at least 40%, at least 50%, at least 60%, at least 70%, at least 80%, at least 90%, at least 95%, or at least 99%. In some embodiments, the percent crystallinity can be substantially 100%, where substantially 100% indicates that the entire amount of diol appears to be crystalline as best can be determined using methods known in the art. Accordingly, therapeutically effective amounts of diol can include amounts that vary in crystallinity. These include instances where an amount of the crystallized diol in a solid form is subsequently dissolved, partially dissolved, or suspended or dispersed in a liquid.

Purification of OXY133

In some embodiments, the crude OXY133 can be separated from the reaction mixture prior to purification. In some embodiments, an organic solvent such as dichloromethane is added to the crude OXY133 reaction mixture and the resulting organic layer is separated. Once separated, the crude OXY133 exists as a semi-solid viscous mass. The crude OXY133 may be dissolved by any suitable means (e.g., dichloromethane, etc.) and placed into a silica gel column with an organic solvent, such as methanol-ethyl acetate, to solvate the crude OXY133. In some embodiments, the crude OXY133 may be crystallized or recrystallized. In some embodiments, purified OXY133 is formed by recrystallizing the crude OXY133 in a 3:1 mixture of acetone/water, as shown below:

Scheme 5

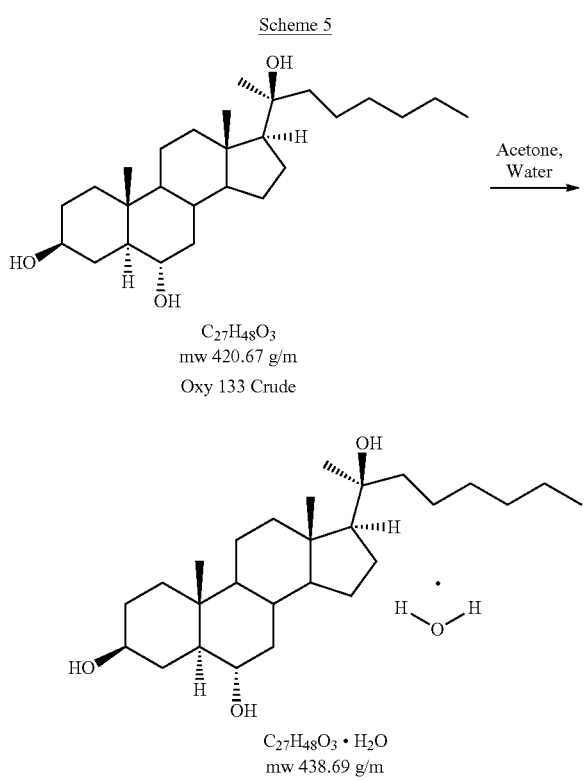

As shown above, upon crystallization, the purified OXY133 forms a hydrate. However, it can be in the anhydrous form, which can be obtained by removing water via ways known in the art. In some embodiments, the percent crystallinity of any of the crystalline forms of OXY133 described herein can vary with respect to the total amount of OXY133.

In certain embodiments the OXY133 can have a percent crystallinity of a salt, hydrate, solvate or crystalline form of OXY133 to be at least 10%, at least 20%, at least 30%, at least 40%, at least 50%, at least 60%, at least 70%, at least 80%, at least 90%, at least 95%, or at least 99%. In some embodiments, the percent crystallinity can be substantially 100%, where substantially 100% indicates that the entire amount of OXY133 appears to be crystalline as best can be determined using methods known in the art. Accordingly, therapeutically effective amounts of OXY133 can include amounts that vary in crystallinity. These include instances where an amount of the crystallized OXY133 in a solid form is subsequently dissolved, partially dissolved, or suspended or dispersed in a liquid.

In one embodiment, the purified OXY133 is crystallized as a monohydrate. However, in other embodiments the purified OXY133 may be crystallized in other hydrous forms, such as, for example, a dihydrate, a hemihydrate, a sesquihydrate, a trihydrate, a tetrahydrate and the like, as well as the corresponding solvated forms. In other embodiments, the purified OXY133 is crystallized as a co-crystal or a pharmaceutically acceptable salt.

In some embodiments, the reaction mixture containing the crude OXY133 may be solidified by mixing with heptanes. The product may subsequently be filtered and suspended in methylene chloride. In some embodiments, the crude OXY133 may be filtered from the suspension and crystal-lized with the use of acetone and water or other organic or inorganic solvents (e.g., diethyl ether, dichloromethane, ethyl acetate, acetone, n,n-dimethylformamide, acetonitrile, dimethyl sulfoxide, ammonia, t-butanol, n-propanol, ethanol, methanol, acetic acid or a combination thereof).

In various embodiments, the crude OXY133 may be isolated and purified by any other traditional means. That is, the crude OXY133 can be isolated and purified to the desired purity, e.g., from about 95% to about 99.9% by filtration, centrifugation, distillation to separate volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. In various embodiments, the hydroboration-oxidation step and the purification step take place in the same reaction vessel. In various embodiments, the alkylation step, the hydroboration-oxidation step and the purification step take place in the same reaction vessel.

The method of synthesizing the intermediary diol (formula 2) is stereoselective and produces a high yield of OXY133. For example, in some embodiments, the yield of the purified OXY133 is between about 20% and about 99%. In some embodiments, the yield of the purified OXY133 is between about 20% and about 80%. In some embodiments, the yield of the purified OXY133 is between about 25% and about 70% or about 28%. However, it is contemplated that the percent yield may be higher or lower than these amounts.

In some embodiments, the purified OXY133 is formed in crystal form via crystallization, which separates the OXY133 from the liquid feed stream by cooling the liquid feed stream or adding precipitants which lower the solubility of byproducts and unused reactants in the reaction mixture so that the OXY133 forms crystals. In some embodiments, the solid crystals are then separated from the remaining liquid by filtration or centrifugation. The crystals can be resolubilized in a solvent and then recrystallized and the crystals are then separated from the remaining liquid by filtration or centrifugation to obtain a highly pure sample of OXY133. In some embodiments, the crystals can then be granulated to the desired particle size.

In some embodiments, the crude OXY133 can be purified where the purified OXY133 is formed in crystallized form in a solvent and then removed from the solvent to form a high purity OXY133 having a purity of from about 95% to about 97% or from about 98% to about 99.99%. In some embodiments, the OXY133 can be recovered via filtration or vacuum filtration before or after purification.

In some embodiments, as illustrated in Scheme 6 below, a method of synthesizing OXY133 includes reacting solid pregnenolone with n-hexylmagnesium bromide in a tetrahydrofuran (THF) solution at about 0° C. to form a diol in a first step. This reaction went to about 80 to 85% completion. In a second step, after the purification of the diol by recrystallization from methanol/water, the diol undergoes hydroboration oxidation including recrystallization from methyl tertbutyl ester (MTBE)/heptane to form OXY133 crude. In a third step, OXY133 crude is recrystallized from 3:1 acetone/water to form OXY133 monohydrate in an overall yield of about 20 to about 35% by weight.

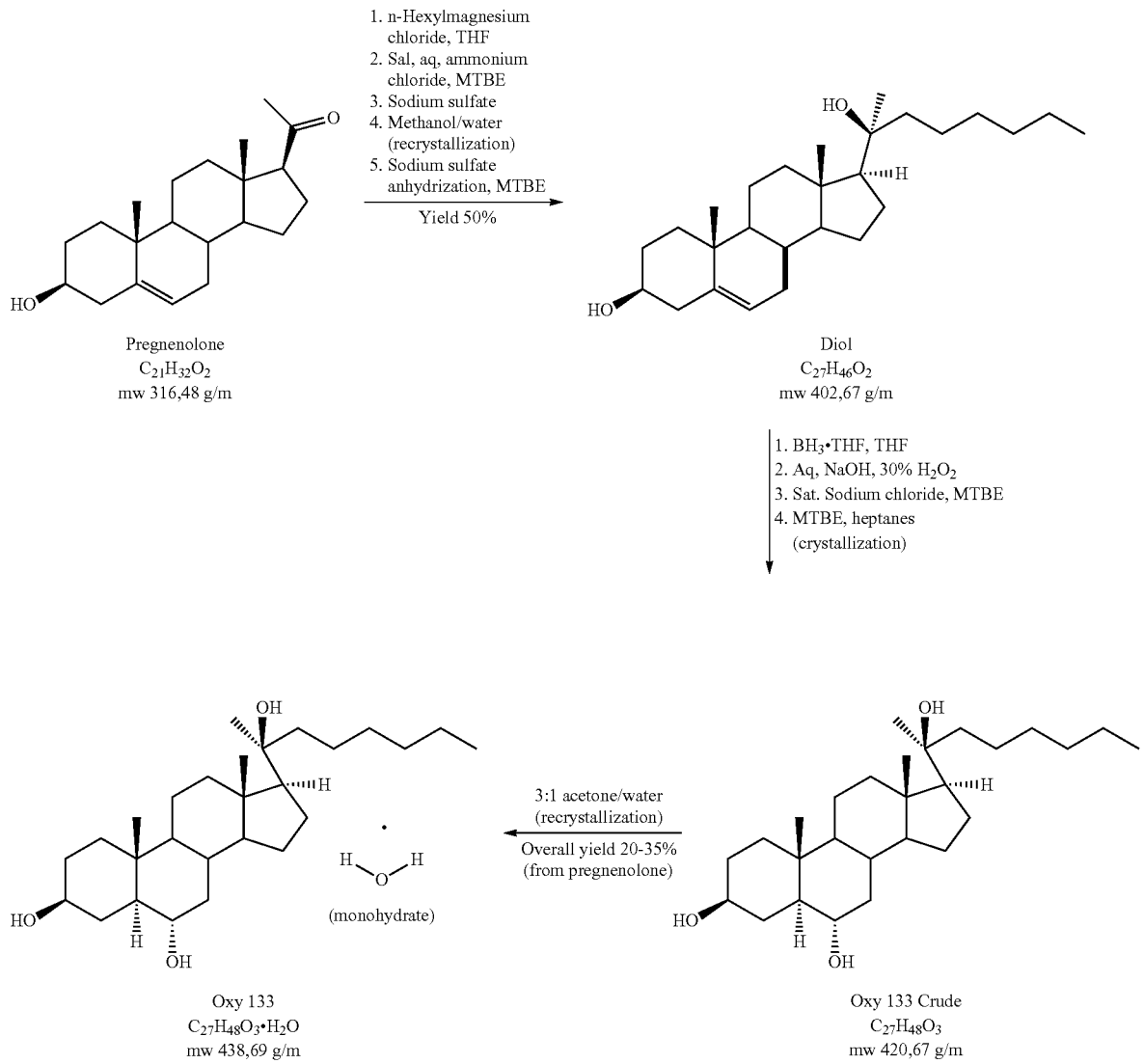

By following the pregnenolone synthetic pathway, batches of 420 grams of OXY133 monohydrate having a purity of 95.5% and 328 grams of OXY133 monohydrate having a purity of 94.8% were produced.

Methods of Making Crystal Polymorphic Forms of OXY133

In certain embodiments, OXY133 anhydrous (polymorph Form B, also referred to as Form B) can be converted to OXY133 monohydrate (polymorph Form A also referred to as Form A) via re-slurry in acetone/water solvent systems. This conversion was slow in that it took about 48 hours and was dependent on the use of the anhydrous OXY133 as the input material.

In other embodiments, several other crystalline forms were produced in various solvent systems when the temperature of the slurry was heated above 30° C. Most of these particular crystalline forms could not be converted to the OXY133 monohydrate via re-slurry.

In order to stop the conversion of OXY133 to polymorph forms other than OXY133 monohydrate (Form A), new solvent systems that would allow for the dissolution of OXY133 at ambient temperatures, below 30° C., followed by precipitation with water were investigated and optimized.

In some embodiments, OXY133 was recrystallized from an acetone/water mixture (3:1) following the reaction scheme 7 below:

Scheme 7

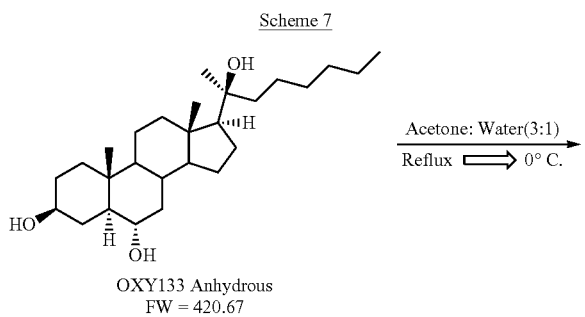

OXY133 Anhydrous
FW = 420.67

-continued

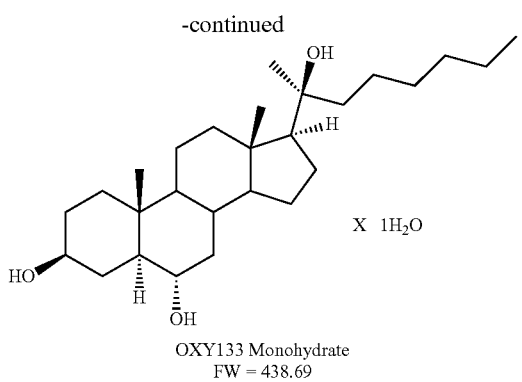

OXY133 Monohydrate
FW = 438.69

In other embodiments, using this procedure OXY133 monohydrate having a theoretical value amount of water present in the solid of about 4.11 wt % was generated. However, in some cases, the OXY133 was isolated as an anhydrous form and as a partial hydrate, for example, a hemihydrate, with varying amounts of water present. Without being bound by theory, it is believed that a higher purity input material of OXY133 could cause the generation of other crystalline forms from the above recrystallization procedure.

In various embodiments, OXY133 anhydrous (Form B) was re-slurried in a slurry-to-slurry conversion in several different solvent systems as summarized in Table 1 below.

TABLE 1

| Solvent System | Temperature (° C.) | Crystal Form |
|---|---|---|
| H$_2$O | 20 | E |
| H$_2$O | 70 | E |
| Acetone/H$_2$O (1:1) | 0 | A |
| Acetone/H$_2$O (1:1) | 10 | A |
| Acetone/H$_2$O (1:1) | 20 | A |
| Acetone/H$_2$O (1:1) | 25 | A |
| Acetone/H$_2$O (1:1) | 30 | C |
| Acetone/H$_2$O (1:1) | 40 | C |
| Acetone/H$_2$O (1:1) | 50 | C |
| Acetone/H$_2$O (1:1) | 60 | C |
| Acetone/H$_2$O (1:1) | 70 | C |
| MeOH/H$_2$O (1:1) | 20 | D |
| MeOH/H$_2$O (1:1) | 70 | D |

In some embodiments, the temperature of the solvent system can be controlled to obtain the polymorphic form and the temperature can be from about 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60, 61, 62, 63, 64, 65, 66, 67, 68, 69, to about 70° C. to obtain the polymorph.

As illustrated in Table 1, acetone/water at a ratio of 1:1 yielded Form A after 48 hours of stirring the anhydrous OXY133 slurry at temperatures from about 15° C. to about 25° C. Additionally, stirring under different conditions, for example acetone/water conditions at about 70° C. yielded several new crystalline forms, in particular OXY133 polymorph Forms C, D, and E. While the acetone/water experiments showed that the OXY133 Form B could be converted to Form A, the conversion was rather slow, taking between 24 and 48 hours to convert fully.

Figure 2A:
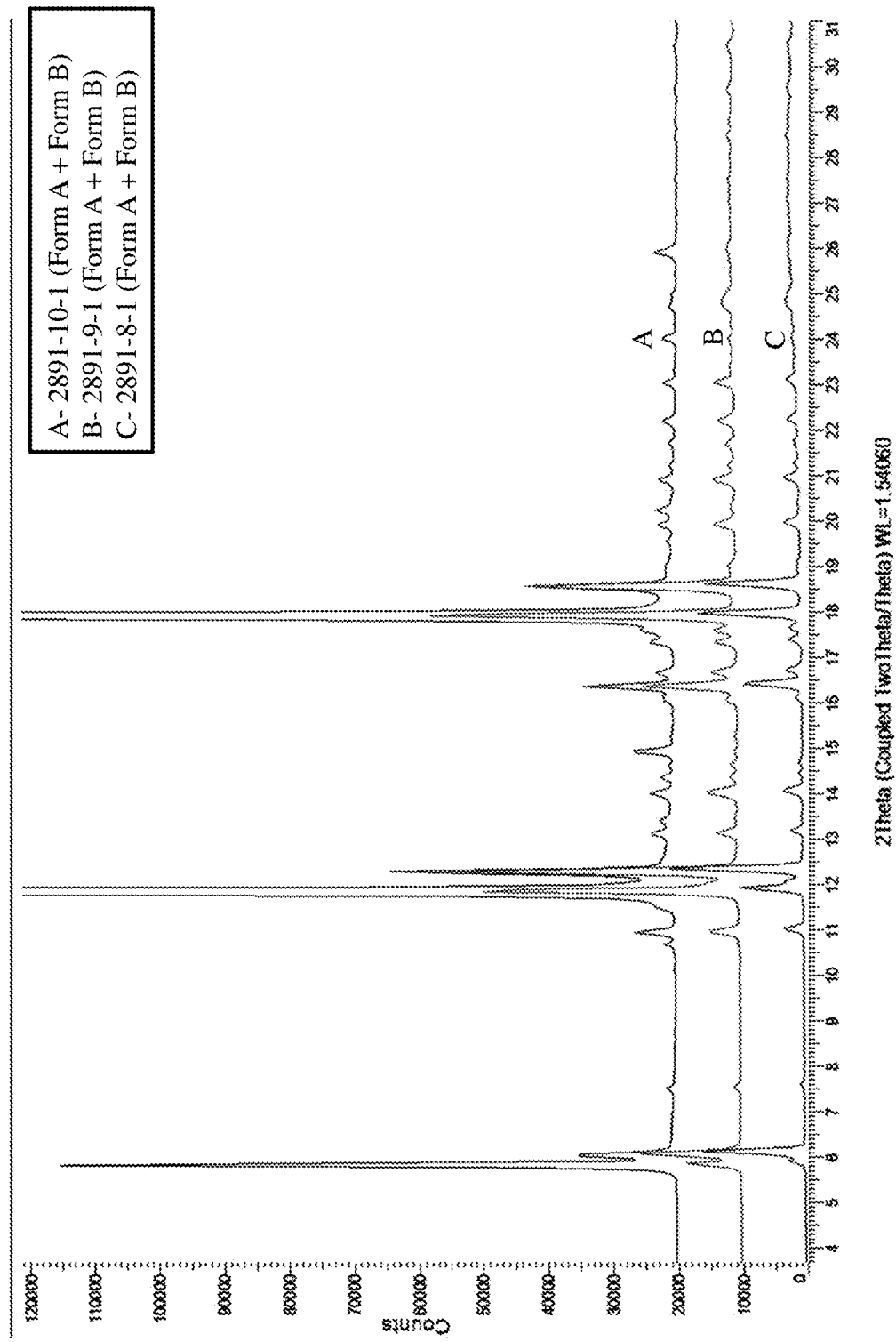
FIGS. 2A, 2B, 2C, 2D, and 2E are XRPDs of OXY133 polymorph Forms A and B.
Figure 2B:
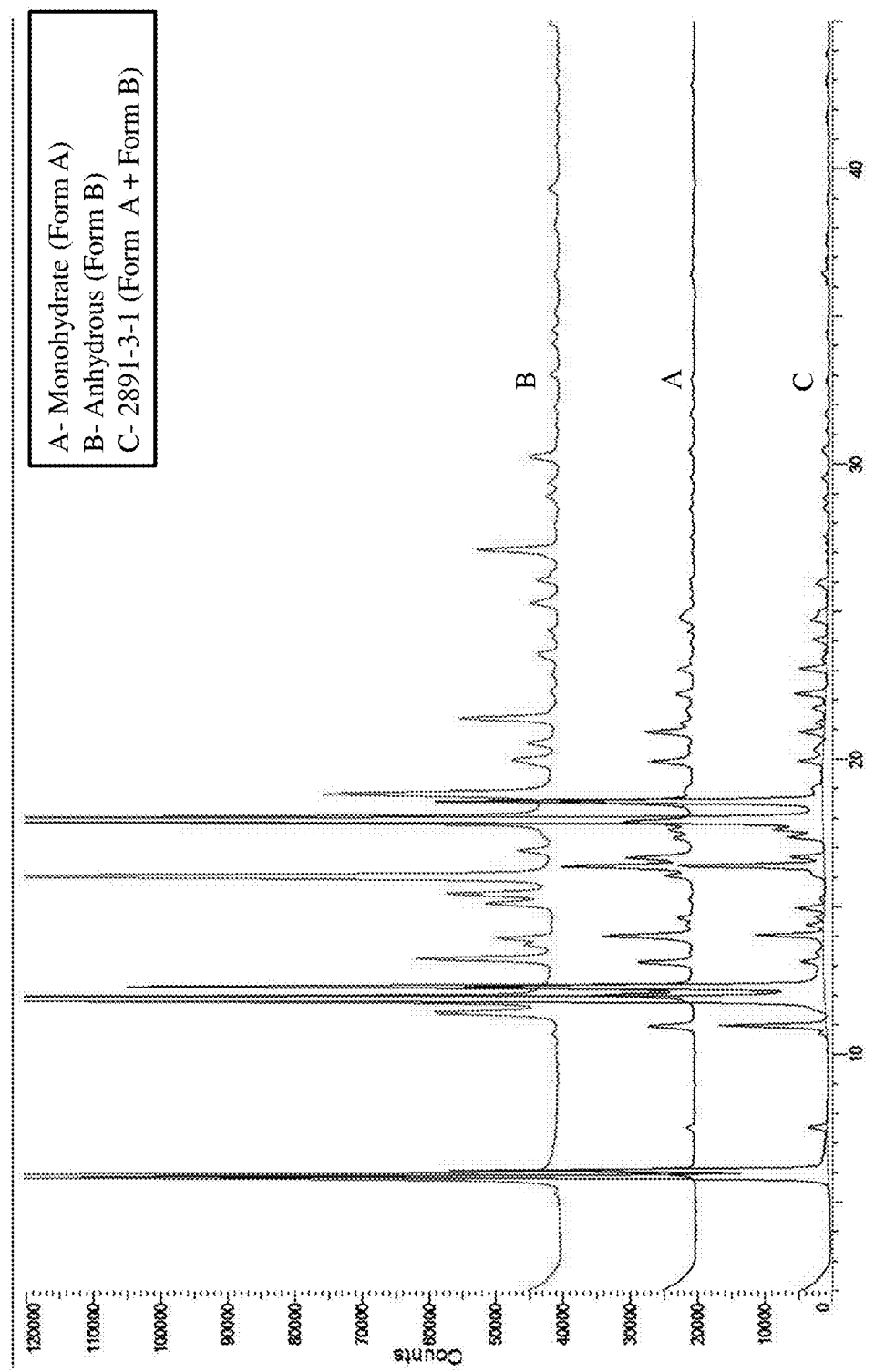
Figure 2C:
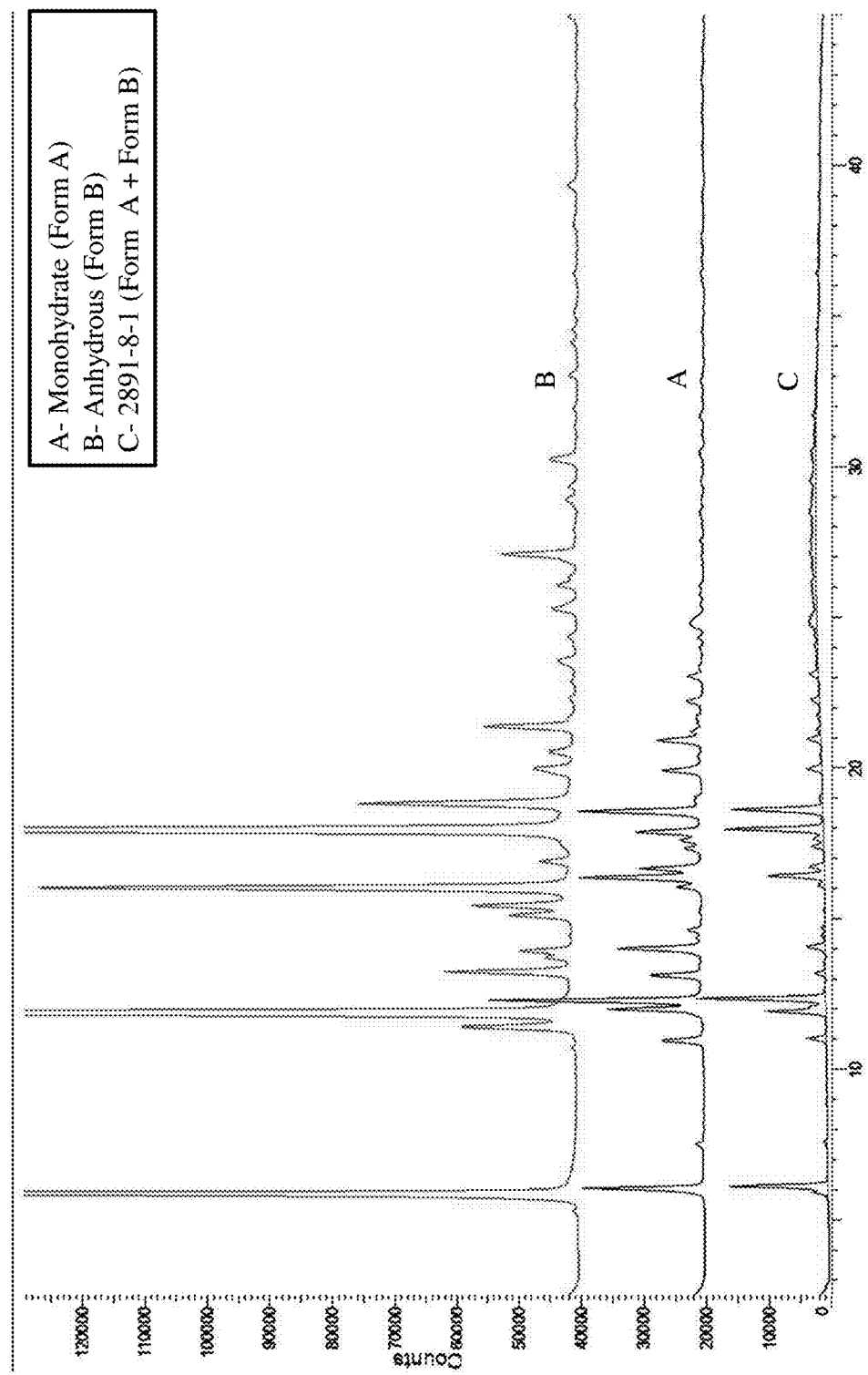
Figure 2D:
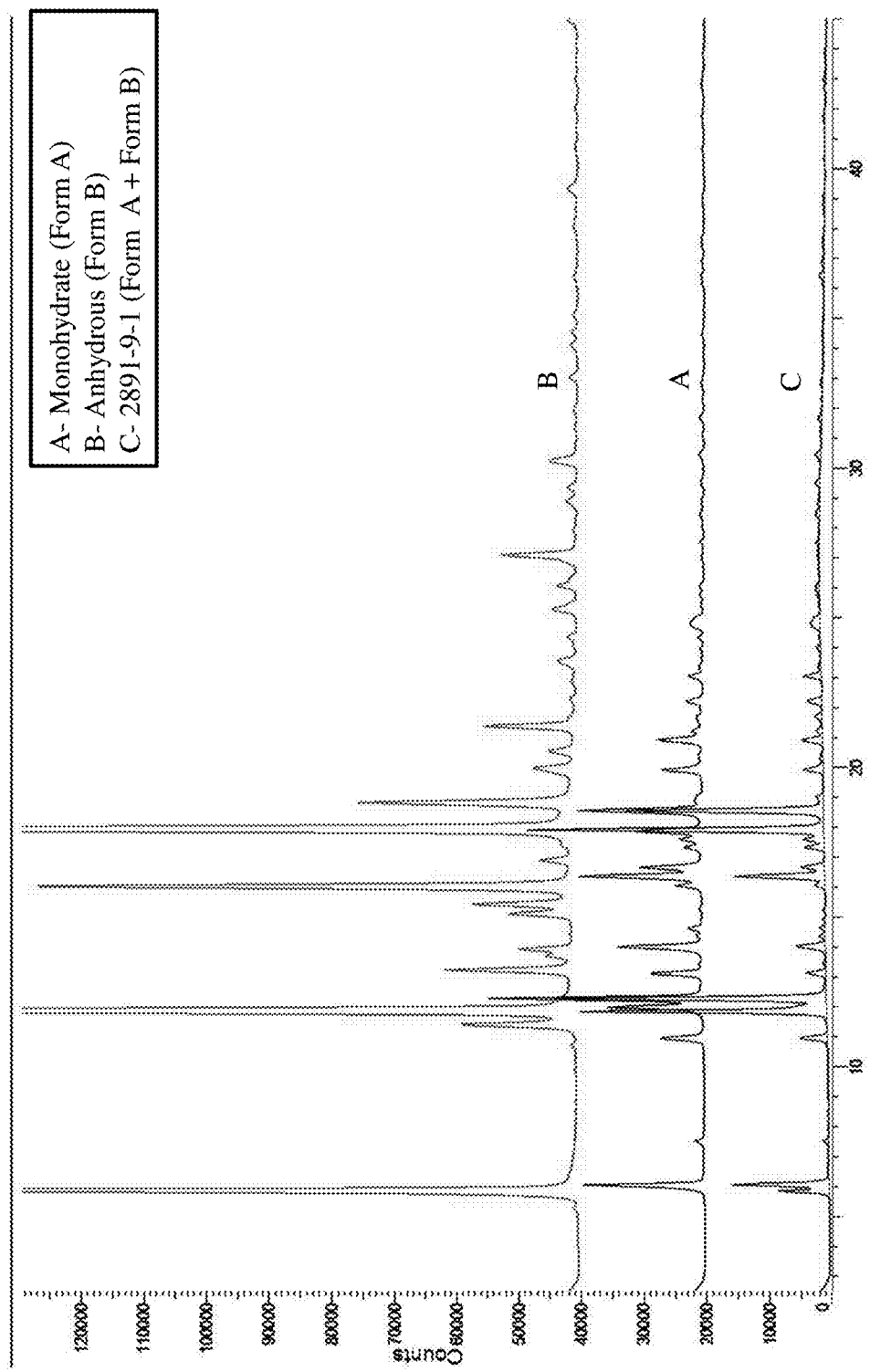
Figure 2E:
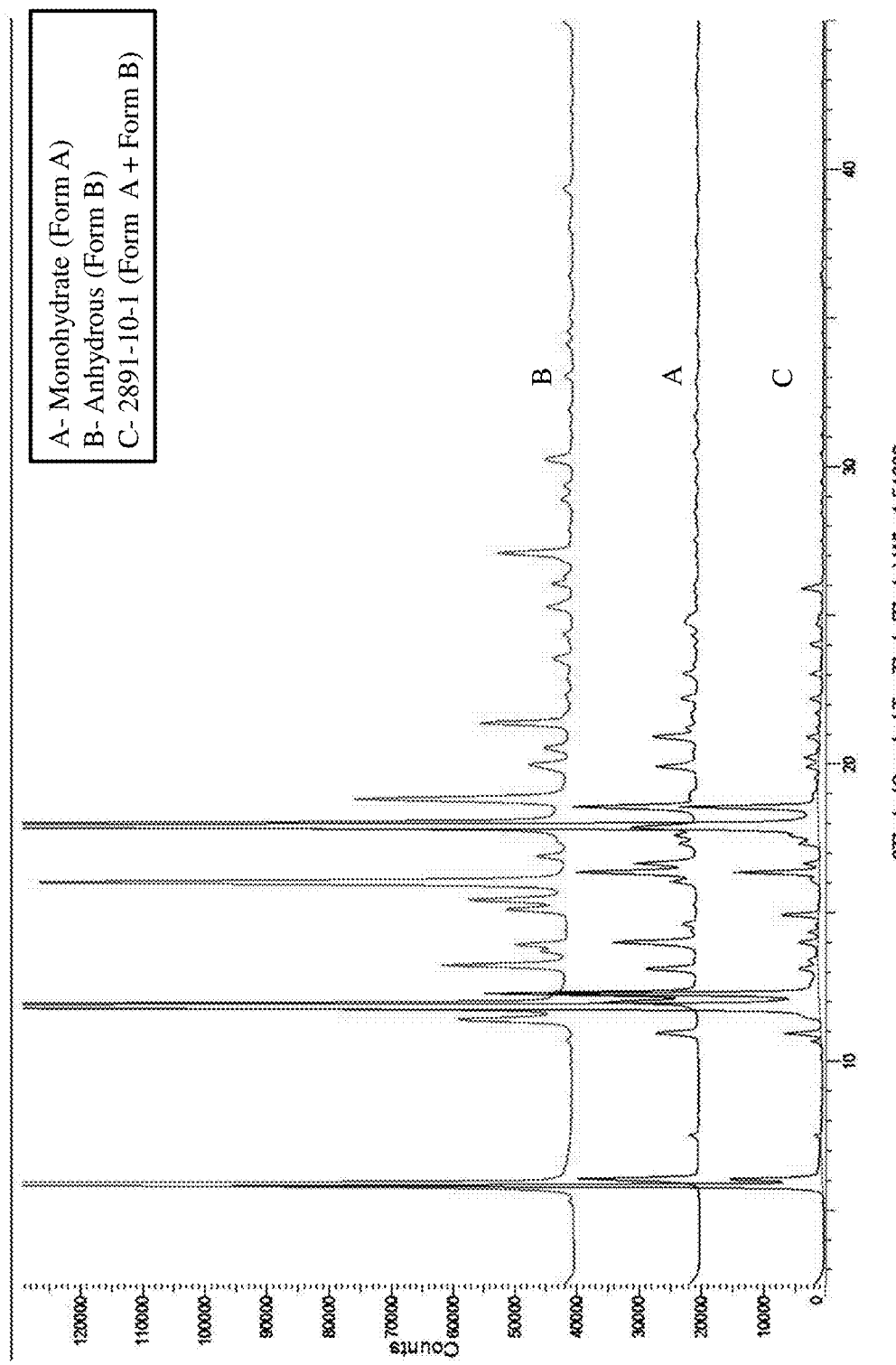

In an effort to improve the rate at which Form B converts to Form A using the re-slurry conditions in acetone/water, the temperature of the slurry was studied. In various embodiments, increasing the slurry temperature to 30° C. and above resulted in the production of Form C. Form C was found to be fairly stable in the acetone/water solvent system. However, no conversion from Form C to Form A or Form B was observed when the slurry was stirred at a temperature of about 20° C. in acetone/water. In other embodiments, since increasing the temperature of the slurry did not yield Form A, temperatures ranging from 0° C. to 25° C. were studied. Surprisingly, the conversion from Form B to Form A was faster with lower temperatures. FIG. 2A shows the difference in XRPDs of a slurry of Form B at the same in-process controls time points after stirring in acetone/water mixtures for 20 minutes. As a result of stirring in acetone/water for the short period of time of 20 minutes, Polymorph Form B was only partially converted to Form A and, as illustrated in FIG. 2A, the XRPDs of the three samples are mixtures of Forms A and B.

At 0° C., most of Form B was successfully converted to Form A. However, it is also important to note that, as illustrated in Table 2 below, the water content measured according to Karl-Fisher (KF) water determination method of the isolated solid increased with increasing slurry temperature between 0° C. and 25° C., even though the XRPD for each sample matches.

TABLE 2

| Lot# | Temperature of Slurry (° C.) | Crystal Form | KF (Wt %) |
|---|---|---|---|
| 2891-8-3 | 0° C. | Form A | 3.25 |
| 2891-9-3 | 10° C. | Form A | 3.83 |
| 2891-10-3 | 25° C. | Form A | 4.02 |

In some embodiments, the crystal form acquired from the first crystallization from acetone/water (3:1) is dependent on purity. The use of this solvent system could lead to crystal forms other than Form B being used as the starting material for the final form conversion, which could result in a failed form conversion attempt.

Accordingly, in some embodiments, crystallization and dissolution/precipitation methods from other acetone/water solvent systems were investigated. Attempts to dissolve OXY133 Form B in acetone showed that the solubility of OXY133 in acetone is fairly low, specifically, about 10 mg/mL at 20° C. and about 80 mg/mL at reflux at 56° C. Additionally, once all solids have been dissolved, they are precipitated from solution rather quickly when cooling to about 54° C. Cooling to 15° C. and charging water to the acetone solvent resulted in the isolation of yet a new crystal form, OXY133 polymorph Form F or Form F. Form F was also shown to be somewhat stable in acetone/water system as it would not convert to any other polymorph forms when stirred at about 20° C. or about 5° C. Due to the low solubility of OXY133 in acetone, we also investigated other solvent compositions with higher solubility of OXY133.

Additional useful solvent systems for dissolving OXY133 included acetone/tetrahydrofuran (THF), methanol/acetone, isopropanol (IPA) and tetrahydrofuran. All of these solvent systems were found to dissolve the OXY133 anhydrous Form B, however, the presence of acetone in the mixtures significantly decreased the solubility of OXY133. Due to the tendency of OXY133 to convert to several other crystal forms while at temperatures elevated above 30° C., it is important to have sufficient solubility at temperatures as low as 0° C. to keep all materials in solution. In addition, to maximize recovery, the solvent system would ideally allow for the use of a reasonable amount of solvent, for example, less than or equal to 10 volumes. Since anhydrous OXY133 or Form B had a good solubility in tetrahydrofuran and isopropanol (IPA) at ambient temperature of about 20° C., solvent systems utilizing tetrahydrofuran/water and IPA/water systems were also investigated.

In some embodiments, OXY133 polymorph Form A was successfully obtained by dissolving Form B in isopropanol or tetrahydrofuran followed by a slow precipitation with water following the reaction scheme 8 below:

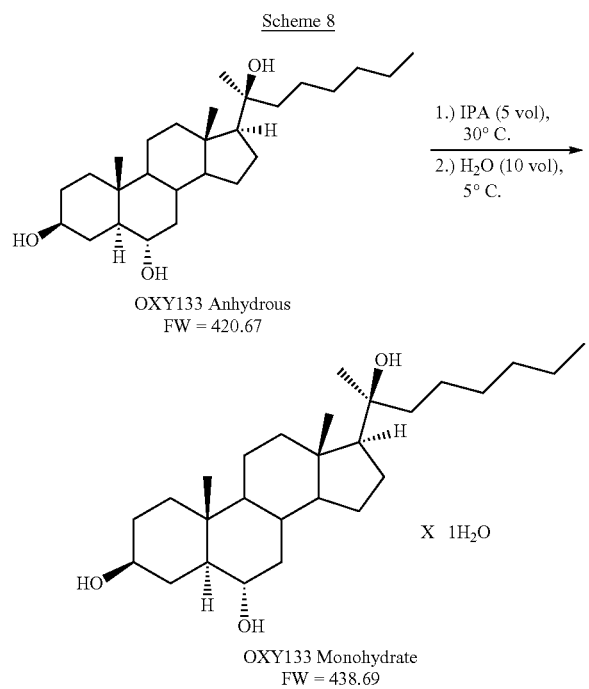

While both solvent systems resulted in OXY133 polymorph Form A, the tetrahydrofuran/water system appeared to precipitate OXY133 from solution as an oil upon addition of water to the solution. This oil appeared to convert to a solid after completion of the water addition and stirring for one (1) hour. Accordingly, the isopropanol/water system did not appear to precipitate OXY133 Form A as an oil before solidifying.

Figure 4:
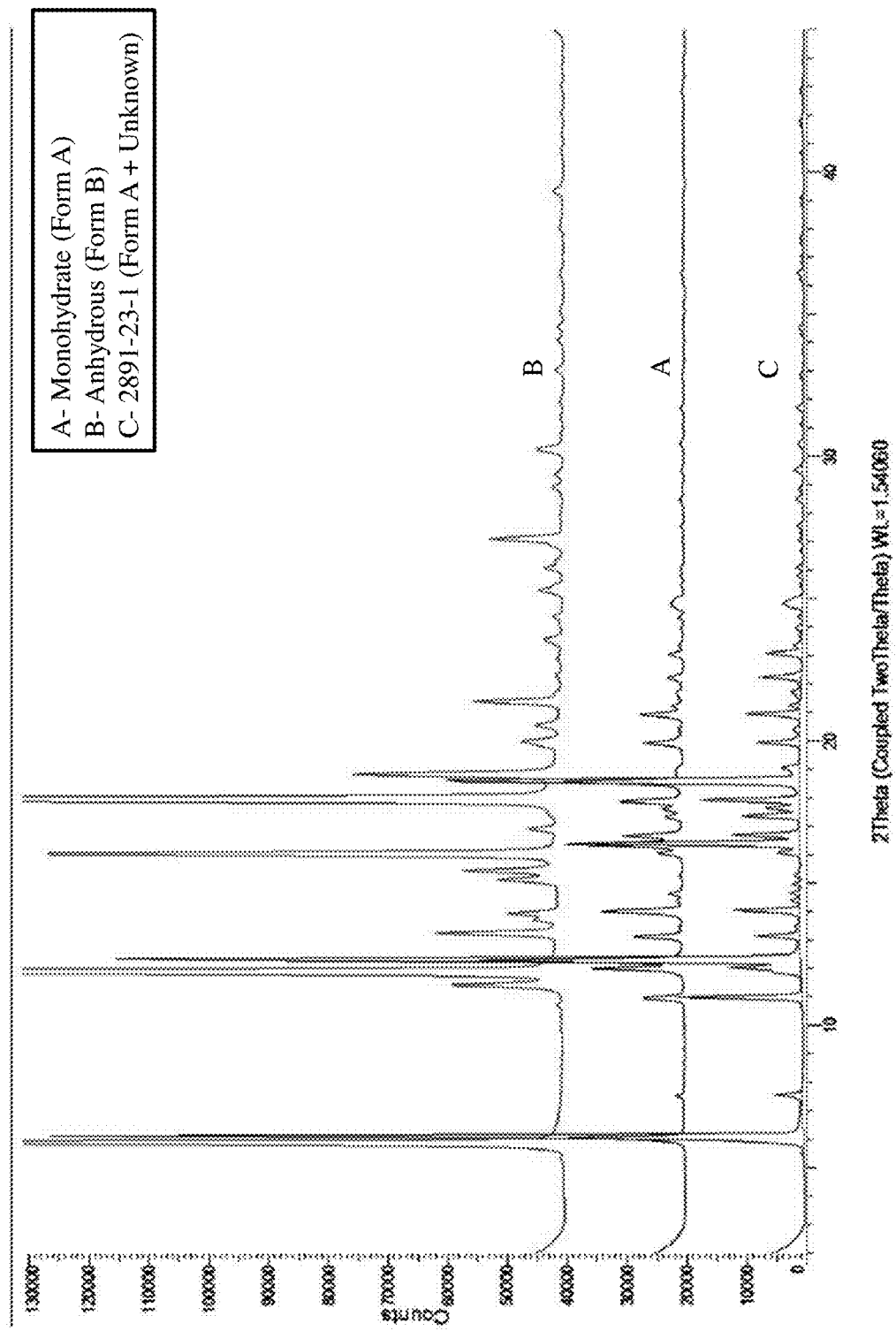
FIG. 4 is an XRPD of OXY133 polymorph Form A and unknown.

In various aspects of this disclosure, the effects of temperature on the crystal form of OXY133 were investigated in the isopropanol/water system. The optimal working range for the precipitation was found to be about 0° C. to about 10° C., where the target was 5° C. Precipitating OXY133 from IPA with water at temperatures of about 15° C. and about 20° C. also provided OXY133 polymorph Form A. However, precipitation with water at about 30° C. produced what may be a mixture of Form A and a small amount of an additional unknown form as illustrated in FIG. 4. Additionally, in other embodiments, precipitation at −10° C. from isopropanol/water yielded a new polymorph form, OXY133 polymorph Form H or Form H. Overall, the isopropanol/water system had a similar temperature dependence for the precipitation of Form A as the acetone/water system. Table 3 below summarizes the experimental results obtained from isopropanol/water solvent systems at different precipitation temperatures.

TABLE 3

| Solvent System | Precipitation Temperature (° C.) | Crystal Form |
| --- | --- | --- |
| IPA/H$_2$O (1:1) | 20 | Form A |
| IPA/H$_2$O (1:2) | 0 | Form A |
| IPA/H$_2$O (1:2) | 10 | Form A |
| IPA/H$_2$O (1:2) | 20 | Form A |
| IPA/H$_2$O (1:2) | 20 | Form A |
| IPA/H$_2$O (1:2) | 30 | Form A + Unknown |
| IPA/H$_2$O (1:2) | 40 | Form G |
| IPA/H$_2$O (1:2) | 5 | Form A |
| IPA/H$_2$O (1:2) | −10 | Form H |
| IPA/H$_2$O (1:2) | 5 | Form A |
| IPA/H$_2$O (1:2) | 5 | Form A |

As illustrated in Table 3 above, the use of isopropanol as the solvent in which Form B was dissolved had several advantages over acetone. The first advantage was being able to keep OXY133 in solution at much lower temperatures, for example about 0° C., avoiding the problem of forming different, stable crystal structures at higher temperatures of greater or equal to 30° C. It also allows for the conversion to Form A from input forms other than Form B, namely solvates or hemihydrates. Further, the cycle time of the dissolution/precipitation process was short, for example, from about 4 to about 6 hours as opposed to the process of re-slurrying OXY133 in acetone/water for about 48 hours.

The many crystalline forms obtained by subjecting a slurry of OXY133 to different conditions of re-slurrying, recrystallizing from different solvent systems at different temperatures may be identified by many analytical methods, for example, XRPD, HPLC-CAD, DSC-TGA and others known in the art. In certain embodiments, the OXY133 polymorphs may be characterized, at least in part, by X-ray Powder Diffraction (XRPD). In particular, crystalline solids produce a distinctive diffraction pattern of peaks, represented in what is referred to as a diffractogram. The peak assignments for a given crystalline material, for example, degree 2θ values, may vary slightly, depending on the instrumentation used to obtain the diffractogram and certain other factors, for example, sample preparation. Nevertheless, these variations should not be more than +/−0.2 degrees 2θ and the relative spacing between the peaks in the diffractogram will always be the same, regardless of the instrumentation used or the method of sample preparation, and the like.

Figure 3:
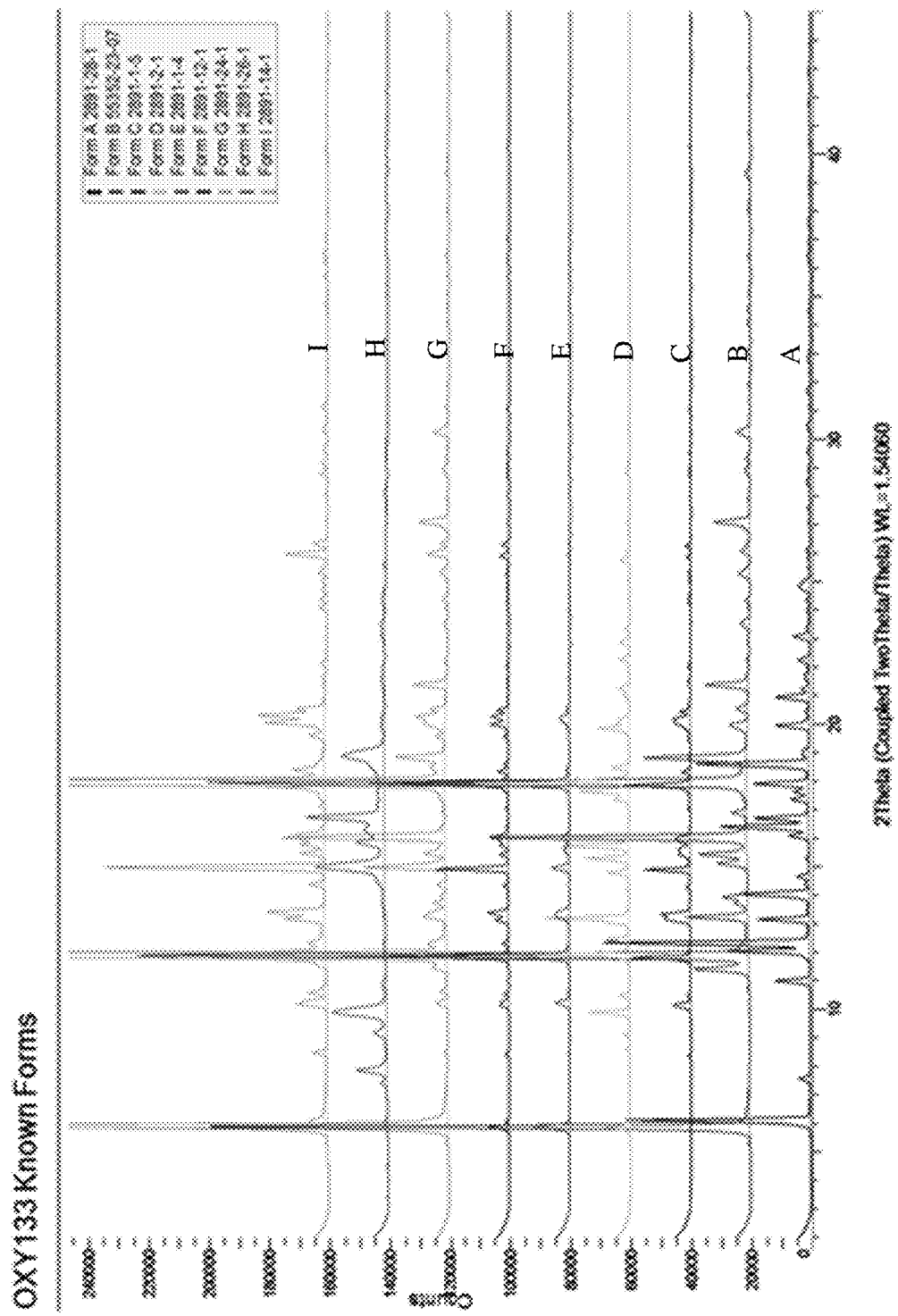
FIG. 3 is a graphic illustration of XRPDs of OXY133 polymorph Forms A, B, C, D, E, F, G, H and I.

For example, XRPD spectral data relating to the many OXY133 polymorphs are depicted in FIGS. 2-13B. In particular, FIGS. 2A to 2E are XRPDs of OXY133 polymorph Forms A and B. FIG. 3 is a graphic illustration of XRPDs of OXY133 polymorph Forms A, B, C, D, E, F, G, H and I. FIG. 4 is an XRPD of OXY133 polymorph Form A and unknown formed when OXY133 is crystallized from an isopropanol/water solvent/anti-solvent system in a ratio of 1:2 v/v at 30° C.

Figure 5:
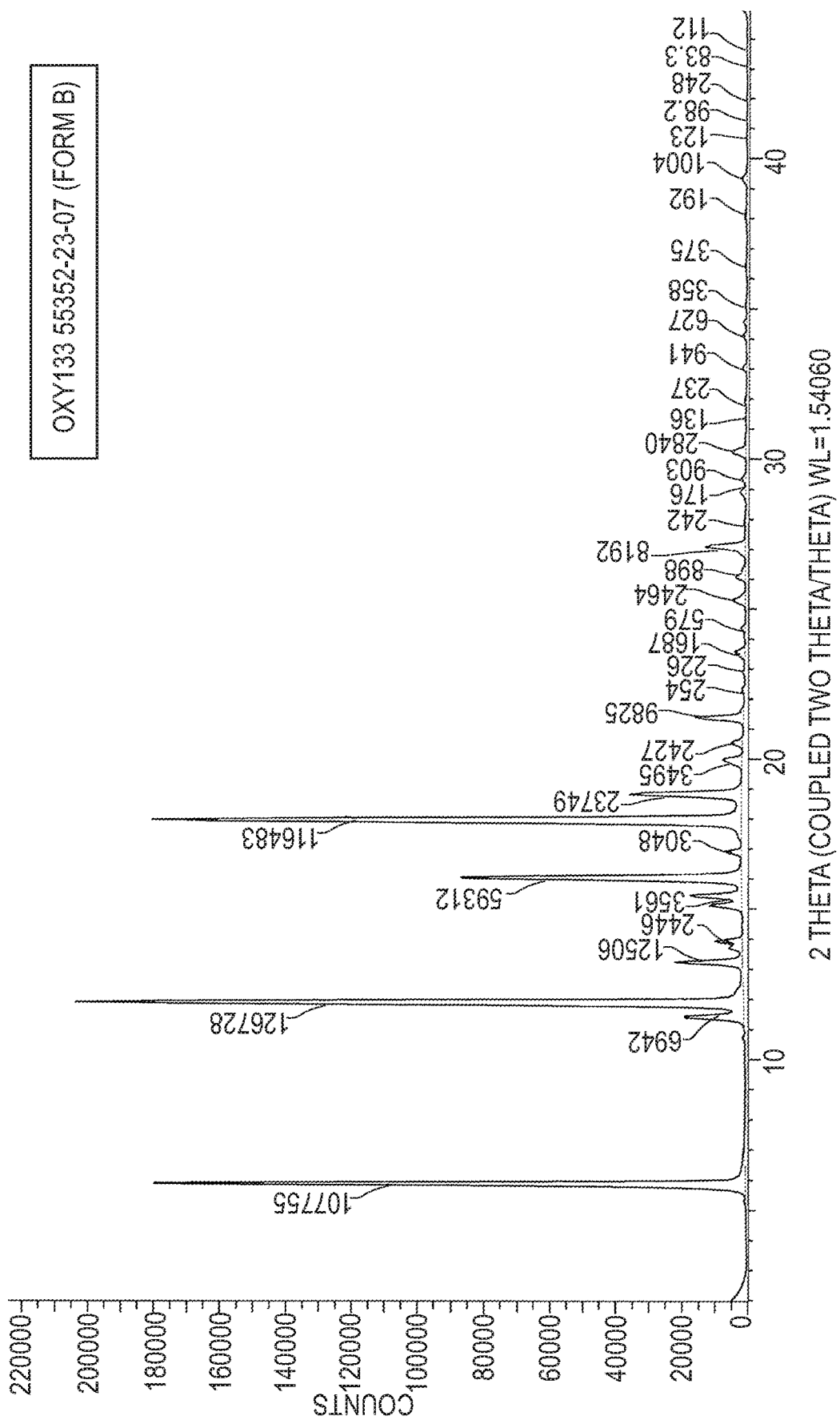
FIG. 5 is an XRPD of OXY133 polymorph Form B.

FIG. 5 is an XRPD of OXY133 polymorph Form B or anhydrous OXY133. Table 4, below lists data taken from the XRPD of FIG. 5. As illustrated in Table 4, OXY133 Form B can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and 36.

TABLE 4

XRPD Data for OXY133 Polymorph Form B, as illustrated in FIG. 5

| Index No. | Angle (2-Theta) | d Value (Angstrom) | Net Intensity (Counts) | Gross Intensity (Counts) | Rel. Intensity (%) |
|---|---|---|---|---|---|
| 0 | 5.87 | 15.0451 | 107755 | 108530 | 85.00% |
| 1 | 11.469 | 7.70901 | 6942 | 8134 | 5.50% |
| 2 | 11.885 | 7.44037 | 126729 | 128030 | 100.00% |
| 3 | 13.25 | 6.6767 | 12506 | 14054 | 9.90% |
| 4 | 13.842 | 6.39245 | 2446 | 4049 | 1.90% |
| 5 | 15.321 | 5.7786 | 3561 | 5356 | 2.80% |
| 6 | 16.015 | 5.5297 | 59312 | 61227 | 46.80% |
| 7 | 16.905 | 5.24066 | 3048 | 5052 | 2.40% |
| 8 | 17.958 | 4.93554 | 116483 | 118500 | 91.90% |
| 9 | 18.815 | 4.71252 | 23749 | 25703 | 18.70% |
| 10 | 19.925 | 4.45255 | 3495 | 5269 | 2.80% |
| 11 | 20.513 | 4.32619 | 2427 | 4060 | 1.90% |
| 12 | 21.383 | 4.15212 | 9825 | 11229 | 7.80% |
| 13 | 22.2 | 4.00108 | 254 | 1413 | 0.20% |
| 14 | 22.953 | 3.87158 | 226 | 1253 | 0.20% |
| 15 | 23.497 | 3.78317 | 1687 | 2681 | 1.30% |
| 16 | 24.283 | 3.66233 | 579 | 1507 | 0.50% |
| 17 | 25.306 | 3.51666 | 2464 | 3378 | 1.90% |
| 18 | 26.144 | 3.40574 | 898 | 1856 | 0.70% |
| 19 | 27.062 | 3.29227 | 8192 | 9143 | 6.50% |
| 20 | 27.804 | 3.20606 | 242 | 1132 | 0.20% |
| 21 | 29.115 | 3.06462 | 176 | 995 | 0.10% |
| 22 | 29.331 | 3.04256 | 903 | 1722 | 0.70% |
| 23 | 30.264 | 2.95083 | 2840 | 3649 | 2.20% |
| 24 | 31.395 | 2.84712 | 136 | 904 | 0.10% |
| 25 | 31.817 | 2.81029 | 237 | 968 | 0.20% |
| 26 | 33.03 | 2.70977 | 941 | 1593 | 0.70% |
| 27 | 34.101 | 2.62707 | 627 | 1313 | 0.50% |
| 28 | 35.073 | 2.55651 | 358 | 1034 | 0.30% |
| 29 | 36.423 | 2.46473 | 375 | 1018 | 0.30% |
| 30 | 38.147 | 2.35726 | 192 | 890 | 0.20% |
| 31 | 39.344 | 2.28825 | 1004 | 1697 | 0.80% |
| 32 | 40.716 | 2.21425 | 123 | 794 | 0.10% |
| 33 | 41.31 | 2.18376 | 98.2 | 785 | 0.10% |
| 34 | 41.969 | 2.15101 | 248 | 915 | 0.20% |
| 35 | 43.121 | 2.09616 | 83.3 | 751 | 0.10% |
| 36 | 43.669 | 2.07112 | 112 | 818 | 0.10% |

Figure 6A:
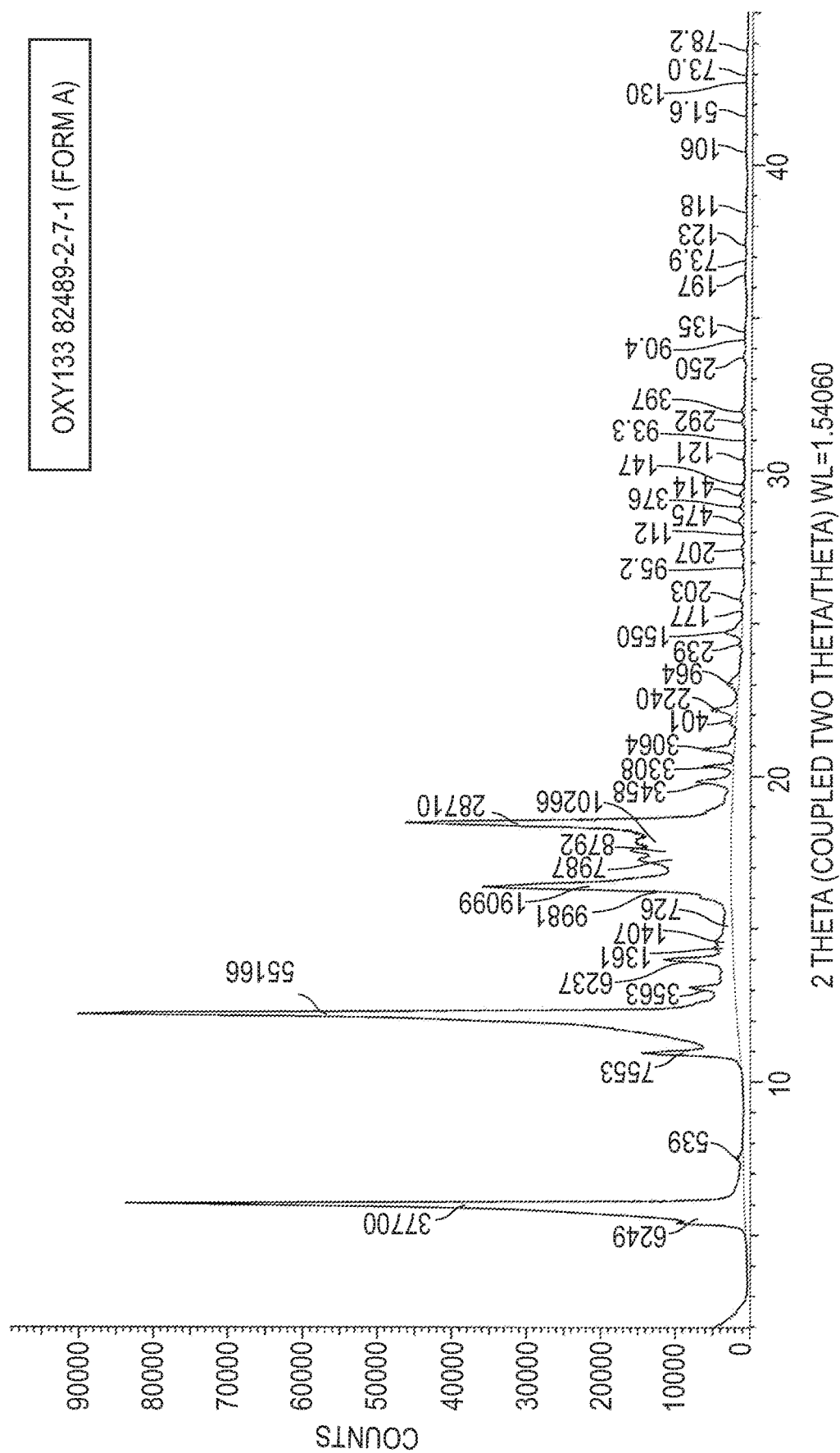
Figure 6B:
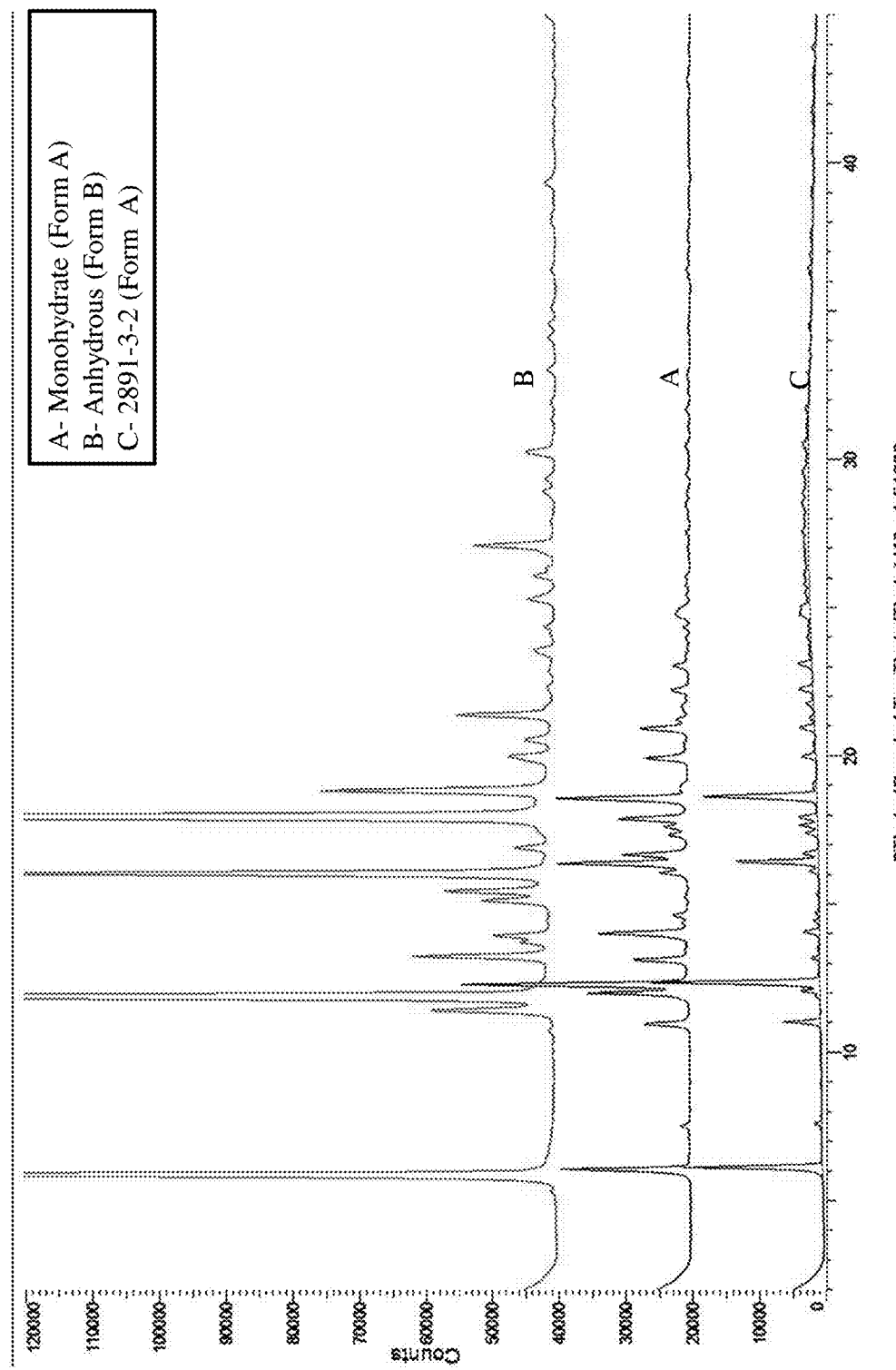
Figure 6C:
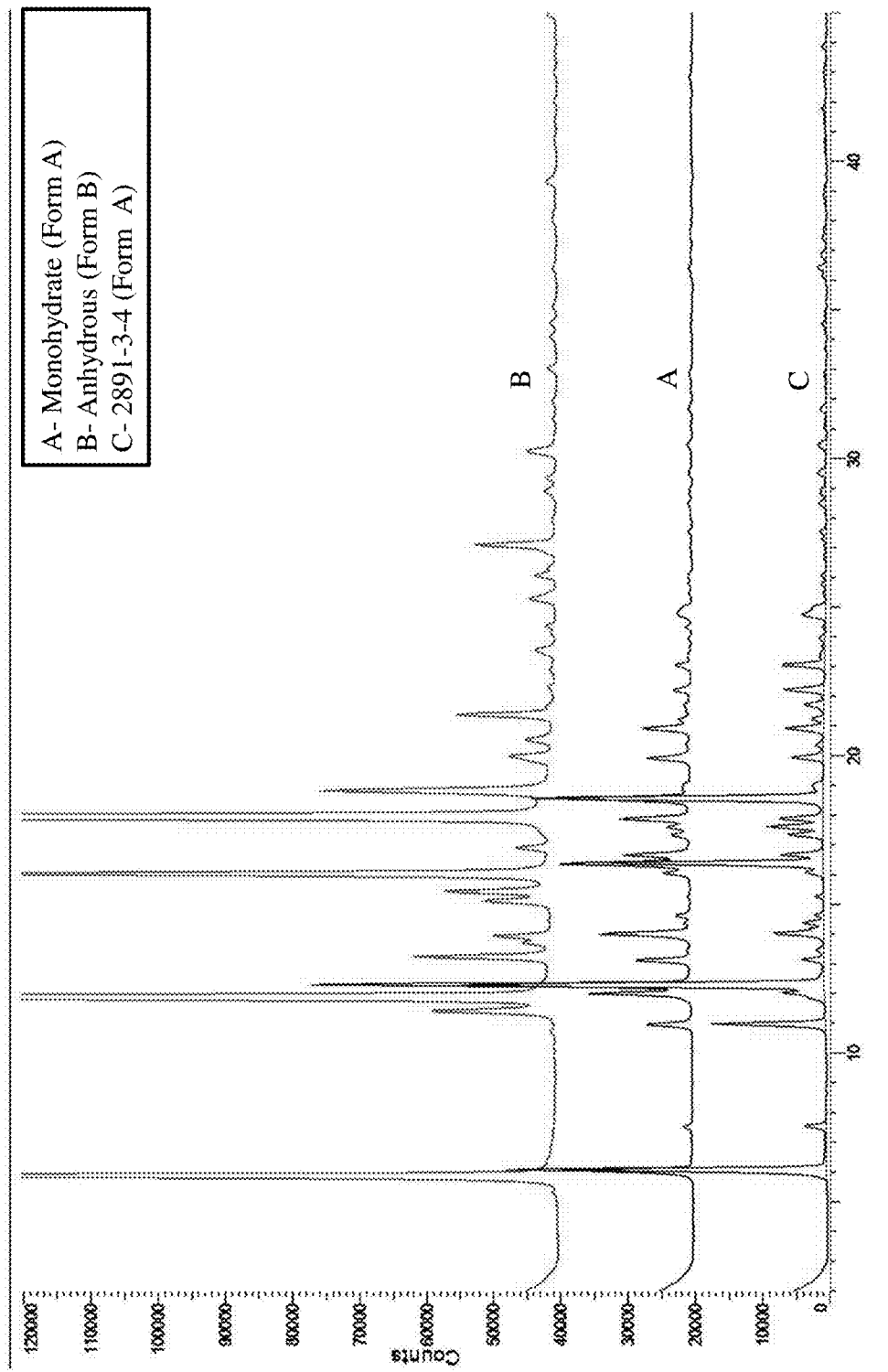
Figure 6D:
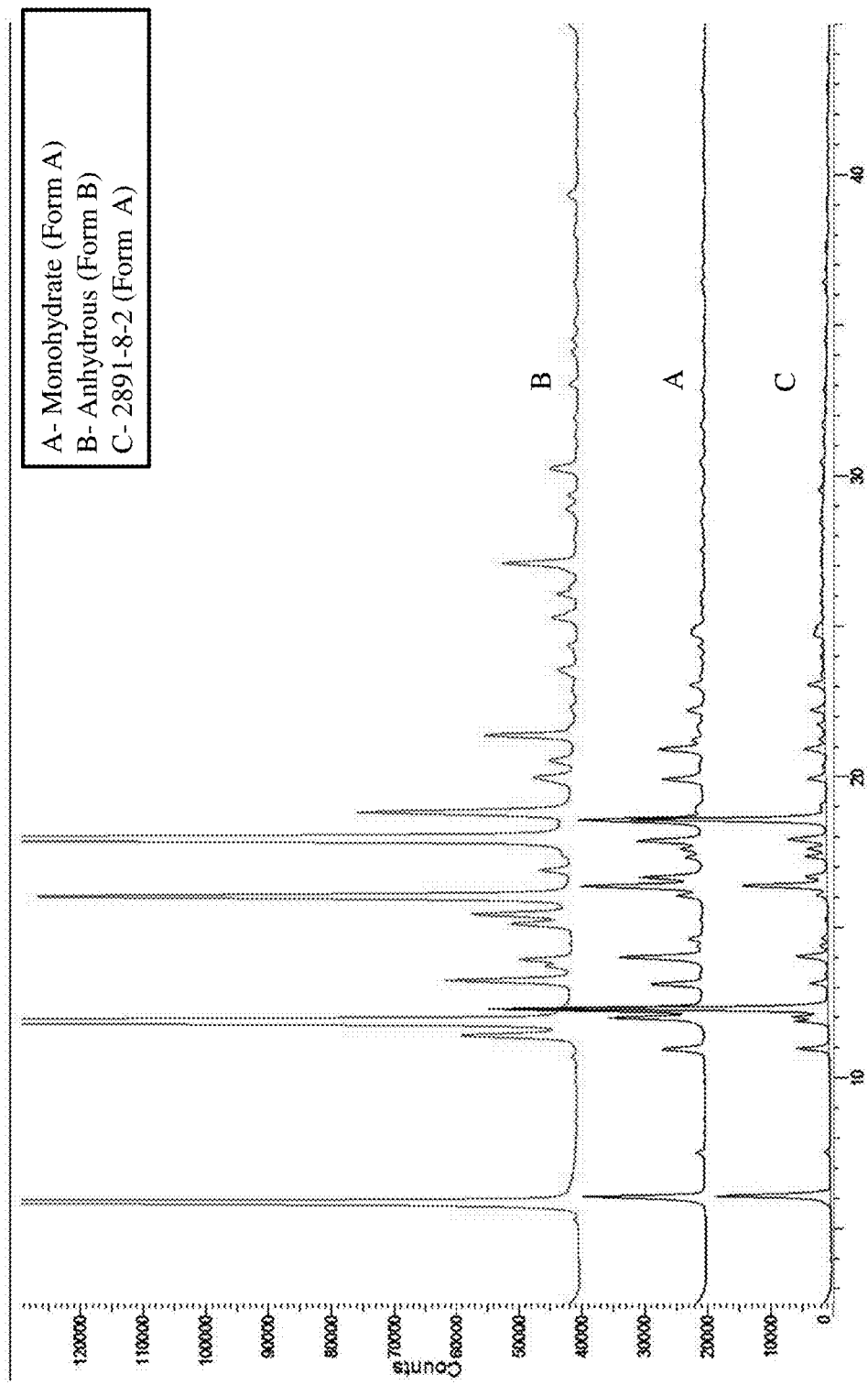
Figure 6E:
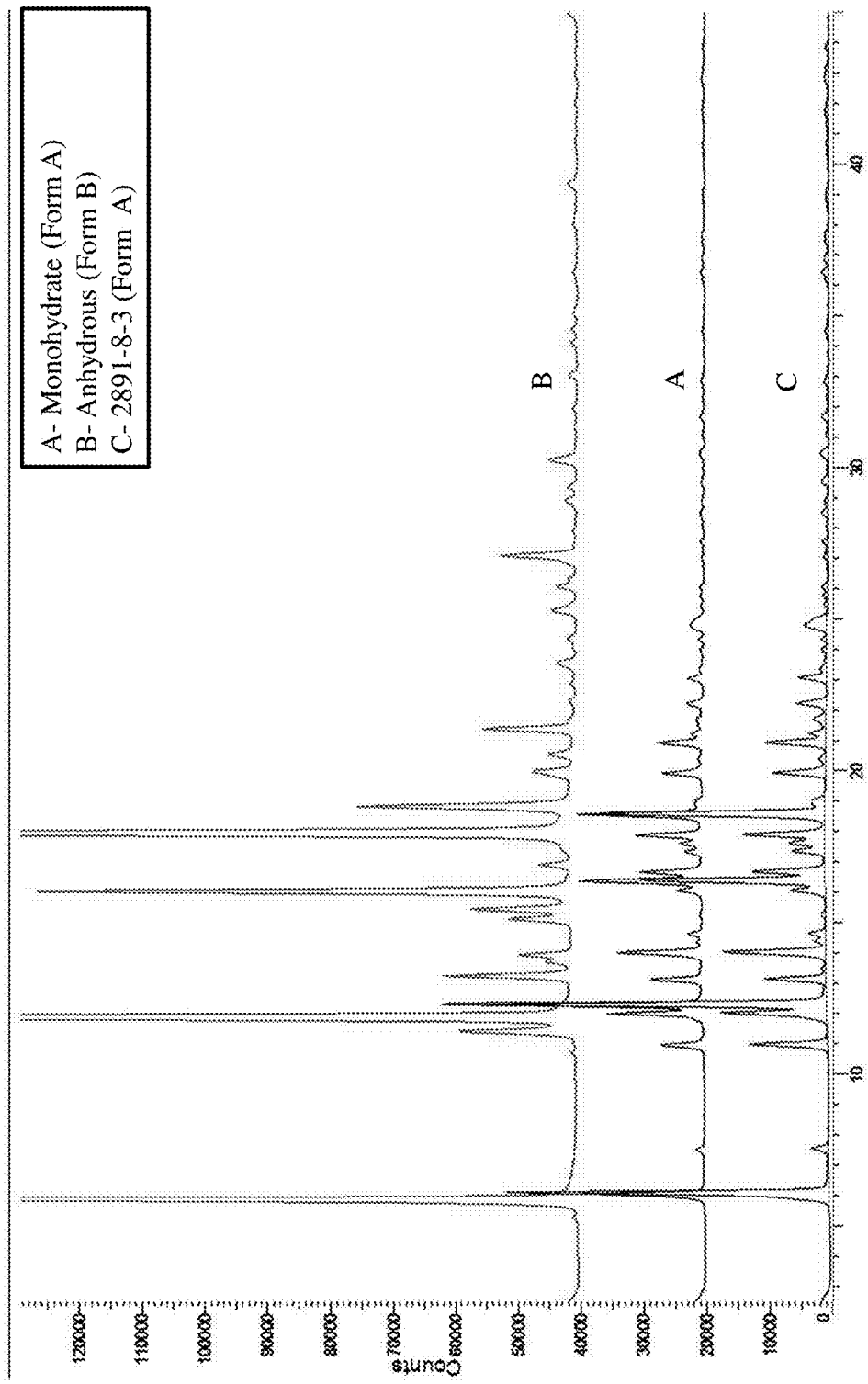
Figure 6F:
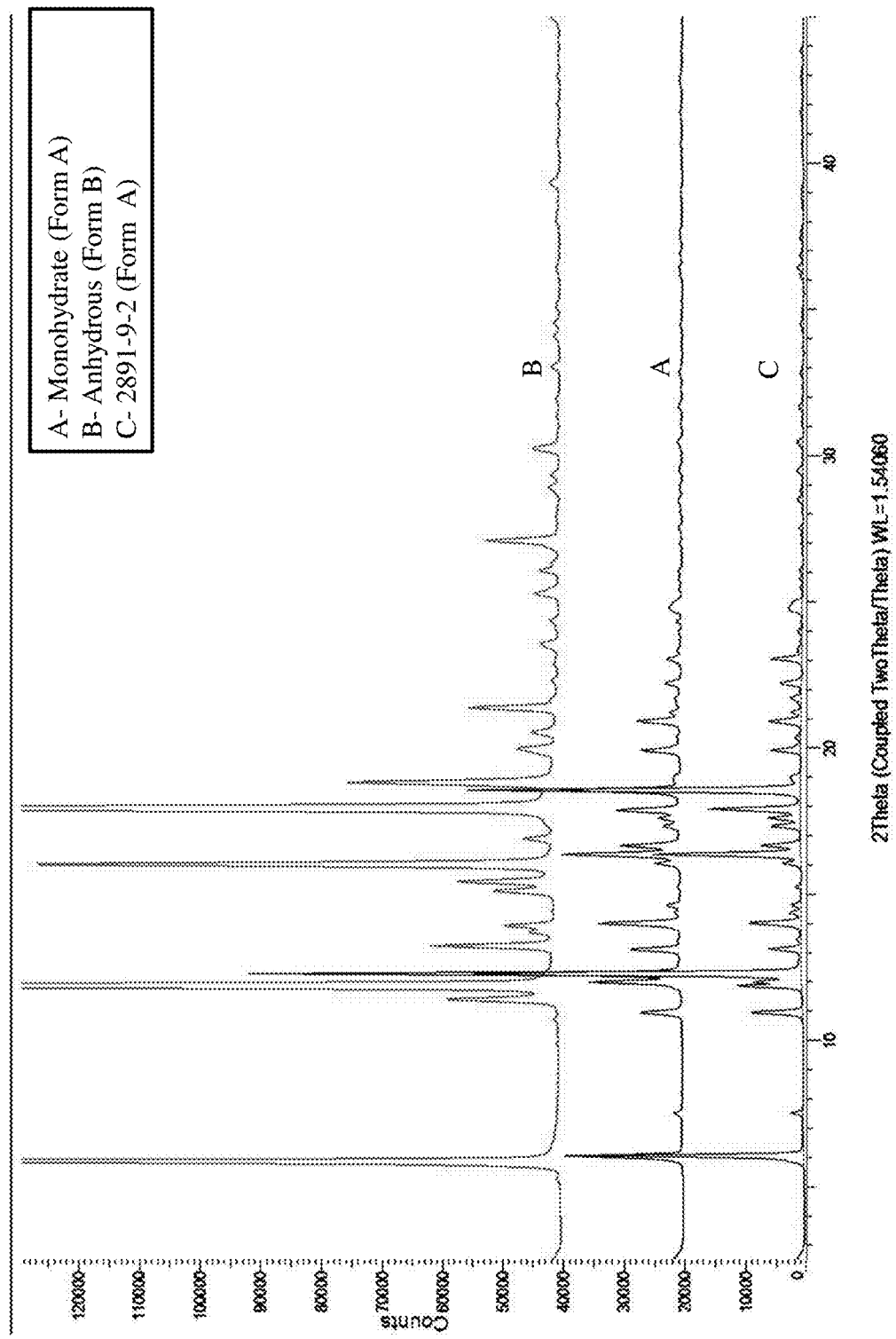
Figure 6G:
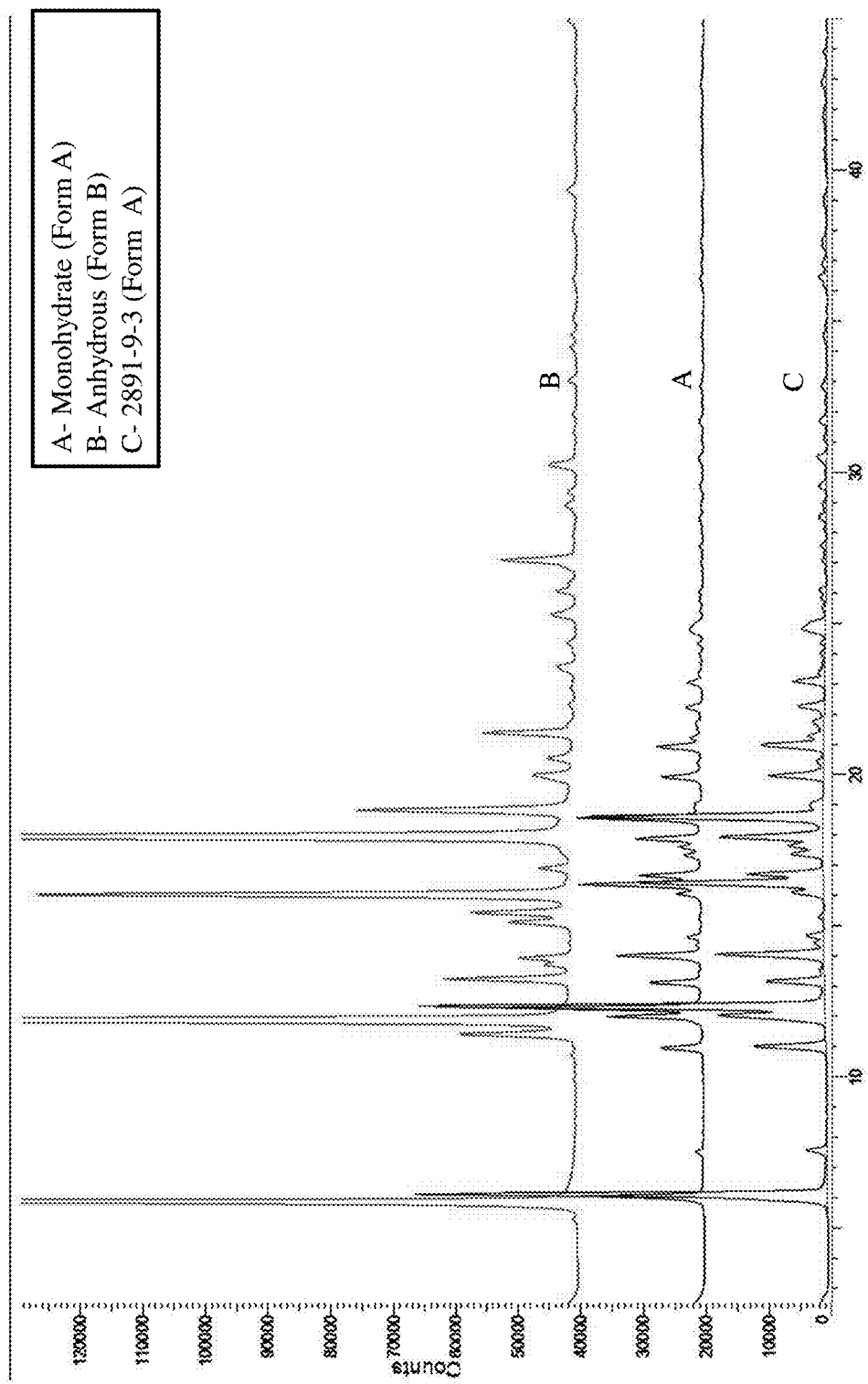
Figure 6H:
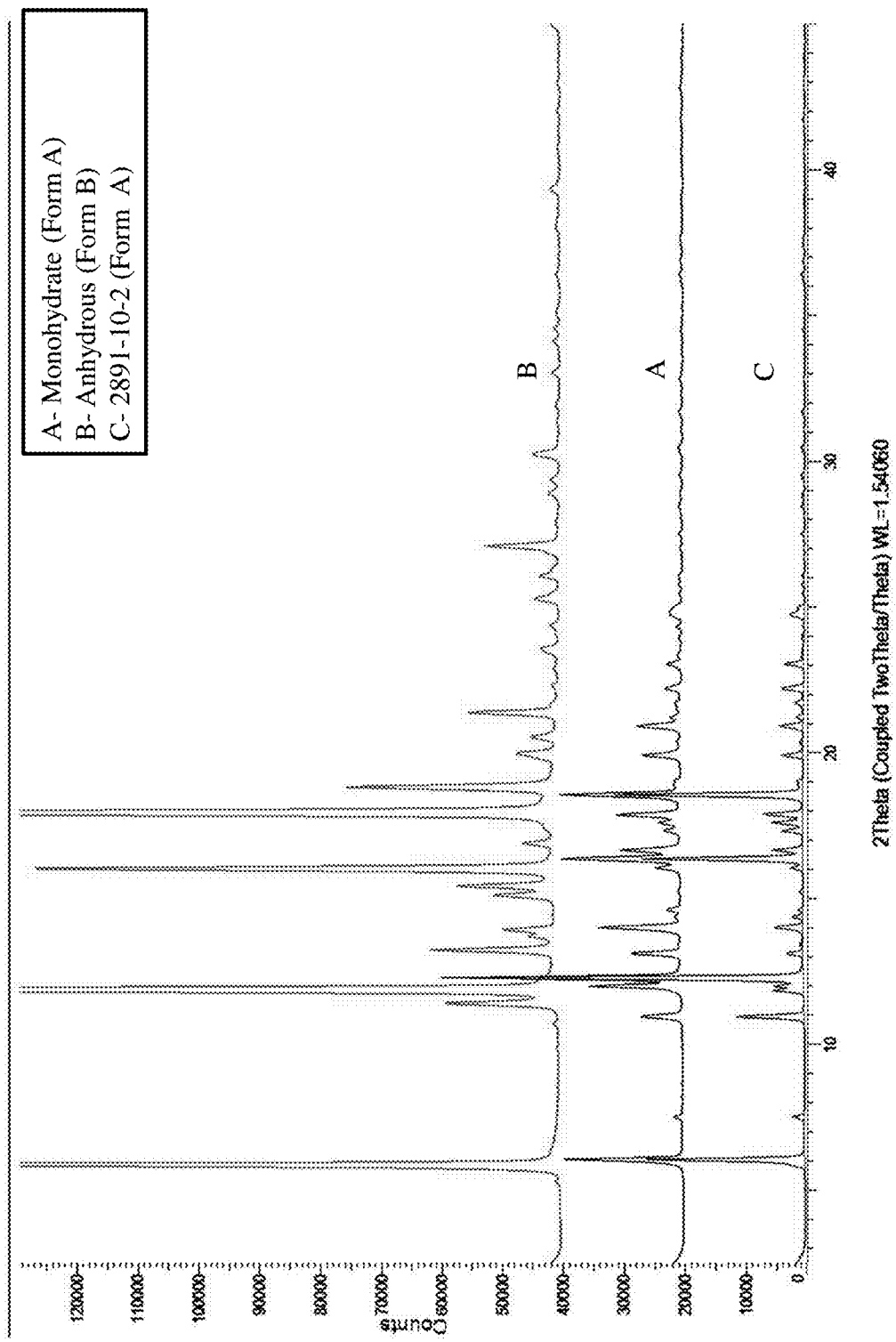
Figure 6I:
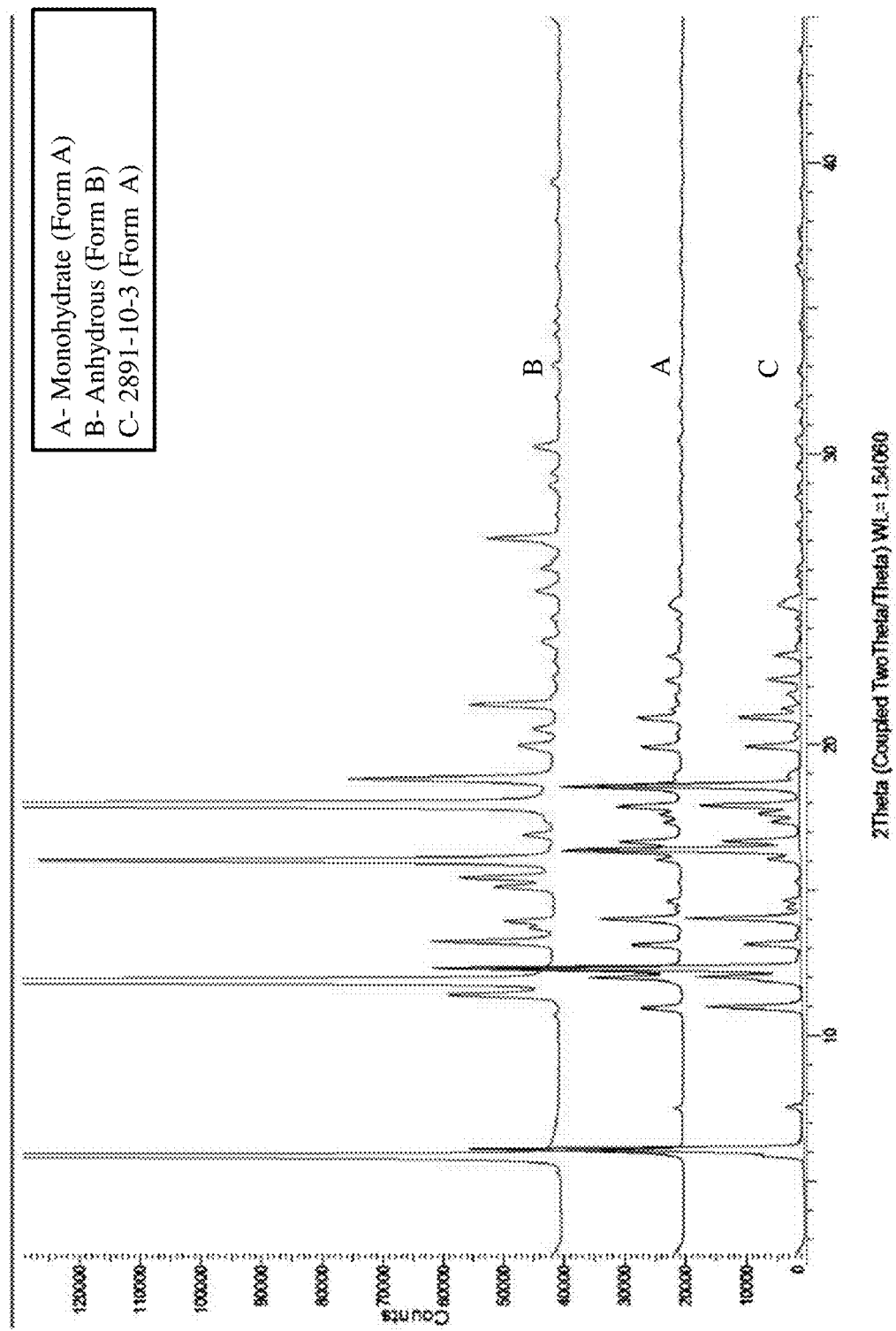

FIGS. 6A, 6B, 6C, 6D, 6E, 6F, 6G, 6H, 6I, 6J, 6K, 6L, 6M, 6N, 6O, 6P, 6Q, 6R, 6S, 6T, 6U, 6V, 6W and 6X are XRPDs of OXY133 polymorph Form A. In particular, FIG. 6A is an XRPD of a solid OXY133 Form A. Table 5, below lists data taken from the XRPD of FIG. 6A. As illustrated in Table 5, OXY133 Form A can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48

TABLE 5

XRPD Data for OXY133 Polymorph Form A, as illustrated in FIG. 6A

| Index No. | Angle (2-Theta) | d Value (Angstrom) | Net Intensity (Counts) | Gross Intensity (Counts) | Rel. Intensity (%) |
|---|---|---|---|---|---|
| 0 | 5.561 | 15.8807 | 6249 | 6906 | 11.30% |
| 1 | 5.967 | 14.799 | 37706 | 38421 | 68.30% |
| 2 | 7.484 | 11.803 | 539 | 1386 | 1.00% |
| 3 | 10.952 | 8.07213 | 7553 | 8876 | 13.70% |
| 4 | 12.183 | 7.25924 | 55166 | 56910 | 100.00% |
| 5 | 13.059 | 6.77383 | 3563 | 5552 | 6.50% |
| 6 | 14.002 | 6.31977 | 6237 | 8436 | 11.30% |
| 7 | 14.423 | 6.13613 | 1361 | 3637 | 2.50% |
| 8 | 14.564 | 6.07711 | 1407 | 3707 | 2.60% |
| 9 | 15.152 | 5.84266 | 726 | 3111 | 1.30% |
| 10 | 16.232 | 5.45628 | 9981 | 12467 | 18.10% |
| 11 | 16.388 | 5.40467 | 19099 | 21594 | 34.60% |
| 12 | 17.278 | 5.12833 | 7987 | 10505 | 14.50% |
| 13 | 17.565 | 5.04494 | 8792 | 11307 | 15.90% |
| 14 | 17.859 | 4.9627 | 10266 | 12773 | 18.60% |
| 15 | 18.447 | 4.80569 | 28710 | 31185 | 52.00% |
| 16 | 19.823 | 4.47519 | 3458 | 5778 | 6.30% |
| 17 | 20.324 | 4.36597 | 3308 | 5543 | 6.00% |
| 18 | 20.885 | 4.24992 | 3064 | 5186 | 5.60% |
| 19 | 21.789 | 4.07571 | 401 | 2307 | 0.70% |
| 20 | 22.173 | 4.00583 | 2240 | 4045 | 4.10% |
| 21 | 23.043 | 3.85655 | 964 | 2507 | 1.70% |
| 22 | 24.351 | 3.65238 | 239 | 1389 | 0.40% |
| 23 | 24.706 | 3.60057 | 1550 | 2669 | 2.80% |
| 24 | 25.419 | 3.50117 | 177 | 1210 | 0.30% |
| 25 | 25.832 | 3.44621 | 203 | 1173 | 0.40% |
| 26 | 26.873 | 3.31496 | 95.2 | 1004 | 0.20% |
| 27 | 27.462 | 3.24523 | 207 | 1132 | 0.40% |
| 28 | 27.964 | 3.18806 | 112 | 1044 | 0.20% |
| 29 | 28.355 | 3.14497 | 475 | 1406 | 0.90% |
| 30 | 28.855 | 3.09163 | 376 | 1294 | 0.70% |
| 31 | 29.247 | 3.05108 | 414 | 1312 | 0.80% |
| 32 | 29.589 | 3.0166 | 147 | 1018 | 0.30% |
| 33 | 30.361 | 2.94166 | 121 | 951 | 0.20% |
| 34 | 31.028 | 2.87987 | 93.3 | 907 | 0.20% |
| 35 | 31.609 | 2.82831 | 292 | 1123 | 0.50% |
| 36 | 31.972 | 2.79704 | 397 | 1229 | 0.70% |
| 37 | 33.731 | 2.65503 | 250 | 1001 | 0.50% |
| 38 | 34.301 | 2.6122 | 90.4 | 829 | 0.20% |
| 39 | 34.568 | 2.59262 | 135 | 860 | 0.20% |
| 40 | 36.421 | 2.46492 | 197 | 911 | 0.40% |
| 41 | 36.926 | 2.43235 | 73.9 | 797 | 0.10% |
| 42 | 37.429 | 2.4008 | 123 | 841 | 0.20% |
| 43 | 38.501 | 2.33638 | 118 | 810 | 0.20% |
| 44 | 40.499 | 2.22559 | 106 | 820 | 0.20% |
| 45 | 41.649 | 2.16678 | 51.6 | 791 | 0.10% |
| 46 | 42.778 | 2.11217 | 130 | 835 | 0.20% |
| 47 | 42.995 | 2.10199 | 73 | 768 | 0.10% |
| 48 | 43.805 | 2.06497 | 78.2 | 715 | 0.10% |

Figure 6J:
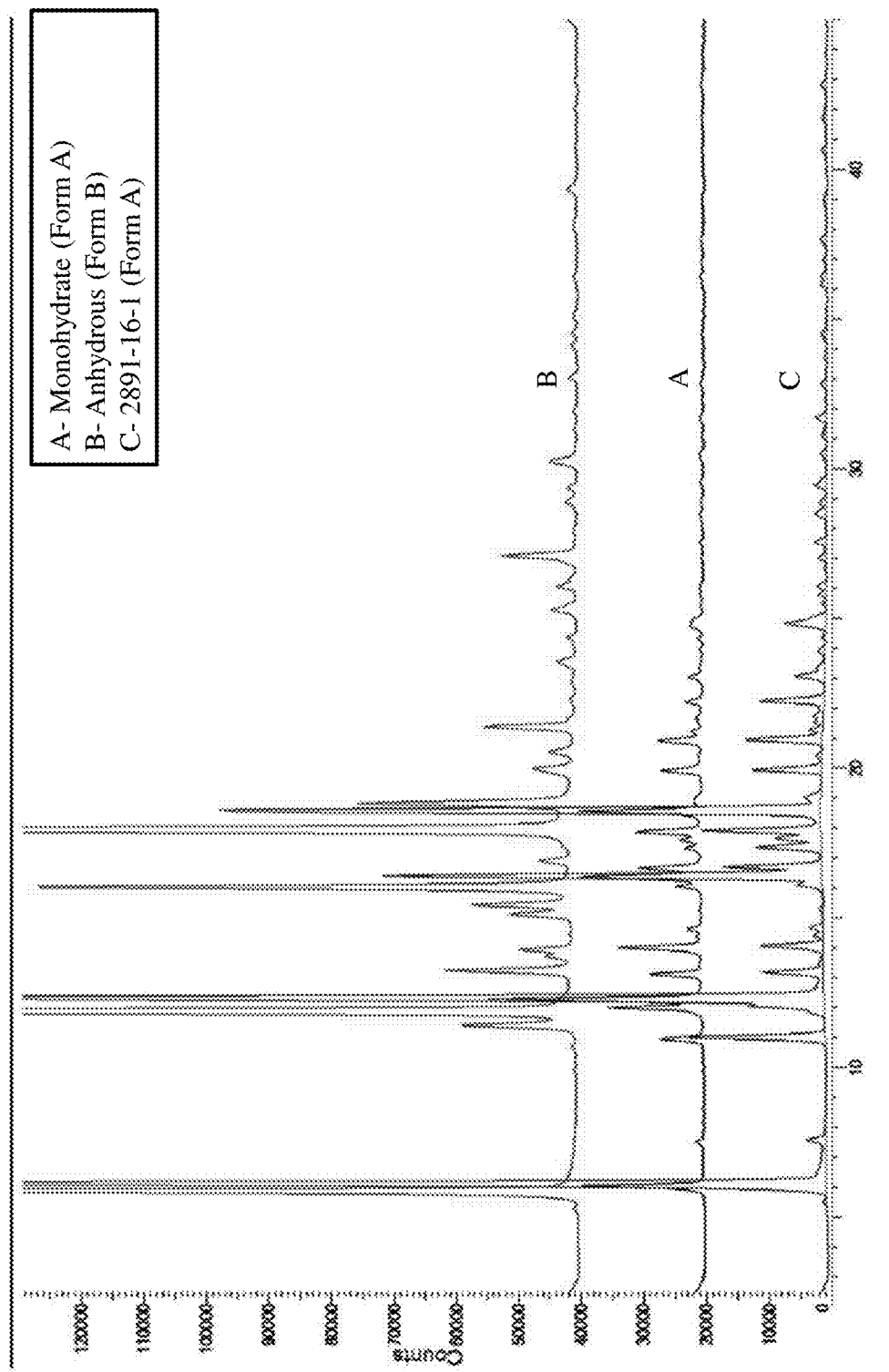
Figure 6K:
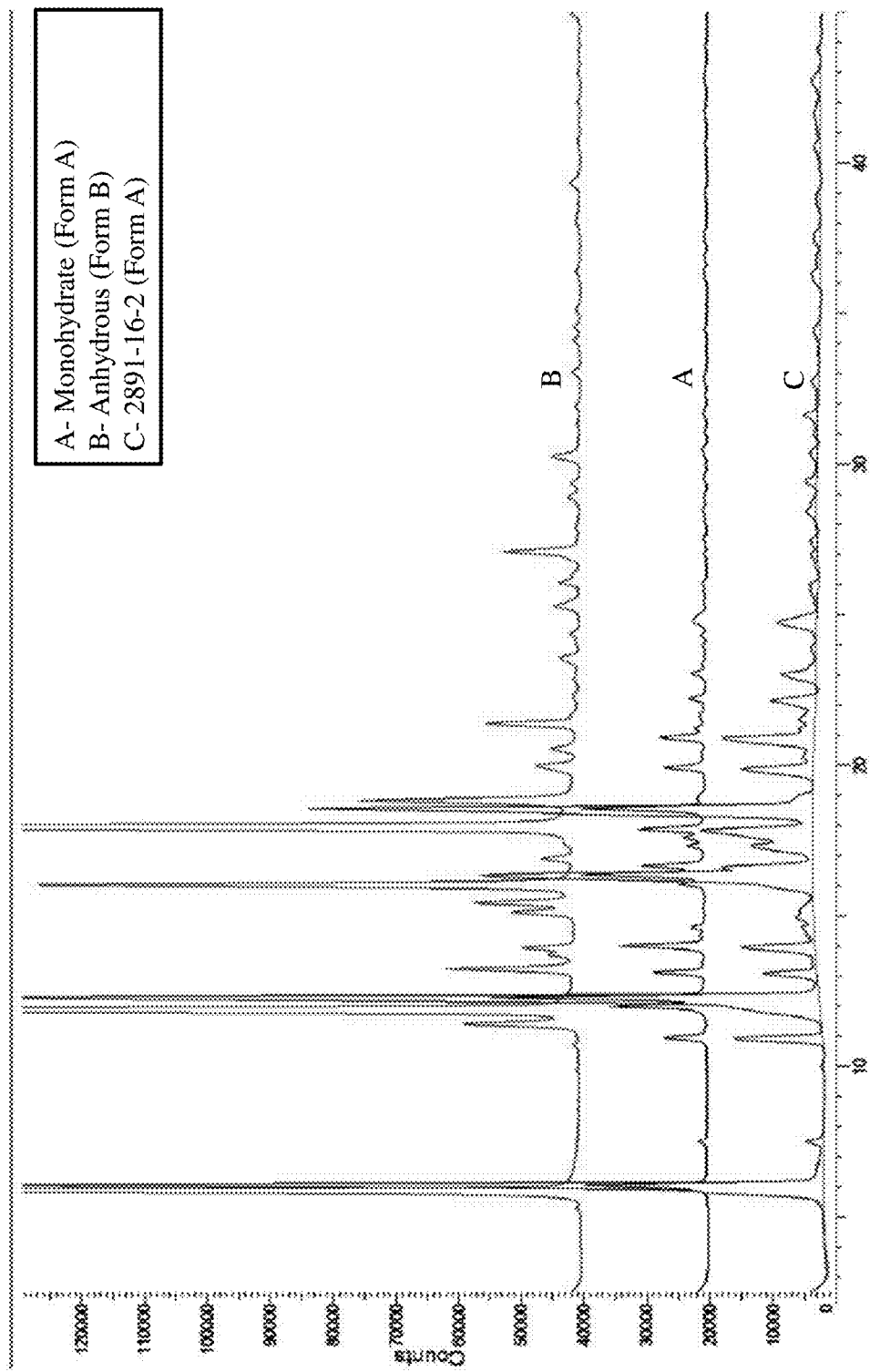
Figure 6L:
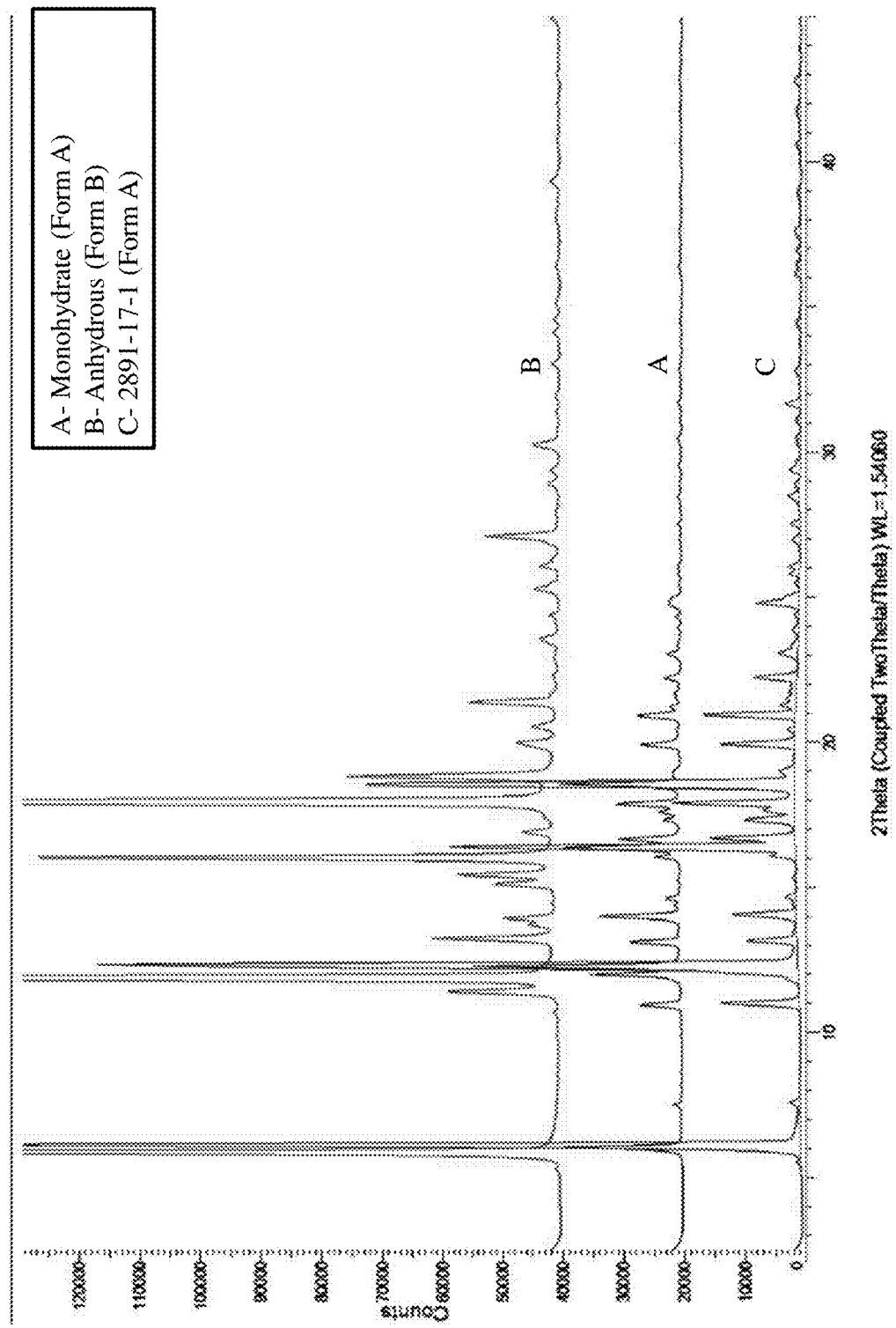
Figure 6M:
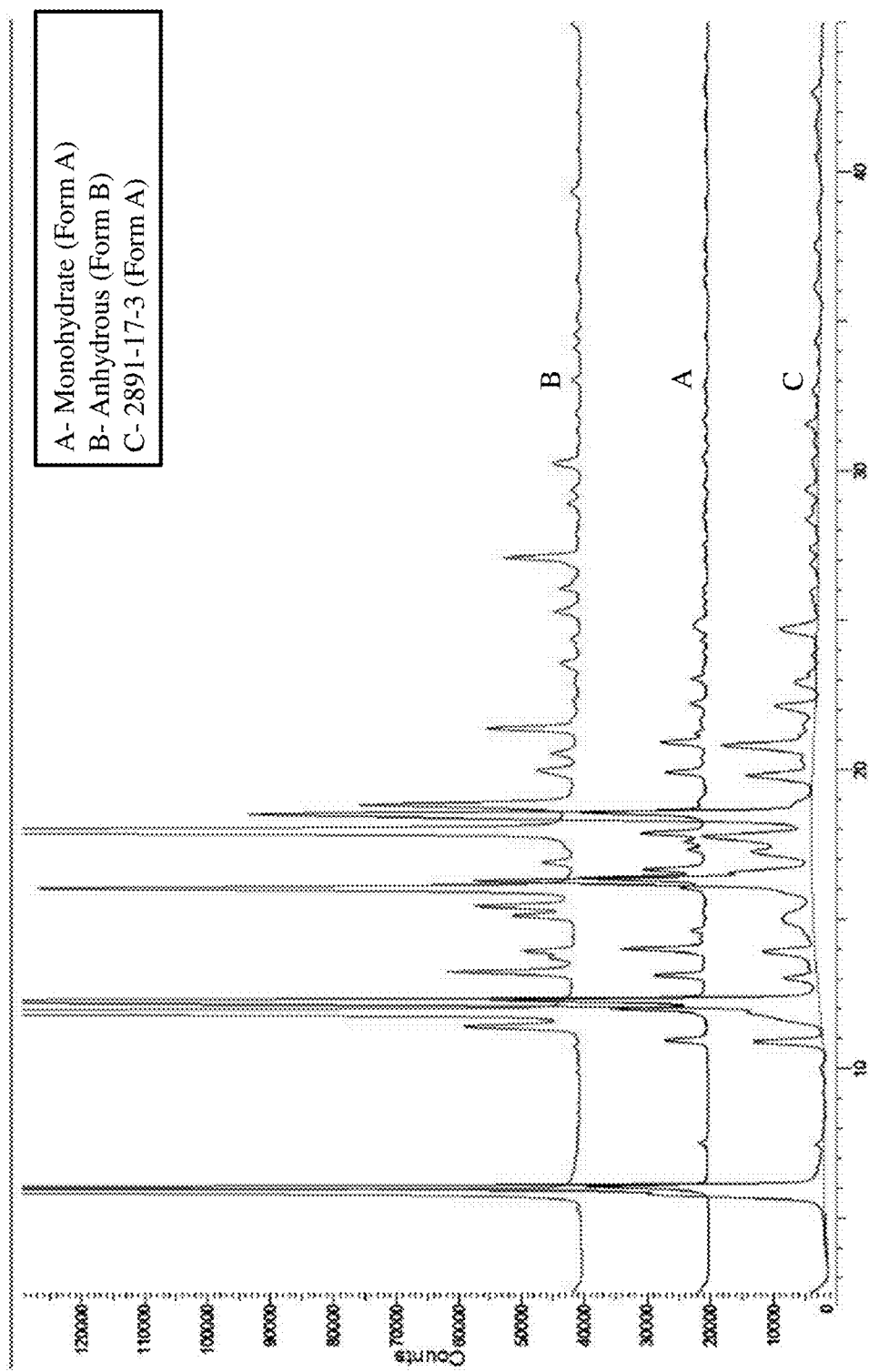
Figure 6N:
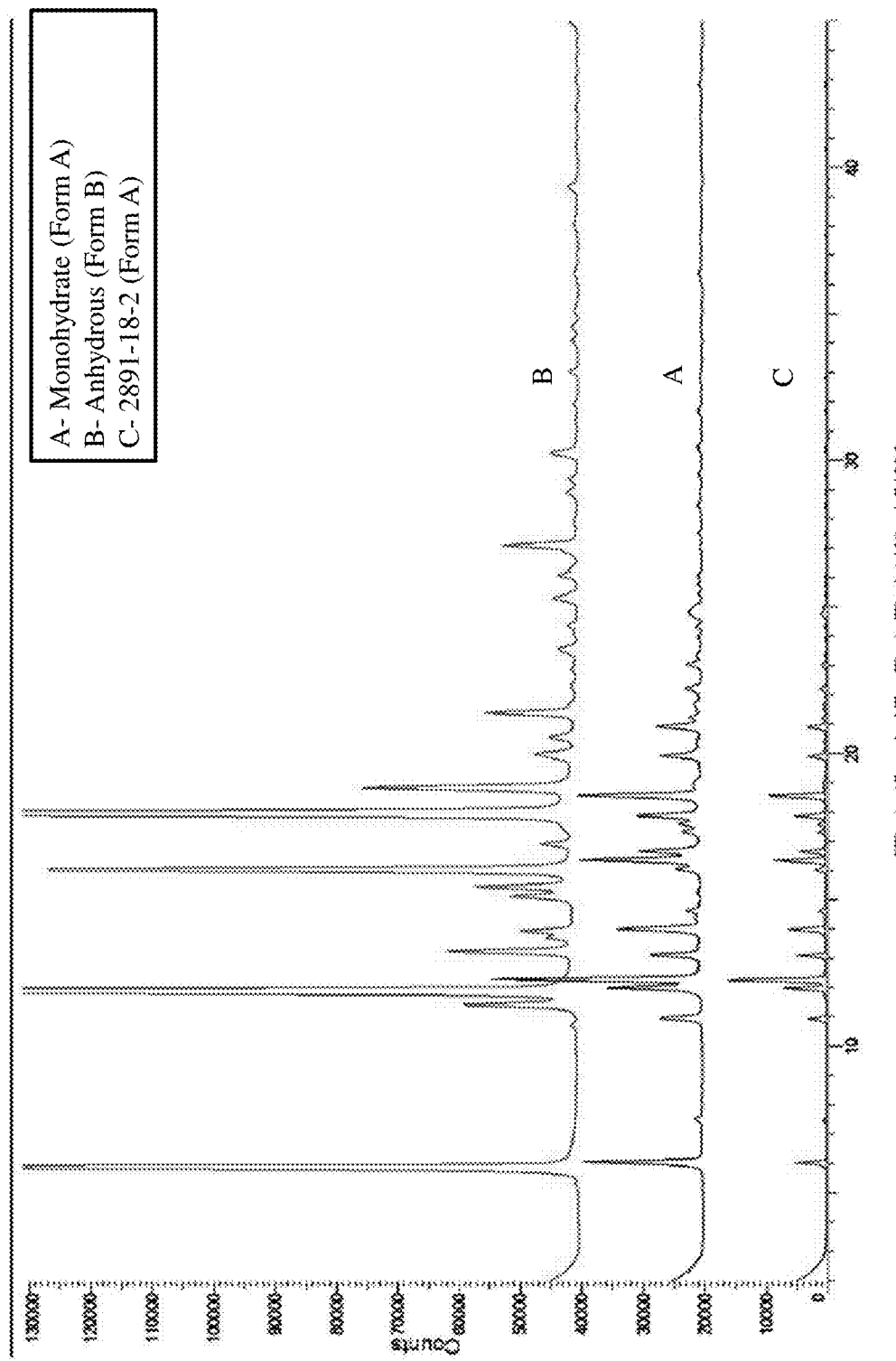
Figure 60:
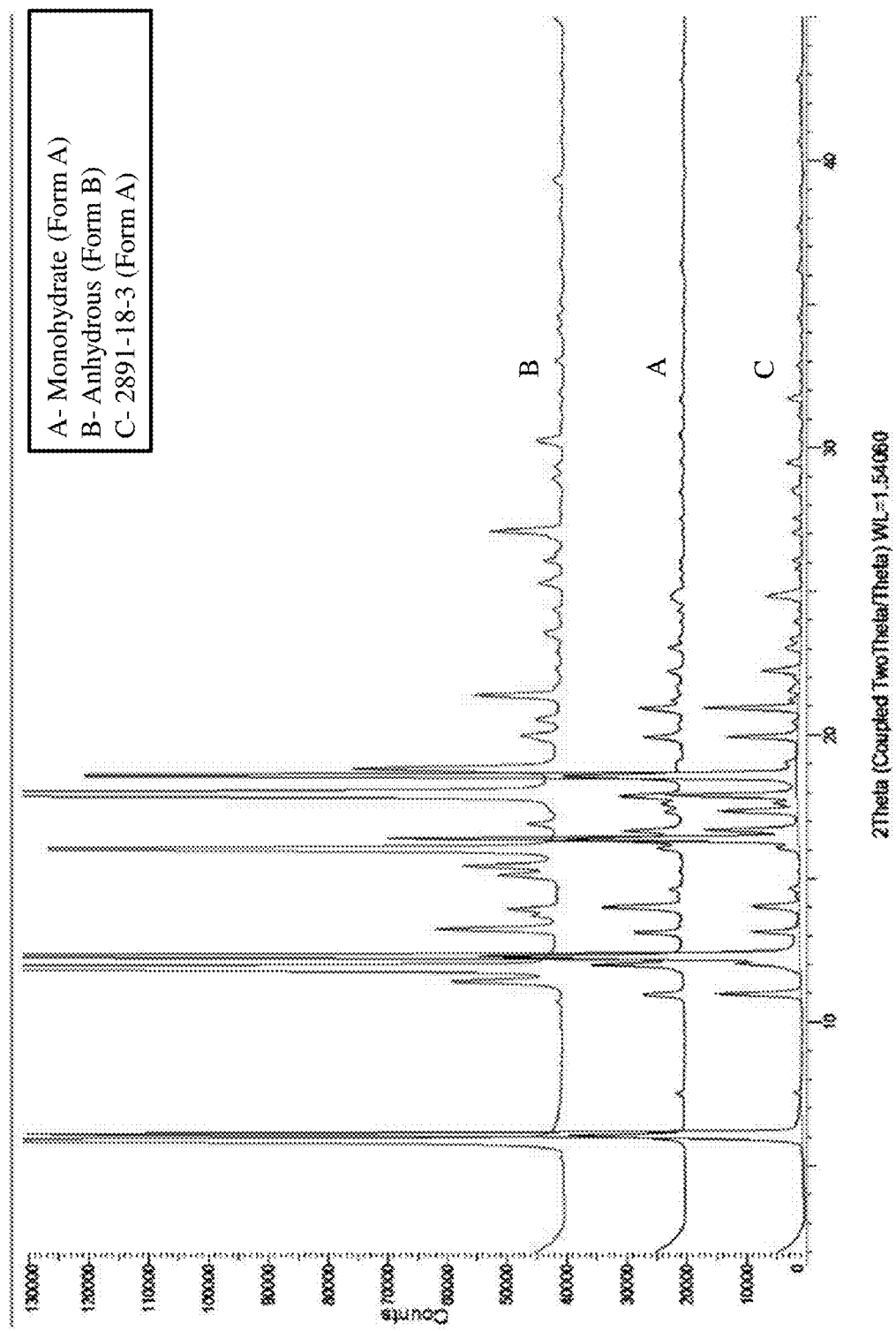
Figure 6P:
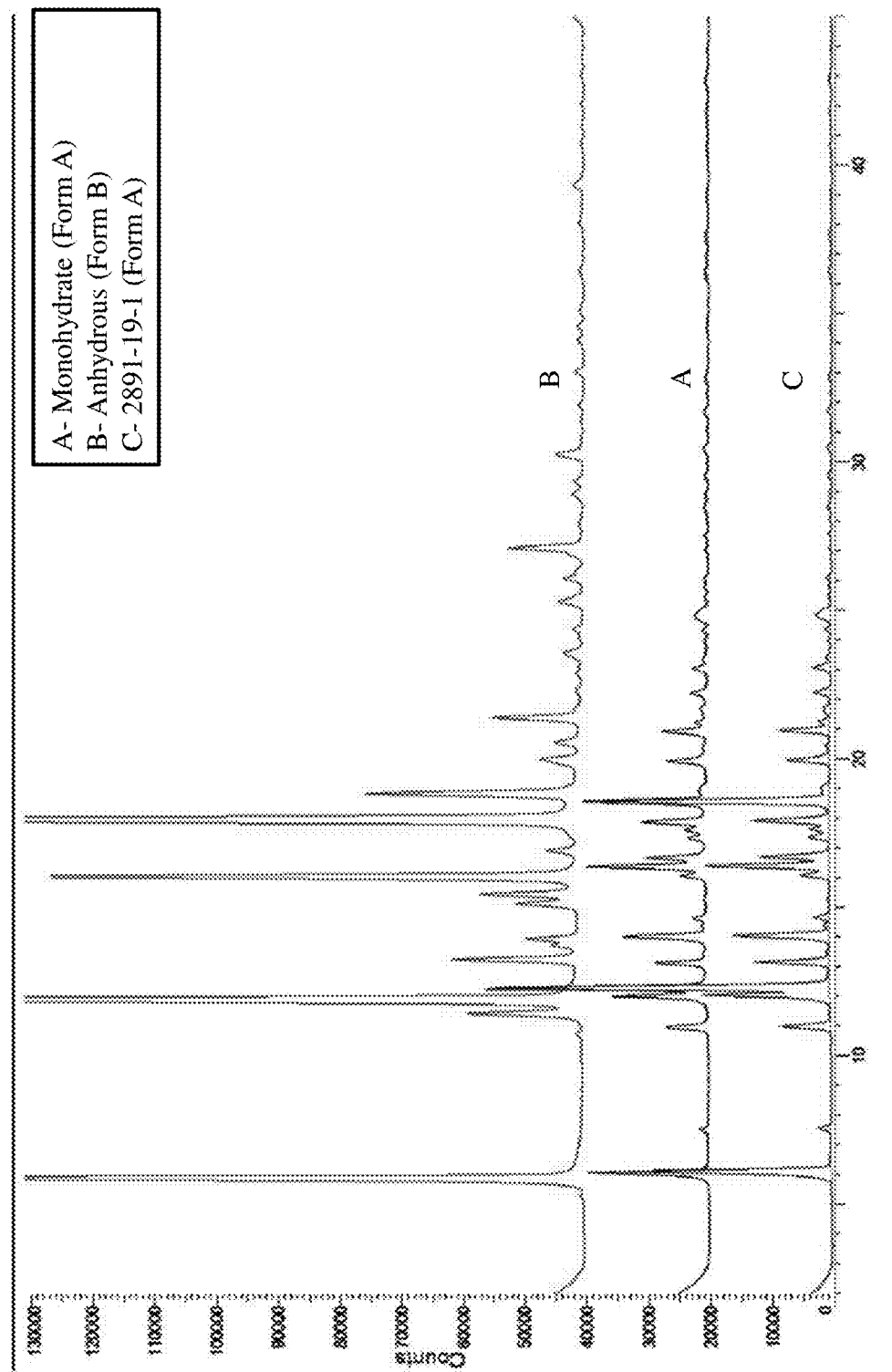
Figure 6Q:
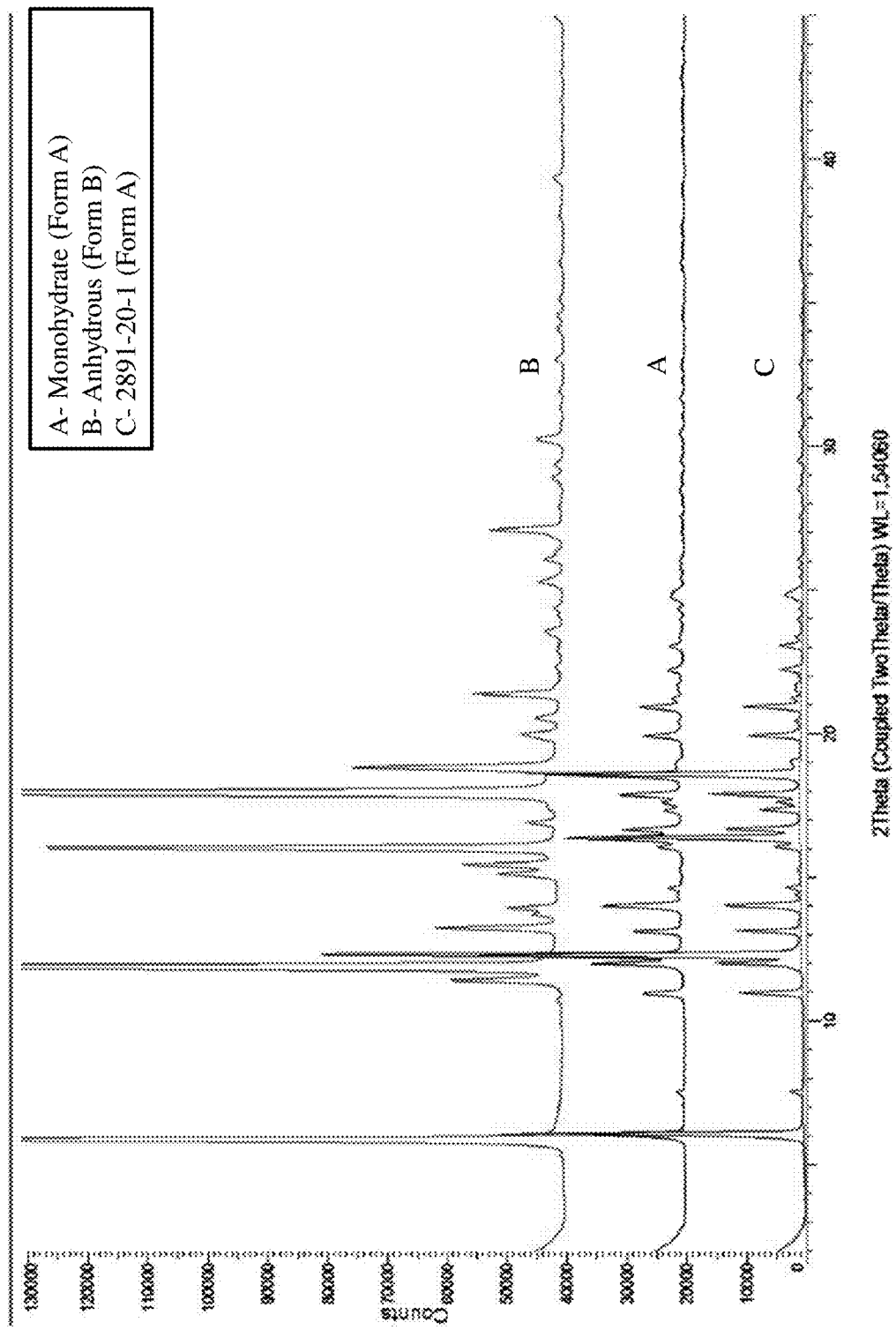
Figure 6R:
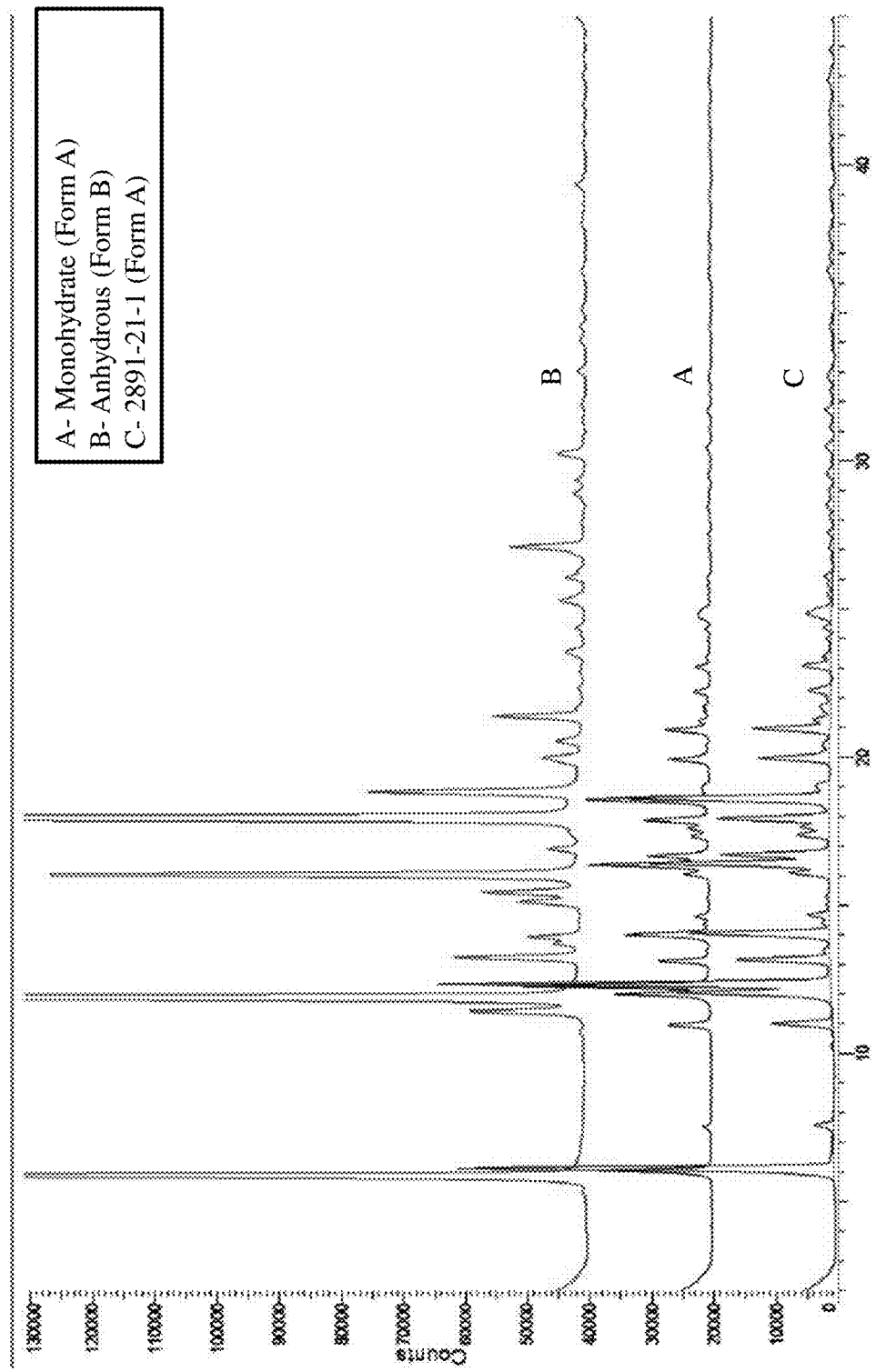
Figure 6S:
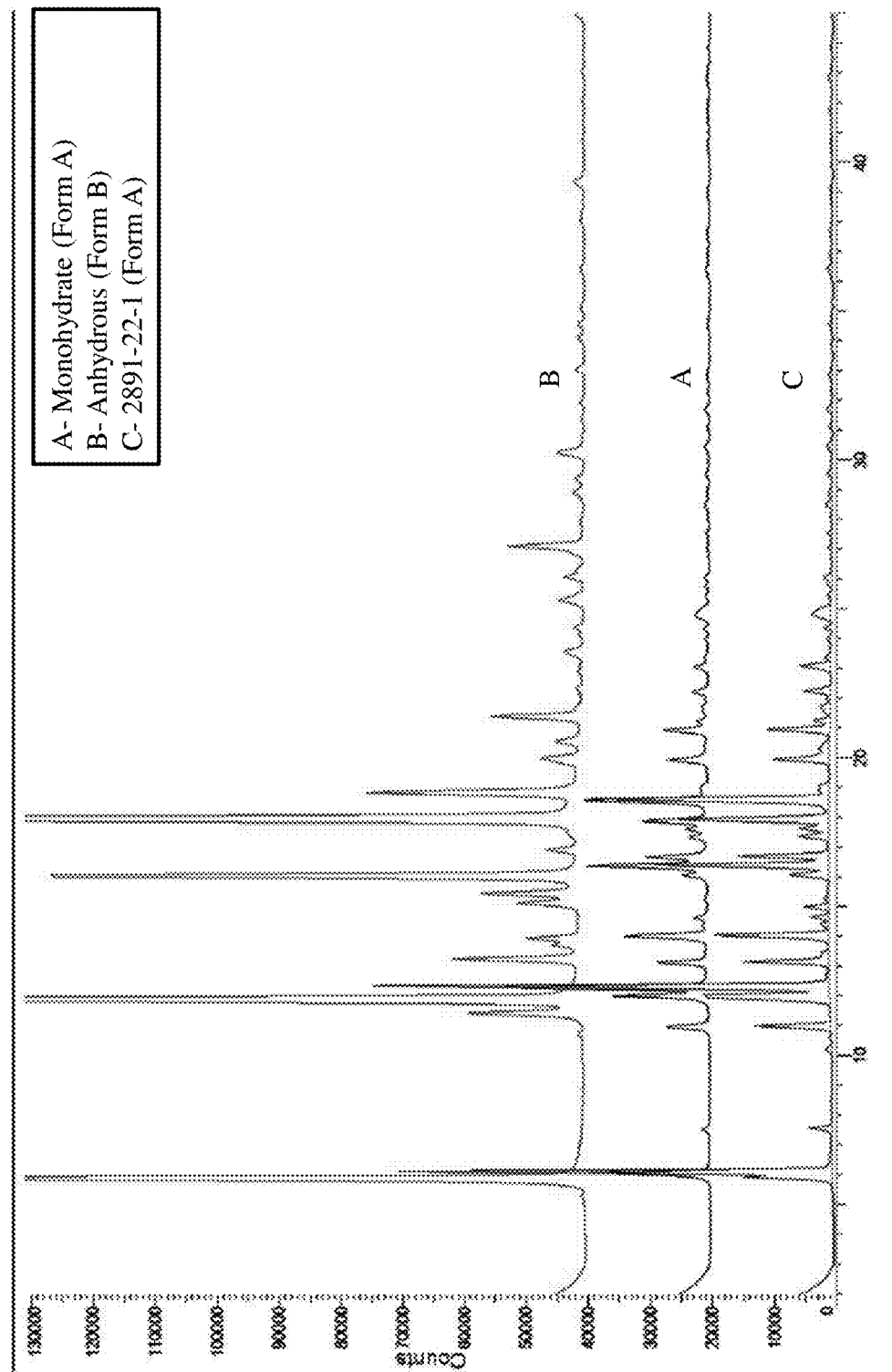
Figure 6T:
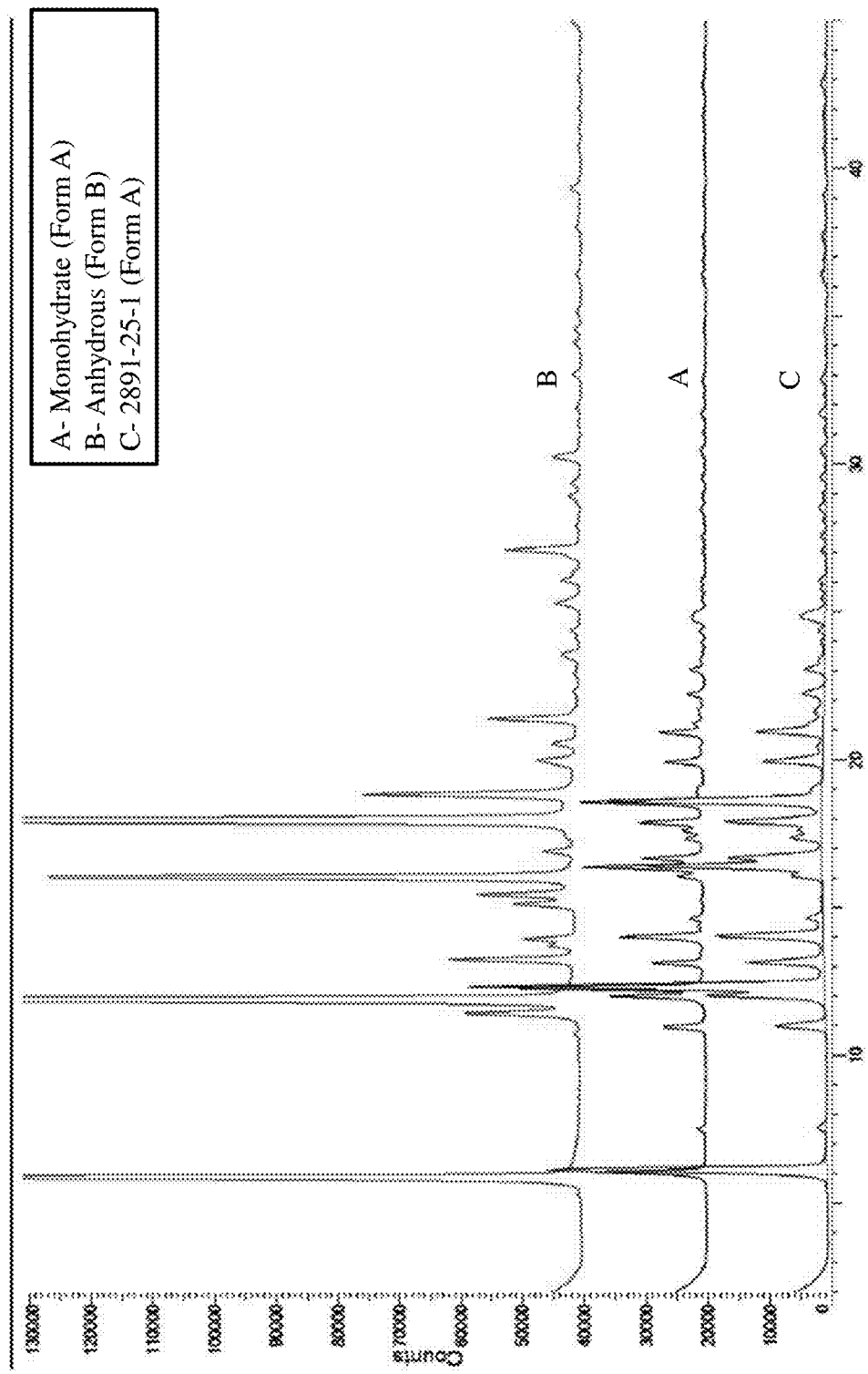
Figure 6U:
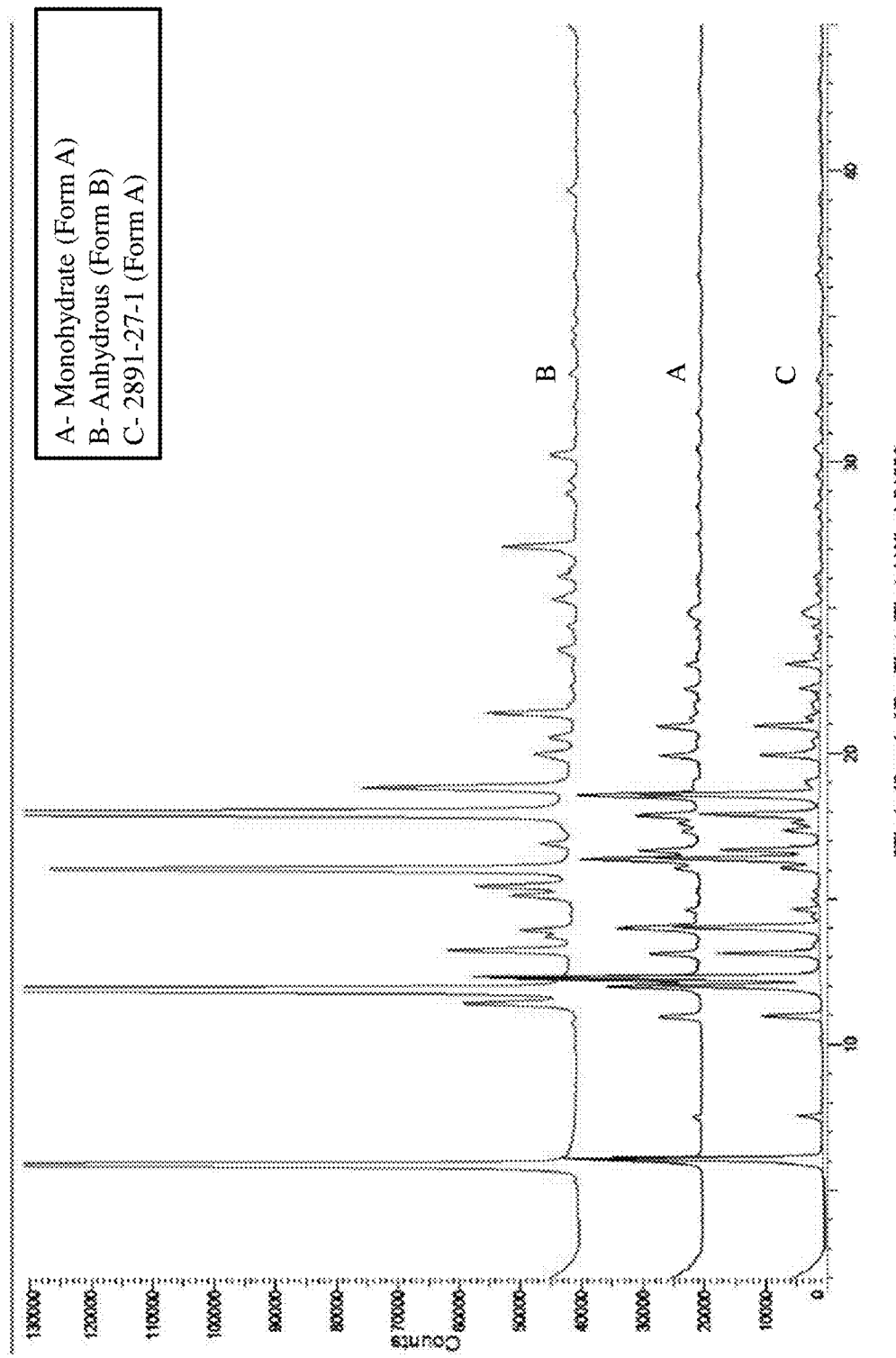
Figure 6V:
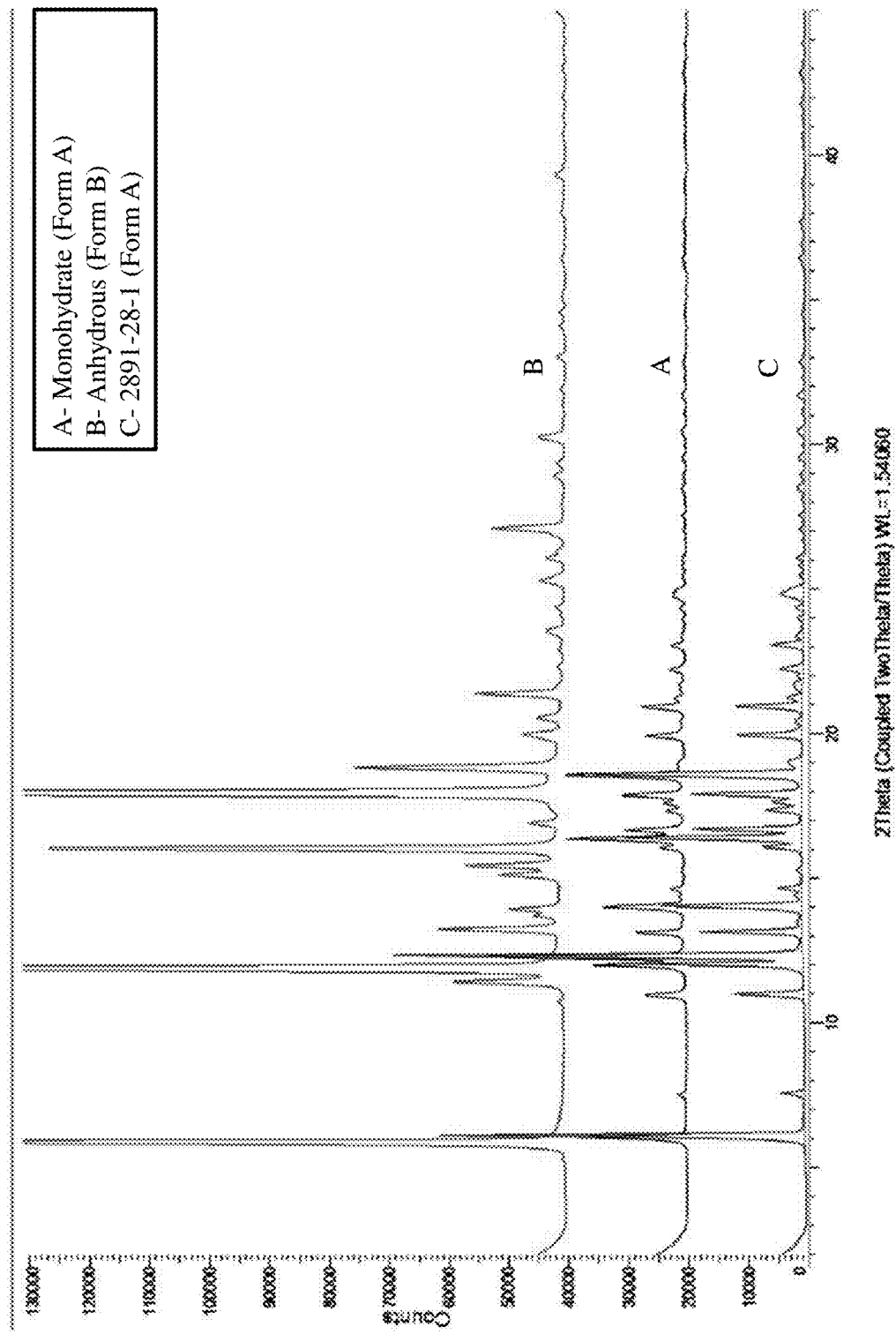

FIGS. 6B-6I are XRPDs of polymorph Form A obtained by re-slurrying from an acetone/water solvent/anti-solvent medium in a ratio of 1:1 v/v at precipitating temperatures of 20° C., 50° C., 0° C., 35° C., 10° C., 25° C., respectively. FIGS. 6J and 6K are XRPDs of polymorph Form A obtained by crystallization from a THF/acetone/water solvent system at temperatures of 35° C. FIGS. 6L and 6M are XRPDs of polymorph Form A by re-slurrying from a THF/water solvent system in a ratio of 1:2 v/v at precipitating temperatures of 20° C. and 35° C., respectively. FIGS. 6N-6V are XRPDs of polymorph Form A obtained by crystallization from IPA/water solvent system in a ratio of 1:2 or 1:1 v/v at temperatures of 0° C., 5° C., 10° C. and 20° C., respectively, as also listed in more detail in Table 15 below. In FIG. 6T, the conversion to polymorph Form A is from a hemihydrate of OXY133.

Figure 6W:
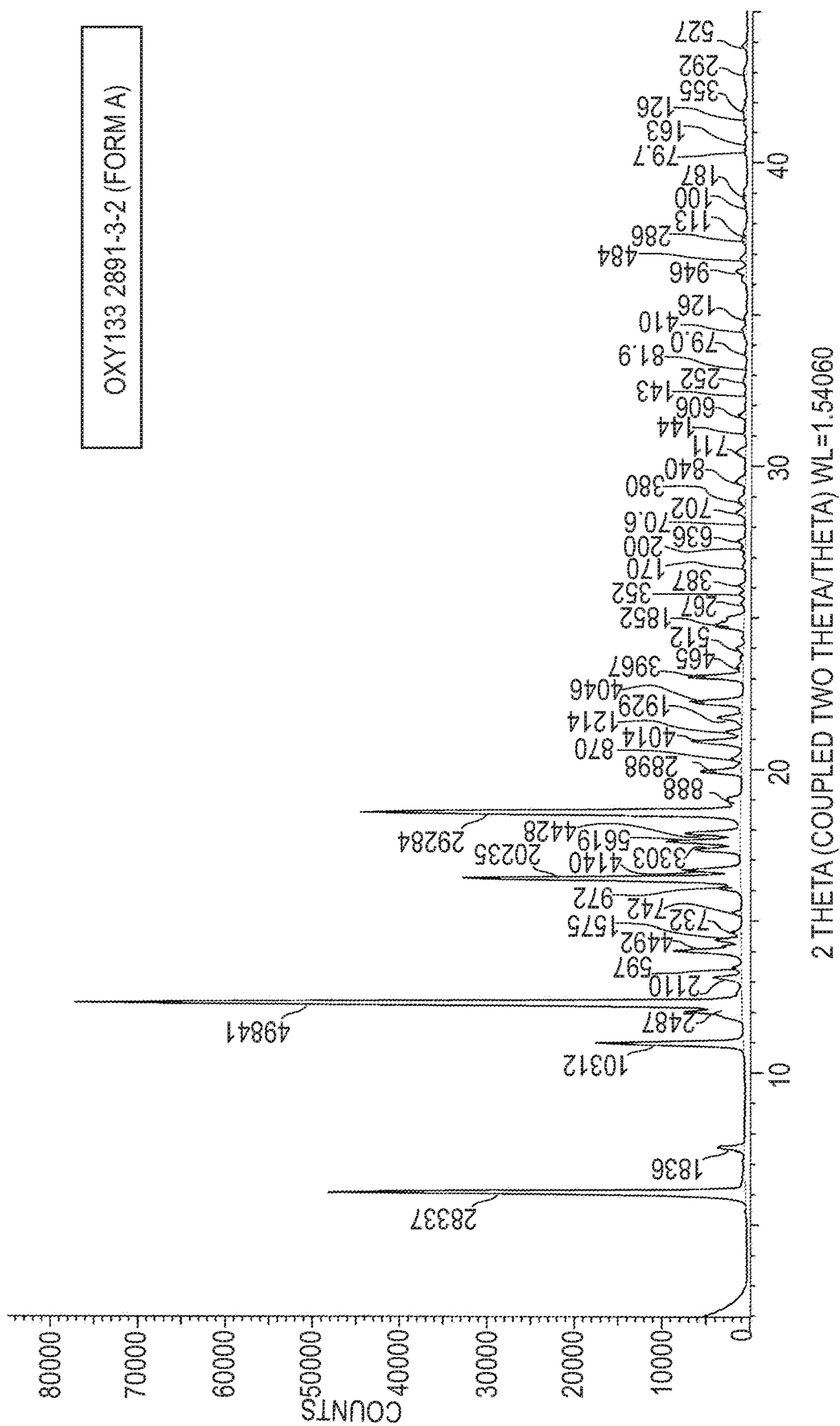

FIG. 6W is an XRPD of polymorph A obtained by re-slurrying from an acetone/water solvent/anti-solvent medium in a ratio of 1:1 v/v at a precipitating temperature of 20° C. FIG. 6W is an XRPD of a solid OXY133 Form A. Table 6, below lists data taken from the XRPD of FIG. 6W. As illustrated in Table 6, OXY133 Form A can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 and 61.

TABLE 6

XRPD Data for OXY133 Polymorph Form A, as illustrated in FIG. 6W

| Index No. | Angle (2-Theta) | d Value (Angstrom) | Net Intensity (Counts) | Gross Intensity (Counts) | Rel. Intensity (%) |
|---|---|---|---|---|---|
| 0 | 6.066 | 14.55919 | 28337 | 28877 | 56.90% |
| 1 | 7.525 | 11.73815 | 1836 | 2450 | 3.70% |
| 2 | 10.98 | 8.05166 | 10312 | 11050 | 20.70% |
| 3 | 12.116 | 7.29894 | 2487 | 3391 | 5.00% |
| 4 | 12.292 | 7.19472 | 49841 | 50764 | 100.00% |
| 5 | 13.141 | 6.73178 | 2110 | 3103 | 4.20% |
| 6 | 13.467 | 6.56952 | 597 | 1605 | 1.20% |
| 7 | 14.043 | 6.30144 | 4492 | 5514 | 9.00% |
| 8 | 14.413 | 6.1407 | 1575 | 2596 | 3.20% |
| 9 | 14.631 | 6.04969 | 732 | 1748 | 1.50% |
| 10 | 15.261 | 5.80105 | 742 | 1742 | 1.50% |
| 11 | 16.141 | 5.48665 | 972 | 2013 | 1.90% |
| 12 | 16.398 | 5.4013 | 20235 | 21297 | 40.60% |
| 13 | 16.648 | 5.32084 | 4140 | 5219 | 8.30% |
| 14 | 17.36 | 5.1042 | 3303 | 4412 | 6.60% |
| 15 | 17.616 | 5.03065 | 5619 | 6731 | 11.30% |
| 16 | 17.881 | 4.95652 | 4428 | 5541 | 8.90% |
| 17 | 18.569 | 4.7745 | 29284 | 30379 | 58.80% |
| 18 | 18.965 | 4.67564 | 888 | 1961 | 1.80% |
| 19 | 19.962 | 4.44445 | 2898 | 3937 | 5.80% |
| 20 | 20.329 | 4.36498 | 870 | 1910 | 1.70% |
| 21 | 20.922 | 4.24243 | 4014 | 5041 | 8.10% |
| 22 | 21.245 | 4.17879 | 1214 | 2225 | 2.40% |
| 23 | 21.72 | 4.0884 | 1929 | 2907 | 3.90% |
| 24 | 22.227 | 3.99629 | 4046 | 4975 | 8.10% |
| 25 | 23.076 | 3.85122 | 3967 | 4821 | 8.00% |
| 26 | 23.362 | 3.80459 | 465 | 1301 | 0.90% |
| 27 | 23.942 | 3.71371 | 512 | 1297 | 1.00% |
| 28 | 24.805 | 3.58646 | 1852 | 2588 | 3.70% |
| 29 | 25.498 | 3.49057 | 267 | 964 | 0.50% |
| 30 | 25.817 | 3.44821 | 352 | 1031 | 0.70% |
| 31 | 26.017 | 3.42212 | 387 | 1053 | 0.80% |
| 32 | 26.711 | 3.33473 | 170 | 799 | 0.30% |
| 33 | 27.337 | 3.25982 | 209 | 843 | 0.40% |
| 34 | 27.528 | 3.2376 | 636 | 1267 | 1.30% |
| 35 | 28.157 | 3.16664 | 70.6 | 707 | 0.10% |
| 36 | 28.504 | 3.1289 | 702 | 1355 | 1.40% |
| 37 | 28.895 | 3.08749 | 380 | 1045 | 0.80% |
| 38 | 29.52 | 3.02352 | 840 | 1505 | 1.70% |
| 39 | 30.458 | 2.9325 | 771 | 1399 | 1.50% |
| 40 | 31.135 | 2.87021 | 144 | 758 | 0.30% |
| 41 | 31.674 | 2.82262 | 606 | 1230 | 1.20% |
| 42 | 32.376 | 2.763 | 143 | 760 | 0.30% |
| 43 | 32.829 | 2.72595 | 252 | 855 | 0.50% |
| 44 | 33.26 | 2.69157 | 81.9 | 661 | 0.20% |
| 45 | 33.746 | 2.65388 | 79 | 652 | 0.20% |
| 46 | 34.479 | 2.59911 | 410 | 988 | 0.80% |
| 47 | 34.856 | 2.57192 | 126 | 695 | 0.30% |
| 48 | 36.397 | 2.46643 | 946 | 1536 | 1.90% |
| 49 | 36.297 | 2.47302 | 315 | 900 | 0.60% |
| 50 | 36.397 | 2.46645 | 946 | 1535 | 1.90% |
| 51 | 36.873 | 2.43568 | 484 | 1090 | 1.00% |
| 52 | 37.502 | 2.39628 | 286 | 895 | 0.60% |
| 53 | 37.601 | 2.39023 | 143 | 752 | 0.30% |
| 54 | 38.553 | 2.33332 | 100 | 692 | 0.20% |
| 55 | 38.923 | 2.31198 | 187 | 775 | 0.40% |
| 56 | 40.424 | 2.22956 | 79.7 | 691 | 0.20% |
| 57 | 40.631 | 2.21868 | 163 | 788 | 0.30% |
| 58 | 41.445 | 2.17698 | 126 | 777 | 0.30% |
| 59 | 41.724 | 2.16302 | 355 | 1008 | 0.70% |
| 60 | 42.97 | 2.10315 | 292 | 922 | 0.60% |
| 61 | 43.865 | 2.06231 | 527 | 1125 | 1.10% |

Figure 6X:
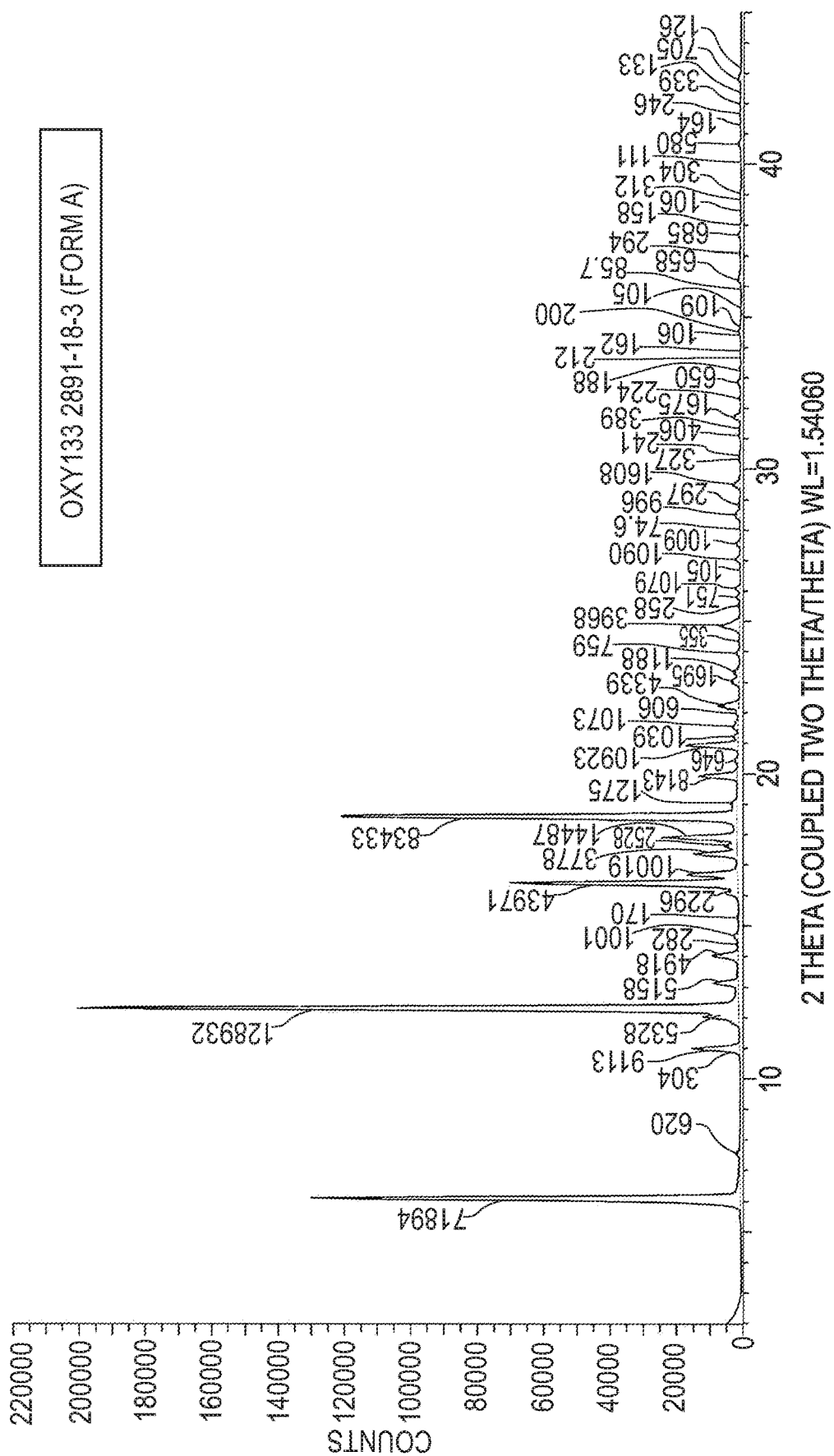
Figure 7A:
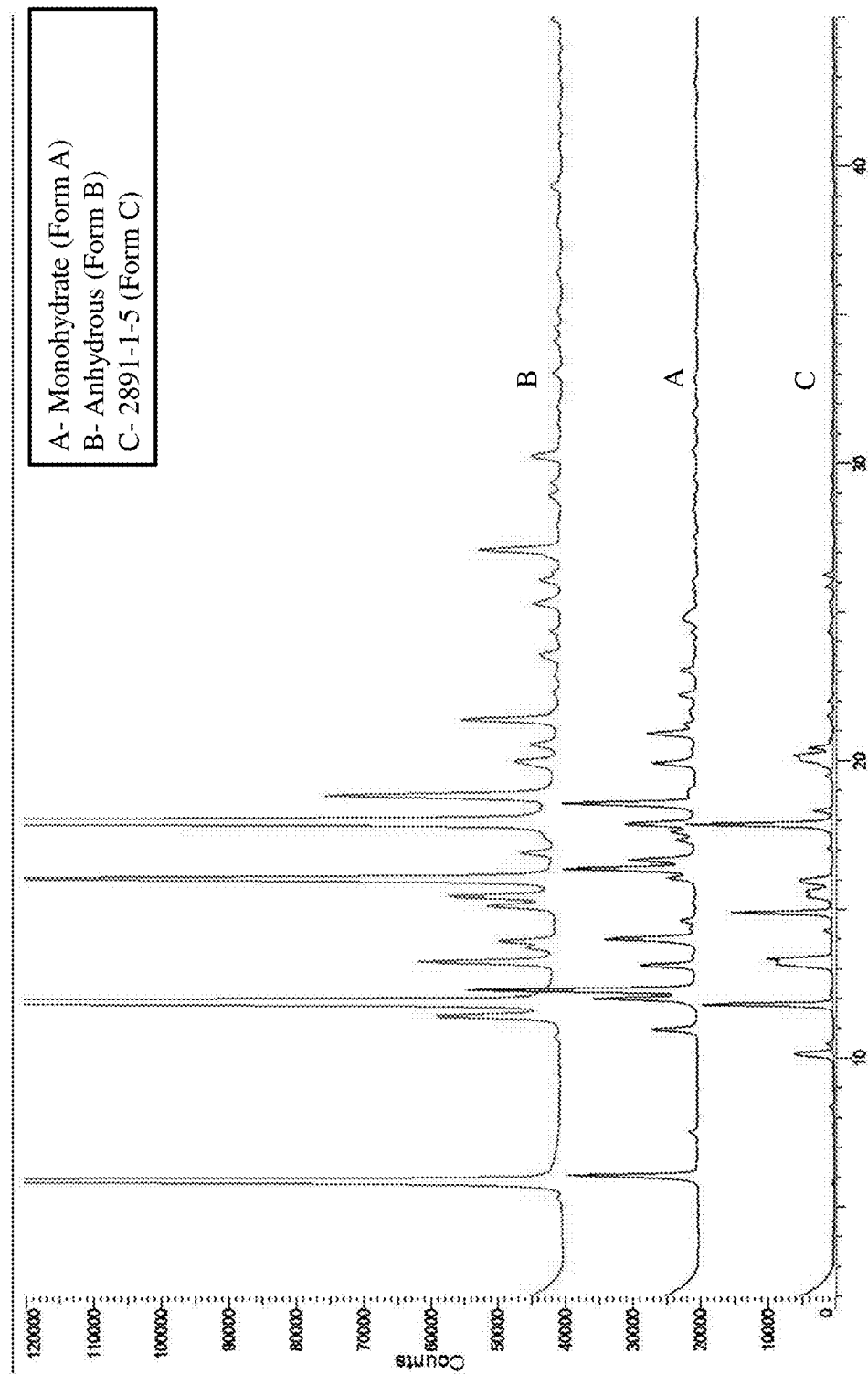
FIGS. 7A, 7B, 7C, 7D, 7E, 7F, 7G, 7H, 7I, 7J, 7K, 7L, 7M, 7N, 7O, and 7P are XRPDs of OXY133 polymorph Form C.
Figure 7B:
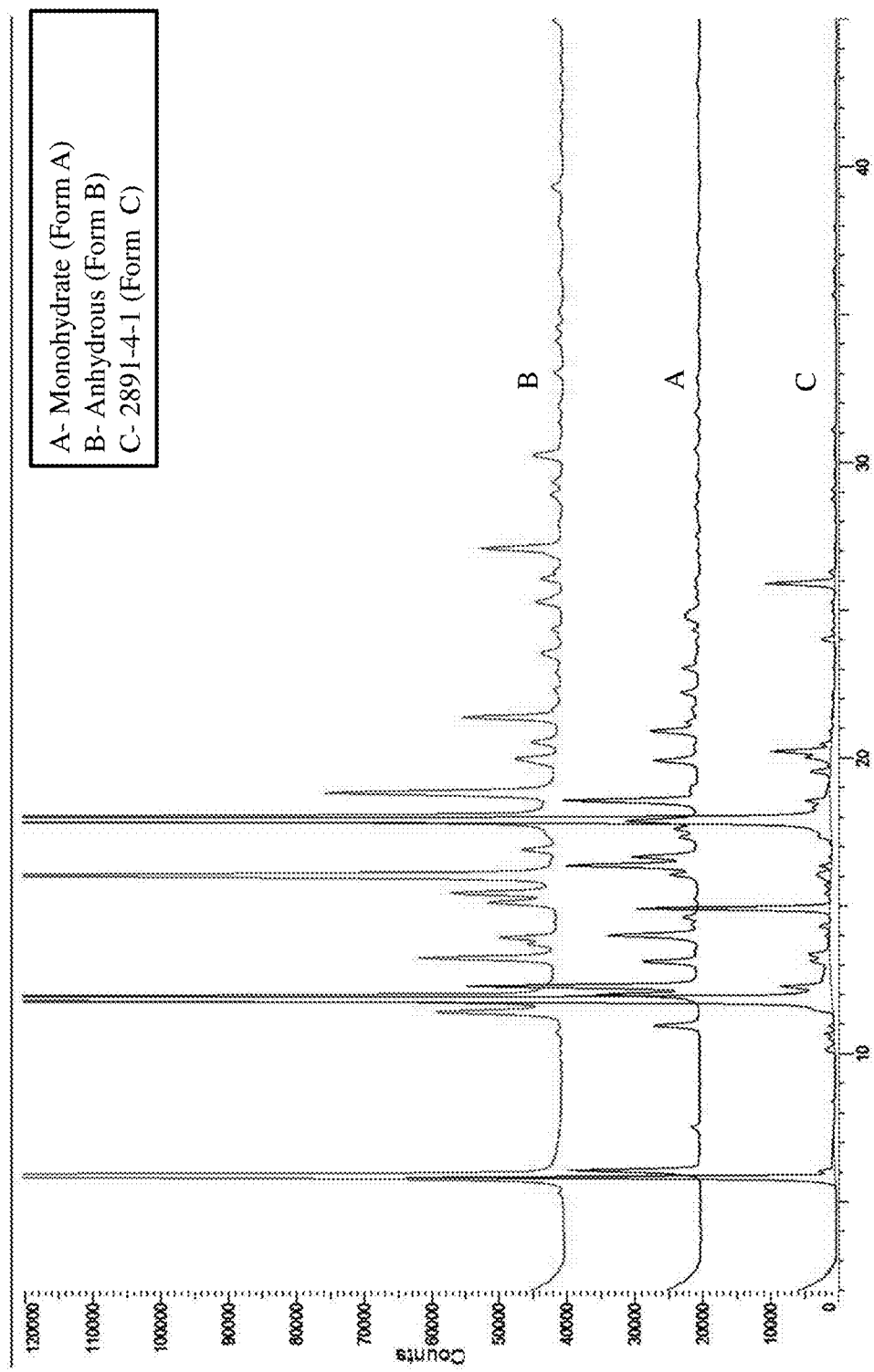
Figure 7C:
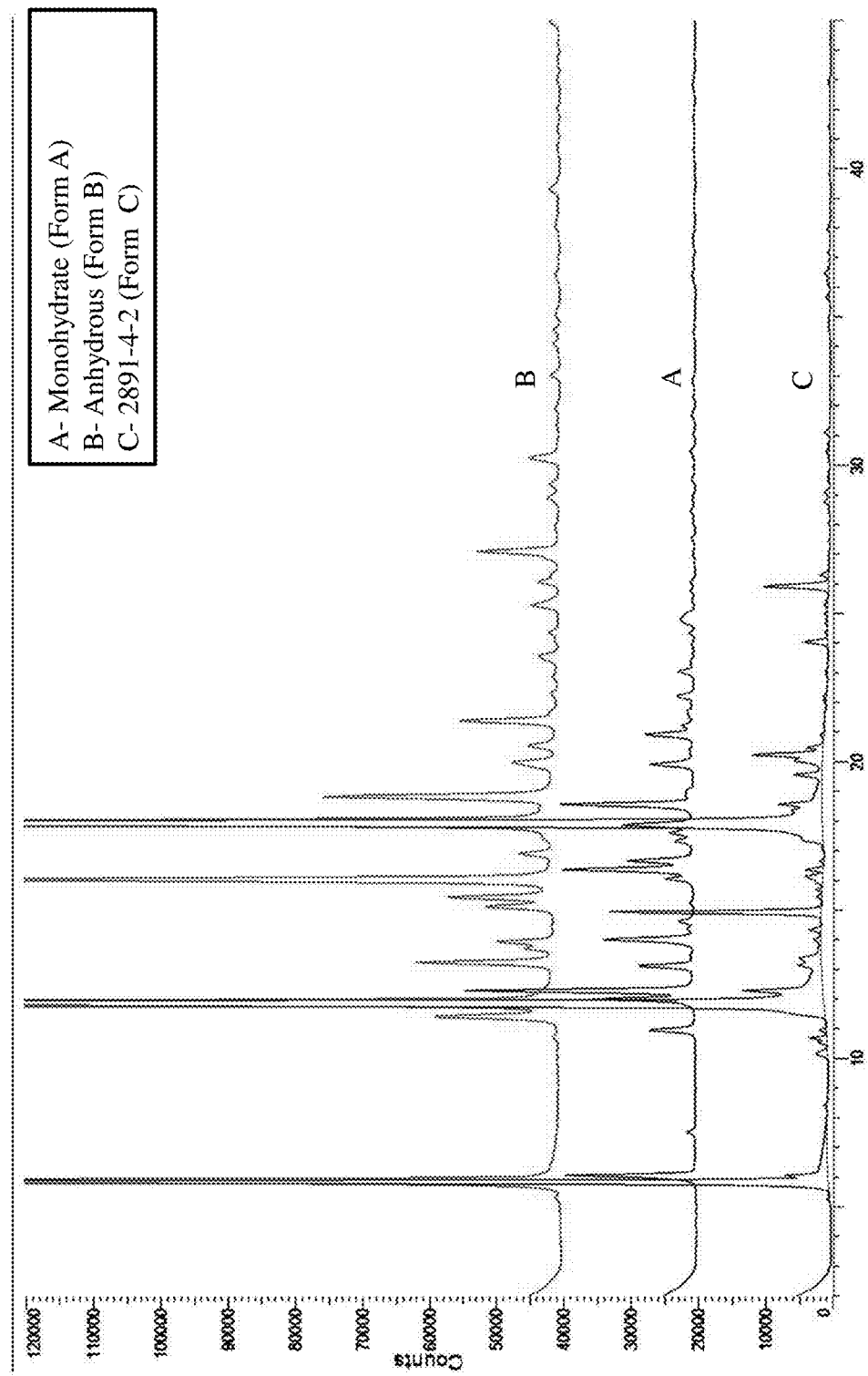
Figure 7D:
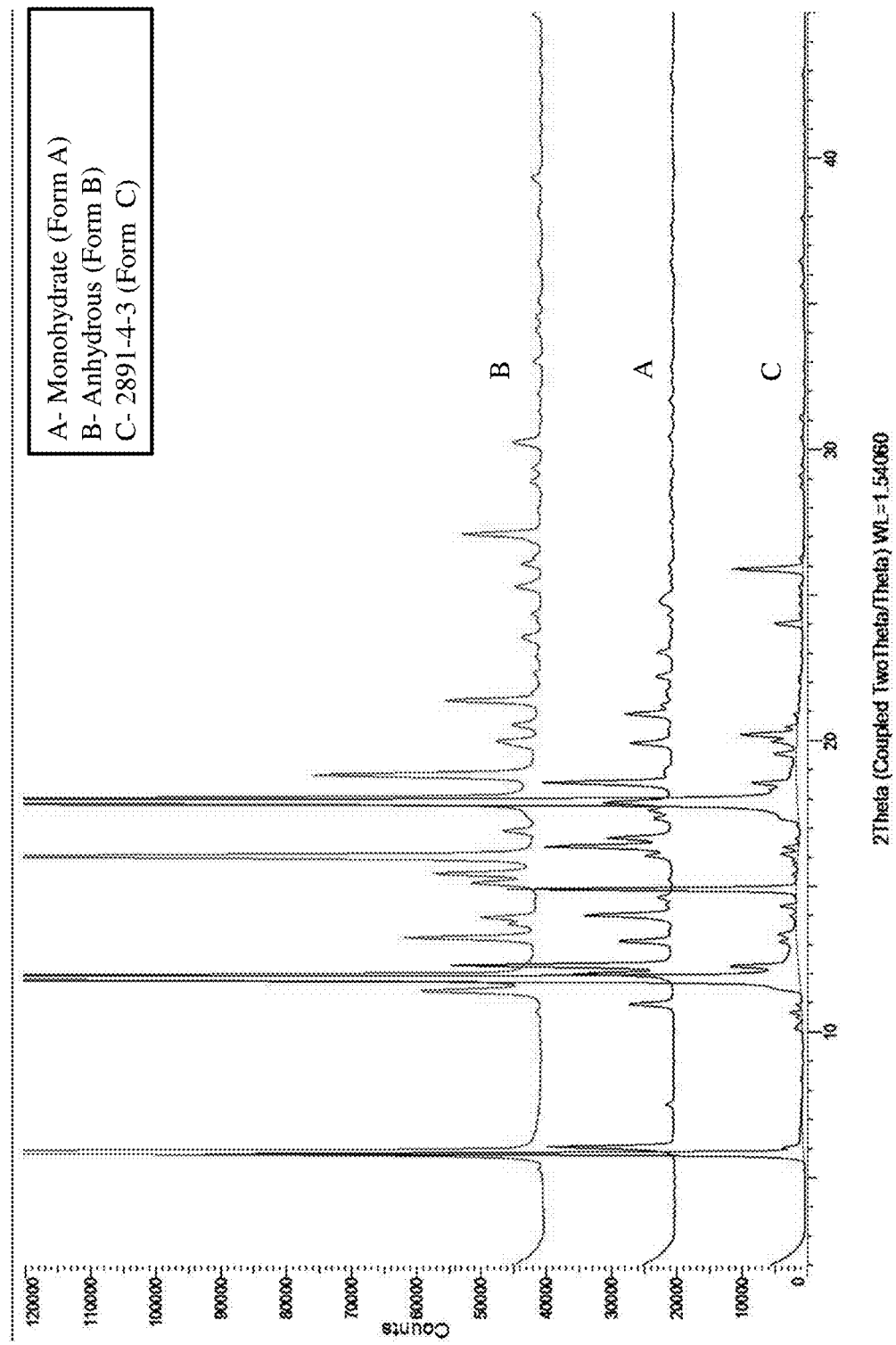
Figure 7E:
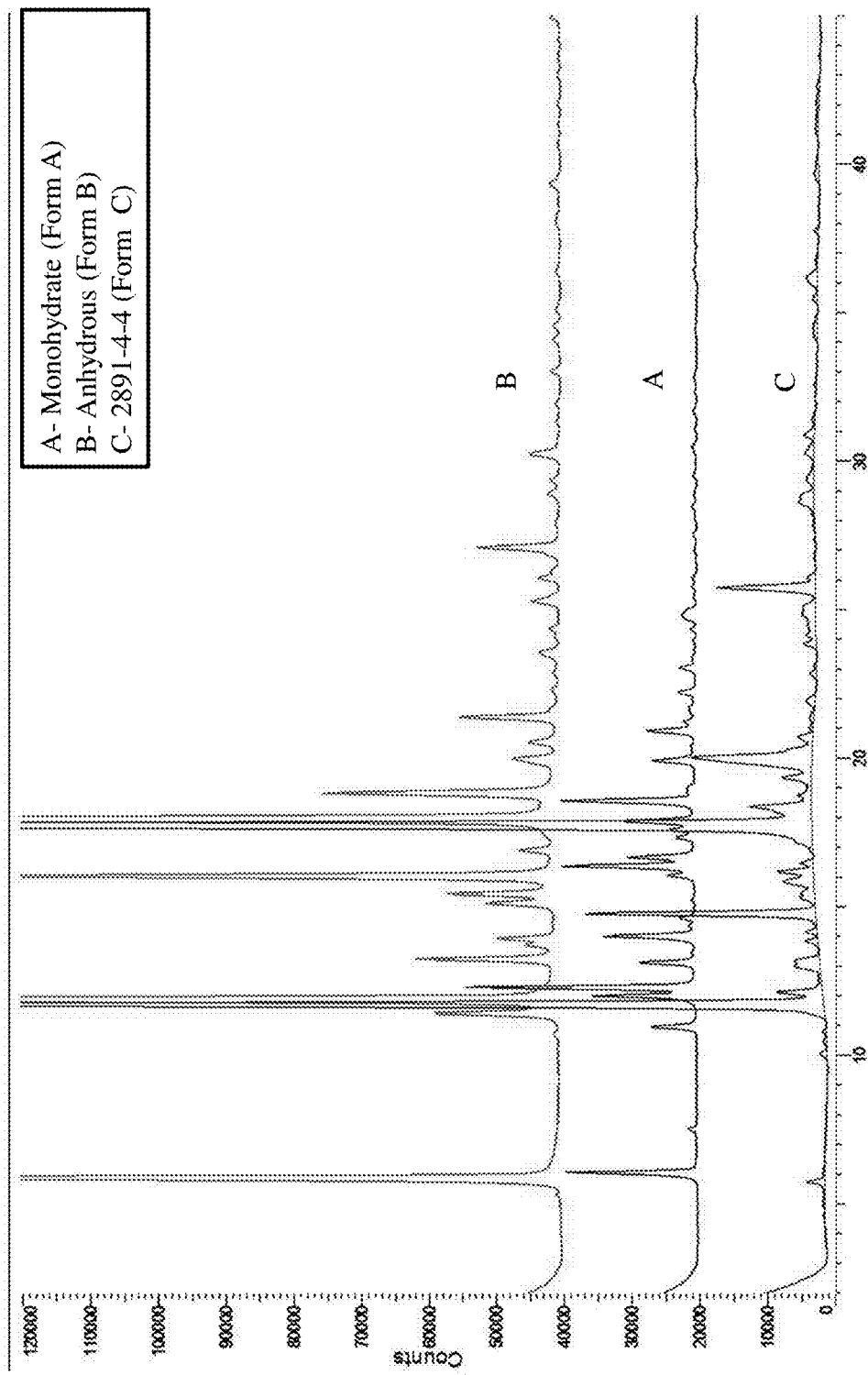
Figure 7F:
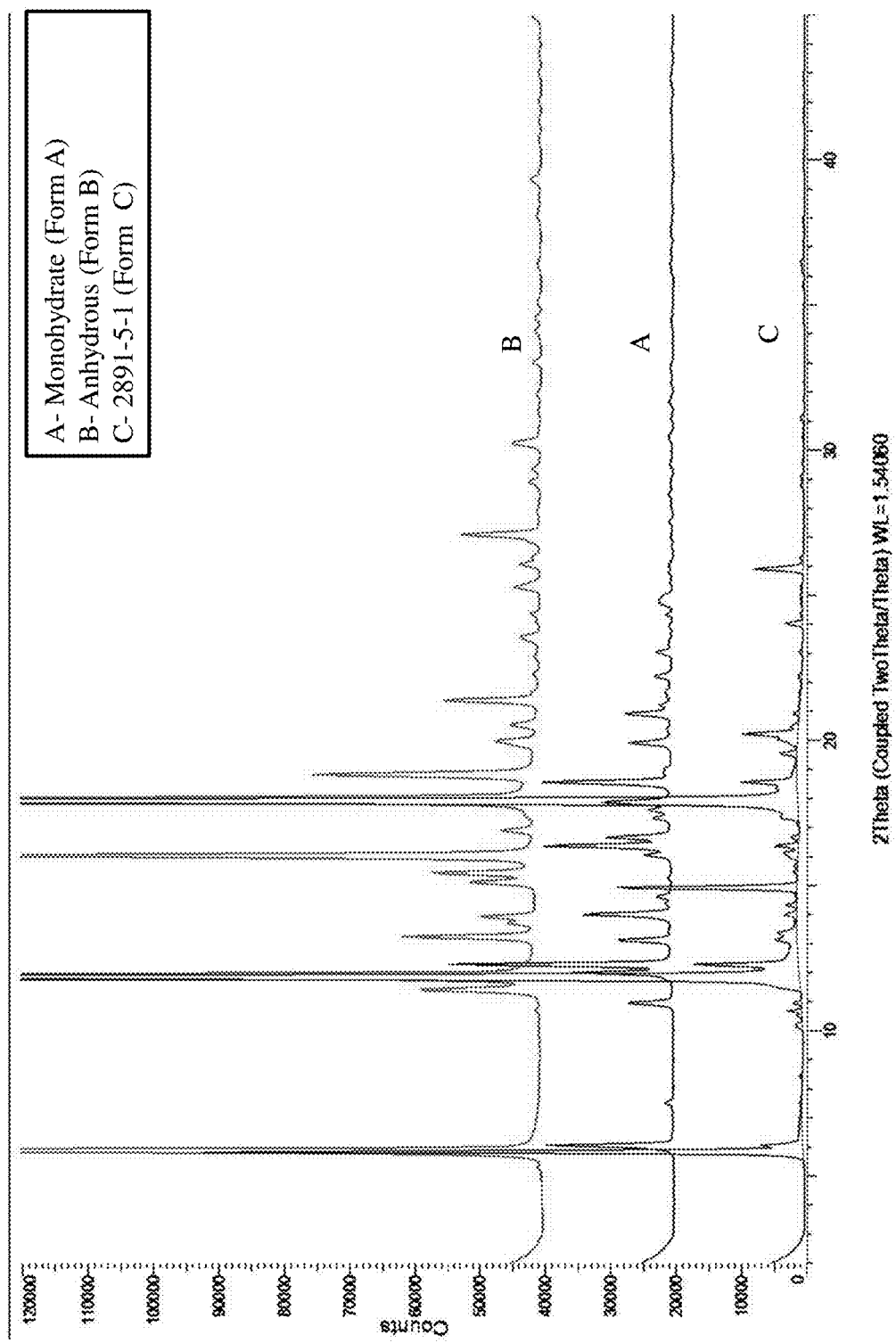
Figure 7G:
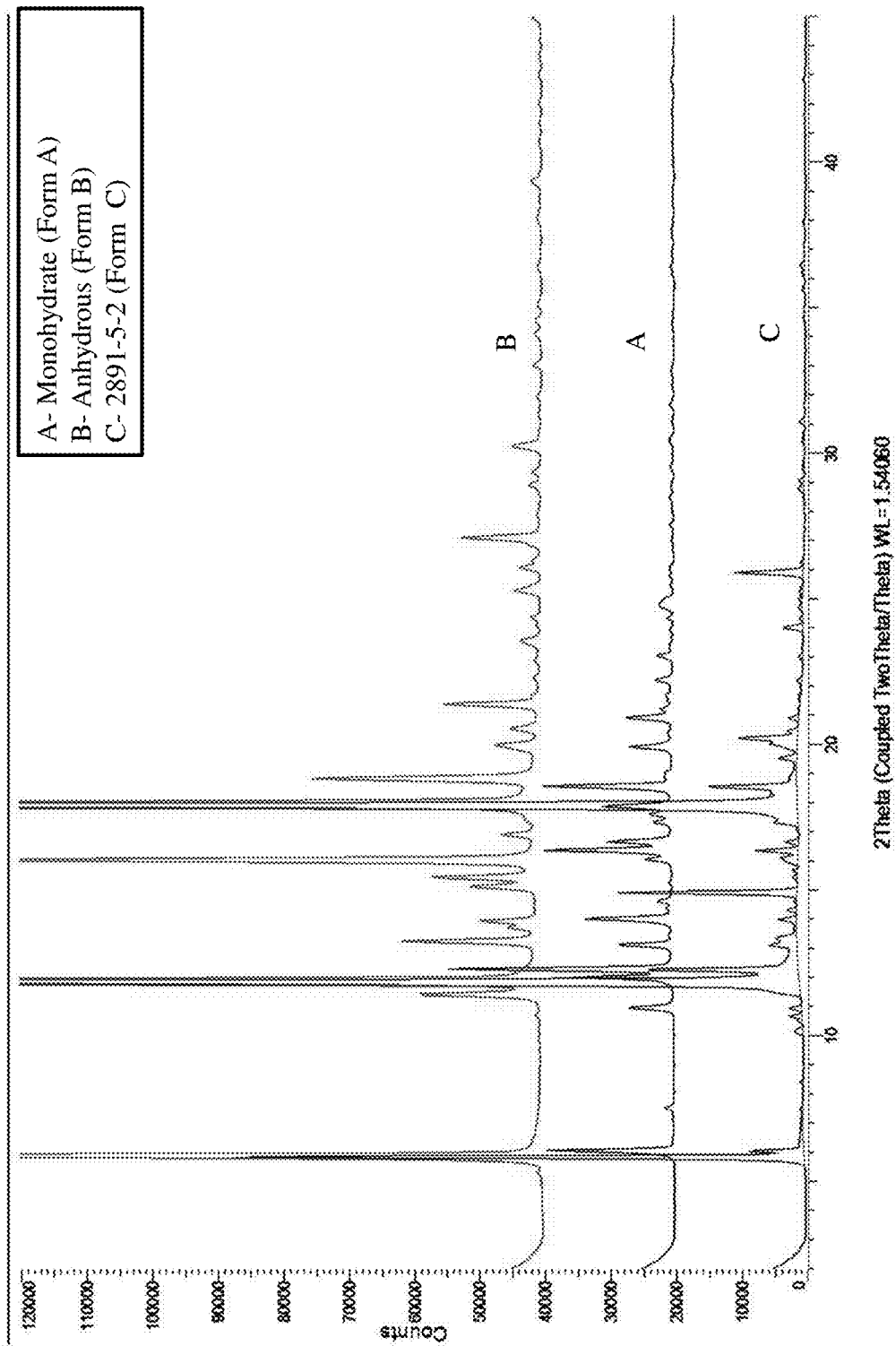
Figure 7H:
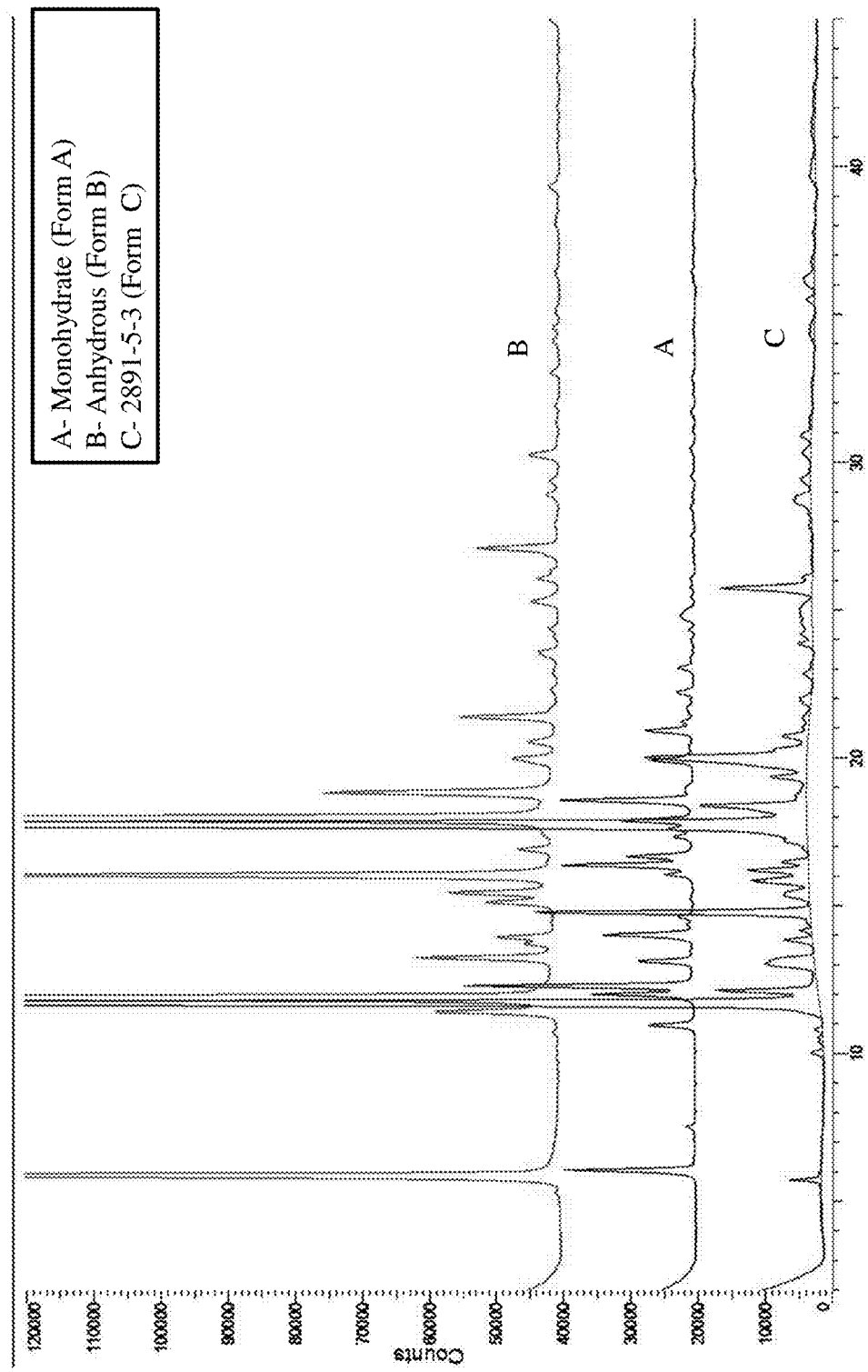
Figure 7I:
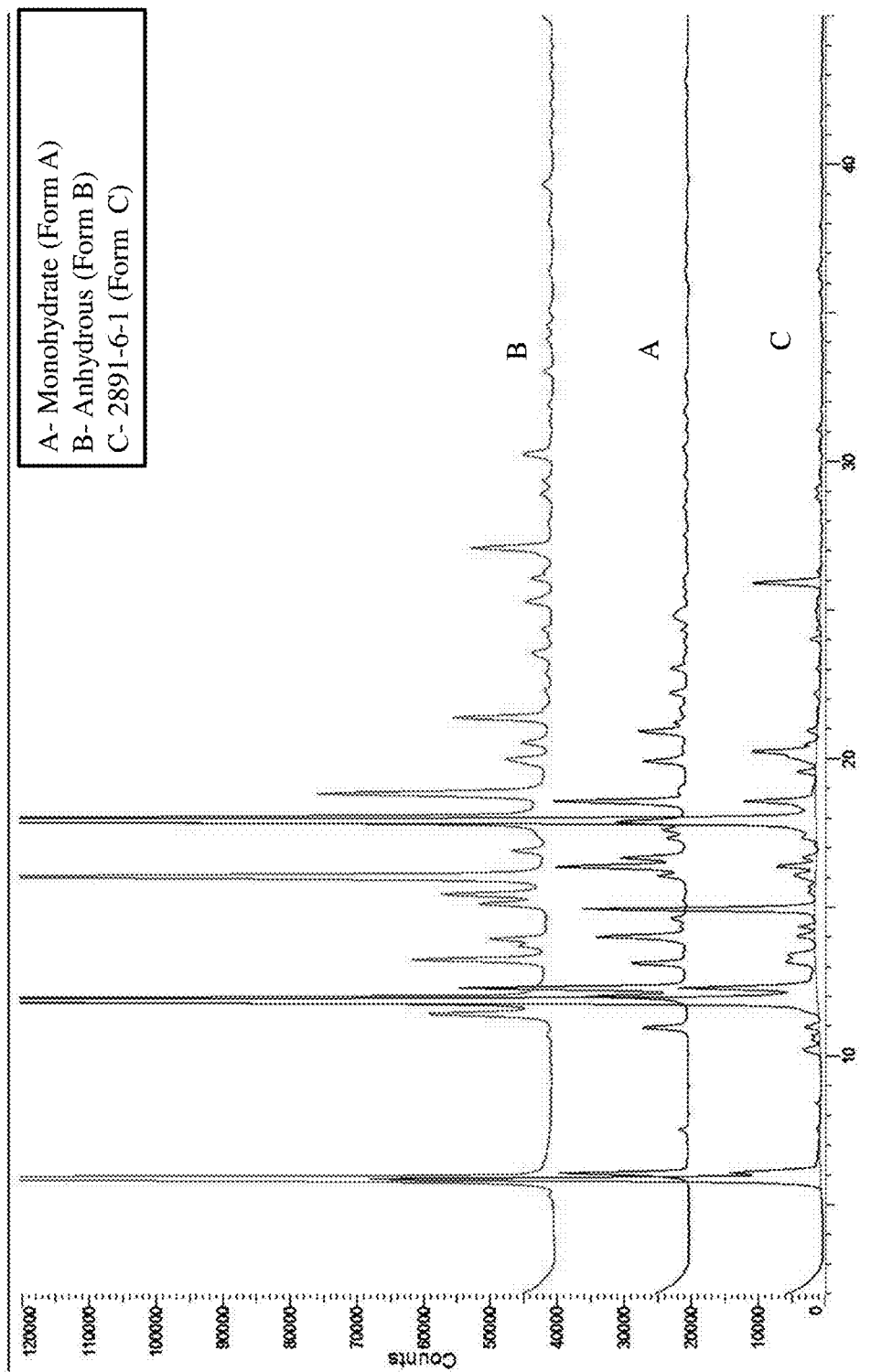
Figure 7J:
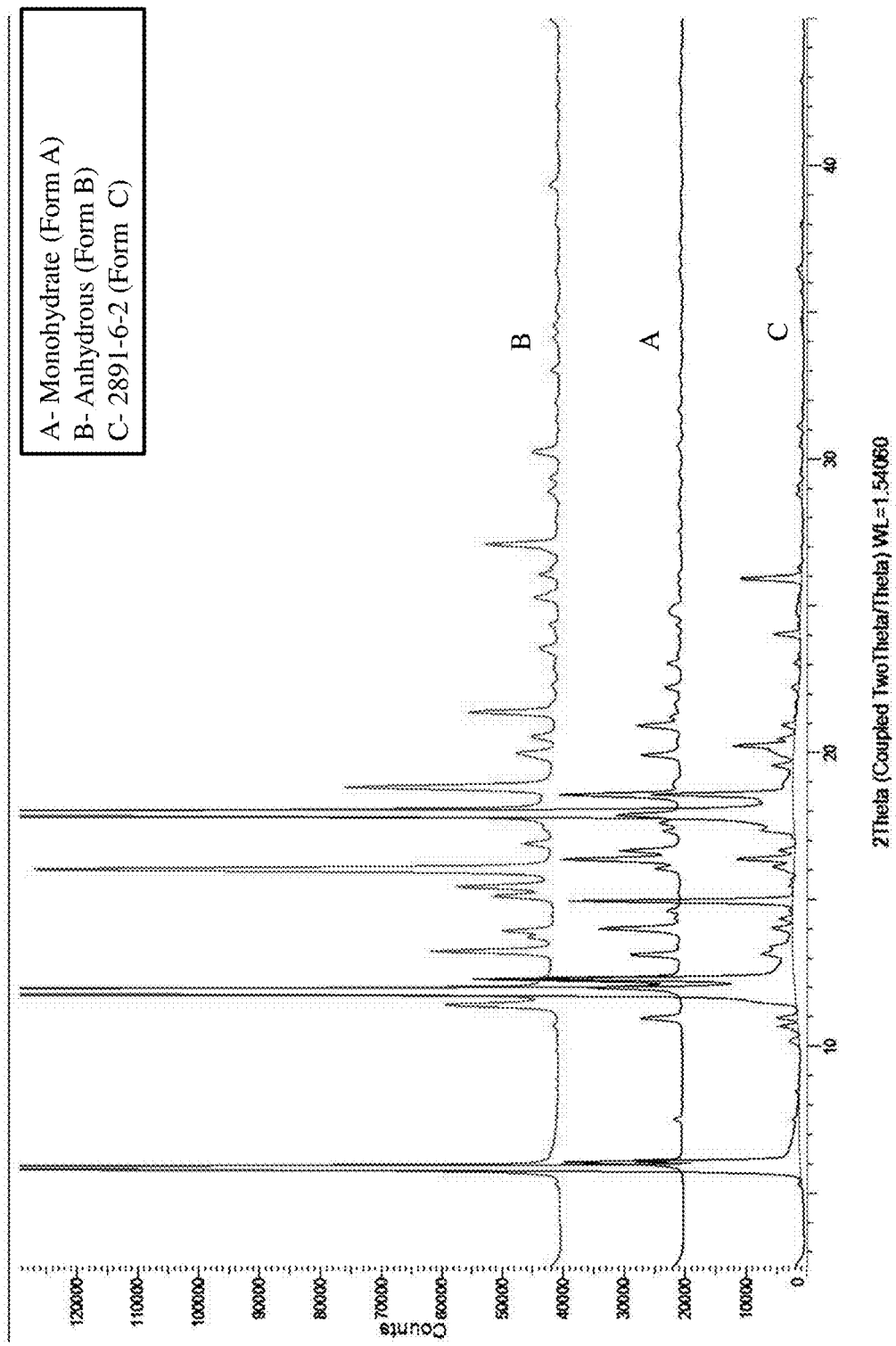
Figure 7K:
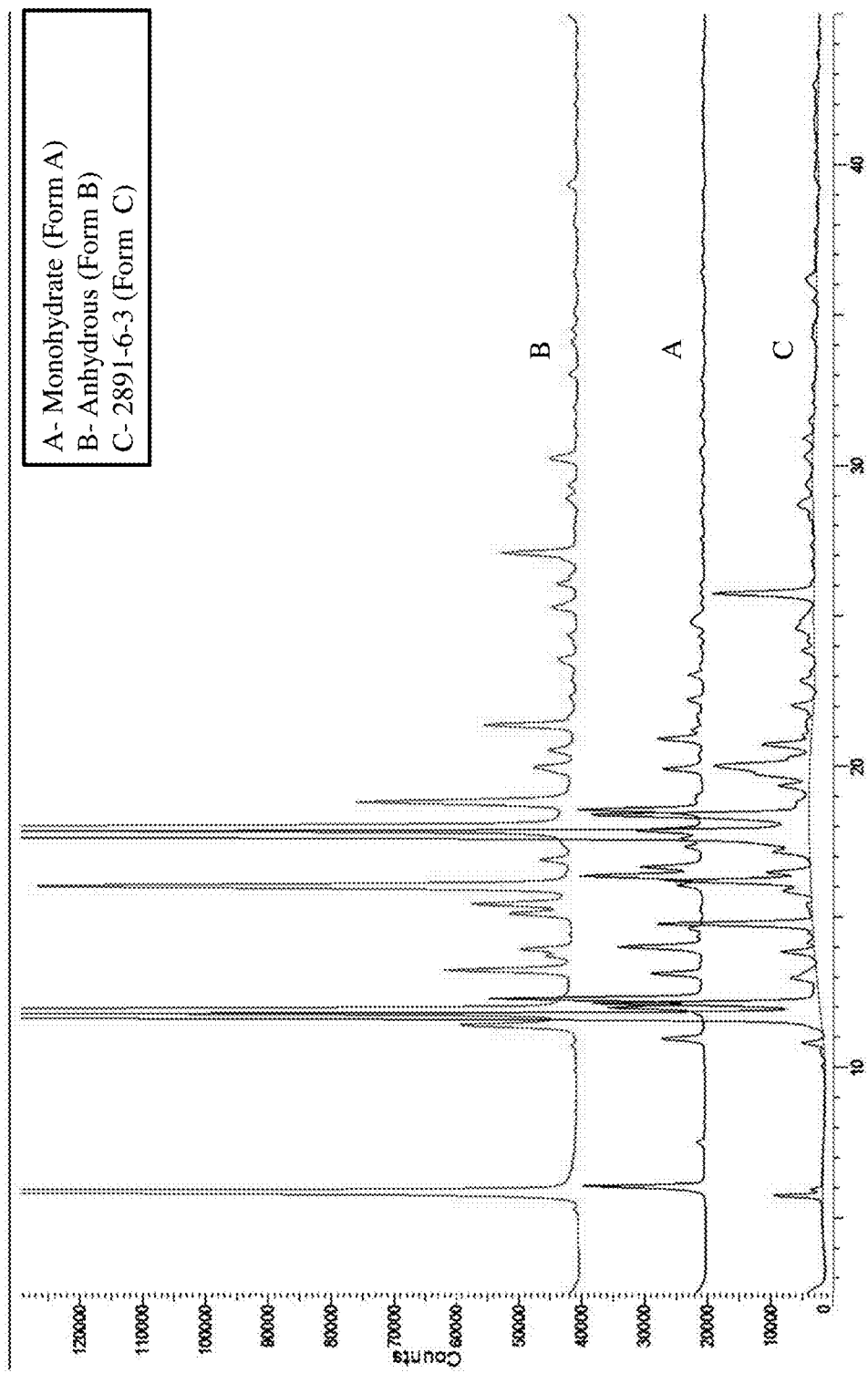
Figure 7L:
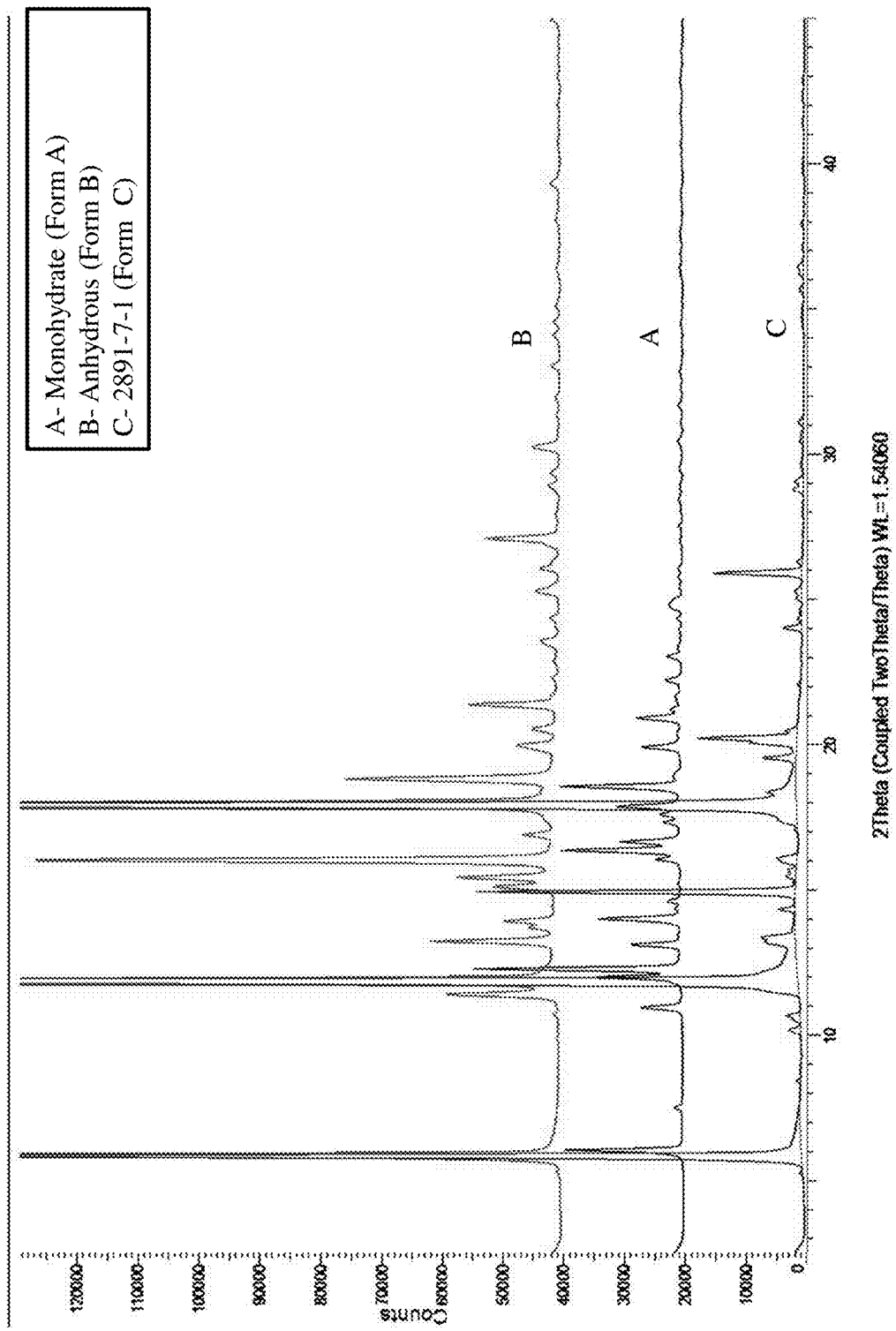
Figure 7M:
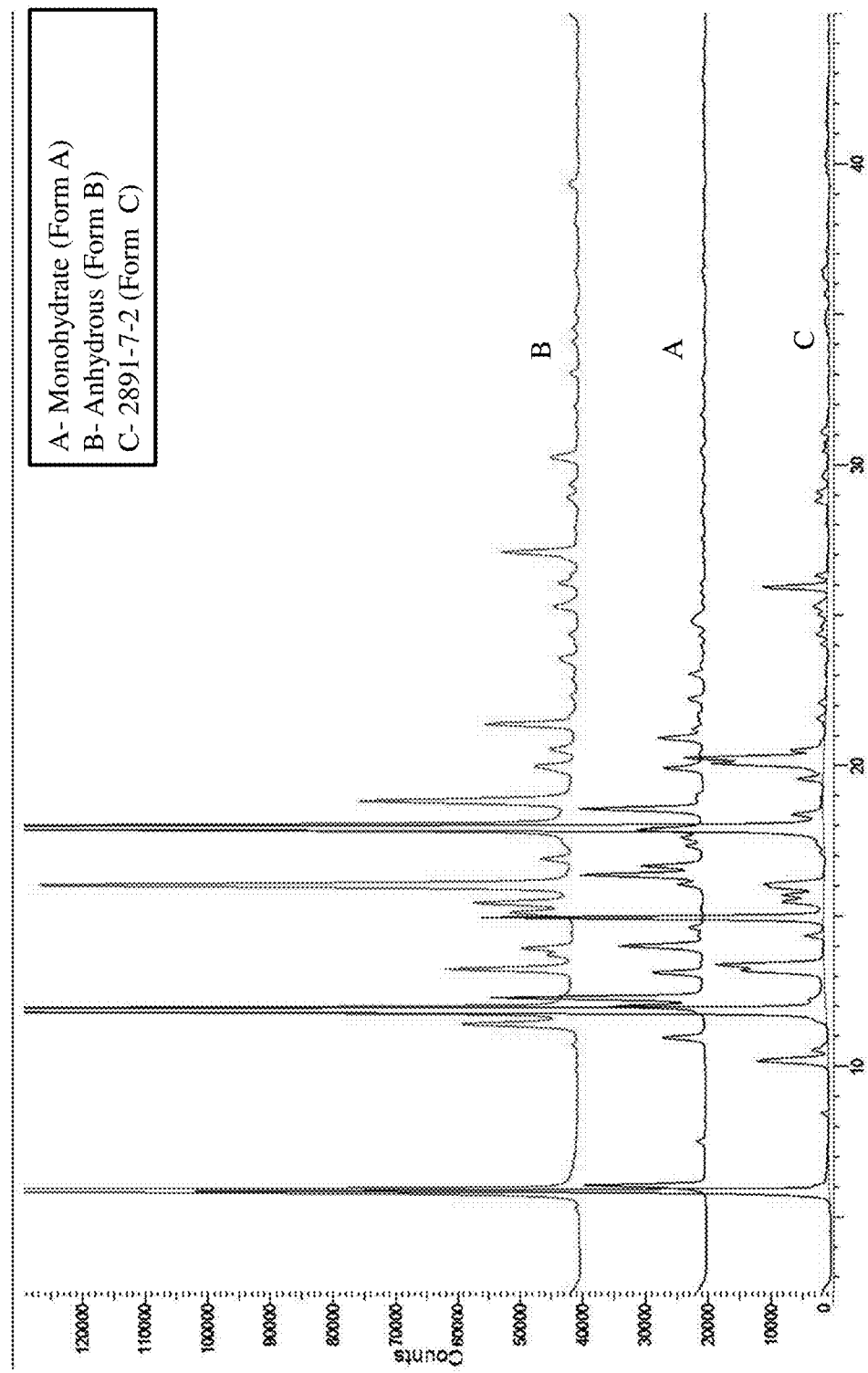
Figure 7N:
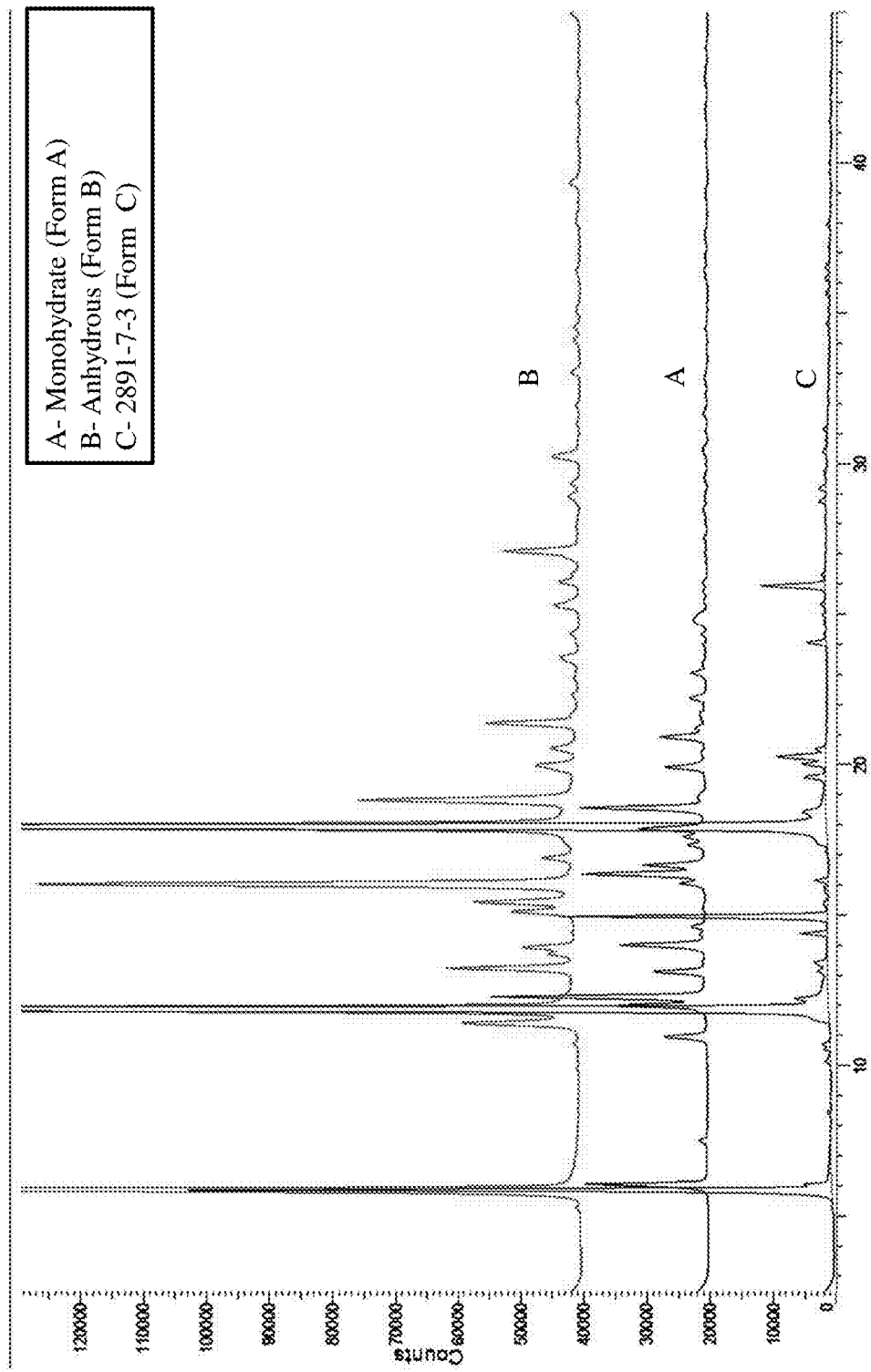
Figure 7O:
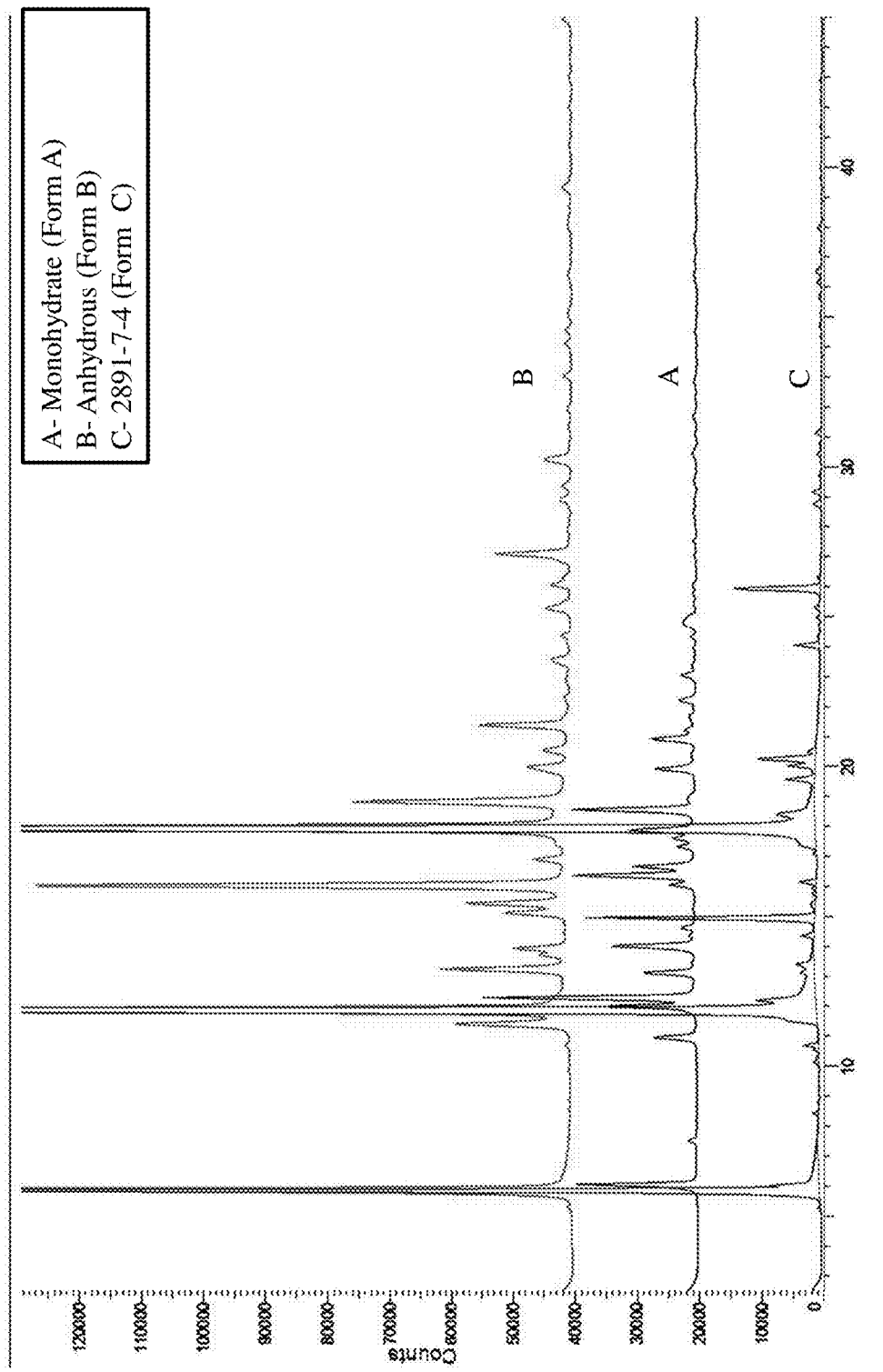
Figure 7P:
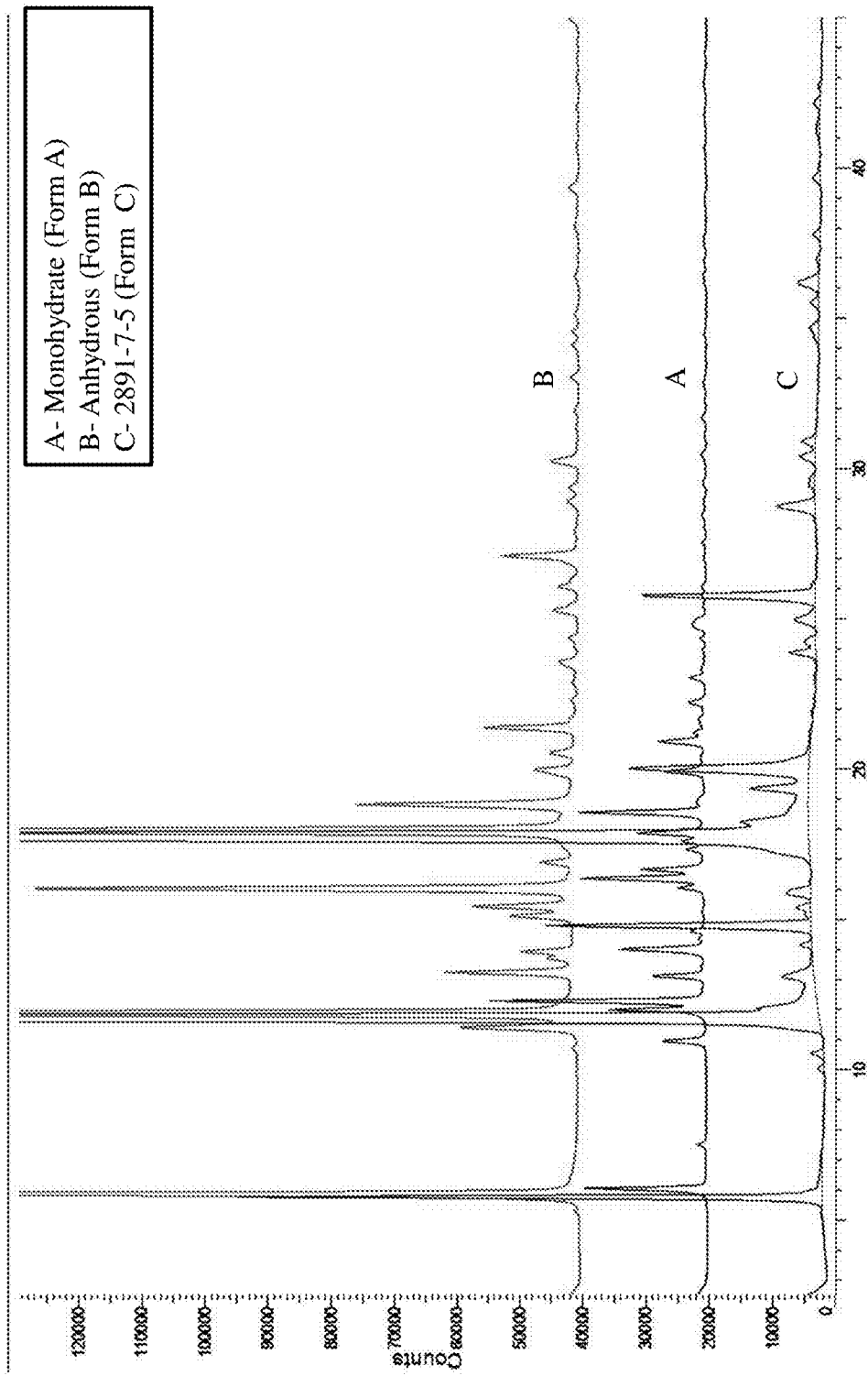

FIG. 6X is an XRPD of solid polymorph A obtained by crystallization from an isopropyl alcohol/water solvent/antisolvent medium in a ratio of 1:1 v/v at a precipitating temperature of 20° C. FIG. 6W is an XRPD of a solid OXY133 Form A. Table 7, below lists data taken from the XRPD of FIG. 6X. As illustrated in Table 7, OXY133 polymorph Form A can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 and 70.

TABLE 7

XRPD Data for OXY133 Polymorph Form A, as illustrated in FIG. 6X

| Index No. | Angle (2-Theta) | d Value (Angstrom) | Net Intensity (Counts) | Gross Intensity (Counts) | Rel. Intensity (%) |
|---|---|---|---|---|---|
| 0 | 6.098 | 14.48166 | 71894 | 72673 | 55.80% |
| 1 | 7.555 | 11.69167 | 620 | 1477 | 0.50% |
| 2 | 10.796 | 8.18802 | 304 | 1200 | 0.20% |
| 3 | 10.984 | 8.04836 | 9113 | 10057 | 7.10% |
| 4 | 12.071 | 7.3264 | 5328 | 6503 | 4.10% |
| 5 | 12.304 | 7.18792 | 128932 | 130146 | 100.00% |
| 6 | 13.144 | 6.73047 | 5158 | 6472 | 4.00% |
| 7 | 14.037 | 6.30435 | 4918 | 6268 | 3.80% |
| 8 | 14.399 | 6.14643 | 282 | 1626 | 0.20% |
| 9 | 14.654 | 6.04022 | 1001 | 2335 | 0.80% |
| 10 | 15.26 | 5.8014 | 170 | 1454 | 0.10% |
| 11 | 16.1 | 5.50083 | 2296 | 3687 | 1.80% |
| 12 | 16.397 | 5.40158 | 43971 | 45425 | 34.10% |
| 13 | 16.695 | 5.30599 | 10019 | 11529 | 7.80% |
| 14 | 17.36 | 5.10419 | 8778 | 10385 | 6.80% |
| 15 | 17.632 | 5.02597 | 2526 | 4161 | 2.00% |
| 16 | 17.91 | 4.94862 | 14487 | 16144 | 11.20% |
| 17 | 18.585 | 4.77037 | 83433 | 85113 | 64.70% |
| 18 | 19.032 | 4.65948 | 1275 | 2949 | 1.00% |
| 19 | 19.934 | 4.45053 | 8143 | 9749 | 6.30% |
| 20 | 20.456 | 4.33802 | 646 | 2180 | 0.50% |
| 21 | 20.94 | 4.23896 | 10923 | 12389 | 8.50% |
| 22 | 21.236 | 4.18054 | 1039 | 2460 | 0.80% |
| 23 | 21.561 | 4.11829 | 1073 | 2437 | 0.80% |
| 24 | 21.999 | 4.03729 | 606 | 1877 | 0.50% |
| 25 | 22.241 | 3.9938 | 4339 | 5551 | 3.40% |
| 26 | 23.036 | 3.85779 | 1695 | 2784 | 1.30% |
| 27 | 23.335 | 3.80903 | 1188 | 2257 | 0.90% |
| 28 | 23.946 | 3.71319 | 759 | 1760 | 0.60% |
| 29 | 24.355 | 3.6518 | 355 | 1319 | 0.30% |
| 30 | 24.849 | 3.58023 | 3968 | 4914 | 3.10% |
| 31 | 25.493 | 3.49128 | 258 | 1156 | 0.20% |
| 32 | 25.8 | 3.45038 | 751 | 1620 | 0.60% |
| 33 | 26.09 | 3.4127 | 1079 | 1914 | 0.80% |
| 34 | 26.697 | 3.33648 | 105 | 924 | 0.10% |
| 35 | 27.048 | 3.29392 | 1090 | 1924 | 0.80% |
| 36 | 27.552 | 3.2348 | 1009 | 1847 | 0.80% |
| 37 | 28.06 | 3.1774 | 74.6 | 925 | 0.10% |
| 38 | 28.531 | 3.12604 | 996 | 1864 | 0.80% |
| 39 | 28.853 | 3.09189 | 297 | 1166 | 0.20% |
| 40 | 29.497 | 3.0258 | 1608 | 2463 | 1.20% |
| 41 | 30.333 | 2.94428 | 327 | 1131 | 0.30% |
| 42 | 30.446 | 2.93364 | 211 | 1004 | 0.20% |
| 43 | 31.115 | 2.87207 | 406 | 1179 | 0.30% |
| 44 | 31.337 | 2.85218 | 369 | 1156 | 0.30% |
| 45 | 31.723 | 2.81839 | 1675 | 2476 | 1.30% |
| 46 | 32.331 | 2.76679 | 224 | 1025 | 0.20% |
| 47 | 32.867 | 2.72284 | 650 | 1431 | 0.50% |
| 48 | 33.302 | 2.68829 | 188 | 934 | 0.10% |
| 49 | 33.694 | 2.65791 | 212 | 939 | 0.20% |
| 50 | 33.908 | 2.6416 | 162 | 893 | 0.10% |
| 51 | 34.422 | 2.60328 | 260 | 982 | 0.20% |
| 52 | 34.531 | 2.59532 | 583 | 1300 | 0.50% |
| 53 | 34.679 | 2.58463 | 109 | 818 | 0.10% |
| 54 | 35.32 | 2.53919 | 105 | 773 | 0.10% |
| 55 | 35.938 | 2.49693 | 85.7 | 764 | 0.10% |
| 56 | 36.216 | 2.47835 | 658 | 1373 | 0.50% |
| 57 | 37.079 | 2.42262 | 294 | 1076 | 0.20% |
| 58 | 37.698 | 2.3843 | 685 | 1473 | 0.50% |
| 59 | 37.996 | 2.36626 | 158 | 938 | 0.10% |
| 60 | 38.486 | 2.33725 | 106 | 862 | 0.10% |
| 61 | 38.869 | 2.31508 | 312 | 1041 | 0.20% |
| 62 | 39.06 | 2.30421 | 304 | 1014 | 0.20% |
| 63 | 40.087 | 2.24749 | 111 | 827 | 0.10% |
| 64 | 40.668 | 2.21676 | 580 | 1364 | 0.40% |
| 65 | 41.302 | 2.18417 | 164 | 988 | 0.10% |

TABLE 7-continued

XRPD Data for OXY133 Polymorph Form
A, as illustrated in FIG. 6X

| Index No. | Angle (2-Theta) | d Value (Angstrom) | Net Intensity (Counts) | Gross Intensity (Counts) | Rel. Intensity (%) |
|---|---|---|---|---|---|
| 66 | 41.677 | 2.16539 | 246 | 1076 | 0.20% |
| 67 | 42.01 | 2.14897 | 339 | 1165 | 0.30% |
| 68 | 42.405 | 2.12988 | 133 | 941 | 0.10% |
| 69 | 42.824 | 2.10999 | 705 | 1478 | 0.50% |
| 70 | 43.206 | 2.09221 | 126 | 853 | 0.10% |

FIGS. 7A, 7B, 7C, 7D, 7E, 7F, 7G, 7H, 7I, 7J, 7K, 7L, 7M, 7N, 7O, and 7P are XRPDs of OXY133 polymorph Form C. In particular, these figures are XRPDs of polymorph Form C obtained by re-slurrying from an acetone/water solvent system, where the acetone is the solvent and the water is the anti-solvent, in a ratio of 1:1 v/v. The precipitating temperatures at which these XRPDs were obtained are listed in more detail in Table 15 below and include 10° C., 20° C., 30° C., 40° C., 50° C., 60° C. and 70° C., respectively.

Figure 26:
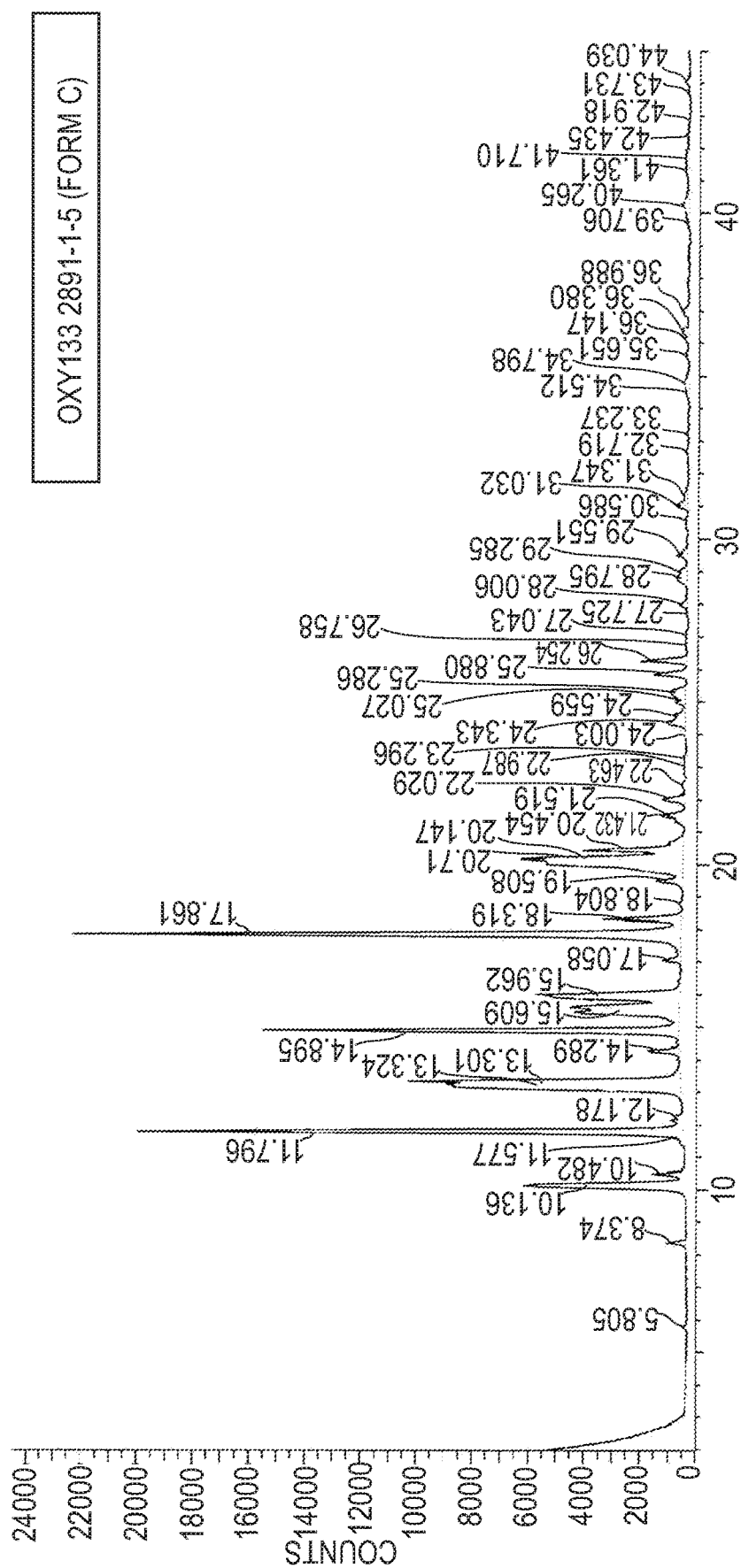
FIG. 26 is an XRPD of OXY133 polymorph Form C.

FIG. 26 is an XRPD of solid polymorph Form C obtained by crystallization from an acetone/water solvent/anti-solvent medium in a ratio of 1:1 v/v at a precipitating temperature of 70° C. Table 8, below lists data taken from the XRPD of FIG. 26. As illustrated in Table 8, OXY133 Form C can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61.

TABLE 8

XRPD Data for OXY133 Polymorph Form
C as illustrated in FIG. 26

| Index No. | Angle (2-Theta) | d Value (Angstrom) | Net Intensity (Counts) | Gross Intensity (Counts) | Rel. Intensity (%) |
|---|---|---|---|---|---|
| 0 | 5.805 | 15.2121 | 91.5 | 376 | 0.60% |
| 1 | 8.374 | 10.5502 | 442 | 767 | 2.90% |
| 2 | 10.136 | 8.71997 | 3499 | 3873 | 22.90% |
| 3 | 10.482 | 8.4332 | 731 | 1120 | 4.8% |
| 4 | 11.577 | 7.63769 | 146 | 585 | 1.00% |
| 5 | 11.796 | 7.49603 | 13179 | 13636 | 86.30% |
| 6 | 12.178 | 7.26185 | 136 | 620 | 0.90% |
| 7 | 13.224 | 6.68973 | 5106 | 5657 | 33.40% |
| 8 | 13.301 | 6.65119 | 4957 | 5511 | 32.50% |
| 9 | 14.289 | 6.19347 | 702 | 1291 | 4.60% |
| 10 | 14.895 | 5.94275 | 9755 | 10351 | 63.90% |
| 11 | 15.477 | 5.72061 | 2129 | 2722 | 13.90% |
| 12 | 15.609 | 5.67263 | 2588 | 3178 | 16.90% |
| 13 | 15.962 | 5.54779 | 2911 | 3493 | 19.10% |
| 14 | 17.058 | 5.19376 | 402 | 958 | 2.60% |
| 15 | 17.861 | 4.96223 | 15268 | 15820 | 100.00% |
| 16 | 18.319 | 4.83902 | 2035 | 2577 | 13.30% |
| 17 | 18.804 | 4.71526 | 64.7 | 588 | 0.40% |
| 18 | 19.508 | 4.54663 | 596 | 1103 | 3.90% |
| 19 | 20.071 | 4.42036 | 3127 | 3625 | 20.50% |
| 20 | 20.147 | 4.40405 | 3688 | 4184 | 24.20% |
| 21 | 20.454 | 4.33862 | 1953 | 2439 | 12.80% |
| 22 | 21.432 | 4.14278 | 282 | 733 | 1.80% |
| 23 | 21.519 | 4.12618 | 546 | 996 | 3.60% |
| 24 | 22.029 | 4.03173 | 538 | 973 | 3.50% |
| 25 | 22.463 | 3.95483 | 70.9 | 489 | 0.50% |
| 26 | 22.987 | 3.86591 | 50 | 447 | 0.30% |
| 27 | 23.296 | 3.81533 | 78.7 | 464 | 0.50% |
| 28 | 24.003 | 3.70451 | 54.5 | 437 | 0.40% |
| 29 | 24.343 | 3.6535 | 491 | 880 | 3.20% |

TABLE 8-continued

XRPD Data for OXY133 Polymorph Form
C as illustrated in FIG. 26

| Index No. | Angle (2-Theta) | d Value (Angstrom) | Net Intensity (Counts) | Gross Intensity (Counts) | Rel. Intensity (%) |
|---|---|---|---|---|---|
| 30 | 24.559 | 3.62187 | 293 | 684 | 1.90% |
| 31 | 25.027 | 3.55517 | 183 | 574 | 1.20% |
| 32 | 25.286 | 3.51938 | 373 | 761 | 2.40% |
| 33 | 25.88 | 3.43991 | 704 | 1083 | 4.60% |
| 34 | 26.254 | 3.39169 | 1226 | 1597 | 8.00% |
| 35 | 26.755 | 3.32934 | 68 | 423 | 0.40% |
| 36 | 26.808 | 3.32293 | 36.7 | 389 | 0.20% |
| 37 | 27.043 | 3.29458 | 50.5 | 392 | 0.30% |
| 38 | 27.725 | 3.215 | 34.6 | 363 | 0.20% |
| 39 | 28.006 | 3.1834 | 218 | 559 | 1.40% |
| 40 | 28.795 | 3.09793 | 234 | 599 | 1.50% |
| 41 | 29.005 | 3.07601 | 243 | 611 | 1.60% |
| 42 | 29.551 | 3.02038 | 192 | 562 | 1.30% |
| 43 | 30.586 | 2.92052 | 41.7 | 407 | 0.30% |
| 44 | 31.032 | 2.87952 | 285 | 645 | 1.90% |
| 45 | 31.347 | 2.85136 | 122 | 475 | 0.80% |
| 46 | 32.719 | 2.73479 | 66.6 | 411 | 0.40% |
| 47 | 33.237 | 2.69338 | 47.6 | 388 | 0.30% |
| 48 | 34.512 | 2.5967 | 75.2 | 407 | 0.50% |
| 49 | 34.798 | 2.57602 | 126 | 462 | 0.80% |
| 50 | 35.651 | 2.51636 | 50.9 | 401 | 0.30% |
| 51 | 36.147 | 2.48292 | 105 | 466 | 0.70% |
| 52 | 36.38 | 2.46755 | 156 | 520 | 1.00% |
| 53 | 36.988 | 2.42836 | 137 | 500 | 0.90% |
| 54 | 39.706 | 2.26822 | 36 | 376 | 0.20% |
| 55 | 40.265 | 2.23798 | 223 | 582 | 1.50% |
| 56 | 41.361 | 2.18118 | 91.4 | 460 | 0.60% |
| 57 | 41.71 | 2.16375 | 97.6 | 462 | 0.60% |
| 58 | 42.435 | 2.12844 | 71.2 | 414 | 0.50% |
| 59 | 42.918 | 2.10561 | 36.6 | 357 | 0.20% |
| 60 | 43.731 | 2.06831 | 40 | 370 | 0.30% |
| 61 | 44.039 | 2.05455 | 78.9 | 418 | 0.50% |

Figure 8A:
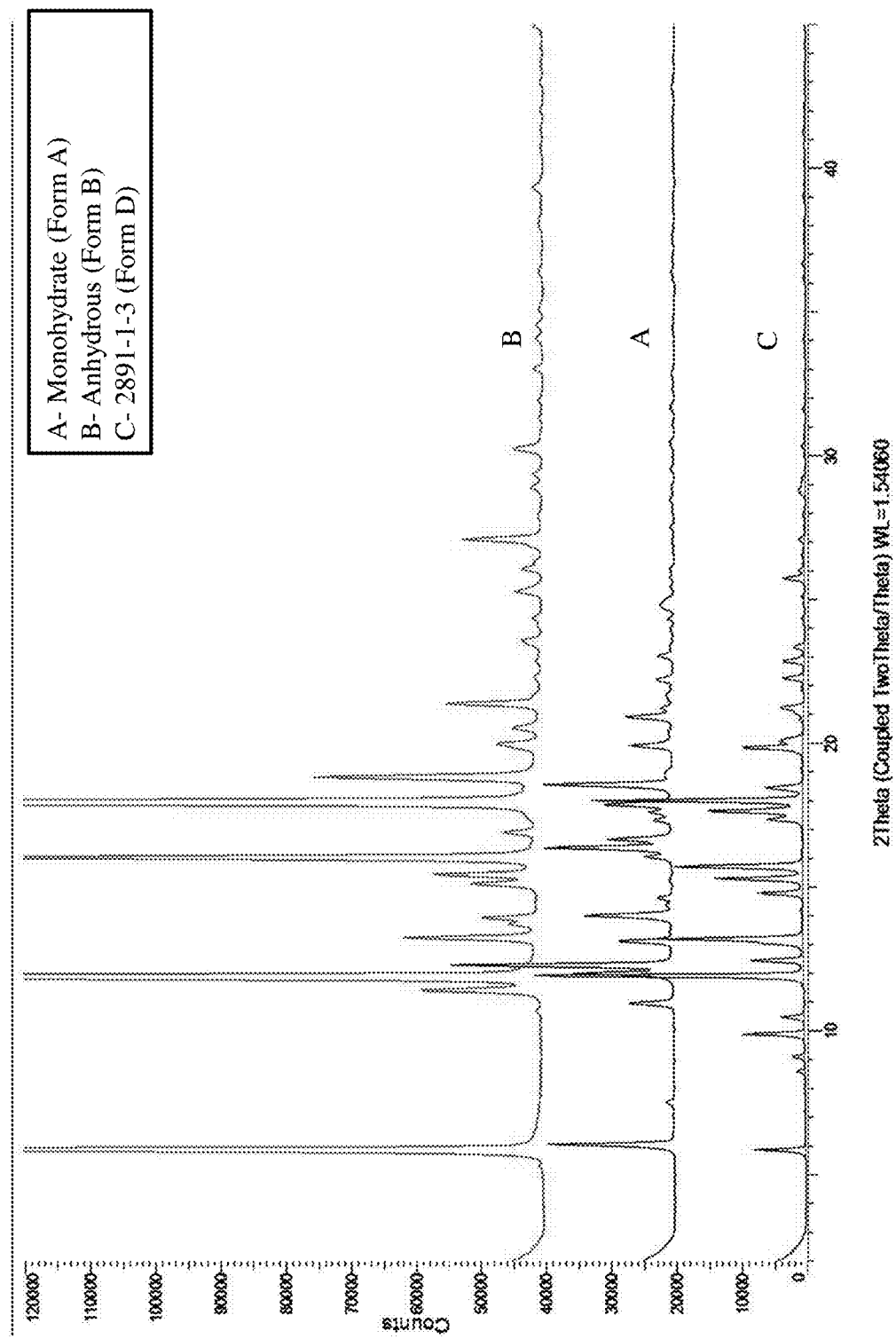
FIGS. 8A and 8B are XRPDs of OXY133 polymorph Form D.
Figure 8B:
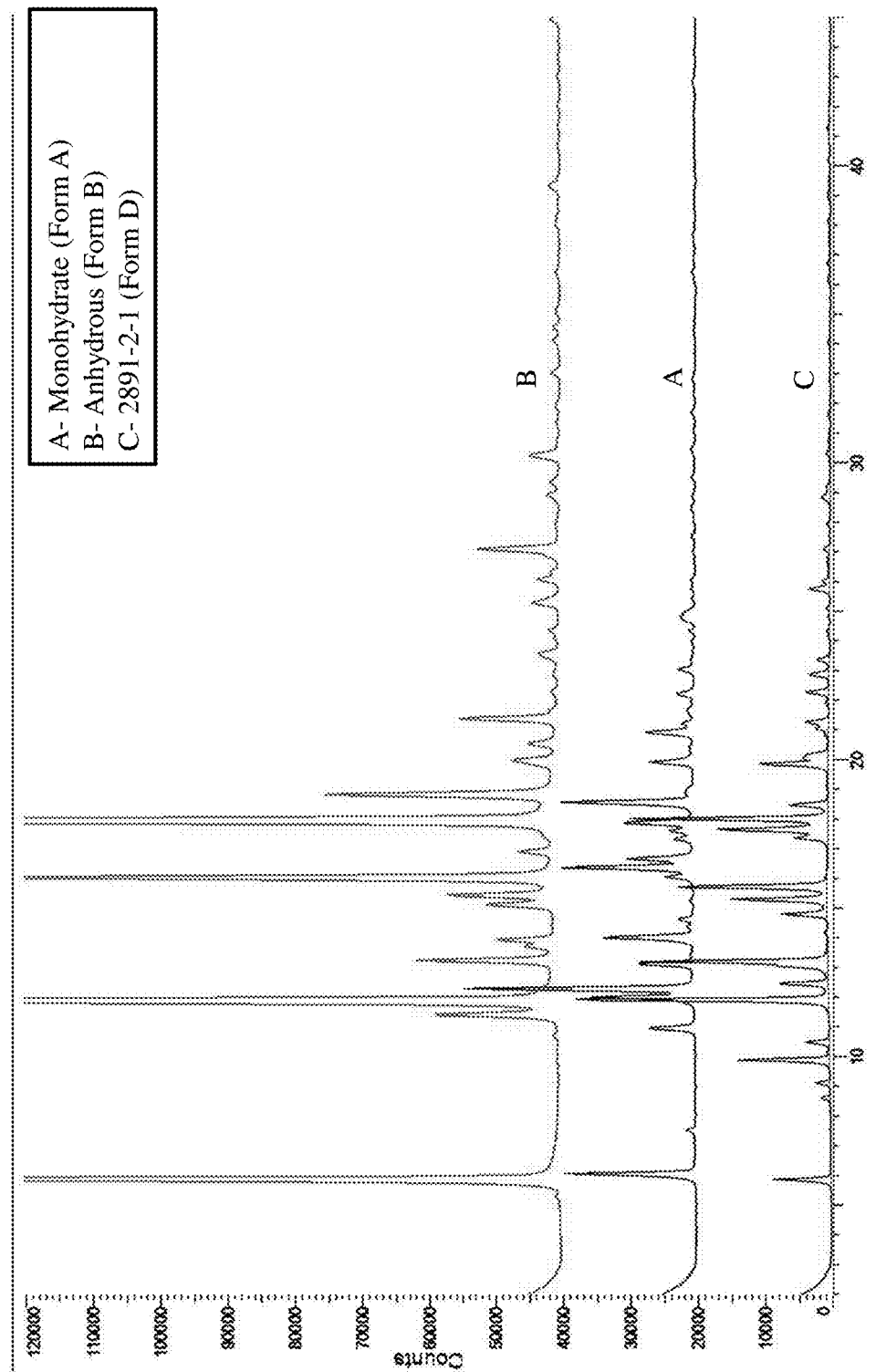
Figure 27:
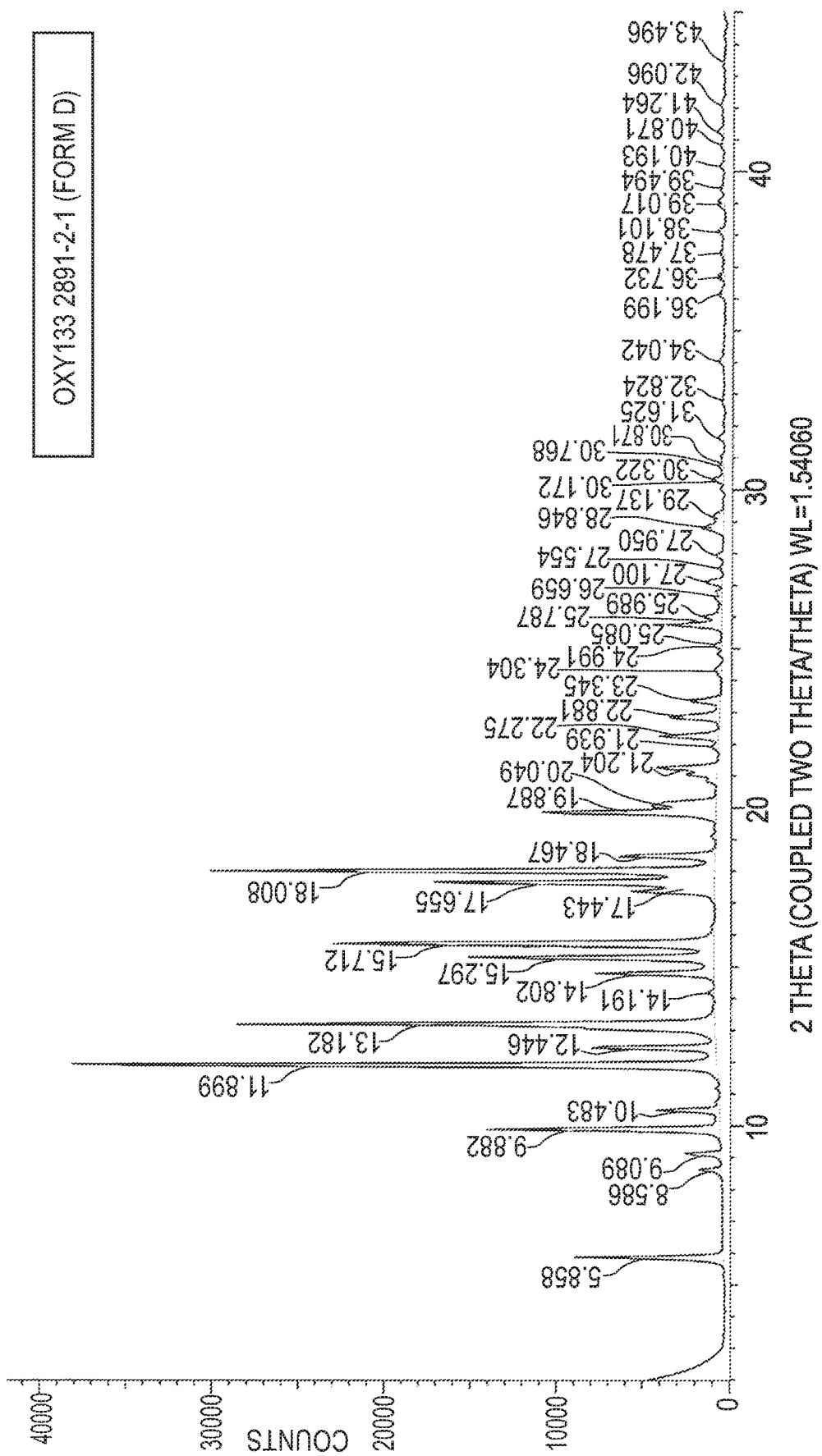
FIG. 27 is an XRPD of OXY133 polymorph Form D.

FIGS. 8A and 8B are XRPDs of OXY133 polymorph Form D obtained by re-slurrying from a methanol/water system at a precipitating temperature of 20° C. and 70° C., respectively. FIG. 27 is an XRPD of solid polymorph Form D obtained by crystallization from a methanol/water system in a ratio of 1:1 methanol/water v/v at a temperature of 70° C. Table 9, below lists data taken from the XRPD of FIG. 27. As illustrated in Table 9, OXY133 Form D can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52.

TABLE 9

XRPD Data for OXY133 Polymorph Form
D as illustrated in FIG. 27

| Index No. | Angle (2-Theta) | d Value (Angstrom) | Net Intensity (Counts) | Gross Intensity (Counts) | Rel. Intensity (%) |
|---|---|---|---|---|---|
| 0 | 5.858 | 15.07603 | 4683 | 5037 | 19.70% |
| 1 | 8.586 | 10.28984 | 656 | 1137 | 2.80% |
| 2 | 9.089 | 9.72157 | 988 | 1510 | 4.2% |
| 3 | 9.882 | 8.94328 | 8863 | 9436 | 37.30% |
| 4 | 10.483 | 8.43241 | 2326 | 2923 | 9.80% |
| 5 | 11.899 | 7.43157 | 23778 | 24503 | 100.00% |
| 6 | 12.446 | 7.106 | 4985 | 5773 | 21.00% |
| 7 | 13.182 | 6.71095 | 17127 | 17982 | 72.00% |
| 8 | 14.191 | 6.23589 | 214 | 1125 | 0.90% |
| 9 | 14.802 | 5.97989 | 4528 | 5455 | 19.00% |
| 10 | 15.297 | 5.78743 | 9207 | 10136 | 38.70% |
| 11 | 15.712 | 5.63571 | 15705 | 16628 | 66.00% |

TABLE 9-continued

XRPD Data for OXY133 Polymorph Form D as illustrated in FIG. 27

| Index No. | Angle (2-Theta) | d Value (Angstrom) | Net Intensity (Counts) | Gross Intensity (Counts) | Rel. Intensity (%) |
|---|---|---|---|---|---|
| 12 | 17.443 | 5.0801 | 1832 | 2721 | 7.70% |
| 13 | 17.655 | 5.01945 | 10402 | 11288 | 43.70% |
| 14 | 18.008 | 4.92205 | 20196 | 21072 | 84.90% |
| 15 | 18.467 | 4.8005 | 4043 | 4898 | 17.00% |
| 16 | 19.887 | 4.46096 | 5123 | 5949 | 21.50% |
| 17 | 20.049 | 4.42535 | 2529 | 3350 | 10.60% |
| 18 | 21.204 | 4.18675 | 1818 | 2577 | 7.60% |
| 19 | 21.939 | 4.04811 | 265 | 974 | 1.10% |
| 20 | 22.275 | 3.98782 | 2347 | 3040 | 9.90% |
| 21 | 22.881 | 3.88351 | 1876 | 2530 | 7.90% |
| 22 | 23.345 | 3.80742 | 1261 | 1876 | 5.30% |
| 23 | 24.304 | 3.65926 | 246 | 815 | 1.00% |
| 24 | 24.991 | 3.56021 | 79.9 | 645 | 0.30% |
| 25 | 25.085 | 3.54713 | 377 | 943 | 1.60% |
| 26 | 25.787 | 3.45209 | 1299 | 1868 | 5.50% |
| 27 | 25.982 | 3.42661 | 729 | 1299 | 3.10% |
| 28 | 26.659 | 3.34107 | 159 | 718 | 0.70% |
| 29 | 27.1 | 3.28777 | 710 | 1253 | 3.00% |
| 30 | 27.554 | 3.23461 | 122 | 648 | 0.50% |
| 31 | 27.95 | 3.18967 | 284 | 795 | 1.20% |
| 32 | 28.846 | 3.09259 | 689 | 1175 | 2.90% |
| 33 | 29.137 | 3.06234 | 356 | 837 | 1.50% |
| 34 | 30.172 | 2.95963 | 82.8 | 545 | 0.30% |
| 35 | 30.322 | 2.94533 | 482 | 947 | 2.00% |
| 36 | 30.768 | 2.90367 | 159 | 626 | 0.70% |
| 37 | 30.871 | 2.89415 | 116 | 582 | 0.50% |
| 38 | 31.625 | 2.82687 | 268 | 718 | 1.10% |
| 39 | 32.824 | 2.72634 | 69.5 | 503 | 0.30% |
| 40 | 34.042 | 2.63154 | 231 | 699 | 1.00% |
| 41 | 36.199 | 2.47947 | 165 | 618 | 0.70% |
| 42 | 36.732 | 2.44472 | 203 | 672 | 0.90% |
| 43 | 37.478 | 2.39777 | 129 | 602 | 0.50% |
| 44 | 38.101 | 2.35995 | 281 | 741 | 1.20% |
| 45 | 39.017 | 2.30666 | 180 | 651 | 0.80% |
| 46 | 39.494 | 2.27986 | 149 | 648 | 0.60% |
| 47 | 40.193 | 2.24182 | 183 | 708 | 0.80% |
| 48 | 40.871 | 2.2062 | 92.1 | 624 | 0.40% |
| 49 | 41.264 | 2.18607 | 338 | 867 | 1.40% |
| 50 | 42.096 | 2.1448 | 135 | 637 | 0.60% |
| 51 | 43.496 | 2.07895 | 84.8 | 552 | 0.40% |
| 52 | 44.291 | 2.04346 | 100 | 528 | 0.40% |

Figure 9A:
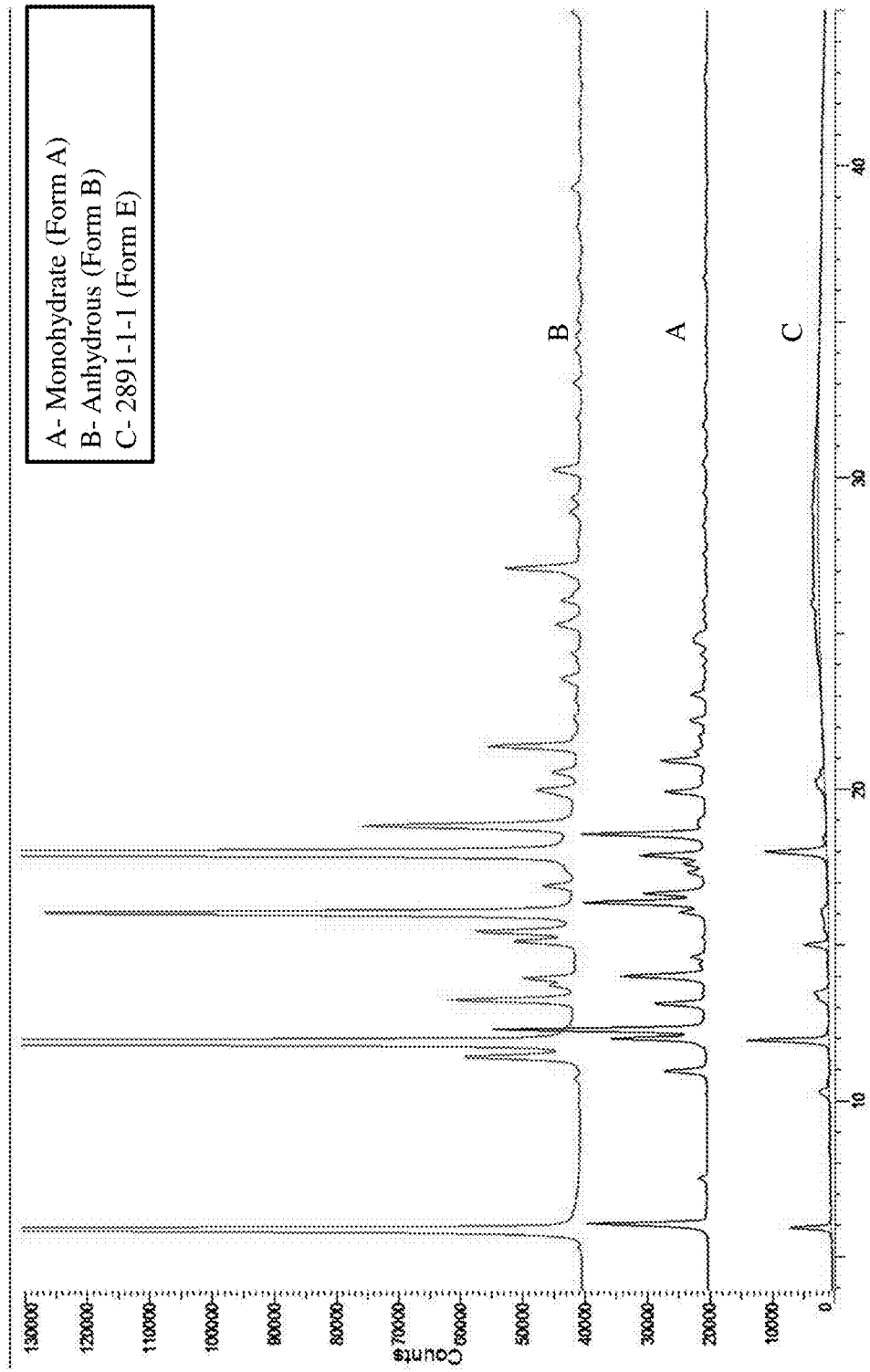
FIGS. 9A and 9B are XRPDs of OXY133 polymorph Form E.
Figure 9B:
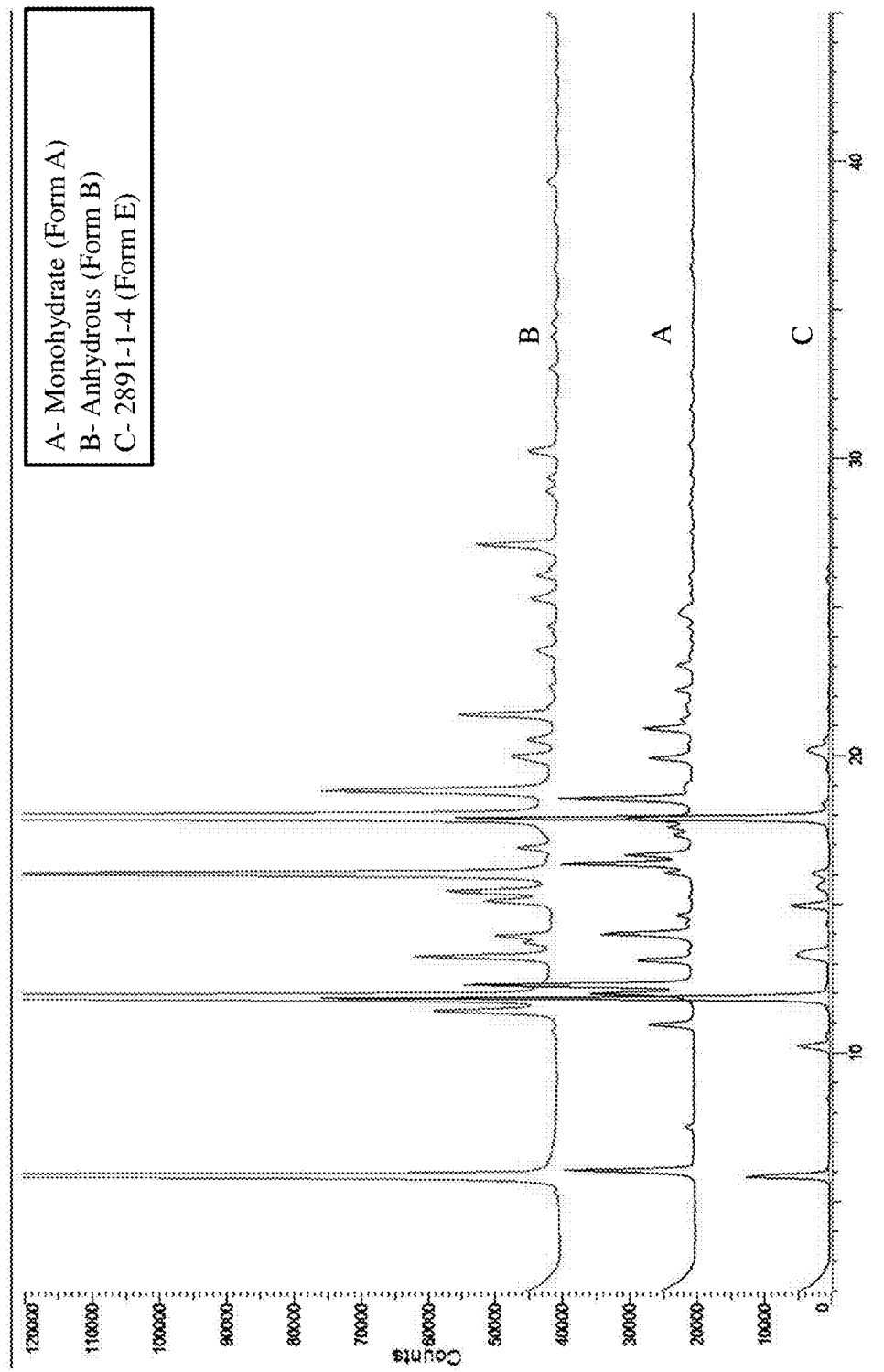
Figure 28:
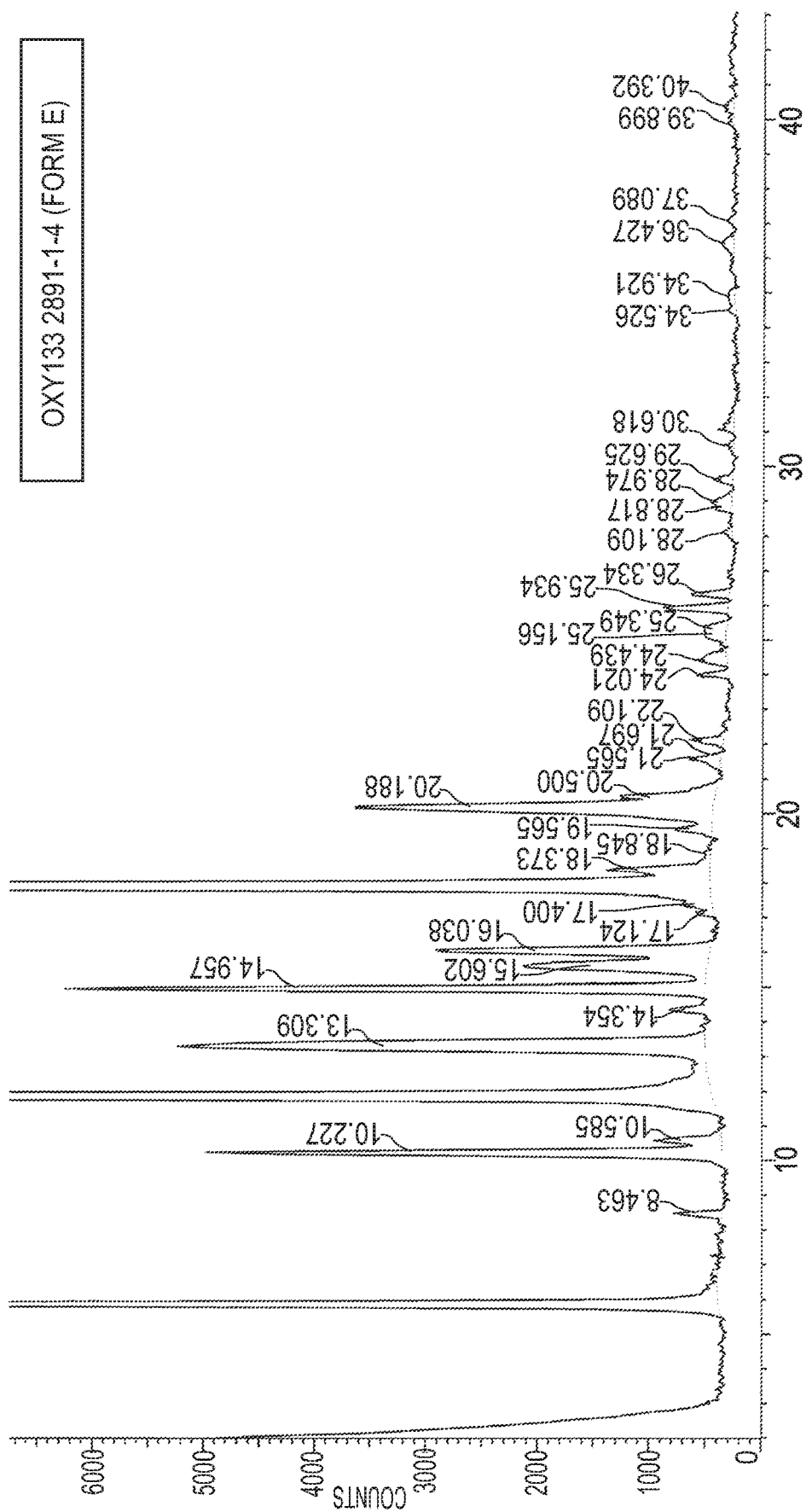
FIG. 28 is an XRPD of OXY133 polymorph Form E.

FIGS. 9A and 9B are XRPDs of OXY133 polymorph Form E obtained from a slurry of OXY133 polymorph Form B in water at temperatures of 20° C. and 70° C., respectively. FIG. 28 is an XRPD of solid polymorph Form E obtained by crystallization of OXY133 polymorph Form B from water at a temperature of 70° C. Table 10, below lists data taken from the XRPD of FIG. 28. As illustrated in Table 10, OXY133 polymorph Form E can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 and 38.

TABLE 10

XRPD Data for OXY 133 Polymorph Form E as illustrated in FIG. 28

| Index No. | Angle (2-Theta) | d Value (Angstrom) | Net Intensity (Counts) | Gross Intensity (Counts) | Rel. Intensity (%) |
|---|---|---|---|---|---|
| 0 | 5.861 | 15.06776 | 6031 | 6409 | 12.00% |
| 1 | 8.463 | 10.44012 | 219 | 569 | 0.40% |
| 2 | 10.227 | 8.64279 | 2774 | 3124 | 5.50% |
| 3 | 10.585 | 8.35089 | 345 | 703 | 0.70% |
| 4 | 11.792 | 7.49876 | 25469 | 25897 | 50.70% |
| 5 | 11.843 | 7.4668 | 50197 | 50630 | 100.00% |
| 6 | 13.309 | 6.64747 | 2884 | 3383 | 5.70% |
| 7 | 14.354 | 6.16576 | 179 | 674 | 0.40% |
| 8 | 14.957 | 5.91844 | 3673 | 4172 | 7.30% |
| 9 | 15.602 | 5.67499 | 1041 | 1521 | 2.10% |
| 10 | 16.038 | 5.52169 | 1568 | 2022 | 3.10% |
| 11 | 17.124 | 5.17408 | 85.2 | 506 | 0.20% |
| 12 | 17.4 | 5.09246 | 159 | 596 | 0.30% |
| 13 | 17.907 | 4.94951 | 35929 | 36384 | 71.60% |
| 14 | 18.373 | 4.82485 | 640 | 1099 | 1.30% |
| 15 | 18.845 | 4.70507 | 41.9 | 494 | 0.10% |
| 16 | 19.565 | 4.53351 | 203 | 641 | 0.40% |
| 17 | 20.188 | 4.39513 | 2162 | 2592 | 4.30% |
| 18 | 20.5 | 4.32894 | 581 | 998 | 1.20% |
| 19 | 21.697 | 4.09278 | 48.4 | 414 | 0.10% |
| 20 | 21.585 | 4.11367 | 208 | 577 | 0.40% |
| 21 | 22.109 | 4.01728 | 184 | 533 | 0.40% |
| 22 | 24.021 | 3.70168 | 163 | 467 | 0.30% |
| 23 | 24.439 | 3.63944 | 193 | 513 | 0.40% |
| 24 | 25.156 | 3.53721 | 119 | 444 | 0.20% |
| 25 | 25.349 | 3.51076 | 126 | 448 | 0.30% |
| 26 | 25.934 | 3.43293 | 413 | 724 | 0.80% |
| 27 | 26.334 | 3.38166 | 228 | 528 | 0.50% |
| 28 | 28.109 | 3.17202 | 85 | 367 | 0.20% |
| 29 | 28.847 | 3.09254 | 76.9 | 366 | 0.20% |
| 30 | 28.974 | 3.07918 | 113 | 399 | 0.20% |
| 31 | 29.625 | 3.013 | 106 | 380 | 0.20% |
| 32 | 30.618 | 2.9175 | 76.9 | 341 | 0.20% |
| 33 | 34.526 | 2.59571 | 58.9 | 312 | 0.10% |
| 34 | 34.921 | 2.56729 | 41.5 | 305 | 0.10% |
| 35 | 36.427 | 2.4645 | 70.5 | 346 | 0.10% |
| 36 | 37.089 | 2.42199 | 53.9 | 322 | 0.10% |
| 37 | 39.899 | 2.25767 | 41.3 | 312 | 0.10% |
| 38 | 40.392 | 2.23124 | 52.7 | 328 | 0.10% |

Figure 10A:
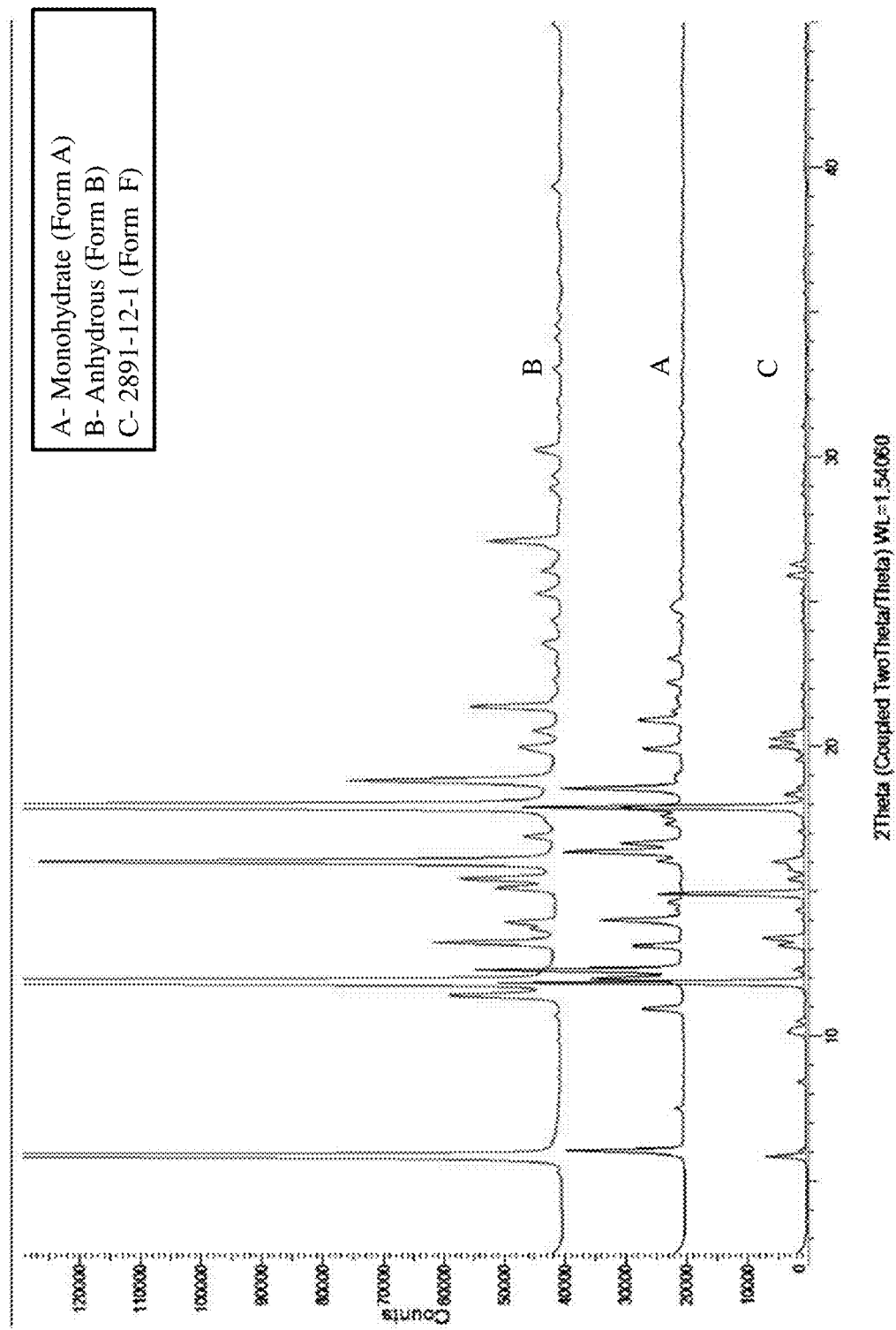
FIGS. 10A, 10B and 10C are XRPDs of OXY133 polymorph Form F.
Figure 10B:
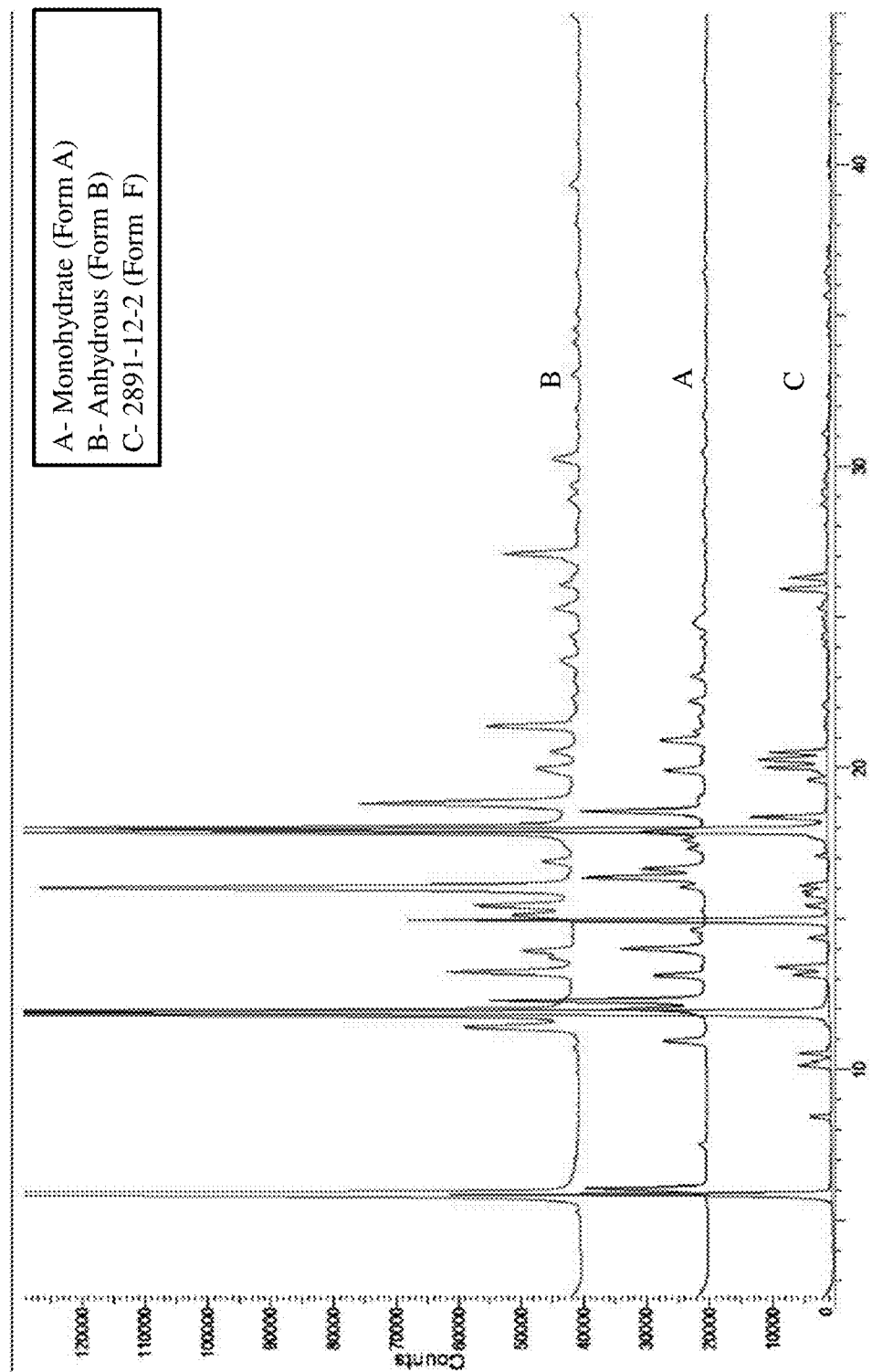
Figure 10C:
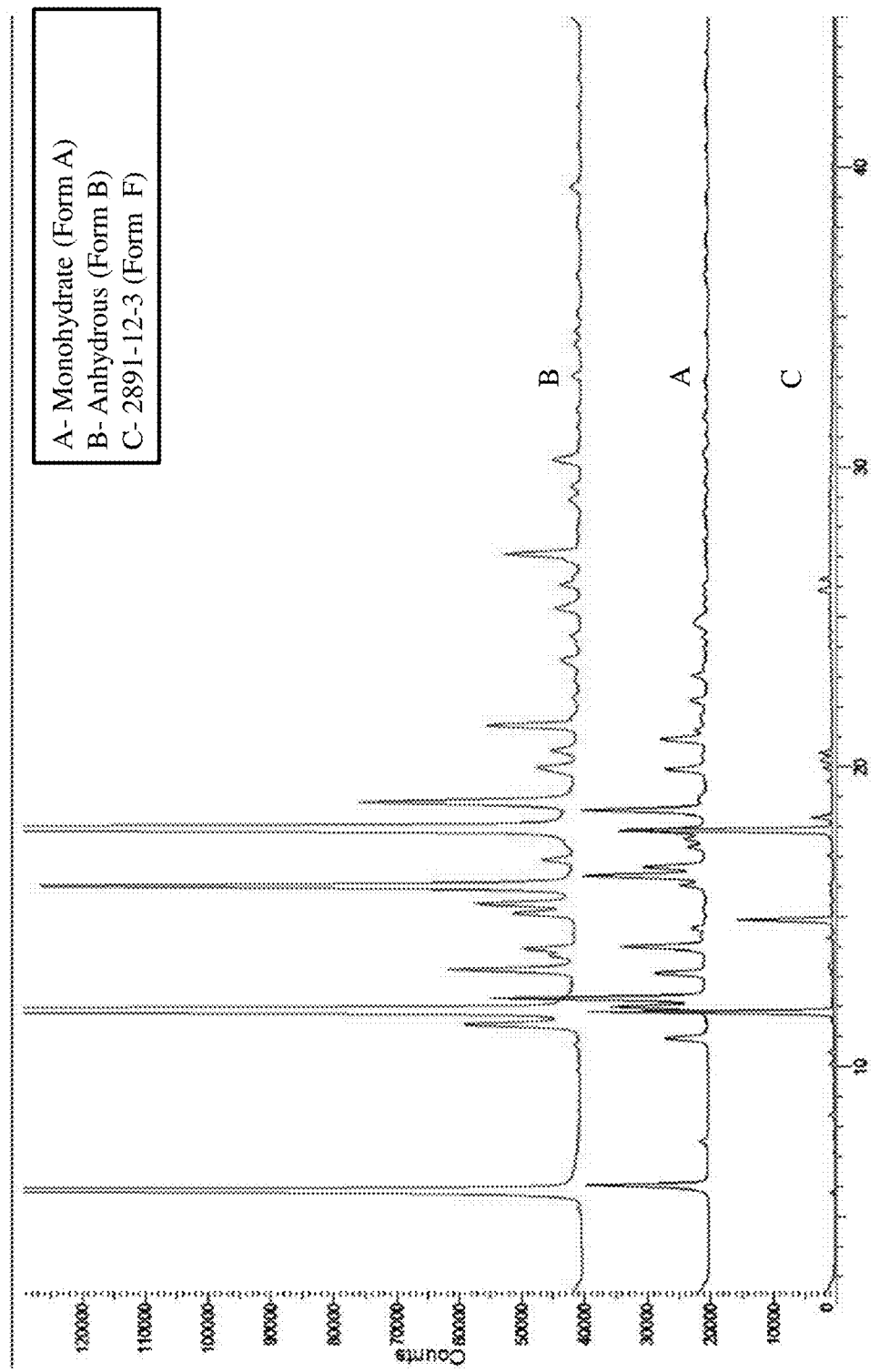
Figure 29:
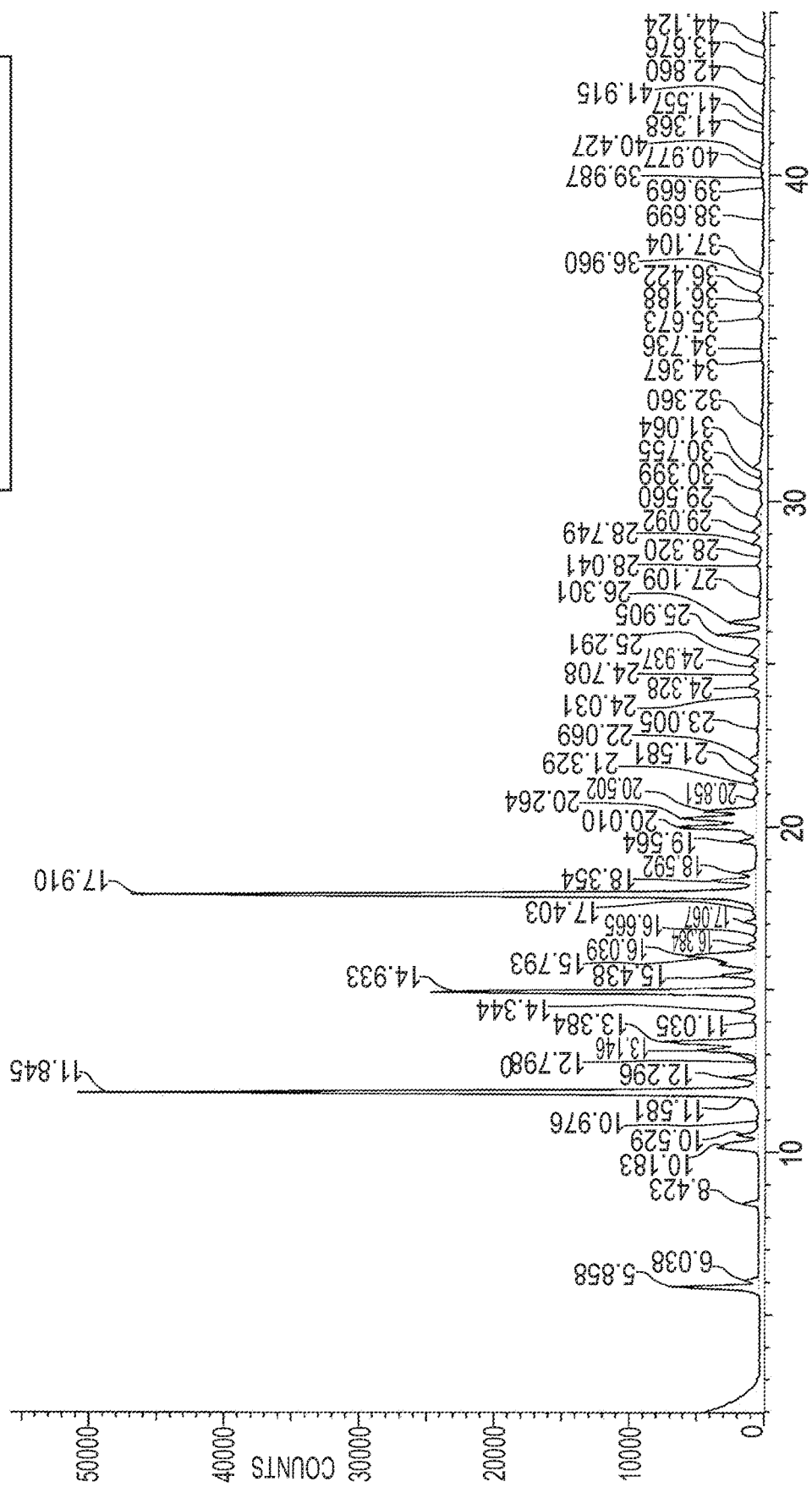
FIG. 29 is an XRPD of OXY133 polymorph Form F.

FIGS. 10A, 10B, and 10C are XRPDs of OXY133 polymorph Form F obtained by a dissolution in acetone/water followed by precipitation at temperatures of 5° C. and 15° C., respectively. FIG. 29 is an XRPD of solid polymorph form F obtained by acetone recrystallization with water after cooling. Table 11, below lists data taken from the XRPD of FIG. 29. As illustrated in Table 11, OXY133 polymorph Form F can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, and 69.

TABLE 11

XRPD Data for OXY133 Polymorph Form F as illustrated in FIG. 29

| Index No. | Angle (2-Theta) | d Value (Angstrom) | Net Intensity (Counts) | Gross Intensity (Counts) | Rel. Intensity (%) |
|---|---|---|---|---|---|
| 0 | 5.858 | 15.07371 | 6401 | 6775 | 13.30% |
| 1 | 6.038 | 14.62591 | 911 | 1296 | 1.90% |
| 2 | 8.423 | 10.48851 | 1258 | 1692 | 2.60% |
| 3 | 10.183 | 8.67999 | 2525 | 2996 | 5.30% |
| 4 | 10.529 | 8.39522 | 1507 | 1991 | 3.10% |
| 5 | 10.976 | 8.05428 | 128 | 620 | 0.30% |
| 6 | 11.581 | 7.63502 | 284 | 821 | 0.60% |
| 7 | 11.845 | 7.4653 | 48013 | 48581 | 100.00% |
| 8 | 12.296 | 7.19232 | 1843 | 2456 | 3.80% |
| 9 | 12.798 | 6.91173 | 85.4 | 738 | 0.20% |

TABLE 11-continued

XRPD Data for OXY133 Polymorph Form F as illustrated in FIG. 29

| Index No. | Angle (2-Theta) | d Value (Angstrom) | Net Intensity (Counts) | Gross Intensity (Counts) | Rel. Intensity (%) |
|---|---|---|---|---|---|
| 10 | 13.146 | 6.72934 | 4250 | 4923 | 8.90% |
| 11 | 13.384 | 6.61009 | 6464 | 7148 | 13.50% |
| 12 | 14.035 | 6.30515 | 214 | 923 | 0.40% |
| 13 | 14.344 | 6.16967 | 1376 | 2100 | 2.90% |
| 14 | 14.933 | 5.92779 | 22122 | 22863 | 46.10% |
| 15 | 15.438 | 5.73496 | 2433 | 3175 | 5.10% |
| 16 | 15.793 | 5.60697 | 2199 | 2935 | 4.60% |
| 17 | 16.039 | 5.52147 | 4733 | 5462 | 9.90% |
| 18 | 16.384 | 5.406 | 536 | 1250 | 1.10% |
| 19 | 16.665 | 5.31559 | 192 | 890 | 0.40% |
| 20 | 17.067 | 5.1911 | 884 | 1577 | 1.80% |
| 21 | 17.403 | 5.09172 | 231 | 934 | 0.50% |
| 22 | 17.91 | 4.94874 | 45219 | 45929 | 94.2% |
| 23 | 18.354 | 4.82995 | 3217 | 3922 | 6.70% |
| 24 | 18.592 | 4.76859 | 1122 | 1822 | 2.30% |
| 25 | 19.564 | 4.53385 | 1341 | 2017 | 2.80% |
| 26 | 20.01 | 4.43386 | 5638 | 6313 | 11.70% |
| 27 | 20.264 | 4.37871 | 5474 | 6144 | 11.40% |
| 28 | 20.502 | 4.32853 | 3495 | 4157 | 7.30% |
| 29 | 20.851 | 4.25674 | 204 | 852 | 0.40% |
| 30 | 21.329 | 4.16243 | 331 | 955 | 0.70% |
| 31 | 21.581 | 4.11452 | 449 | 1061 | 0.90% |
| 32 | 22.069 | 4.02458 | 551 | 1143 | 1.10% |
| 33 | 23.005 | 3.86289 | 105 | 662 | 0.20% |
| 34 | 24.031 | 3.7002 | 301 | 834 | 0.60% |
| 35 | 24.328 | 3.65573 | 680 | 1225 | 1.40% |
| 36 | 24.708 | 3.60033 | 467 | 1020 | 1.00% |
| 37 | 24.937 | 3.56787 | 469 | 1024 | 1.00% |
| 38 | 25.291 | 3.51871 | 809 | 1363 | 1.70% |
| 39 | 25.905 | 3.43669 | 2869 | 3407 | 6.00% |
| 40 | 26.301 | 3.38579 | 2283 | 2802 | 4.80% |
| 41 | 27.109 | 3.2867 | 171 | 630 | 0.40% |
| 42 | 28.041 | 3.17955 | 262 | 699 | 0.50% |
| 43 | 28.32 | 3.14883 | 53.8 | 489 | 0.10% |
| 44 | 28.749 | 3.10286 | 554 | 986 | 1.20% |
| 45 | 29.092 | 3.06705 | 497 | 926 | 1.00% |
| 46 | 29.56 | 3.01949 | 358 | 774 | 0.70% |
| 47 | 29.551 | 3.02045 | 375 | 791 | 0.80% |
| 48 | 30.399 | 2.93805 | 225 | 636 | 0.50% |
| 49 | 30.755 | 2.90486 | 103 | 517 | 0.20% |
| 50 | 31.064 | 2.87668 | 612 | 1024 | 1.30% |
| 51 | 32.36 | 2.76431 | 75.5 | 449 | 0.20% |
| 52 | 34.367 | 2.60735 | 99 | 459 | 0.20% |
| 53 | 34.736 | 2.58049 | 155 | 534 | 0.30% |
| 54 | 35.673 | 2.51486 | 274 | 682 | 0.60% |
| 55 | 36.188 | 2.4802 | 242 | 661 | 0.50% |
| 56 | 36.422 | 2.46479 | 381 | 803 | 0.80% |
| 57 | 36.96 | 2.4302 | 164 | 580 | 0.30% |
| 58 | 37.104 | 2.42105 | 200 | 612 | 0.40% |
| 59 | 38.699 | 2.32486 | 95.8 | 463 | 0.20% |
| 60 | 39.669 | 2.27022 | 129 | 507 | 0.30% |
| 61 | 39.983 | 2.25313 | 126 | 522 | 0.30% |
| 62 | 40.227 | 2.24001 | 163 | 570 | 0.30% |
| 63 | 40.427 | 2.2294 | 128 | 541 | 0.30% |
| 64 | 41.368 | 2.18081 | 98.9 | 522 | 0.20% |
| 65 | 41.667 | 2.16585 | 95.6 | 513 | 0.20% |
| 66 | 41.915 | 2.15361 | 73 | 483 | 0.20% |
| 67 | 42.86 | 2.1083 | 53.5 | 414 | 0.10% |
| 68 | 43.676 | 2.07078 | 71.6 | 430 | 0.10% |
| 69 | 44.124 | 2.05078 | 142 | 497 | 0.30% |

Figure 11:
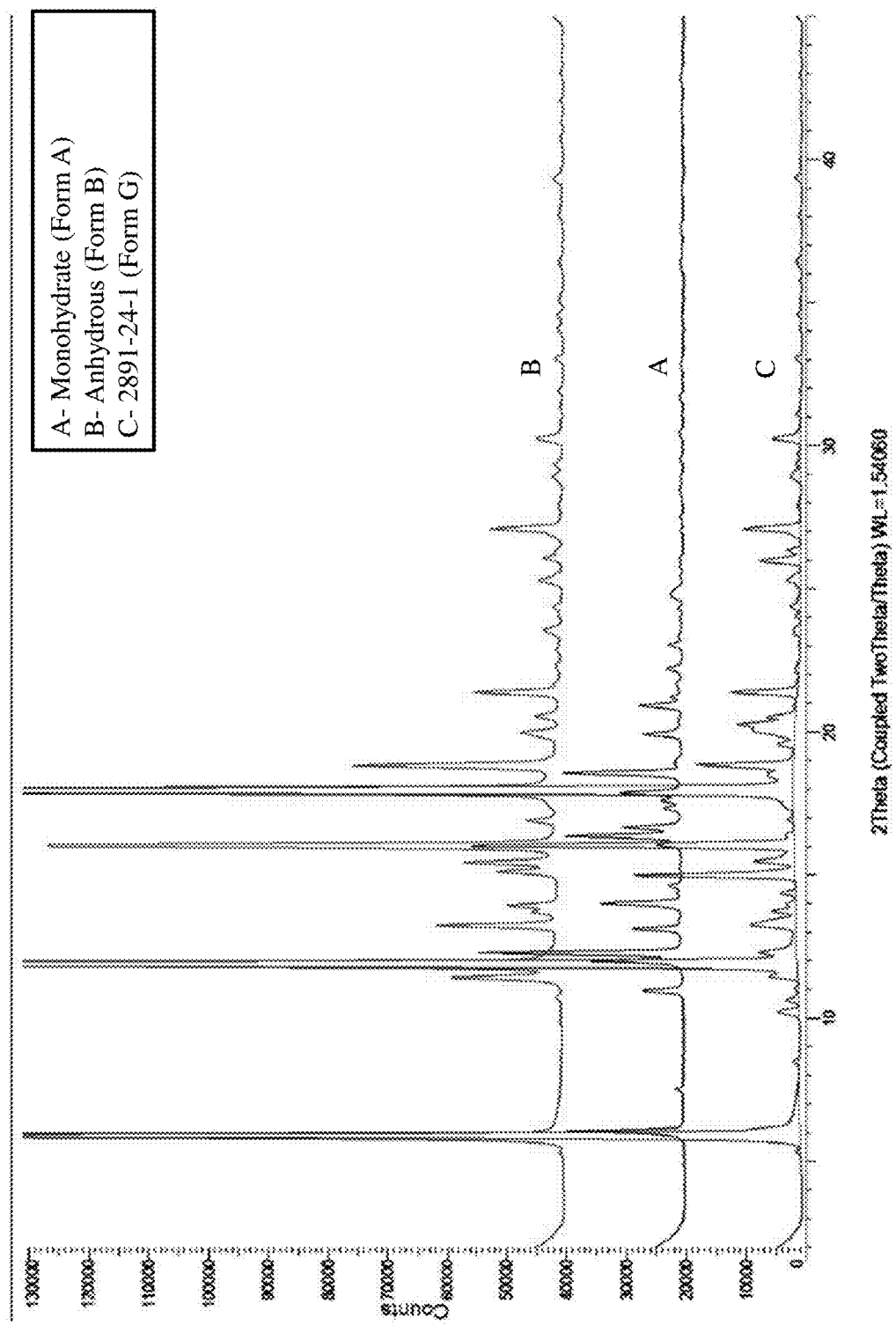
FIG. 11 is an XRPD of OXY133 polymorph Form G.
Figure 30:
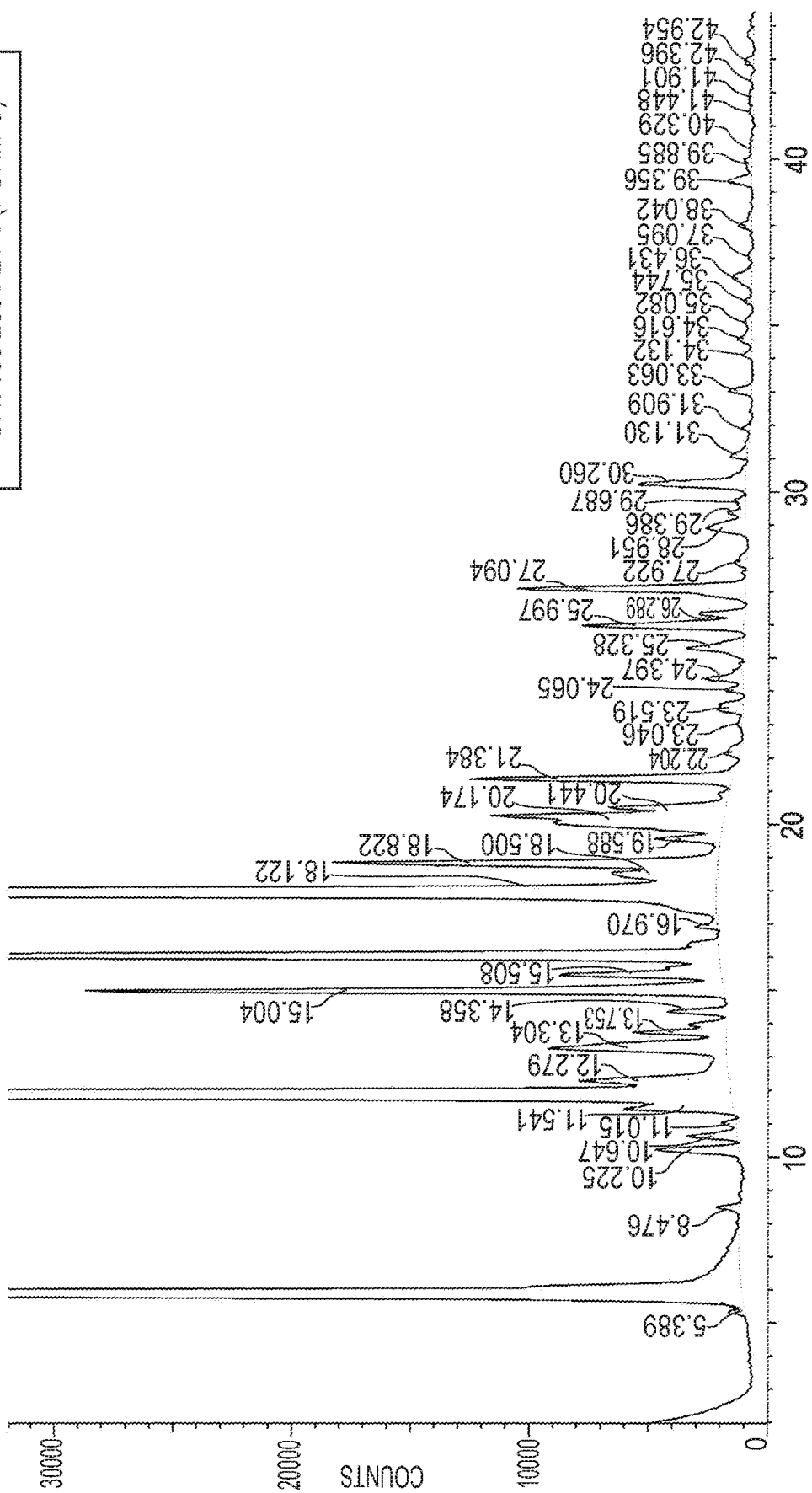
FIG. 30 is an XRPD of OXY133 polymorph Form G.

FIG. 11 is an XRPD of OXY133 polymorph Form G obtained by crystallization from IPA/water solvent system in a ratio of 1:2 v/v at a temperature of 40° C. FIG. 30 is an XRPD of solid polymorph Form G obtained by IPA/water solvent system in a ratio of 1:2 v/v at a temperature of 40° C. Table 12, below lists data taken from the XRPD of FIG. 30. As illustrated in Table 12, OXY133 Form G can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, and 56.

TABLE 12

XRPD Data for OXY133 Polymorph Form G as illustrated in FIG. 30

| Index No. | Angle (2-Theta) | d Value (Angstrom) | Net Intensity (Counts) | Gross Intensity (Counts) | Rel. Intensity (%) |
|---|---|---|---|---|---|
| 0 | 5.389 | 16.38447 | 172 | 1127 | 0.10% |
| 1 | 5.913 | 14.93454 | 149287 | 150350 | 85.10% |
| 2 | 8.476 | 10.42353 | 526 | 1685 | 0.30% |
| 3 | 10.225 | 8.64412 | 2036 | 3239 | 1.20% |
| 4 | 10.647 | 8.30276 | 1118 | 2393 | 0.60% |
| 5 | 11.015 | 8.02616 | 251 | 1575 | 0.10% |
| 6 | 11.541 | 7.66118 | 2081 | 3523 | 1.20% |
| 7 | 11.893 | 7.43524 | 175415 | 176944 | 100.00% |
| 8 | 12.279 | 7.20257 | 3790 | 5399 | 2.20% |
| 9 | 13.304 | 6.64985 | 4196 | 5938 | 2.40% |
| 10 | 13.753 | 6.43346 | 2241 | 4005 | 1.30% |
| 11 | 14.358 | 6.16397 | 1601 | 3360 | 0.90% |
| 12 | 15.004 | 5.89985 | 15936 | 17787 | 9.10% |
| 13 | 15.508 | 5.70918 | 3795 | 5751 | 2.20% |
| 14 | 16.05 | 5.51775 | 31595 | 33633 | 18.00% |
| 15 | 16.97 | 5.22071 | 362 | 2482 | 0.20% |
| 16 | 18.122 | 4.8913 | 7912 | 10068 | 4.5% |
| 17 | 17.958 | 4.93562 | 172190 | 174350 | 98.20% |
| 18 | 18.5 | 4.79221 | 2853 | 4990 | 1.60% |
| 19 | 18.822 | 4.71094 | 10445 | 12553 | 6.00% |
| 20 | 19.588 | 4.52832 | 1675 | 3670 | 1.00% |
| 21 | 20.174 | 4.39821 | 4778 | 6643 | 2.70% |
| 22 | 20.441 | 4.34134 | 2462 | 4257 | 1.40% |
| 23 | 21.384 | 4.15192 | 7374 | 8854 | 4.20% |
| 24 | 22.204 | 4.00034 | 300 | 1501 | 0.20% |
| 25 | 23.046 | 3.85606 | 122 | 1211 | 0.10% |
| 26 | 23.519 | 3.77953 | 591 | 1663 | 0.30% |
| 27 | 24.065 | 3.69511 | 427 | 1495 | 0.20% |
| 28 | 24.397 | 3.64547 | 986 | 2074 | 0.60% |
| 29 | 25.328 | 3.51363 | 1381 | 2468 | 0.80% |
| 30 | 25.997 | 3.42472 | 4490 | 5531 | 2.60% |
| 31 | 26.289 | 3.38731 | 1368 | 2378 | 0.80% |
| 32 | 27.094 | 3.28846 | 6612 | 7593 | 3.80% |
| 33 | 27.922 | 3.19278 | 277 | 1220 | 0.20% |
| 34 | 28.951 | 3.08162 | 1002 | 1962 | 0.60% |
| 35 | 29.386 | 3.03696 | 519 | 1511 | 0.30% |
| 36 | 29.687 | 3.00684 | 273 | 1275 | 0.20% |
| 37 | 30.26 | 2.9512 | 3003 | 3996 | 1.70% |
| 38 | 31.13 | 2.87072 | 395 | 1317 | 0.20% |
| 39 | 31.909 | 2.80237 | 344 | 1157 | 0.20% |
| 40 | 33.063 | 2.70719 | 621 | 1376 | 0.40% |
| 41 | 34.132 | 2.62474 | 291 | 1050 | 0.20% |
| 42 | 34.616 | 2.58915 | 372 | 1139 | 0.20% |
| 43 | 35.082 | 2.55587 | 209 | 961 | 0.10% |
| 44 | 35.744 | 2.50999 | 218 | 962 | 0.10% |
| 45 | 36.431 | 2.46421 | 605 | 1380 | 0.30% |
| 46 | 37.095 | 2.42162 | 142 | 897 | 0.10% |
| 47 | 38.042 | 2.36348 | 288 | 1067 | 0.20% |
| 48 | 39.356 | 2.28756 | 710 | 1486 | 0.40% |
| 49 | 39.885 | 2.25841 | 142 | 918 | 0.10% |
| 50 | 40.329 | 2.23457 | 65.8 | 817 | 0.00% |
| 51 | 41.448 | 2.17679 | 134 | 845 | 0.10% |
| 52 | 41.901 | 2.15432 | 83.3 | 813 | 0.00% |
| 53 | 42.396 | 2.13032 | 87.5 | 810 | 0.00% |
| 54 | 42.954 | 2.10389 | 206 | 913 | 0.10% |
| 55 | 43.753 | 2.06732 | 160 | 861 | 0.10% |
| 56 | 44.124 | 2.05079 | 91.5 | 785 | 0.10% |

Figure 12:
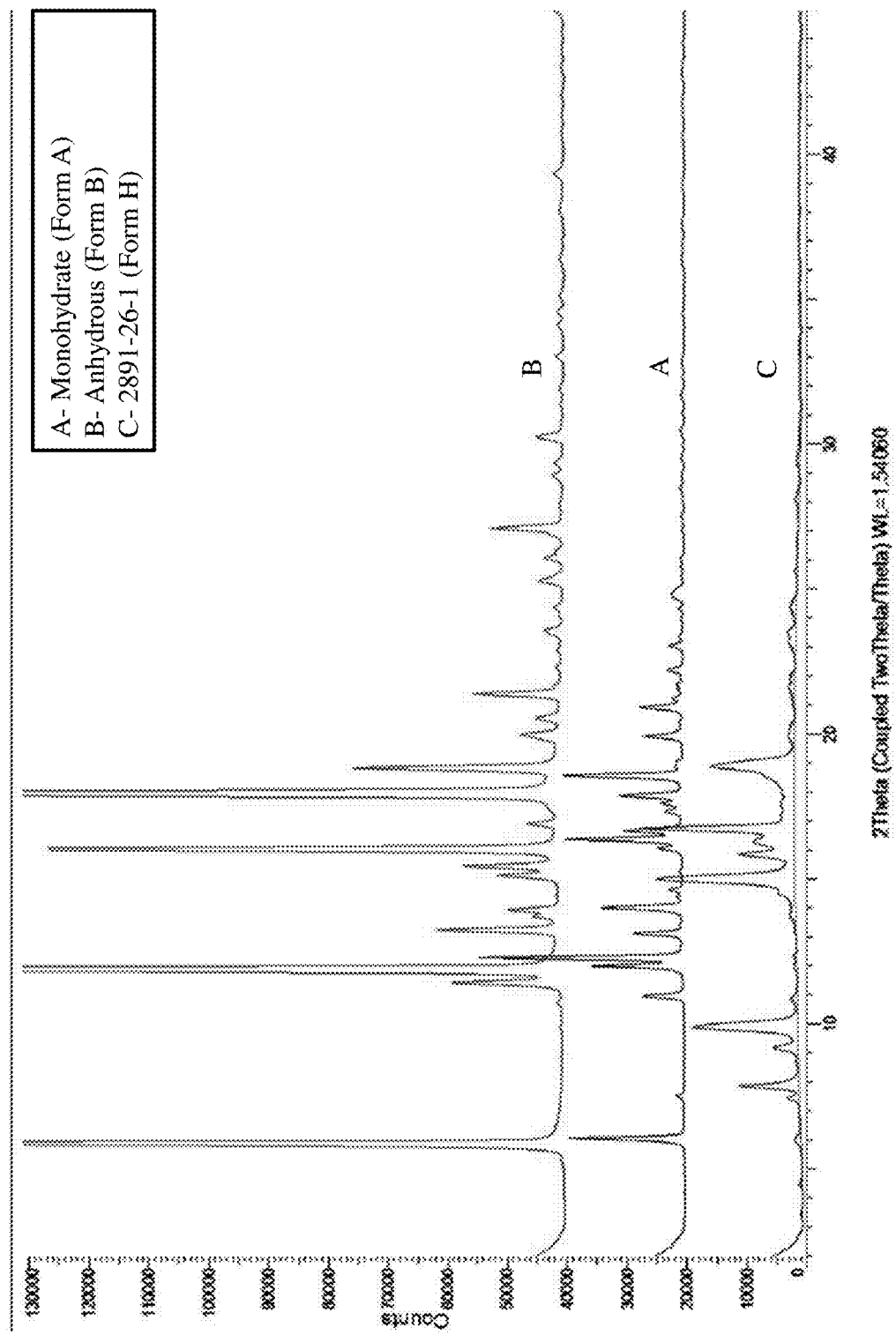
FIG. 12 is an XRPD of OXY133 polymorph Form H.
Figure 31:
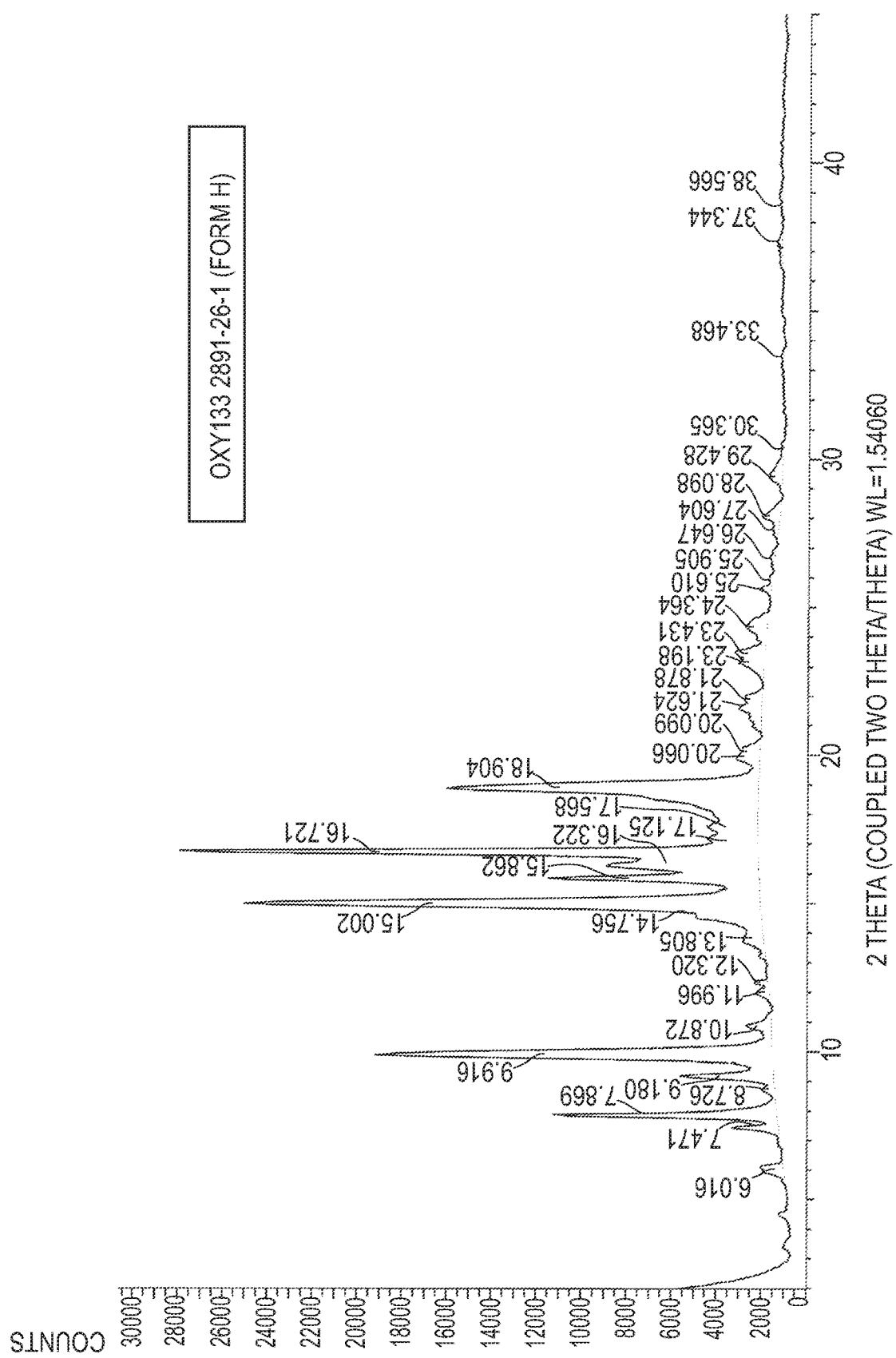
FIG. 31 is an XRPD of OXY133 polymorph Form H.

FIG. 12 is an XRPD of OXY133 polymorph Form H obtained by crystallization from IPA/water solvent system in a ratio of 1:2 v/v at a temperature of −10° C. FIG. 31 is an XRPD of solid polymorph Form H obtained by crystallization from IPA/water solvent system in a ratio of 1:2 v/v at a temperature of −10° C. Table 13, below lists data taken from the XRPD of FIG. 31. As illustrated in Table 13, OXY133 polymorph Form H can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, and 34.

TABLE 13

XRPD Data for OXY133 Polymorph Form H as illustrated in FIG. 31

| Index No. | Angle (2-Theta) | d Value (Angstrom) | Net Intensity (Counts) | Gross Intensity (Counts) | Rel. Intensity (%) |
|---|---|---|---|---|---|
| 0 | 6.016 | 14.6791 | 370 | 1366 | 2.20% |
| 1 | 7.471 | 11.82347 | 939 | 2168 | 5.60% |
| 2 | 7.869 | 11.22605 | 5683 | 6970 | 33.80% |
| 3 | 8.726 | 10.1252 | 234 | 1626 | 1.40% |
| 4 | 9.18 | 9.62563 | 2392 | 3829 | 14.20% |
| 5 | 9.916 | 8.913 | 10104 | 11601 | 60.10% |
| 6 | 10.872 | 8.13087 | 592 | 2139 | 3.50% |
| 7 | 11.996 | 7.3717 | 204 | 1851 | 1.20% |
| 8 | 12.32 | 7.17876 | 305 | 2002 | 1.80% |
| 9 | 13.805 | 6.40942 | 496 | 2404 | 3.00% |
| 10 | 14.756 | 5.99864 | 3324 | 5343 | 19.80% |
| 11 | 15.002 | 5.90075 | 14585 | 16627 | 86.80% |
| 12 | 15.862 | 5.58261 | 5789 | 7898 | 34.50% |
| 13 | 16.322 | 5.42647 | 4126 | 6261 | 24.6% |
| 14 | 16.721 | 5.29782 | 16799 | 18950 | 100.00% |
| 15 | 17.125 | 5.17379 | 1363 | 3525 | 8.10% |
| 16 | 17.568 | 5.04432 | 1441 | 3610 | 8.60% |
| 17 | 18.904 | 4.69057 | 8872 | 11019 | 52.80% |
| 18 | 19.966 | 4.44348 | 626 | 2713 | 3.70% |
| 19 | 20.093 | 4.41569 | 575 | 2653 | 3.40% |
| 20 | 21.624 | 4.10630 | 637 | 2647 | 3.80% |
| 21 | 21.878 | 4.05931 | 527 | 2527 | 3.10% |
| 22 | 23.198 | 3.83111 | 679 | 2588 | 4.0% |
| 23 | 23.431 | 3.79356 | 775 | 2662 | 4.60% |
| 24 | 24.364 | 3.65037 | 646 | 2427 | 3.80% |
| 25 | 25.61 | 3.47553 | 350 | 1965 | 2.10% |
| 26 | 25.905 | 3.43667 | 88.3 | 1663 | 0.50% |
| 27 | 26.647 | 3.34264 | 158 | 1619 | 0.90% |
| 28 | 27.604 | 3.22888 | 168 | 1487 | 1.00% |
| 29 | 28.098 | 3.17319 | 487 | 1738 | 2.90% |
| 30 | 29.428 | 3.03275 | 362 | 1497 | 2.20% |
| 31 | 30.365 | 2.94128 | 81 | 1172 | 0.50% |
| 32 | 33.468 | 2.67532 | 153 | 1218 | 0.90% |
| 33 | 37.344 | 2.40606 | 157 | 1356 | 0.90% |
| 34 | 38.566 | 2.33259 | 71.8 | 1280 | 0.40% |

Figure 13A:
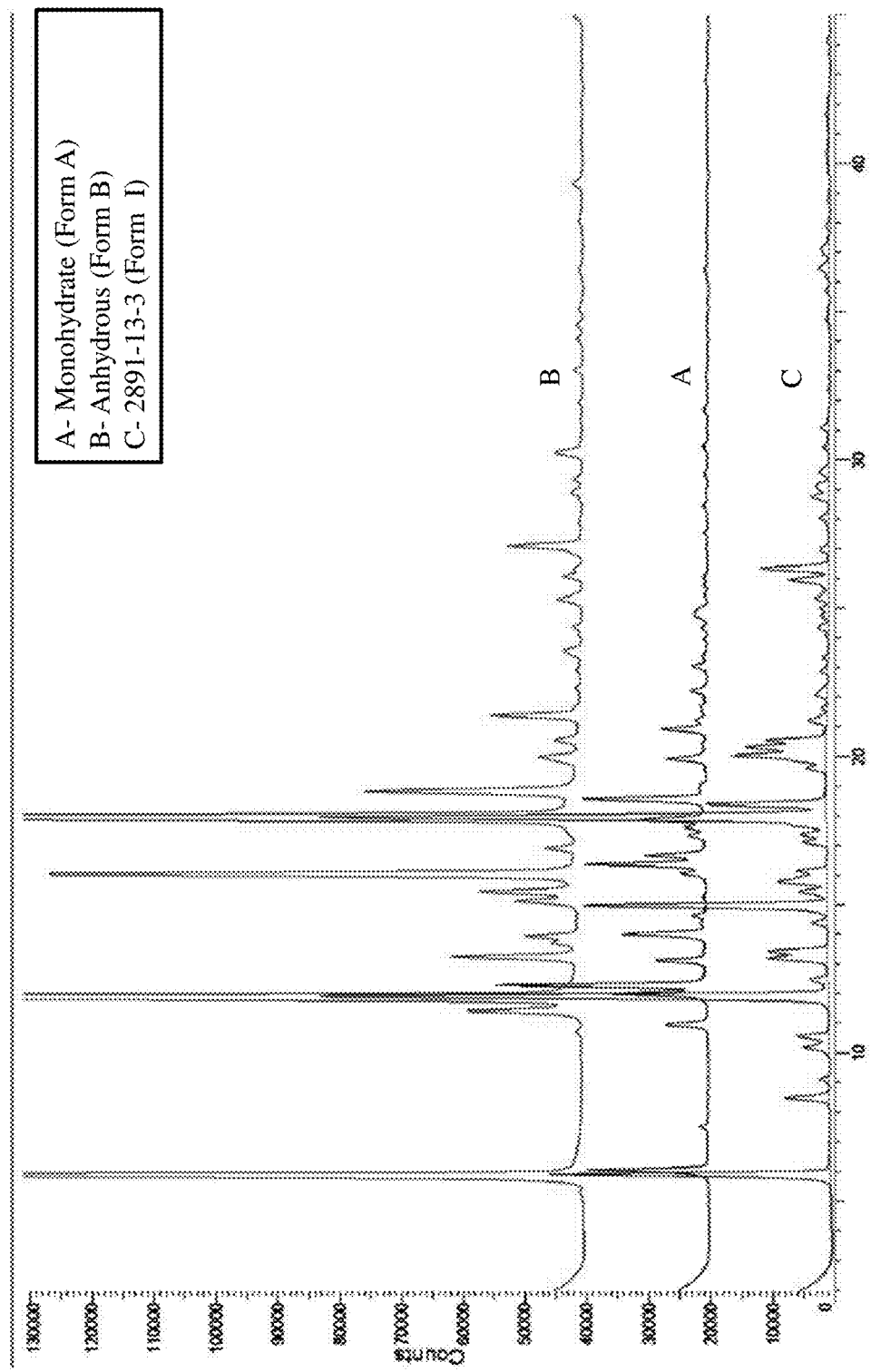
FIGS. 13A and 13B are XRPDs of OXY133 polymorph Form I.
Figure 13B:
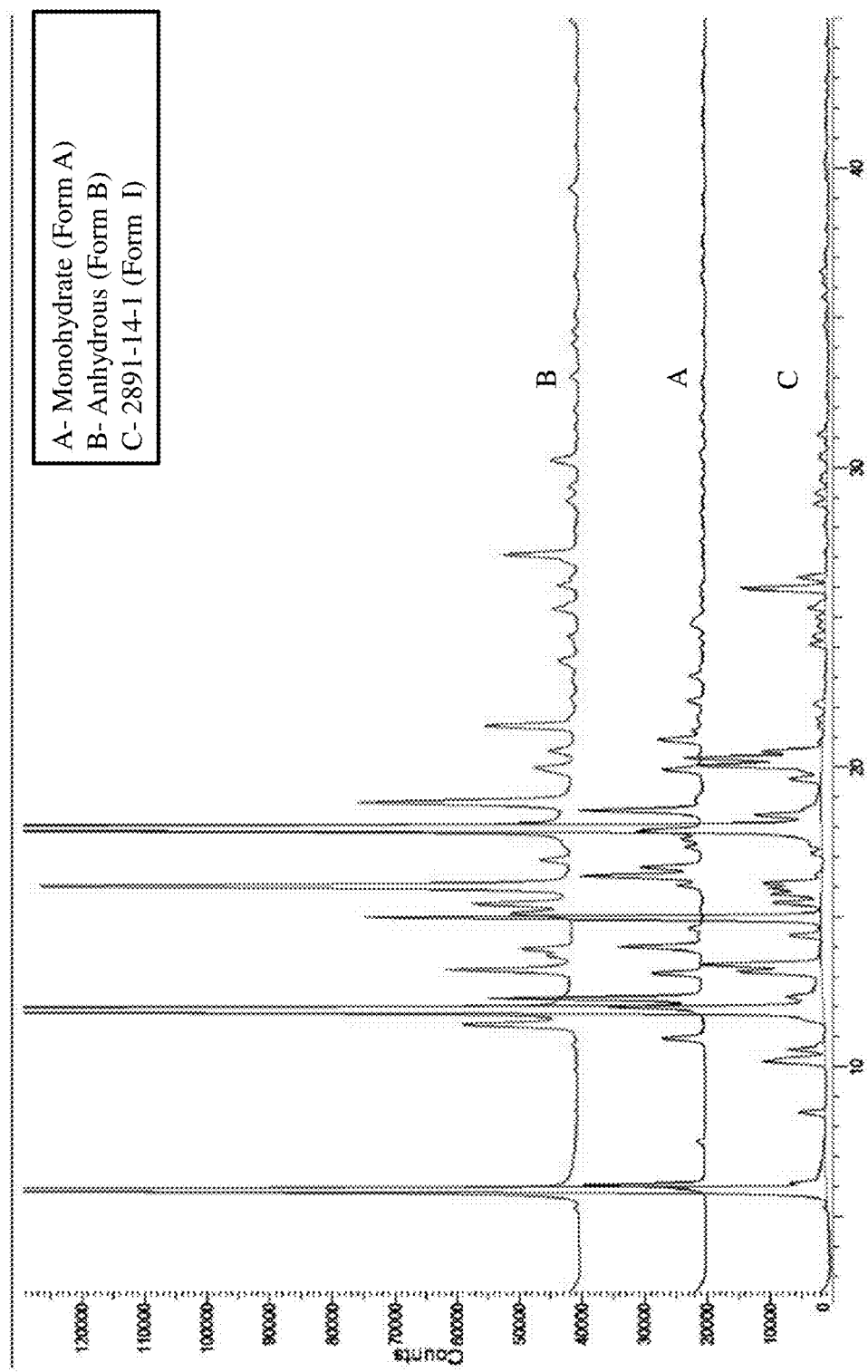
Figure 32:
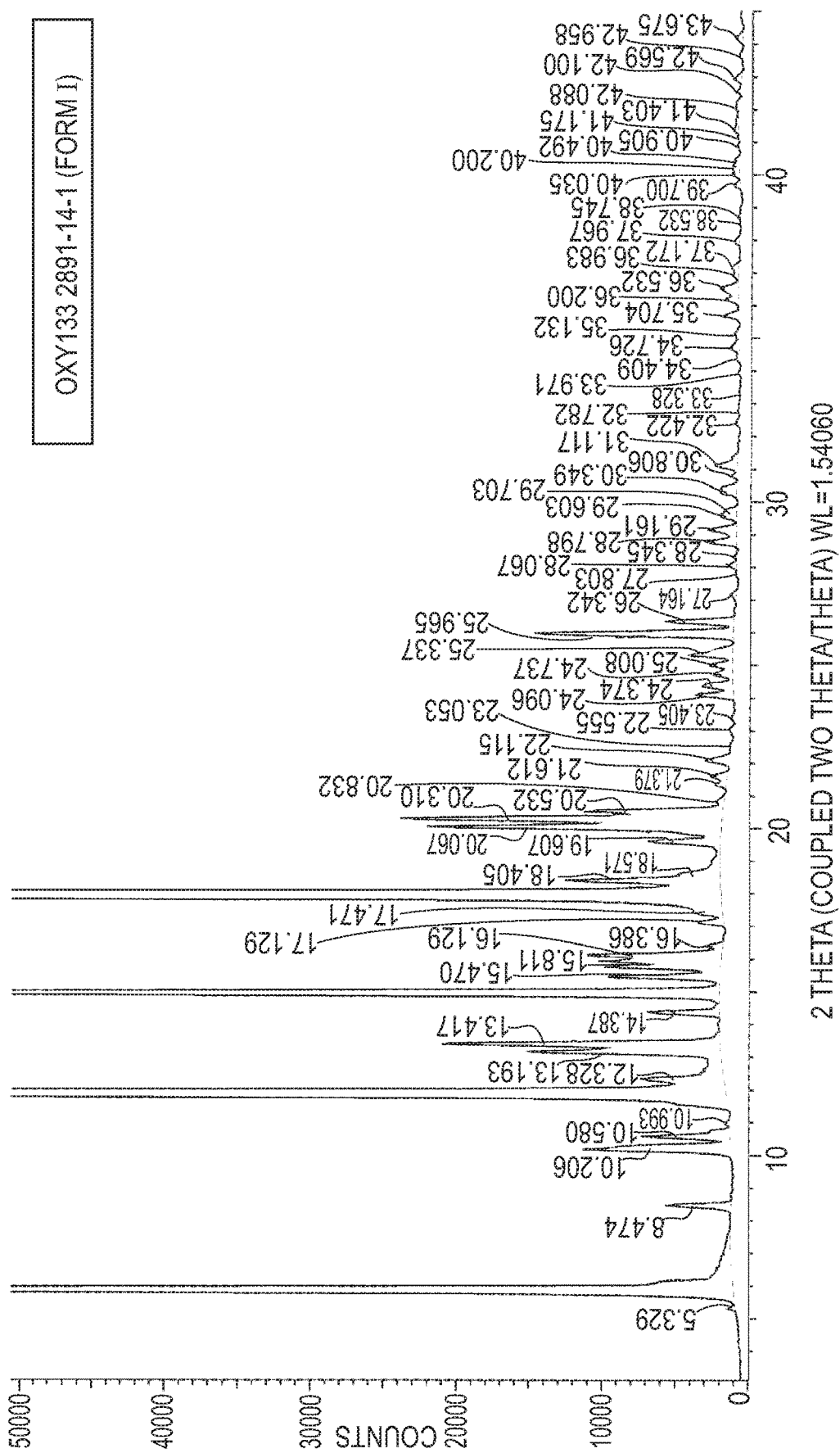
FIG. 32 is an XRPD of OXY133 polymorph Form I.

FIGS. 13A and 13B are XRPDs of OXY133 polymorph Form I formed by re-slurrying from a methanol/acetone/water solvent system or by recrystallization from acetone at 20° C., respectively. FIG. 32 is an XRPD of solid polymorph Form I obtained by acetone recrystallization at 20° C. Table 14, below lists data taken from the XRPD of FIG. 32. As illustrated in Table 14, OXY133 polymorph Form I can have one or more reflections of different relative intensities at index numbers 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, and 77.

TABLE 14

XRPD Data for OXY133 Polymorph Form I as illustrated in FIG. 32

| Index No. | Angle (2-Theta) | d Value (Angstrom) | Net Intensity (Counts) | Gross Intensity (Counts) | Rel. Intensity (%) |
|---|---|---|---|---|---|
| 0 | 5.32 | 16.59697 | 236 | 1104 | 0.10% |
| 1 | 5.905 | 14.95526 | 137036 | 138063 | 45.80% |
| 2 | 8.474 | 10.42561 | 2653 | 3812 | 0.90% |
| 3 | 10.206 | 8.66055 | 5408 | 6618 | 1.80% |
| 4 | 10.58 | 8.35469 | 3648 | 4893 | 1.20% |
| 5 | 10.993 | 8.04169 | 183 | 1445 | 0.10% |
| 6 | 11.921 | 7.41816 | 299152 | 300681 | 100.00% |
| 7 | 12.328 | 7.1739 | 3415 | 5083 | 1.10% |
| 8 | 13.193 | 6.70566 | 8128 | 10013 | 2.70% |
| 9 | 13.417 | 6.59395 | 12053 | 13977 | 4.00% |
| 10 | 14.387 | 6.15162 | 3020 | 5033 | 1.00% |
| 11 | 14.984 | 5.90766 | 46352 | 48356 | 15.50% |
| 12 | 15.47 | 5.72325 | 5158 | 7116 | 1.70% |
| 13 | 15.811 | 5.60052 | 4256 | 6162 | 1.40% |
| 14 | 16.129 | 5.49095 | 6107 | 7951 | 2.00% |
| 15 | 16.386 | 5.40518 | 691 | 2474 | 0.20% |
| 16 | 17.129 | 5.17241 | 1129 | 2847 | 0.40% |
| 17 | 17.471 | 5.0721 | 1286 | 3086 | 0.40% |
| 18 | 17.973 | 4.9314 | 273229 | 275118 | 91.30% |
| 19 | 18.405 | 4.81673 | 6960 | 8899 | 2.30% |
| 20 | 18.571 | 4.77395 | 1895 | 3845 | 0.60% |
| 21 | 19.607 | 4.52391 | 3256 | 5195 | 1.10% |
| 22 | 20.067 | 4.4214 | 13294 | 15178 | 4.40% |
| 23 | 20.31 | 4.36904 | 14645 | 16489 | 4.90% |
| 24 | 20.532 | 4.32223 | 6524 | 8323 | 2.20% |
| 25 | 20.832 | 4.26069 | 451 | 2180 | 0.20% |
| 26 | 21.379 | 4.15295 | 502 | 2081 | 0.20% |
| 27 | 21.612 | 4.10866 | 765 | 2276 | 0.30% |
| 28 | 22.115 | 4.01636 | 1077 | 2444 | 0.40% |
| 29 | 22.555 | 3.93886 | 70.6 | 1314 | 0.00% |
| 30 | 23.053 | 3.85501 | 161 | 1298 | 0.10% |
| 31 | 23.405 | 3.79778 | 131 | 1212 | 0.00% |
| 32 | 24.096 | 3.69039 | 1821 | 2936 | 0.60% |
| 33 | 24.374 | 3.64887 | 1336 | 2488 | 0.40% |
| 34 | 24.737 | 3.59615 | 754 | 1939 | 0.30% |
| 35 | 25.008 | 3.55782 | 1101 | 2297 | 0.40% |
| 36 | 25.337 | 3.51239 | 1882 | 3080 | 0.60% |
| 37 | 25.965 | 3.4288 | 9581 | 10738 | 3.20% |
| 38 | 26.342 | 3.38056 | 3315 | 4422 | 1.10% |
| 39 | 27.164 | 3.28019 | 306 | 1236 | 0.10% |
| 40 | 27.803 | 3.20623 | 53.8 | 928 | 0.00% |
| 41 | 28.067 | 3.17668 | 466 | 1362 | 0.20% |
| 42 | 28.345 | 3.14614 | 132 | 1041 | 0.00% |
| 43 | 28.798 | 3.09769 | 1581 | 2510 | 0.50% |
| 44 | 29.161 | 3.05993 | 1481 | 2423 | 0.50% |
| 45 | 29.603 | 3.01525 | 743 | 1676 | 0.20% |
| 46 | 29.703 | 3.00526 | 557 | 1485 | 0.20% |
| 47 | 30.349 | 2.94281 | 722 | 1640 | 0.20% |
| 48 | 30.806 | 2.90016 | 337 | 1256 | 0.10% |
| 49 | 31.117 | 2.87188 | 1129 | 2031 | 0.40% |
| 50 | 32.422 | 2.75919 | 139 | 928 | 0.00% |
| 51 | 32.782 | 2.72975 | 139 | 933 | 0.00% |
| 52 | 33.328 | 2.68623 | 83.8 | 851 | 0.00% |
| 53 | 33.971 | 2.63682 | 89.3 | 818 | 0.00% |
| 54 | 34.409 | 2.60426 | 191 | 955 | 0.10% |
| 55 | 34.726 | 2.58126 | 467 | 1263 | 0.20% |
| 56 | 35.132 | 2.55231 | 231 | 1049 | 0.10% |
| 57 | 35.704 | 2.51275 | 803 | 1656 | 0.30% |
| 58 | 36.2 | 2.47944 | 680 | 1571 | 0.20% |
| 59 | 36.532 | 2.45768 | 877 | 1774 | 0.30% |
| 60 | 36.983 | 2.42873 | 286 | 1166 | 0.10% |
| 61 | 37.172 | 2.41681 | 388 | 1253 | 0.10% |
| 62 | 37.967 | 2.36802 | 282 | 1088 | 0.10% |
| 63 | 38.532 | 2.33454 | 68.1 | 838 | 0.00% |
| 64 | 38.745 | 2.32221 | 188 | 945 | 0.10% |
| 65 | 39.7 | 2.26851 | 317 | 1087 | 0.10% |
| 66 | 40.035 | 2.25032 | 322 | 1137 | 0.10% |
| 67 | 40.26 | 2.23823 | 301 | 1137 | 0.10% |
| 68 | 40.432 | 2.22915 | 192 | 1040 | 0.10% |
| 69 | 40.905 | 2.20446 | 73.9 | 950 | 0.00% |
| 70 | 41.175 | 2.19058 | 97.6 | 990 | 0.00% |
| 71 | 41.403 | 2.17907 | 276 | 1175 | 0.10% |
| 72 | 42.088 | 2.14516 | 154 | 1027 | 0.10% |
| 73 | 42.186 | 2.14043 | 168 | 1033 | 0.10% |
| 74 | 42.569 | 2.12206 | 212 | 1030 | 0.10% |
| 75 | 42.958 | 2.10375 | 363 | 1114 | 0.10% |
| 76 | 43.675 | 2.07083 | 136 | 827 | 0.00% |
| 77 | 44.199 | 2.04749 | 287 | 971 | 0.10% |

The equipment utilized to collect the XRPD patterns depicted in FIGS. 2A-13B was a Bruker D8 Advance diffractometer using Cu radiation (40 kV, 25 mA) with a divergence slit of 0.3° (0.6 mm), wherein variable slits must be operated in fixed mode. The axial Soller slits, primary and secondary were each set at 2.50. The anti-scatter slit was set at 0.3° (0.6 mm). The secondary monochromator anti-scatter slit was set at 1 mm and the detector slit at 0.1 mm. If a secondary monochromator is not used, then a suitable β filter must be used, namely a Ni filter for Cu radiation. The linear detector LYNXEYE was set at 3° detector opening with the angle scanned from 2 to 45° 2θ.

Further, Table 15 below is a list of OXY133 polymorphs Forms A, B, C, D, E, F, G, H and I identified by a high performance liquid chromatography (HPLC) followed by charged aerosol detector (CAD) method. Table 15 also lists the starting products, the solvent system including solvent and anti-solvent, the temperature at which a polymorph was formed, the water content of the polymorph as determined by the Karl-Fisher (KF) method of water determination, and where available, the yield and purity of the resulting polymorph.

TABLE 15

HPLC Method: OXY133 Polymorphs (CAD)

| Item | Method | Sample | Processing Point | Temp (C.) | Scale | time (h) | KF | TGA (% LOD) | Crystal Form (XRPD) | Yield (%) | Purity (%) |
|---|---|---|---|---|---|---|---|---|---|---|---|
| 1 | OXY133 Anhydrous From Medtronic | 55352-23-07 | Solid | 20 | NA | NA | NA | 0.34 | Form B | NA | 96.88 |
| 2 | OXY133 Monohydrate From Medtronic | 82489-2-7-1 | Solid | 20 | NA | NA | 4.1 | 5.28 | Form A | NA | NA |
| 3 | Slurry of Form B in Water at 20° C. | 2891-1-1 | Slurry | 20 | 24.6 mg | 24 | NA | NA | Form E | NA | NA |
| 4 | Slurry of Form B in Water at 70° C. | 2891-1-4 | Slurry | 70 | 19.6 mg | 24 | NA | NA | Form E | NA | NA |
| 5 | Acetone/Water (1:1) at 20° C. | 2891-1-2 | Slurry | 20 | 28.0 mg | 24 | NA | NA | Form A | NA | NA |
| 6 | Acetone/Water (1:1) at 70° C. | 2891-1-5 | Slurry | 70 | 19.4 mg | 24 | NA | NA | Form C | NA | NA |
| 7 | MeOH/Water (1:1) at 20° C. | 2891-1-3 | Slurry | 20 | 22.5 mg | 24 | NA | NA | Form D | NA | NA |
| 8 | MeOH/Water (1:1) at 70° C. | 2891-2-1 | Slurry | 70 | 22.0 mg | 24 | NA | NA | Form D | NA | NA |
| 9 | Acetone/Water (1:1) Overhead stirring | 2891-3-1 | Slurry | 20 | 2.0 g | 22 | NA | NA | Form A + Form B | NA | NA |
| 10 | Acetone/Water (1:1) Overhead stirring | 2891-3-2 | Slurry | 20 | 2.0 g | 51 | NA | NA | Form A | NA | NA |
| 11 | Acetone/Water (1:1) Overhead stirring | 2891-3-4 | Solid after drying at 50° C | 50 | 2.0 g | NA | NA | 4.1 | Form A | 75.0 | NA |
| 12 | Acetone/Water (1:1) 30° C. | 2891-4-1 | Slurry | 30 | 2.0 g | 3 | NA | NA | Form C | NA | NA |
| 13 | Acetone/Water (1:1) 30° C. | 2891-4-2 | Slurry | 30 | 2.0 g | 23 | NA | NA | Form C | NA | NA |
| 14 | Acetone/Water (1:1) 30° C. | 2891-4-3 | Slurry | 30 | 2.0 g | 47 | NA | NA | Form C | NA | NA |
| 15 | Acetone/Water (1:1) 30° C. | 2891-4-4 | Solid after drying at 35° C. | 30 | 2.0 g | NA | NA | NA | Form C | 78.9 | NA |
| 16 | Acetone/Water (1:1) 40° C. | 2891-5-1 | Slurry | 40 | 2.0 g | 3 | NA | NA | Form C | NA | NA |
| 17 | Acetone/Water (1:1) 40° C. | 2891-5-2 | Slurry | 40 | 2.0 g | 23 | NA | NA | Form C | NA | NA |
| 18 | Acetone/Water (1:1) 40° C. | 2891-5-3 | Solid after drying at 35° C. | 40 | 2.0 g | NA | NA | NA | Form C | 80.9 | NA |
| 19 | Acetone/Water (1:1) 50° C. | 2891-6-1 | Slurry | 50 | 2.0 g | 3 | NA | NA | Form C | NA | NA |
| 20 | Acetone/Water (1:1) 50° C. | 2891-6-2 | Slurry | 50 | 2.0 g | 23 | NA | NA | Form C | NA | NA |
| 21 | Acetone/Water (1:1) 50° C. | 2891-6-3 | Solid after drying at 35° C. | 50 | 2.0 g | NA | NA | NA | Form C | 84.7 | NA |
| 22 | Acetone/Water (1:1) 60° C. | 2891-7-1 | Slurry | 60 | 2.0 g | 3 | NA | NA | Form C | NA | NA |
| 23 | Acetone/Water (1:1) 60° C. | 2891-7-2 | Slurry | 60 | 2.0 g | 23 | NA | NA | Form C | NA | NA |
| 24 | Acetone/Water (1:1) 60° C. | 2891-7-3 | Slurry | 10 | 2.0 g | 43 | NA | NA | Form C | NA | NA |
| 25 | Acetone/Water (1:1) 60° C. | 2891-7-4 | Slurry | 20 | 2.0 g | 65 | NA | 1.9 | Form C | NA | NA |

TABLE 15-continued

HPLC Method: OXY133 Polymorphs (CAD)

| Item | Method | Sample | Processing Point | Temp (C.) | Scale | time (h) | KF | TGA (% LOD) | Crystal Form (XRPD) | Yield (%) | Purity (%) |
|---|---|---|---|---|---|---|---|---|---|---|---|
| 26 | Acetone/Water (1:1) 60° C. | 2891-7-5 | Solid after drying at 35° C. | 20 | 2.0 g | NA | 1.45 | NA | Form C | 84.2 | NA |
| 27 | Acetone/Water (1:1) 0° C. | 2891-8-1 | Slurry | 0 | 2.0 g | 20 | NA | NA | Form A + Form B | NA | NA |
| 28 | Acetone/Water (1:1) 0° C. | 2891-8-2 | Slurry | 0 | 2.0 g | 46 | NA | NA | Form A | NA | NA |
| 29 | Acetone/Water (1:1) 0° C. | 2891-8-3 | Solid after drying at 35° C. | 35 | 2.0 g | NA | 3.25 | NA | Form A | 89.5 | 96.79 |
| 30 | Acetone/Water (1:1) 10° C. | 2891-9-1 | Slurry | 10 | 2.0 g | 20 | NA | NA | Form A + Form B | NA | NA |
| 31 | Acetone/Water (1:1) 10° C. | 2891-9-2 | Slurry | 10 | 2.0 g | 46 | NA | NA | Form A | NA | NA |
| 32 | Acetone/Water (1:1) 10° C. | 2891-9-3 | Solid after drying at 35° C. | 35 | 2.0 g | NA | 3.83 | NA | Form A | 99.0 | 96.75 |
| 33 | Acetone/Water (1:1) 25° C. | 2891-10-1 | Slurry | 25 | 2.0 g | 20 | NA | NA | Form A + Form B | NA | NA |
| 34 | Acetone/Water (1:1) 25° C. | 2891-10-2 | Slurry | 25 | 2.0 g | 46 | NA | NA | Form A | NA | NA |
| 35 | Acetone/Water (1:1) 25° C. | 2891-10-3 | Solid after drying at 35° C. | 35 | 2.0 g | NA | 4.02 | NA | Form A | 82.6 | 96.97 |
| 36 | Acetone/Water Dissolution/ Precipitation | 2891-12-1 | Slurry after charging water | 15 | 4.0 g | 0 | NA | NA | Form F | NA | NA |
| 37 | Acetone/Water Dissolution/ Precipitation | 2891-12-2 | Slurry | 5 | 4.0 g | 20 | NA | NA | Form F | NA | NA |
| 38 | Acetone/Water Dissolution/ Precipitation | 2891-12-3 | Slurry | 5 | 4.0 g | 45 | NA | NA | Form F | NA | NA |
| 39 | Acetone Recrystallization | 2891-14-1 | Solid | 20 | 2.0 g | 1 | NA | NA | Form I | NA | 98.87 |
| 40 | THF/Acetone/Water Crystallization | 2891-16-1 | Solid before drying | 35 | 4.0 g | NA | NA | NA | Form A | NA | NA |
| 41 | THF/Acetone/Water Crystallization | 2891-16-2 | Solid after drying at 35° C. | 35 | 4.0 g | NA | 3.37 | NA | Form A | 60.0 | 99.31 |
| 42 | THF/Water (1:2) | 2891-17-1 | Oil/Slurry | 20 | 5.0 g | NA | NA | NA | Form A | NA | NA |
| 43 | THF/Water (1:2) | 2891-17-3 | Solid after drying at 35° C. | 35 | 5.0 g | NA | 2.71 | NA | Form A | 90.4 | 96.57 |
| 44 | MeOH/Acetone/Water | 2891-13-3 | Slurry | 20 | 165 mg | 1 | NA | NA | Form I | NA | NA |
| 45 | IPA/Water (1:1) Crystallization | 2891-18-2 | Slurry | 20 | 102 mg | 0 | NA | NA | Form A | NA | NA |
| 46 | IPA/Water (1:1) Crystallization | 2891-18-3 | Solid | 20 | 102 mg | 1 | NA | NA | Form A | NA | NA |
| 47 | IPA/Water (1:2) Crystallization 0° C. | 2891-20-1 | Solid after drying at 20° C. | 0 | 2.0 g | 1 | 4.1 | 4.51 | Form A | 85.0 | |
| 48 | IPA/Water (1:2) Crystallization 10° C. | 2891-21-1 | Solid after drying at 20° C. | 10 | 2.0 g | 1 | 4.04 | 4.95 | Form A | 77.0 | |
| 49 | IPA/Water (1:2) Crystallization 15° C. | 2891-19-1 | Solid after drying at 20° C. | 20 | 2.0 g | 1 | NA | NA | Form A | 73.0 | 97.94 |
| 50 | IPA/Water (1:2) Crystallization 20° C. | 2891-22-1 | Solid after drying at 20° C. | 20 | 2.0 g | 1 | 3.9 | 4.42 | Form A | 79.0 | |
| 51 | IPA/Water (1:2) Crystallization 30° C. | 2891-23-1 | Solid after drying at 20° C. | 30 | 2.0 g | 1 | 4.1 | 4.37 | Form A + Unknown | 79.0 | |
| 52 | IPA/Water (1:2) Crystallization 40° C. | 2891-24-1 | Solid after drying at 20° C. | 40 | 2.0 g | 1 | 0.99 | 1.23 | Form G | 87.0 | |
| 53 | IPA/Water (1:2) Conversion of Hemihydrate | 2891-25-1 | Solid after drying at 20° C. | 5 | 2.0 g | 18 | 4.07 | 4.5 | Form A | 90.0 | 97.08 |

TABLE 15-continued

| | | | | Temp | | time | | TGA | Crystal Form | Yield | Purity |
|---|---|---|---|---|---|---|---|---|---|---|---|
| Item | Method | Sample | Processing Point | (C.) | Scale | (h) | KF | (% LOD) | (XRPD) | (%) | (%) |
| 54 | IPA/Water (1:2) Crystallization −10° C. | 2891-26-1 | Solid after drying at 20° C. | −10 | 2.0 g | 18 | 1.61 | 5.54 | Form H | 87.0 | 97.27 |
| 55 | IPA/Water (1:2) 30 min addition of Water | 2891-27-1 | Solid after drying at 20° C. | 5 | 2.0 g | 18 | 4.05 | 4.65 | Form A | 88.0 | 97.03 |
| 56 | IPA/Water (1:2) 120 min addition of Water | 2891-28-1 | Solid after drying at 20° C. | 5 | 2.0 g | 18 | 4.07 | 4.76 | Form A | 94.0 | 97.16 |

NA—Not Available
ND—Not Determined
KF—water content determined by Karl Fischer water determination method Table 16 below correlates OXY133 polymorph Forms A to I with impurities found in some of these crystal forms.

TABLE 16

HPLC Method: OXY133 Polymorph Impurities (CAD)

| | | | | | | Area Percent (AP) | | | |
|---|---|---|---|---|---|---|---|---|---|
| | | | | | | OXY133 | Imp-1 | Imp-2 | Imp-3 |
| | | | | | | | rt (min) | | |
| | | | | | Crystal | 12.97 | 14.64 | 17.12 | 17.3 |
| | | | | Temp | Form | | rtt | | |
| Item | Method | Sample | Processing Point | (C.) | (XRPD) | 1.00 | 1.13 | 1.32 | 1.33 |
| 1 | OXY133 Anhydrous From Medtronic | 55352-23-07 | Solid | 20 | Form B | 96.88 | 2.35 | 0.77 | ND |
| 2 | OXY133 Monohydrate From Medtronic | 82489-2-7-1 | Solid | 20 | Form A | | | | |
| 3 | Slurry of Form B in Water at 20° C. | 2891-1-1 | Slurry | 20 | Form E | | | | |
| 4 | Slurry of Form B in Water at 70° C. | 2891-1-4 | Slurry | 70 | Form E | | | | |
| 5 | Acetone/Water (1:1) at 20° C. | 2891-1-2 | Slurry | 20 | Form A | | | | |
| 6 | Acetone/Water (1:1) at 70° C. | 2891-1-5 | Slurry | 70 | Form C | | | | |
| 7 | MeOH/Water (1:1) at 20° C. | 2891-1-3 | Slurry | 20 | Form D | | | | |
| 8 | MeOH/Water (1:1) at 70° C. | 2891-2-1 | Slurry | 70 | Form D | | | | |
| 9 | Acetone/Water (1:1) Overhead stirring | 2891-3-1 | Slurry | 20 | Form A + Form B | | | | |
| 10 | Acetone/Water (1:1) Overhead stirring | 2891-3-2 | Slurry | 20 | Form A | | | | |
| 11 | Acetone/Water (1:1) Overhead stirring | 2891-3-4 | Solid after drying at 50° C. | 50 | Form A | | | | |
| 12 | Acetone/Water (1:1) 30° C. | 2891-4-1 | Slurry | 30 | Form C | | | | |
| 13 | Acetone/Water (1:1) 30° C. | 2891-4-2 | Slurry | 30 | Form C | | | | |
| 14 | Acetone/Water (1:1) 30° C. | 2891-4-3 | Slurry | 30 | Form C | | | | |
| 15 | Acetone/Water (1:1) 30° C. | 2891-4-4 | Solid after drying at 35° C. | 30 | Form C | | | | |
| 16 | Acetone/Water (1:1) 40° C. | 2891-5-1 | Slurry | 40 | Form C | | | | |
| 17 | Acetone/Water (1:1) 40° C. | 2891-5-2 | Slurry | 40 | Form C | | | | |
| 18 | Acetone/Water (1:1) 40° C. | 2891-5-3 | Solid after drying at 35° C. | 40 | Form C | | | | |
| 19 | Acetone/Water (1:1) 50° C. | 2891-6-1 | Slurry | 50 | Form C | | | | |
| 20 | Acetone/Water (1:1) 50° C. | 2891-6-2 | Slurry | 50 | Form C | | | | |

TABLE 16-continued

HPLC Method: OXY133 Polymorph Impurities (CAD)

| | | | | | | Area Percent (AP) | | | |
|---|---|---|---|---|---|---|---|---|---|
| | | | | | | OXY133 | Imp-1 | Imp-2 | Imp-3 |
| | | | | | | | rt (min) | | |
| | | | | | Crystal | 12.97 | 14.64 | 17.12 | 17.3 |
| | | | | Temp | Form | | rtt | | |
| Item | Method | Sample | Processing Point | (C.) | (XRPD) | 1.00 | 1.13 | 1.32 | 1.33 |
| 21 | Acetone/Water (1:1) 50° C. | 2891-6-3 | Solid after drying at 35° C. | 50 | Form C | | | | |
| 22 | Acetone/Water (1:1) 60° C. | 2891-7-1 | Slurry | 60 | Form C | | | | |
| 23 | Acetone/Water (1:1) 60° C. | 2891-7-2 | Slurry | 60 | Form C | | | | |
| 24 | Acetone/Water (1:1) 60° C. | 2891-7-3 | Slurry | 10 | Form C | | | | |
| 25 | Acetone/Water (1:1) 60° C. | 2891-7-4 | Slurry | 20 | Form C | | | | |
| 26 | Acetone/Water (1:1) 60° C. | 2891-7-5 | Solid after drying at 35° C. | 20 | Form C | | | | |
| 27 | Acetone/Water (1:1) 0° C. | 2891-8-1 | Slurry | 0 | Form A + Form B | | | | |
| 28 | Acetone/Water (1:1) 0° C. | 2891-8-2 | Slurry | 0 | Form A | | | | |
| 29 | Acetone/Water (1:1) 0° C. | 2891-8-3 | Solid after drying at 35° C. | 35 | Form A | 96.79 | 2.44 | 0.77 | ND |
| 30 | Acetone/Water (1:1) 10° C. | 2891-9-1 | Slurry | 10 | Form A + Form B | | | | |
| 31 | Acetone/Water (1:1) 10° C. | 2891-9-2 | Slurry | 10 | Form A | | | | |
| 32 | Acetone/Water (1:1) 10° C. | 2891-9-3 | Solid after drying at 35° C. | 35 | Form A | 96.75 | 2.30 | 0.92 | ND |
| 33 | Acetone/Water (1:1) 25° C. | 2891-10-1 | Slurry | 25 | Form A + Form B | | | | |
| 34 | Acetone/Water (1:1) 25° C. | 2891-10-2 | Slurry | 25 | Form A | | | | |
| 35 | Acetone/Water (1:1) 25° C. | 2891-10-3 | Solid after drying at 35° C. | 35 | Form A | 96.97 | 2.25 | 0.78 | ND |
| 36 | Acetone/Water Dissolution/ Precipitation | 2891-12-1 | Slurry after charging water | 15 | Form F | | | | |
| 37 | Acetone/Water Dissolution/ Precipitation | 2891-12-2 | Slurry | 5 | Form F | | | | |
| 38 | Acetone/Water Dissolution/ Precipitation | 2891-12-3 | Slurry | 5 | Form F | | | | |
| 39 | Acetone Recrystallization | 2891-14-1 | Solid | 20 | Form I | 98.87 | ND | 1.13 | ND |
| 40 | THF/Acetone/ Water Crystallization | 2891-16-1 | Solid before drying | 35 | Form A | | | | |
| 41 | THF/Acetone/ Water Crystallization | 2891-16-2 | Solid after drying at 35° C. | 35 | Form A | 99.31 | ND | 0.67 | ND |
| 42 | THF/Water (1:2) | 2891-17-1 | Oil/Slurry | 20 | Form A | | | | |
| 43 | THF/Water (1:2) | 2891-17-3 | Solid after drying at 35° C. | 35 | Form A | 96.57 | 2.18 | 0.76 | 0.48 |
| 44 | MeOH/Acetone/Water | 2891-13-3 | Slurry | 20 | Form I | | | | |
| 45 | IPA/Water (1:1) Crystallization | 2891-18-2 | Slurry | 20 | Form A | | | | |
| 46 | IPA/Water (1:1) Crystallization | 2891-18-3 | Solid | 20 | Form A | | | | |
| 47 | IPA/ Water (1:2) Crystallization 0° C. | 2891-20-1 | Solid after drying at 20° C. | 0 | Form A | | | | |
| 48 | IPA/Water (1:2) Crystallization 10° C. | 2891-21-1 | Solid after drying at 20° C. | 10 | Form A | | | | |
| 49 | IPA/Water (1:2) Crystallization 15° C. | 2891-19-1 | Solid after drying at 20° C. | 20 | Form A | 97.94 | 1.15 | 0.91 | ND |
| 50 | IPA/Water (1:2) Crystallization 20° C. | 2891-22-1 | Solid after drying at 20° C. | 20 | Form A | | | | |
| 51 | IPA/Water (1:2) Crystallization 30° C. | 2891-23-1 | Solid after drying at 20° C. | 30 | Form A + Unknown | | | | |
| 52 | IPA/Water (1:2) Crystallization 40° C. | 2891-24-1 | Solid after drying at 20° C. | 40 | Form G | | | | |
| 53 | IPA/Water (1:2) Conversion of Hemihydrate | 2891-25-1 | Solid after drying at 20° C. | 5 | Form A | 97.08 | 2.12 | 0.80 | ND |

TABLE 16-continued

HPLC Method: OXY133 Polymorph Impurities (CAD)

| | | | | | Area Percent (AP) | | | |
|---|---|---|---|---|---|---|---|---|
| | | | | | OXY133 | Imp-1 | Imp-2 | Imp-3 |
| | | | | | | rt (min) | | |
| | | | | Crystal | 12.97 | 14.64 | 17.12 | 17.3 |
| | | | Temp | Form | | rtt | | |
| Item | Method | Sample | Processing Point | (C.) | (XRPD) | 1.00 | 1.13 | 1.32 | 1.33 |
| 54 | IPA/Water (1:2) Crystallization −10° C. | 2891-26-1 | Solid after drying at 20° C. | −10 | Form H | 97.27 | 2.02 | 0.72 | ND |
| 55 | IPA/Water (1:2) 30 min addition of Water | 2891-27-1 | Solid after drying at 20° C. | 5 | Form A | 97.03 | 2.33 | 0.65 | ND |
| 56 | IPA/Water (1:2) 120 min addition of Water | 2891-28-1 | Solid after drying at 20° C. | 5 | Form A | 97.16 | 2.12 | 0.72 | ND |

NA—Not Available
ND—Not Determined
rt—Retention Time
rrt—Relative Retention Time The HPLC-CAD data summarized in Tables 15 and 16 above was collected on a HPLC Agilent 1100 instrument equipped with a Waters XBridge phenyl, 4.6 mm by 150 mm, 3.5 μm column, at a column temperature of 40±2° C., the mobile phases, MPA and MPB were 100% water and methanol (MeOH), respectively, and the flow rate was 1.0 mL/min.

The CAD equipment utilized for the experimental work of this disclosure was Dionex Corona ultra RS, wherein the unit settings included a range of 100 pA, offset of 0, and no filter. The CAD's nebulizer temperature was 35±5° C. and the gas pressure about 35 psi. The HPLC's sample tray was kept at ambient temperature, the injection volume was 5 μl, the needle wash used was the method diluent, the run time 35 minutes and the retention time for OXY133 approximately 13.1 minutes.

Figure 14:
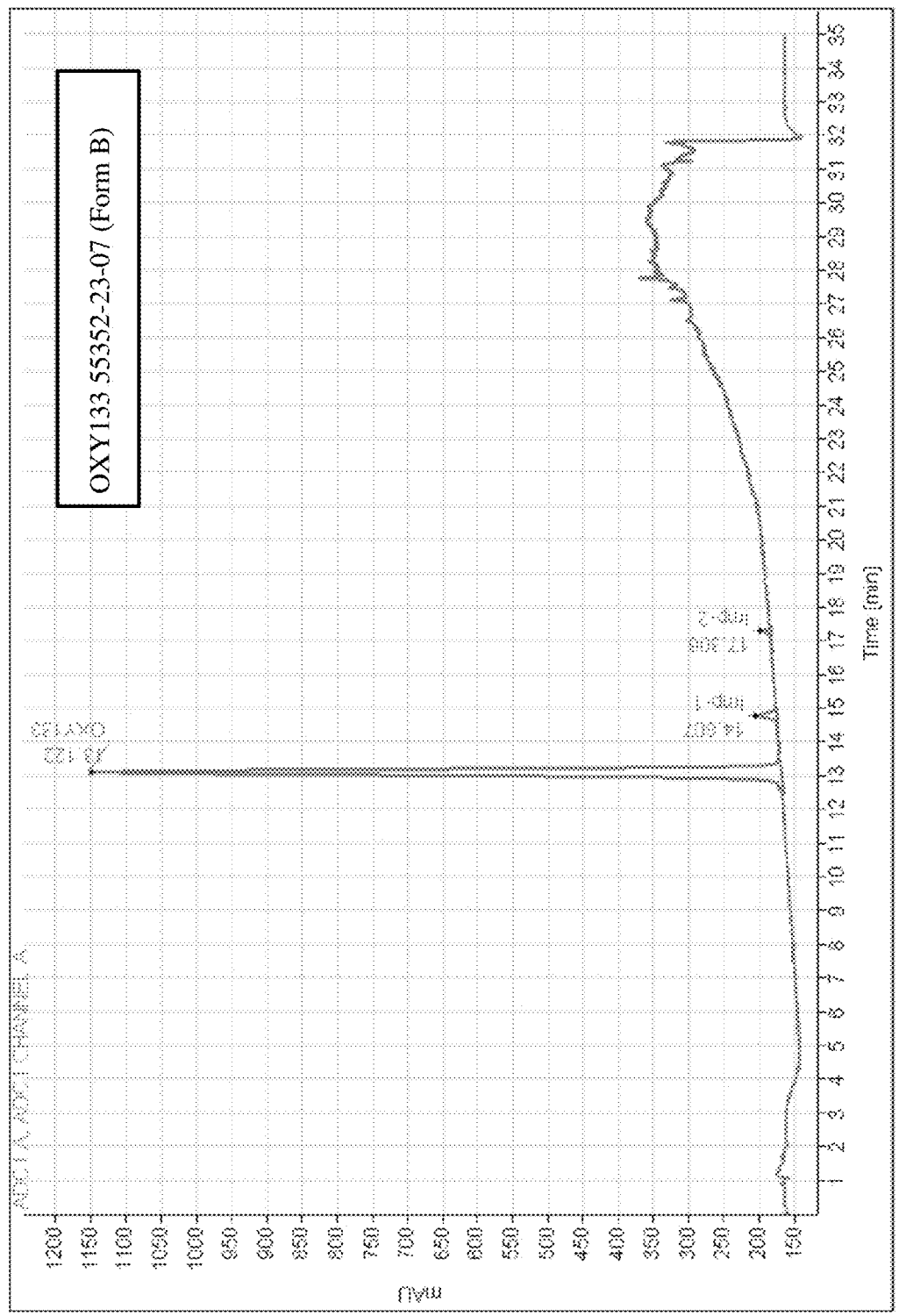
FIG. 14 is an HPLC/CAD single injection report of OXY133 polymorph Form B.
Figure 15A:
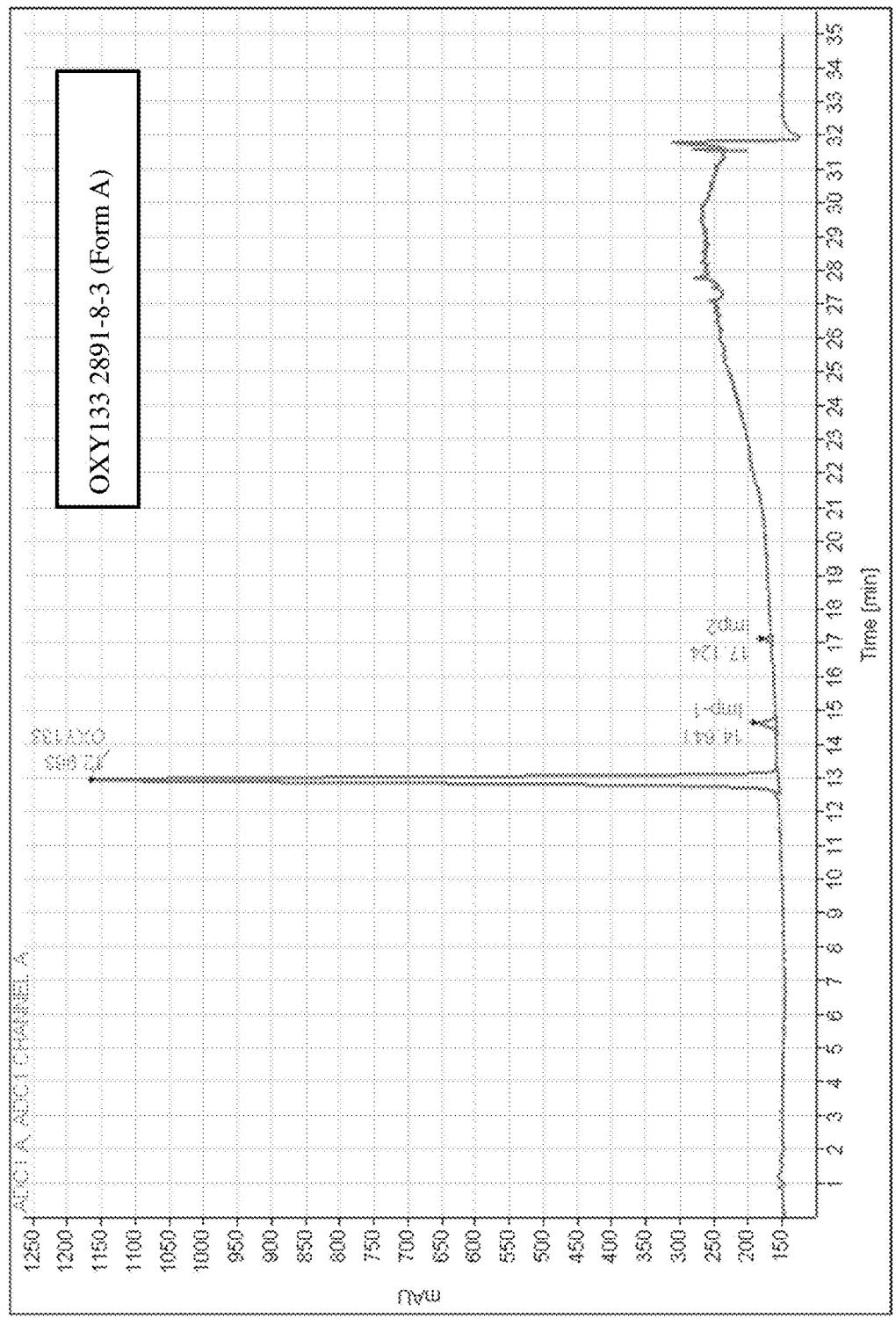
FIGS. 15A, 15B, 15C, 15D, 15E, 15F, 15G, 15H and 15I are HPLC/CAD single injection reports of OXY133 polymorph Form A.
Figure 15B:
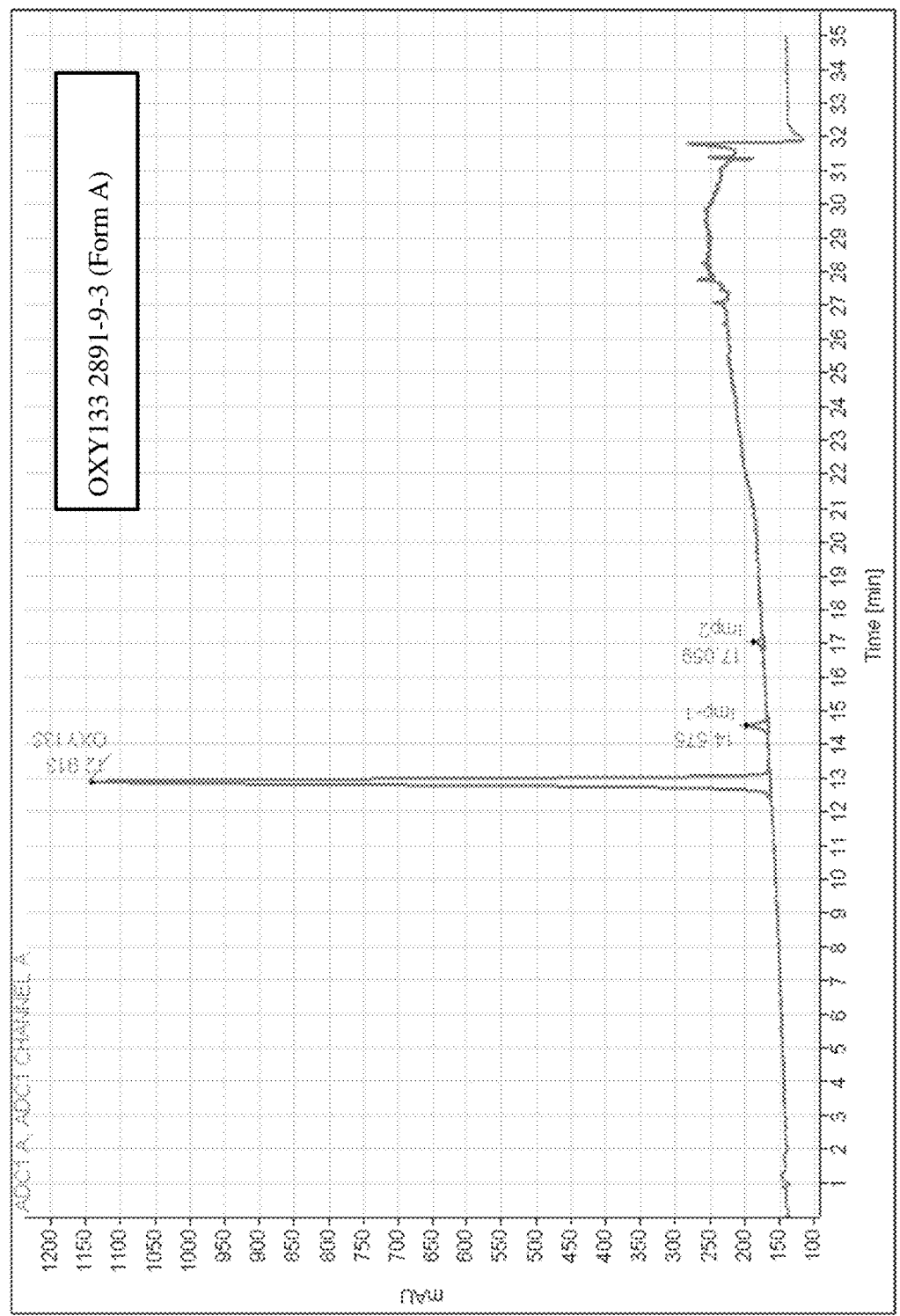
Figure 15C:
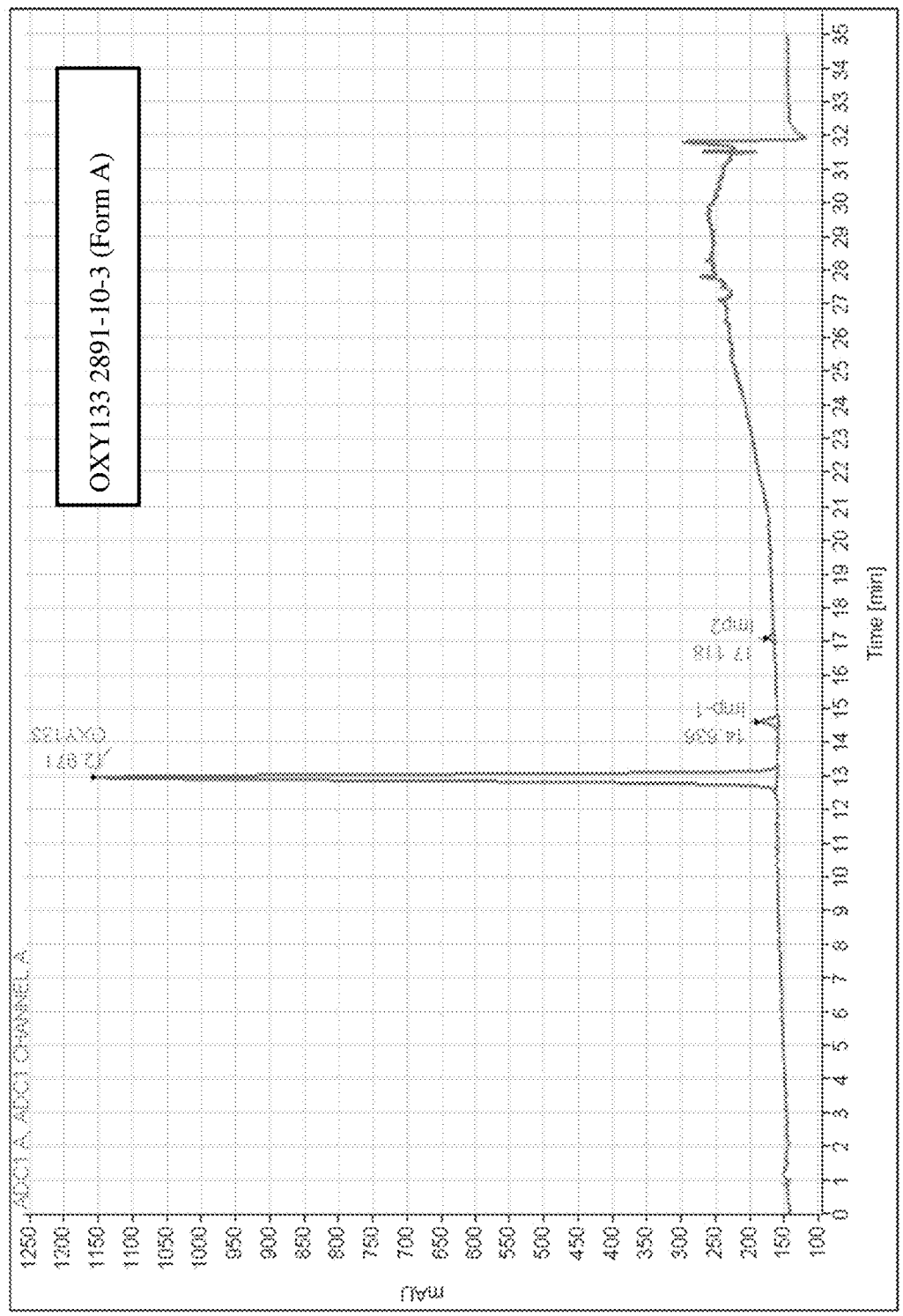
Figure 15D:
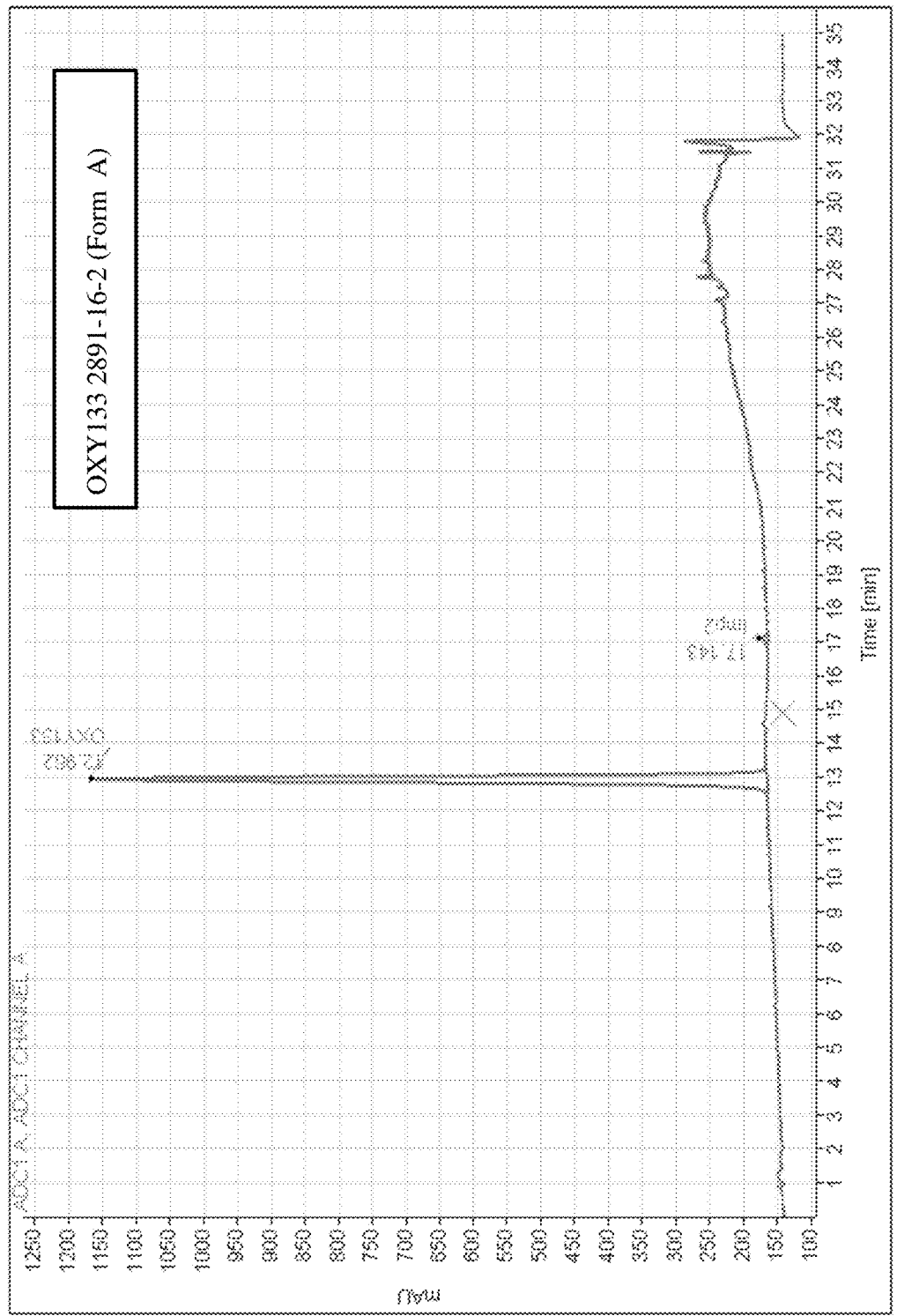
Figure 15E:
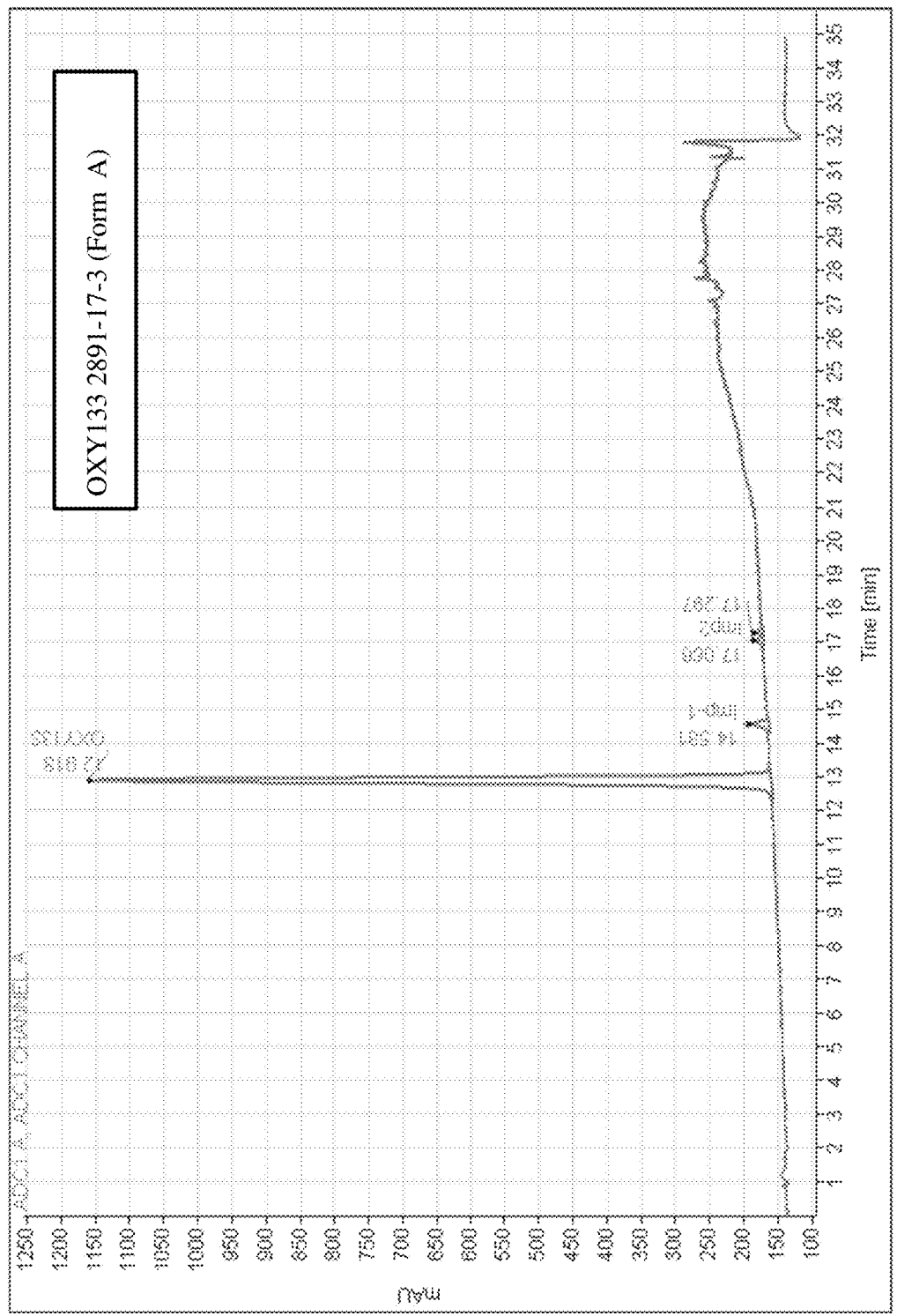
Figure 15F:
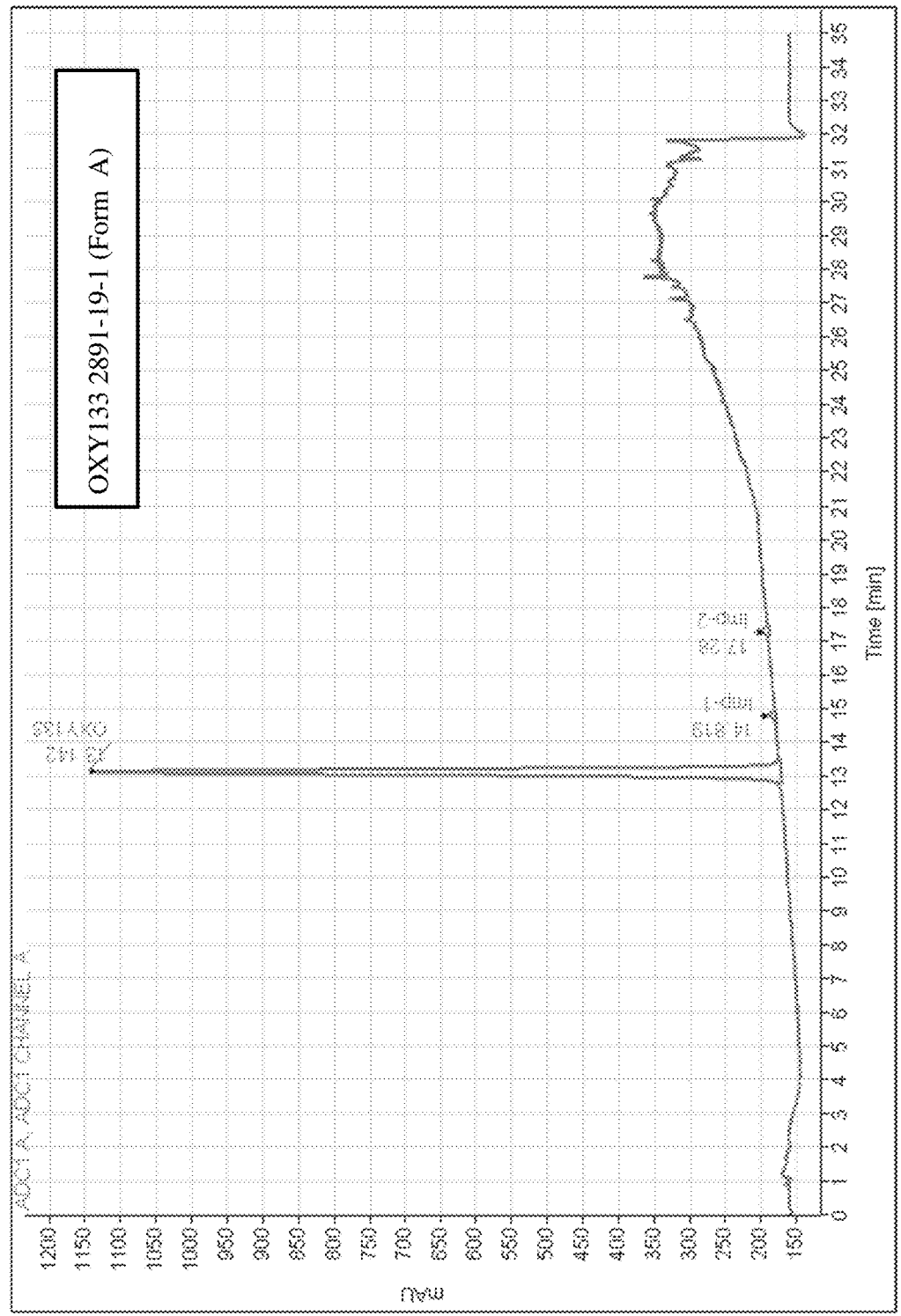
Figure 15G:
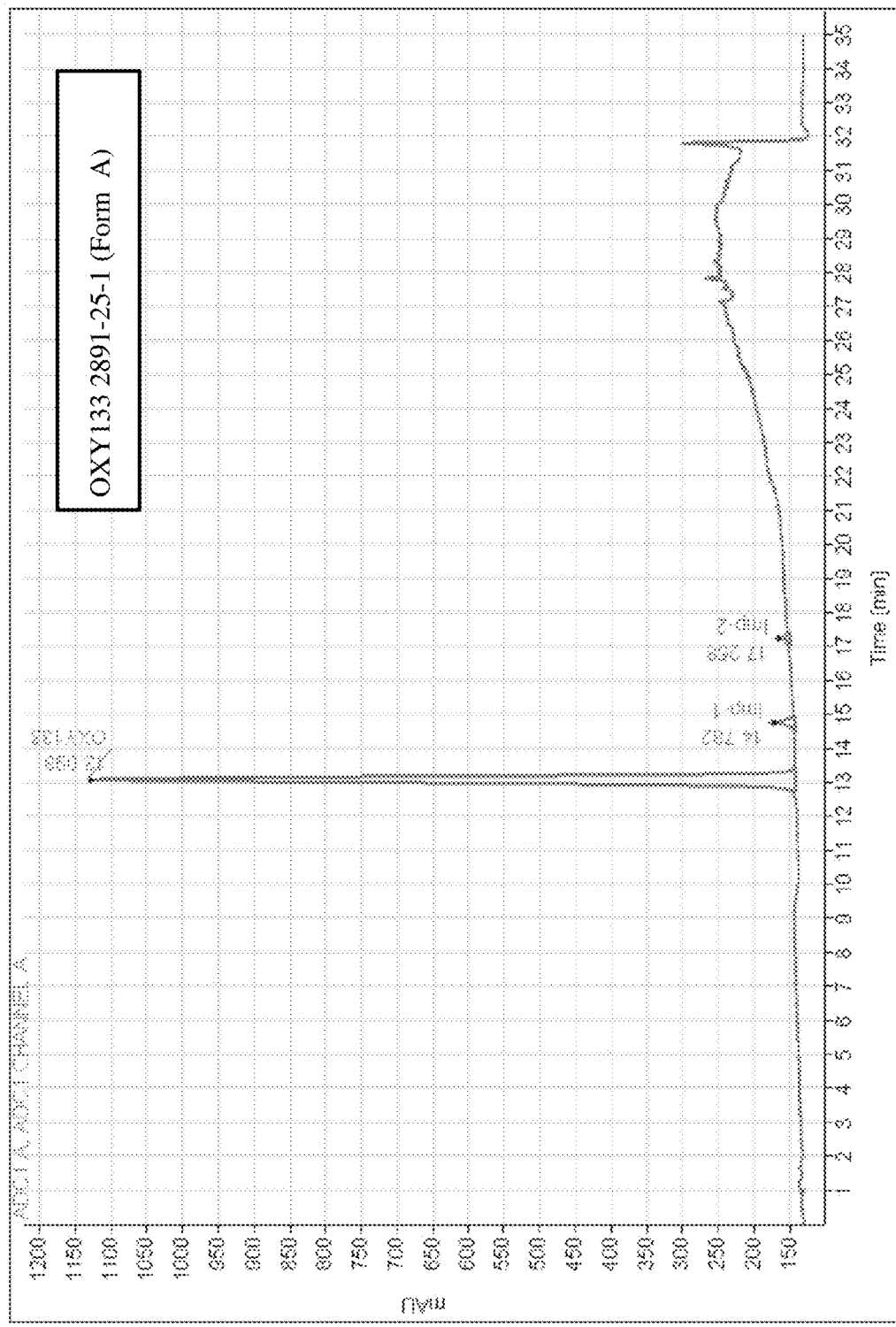
Figure 15H:
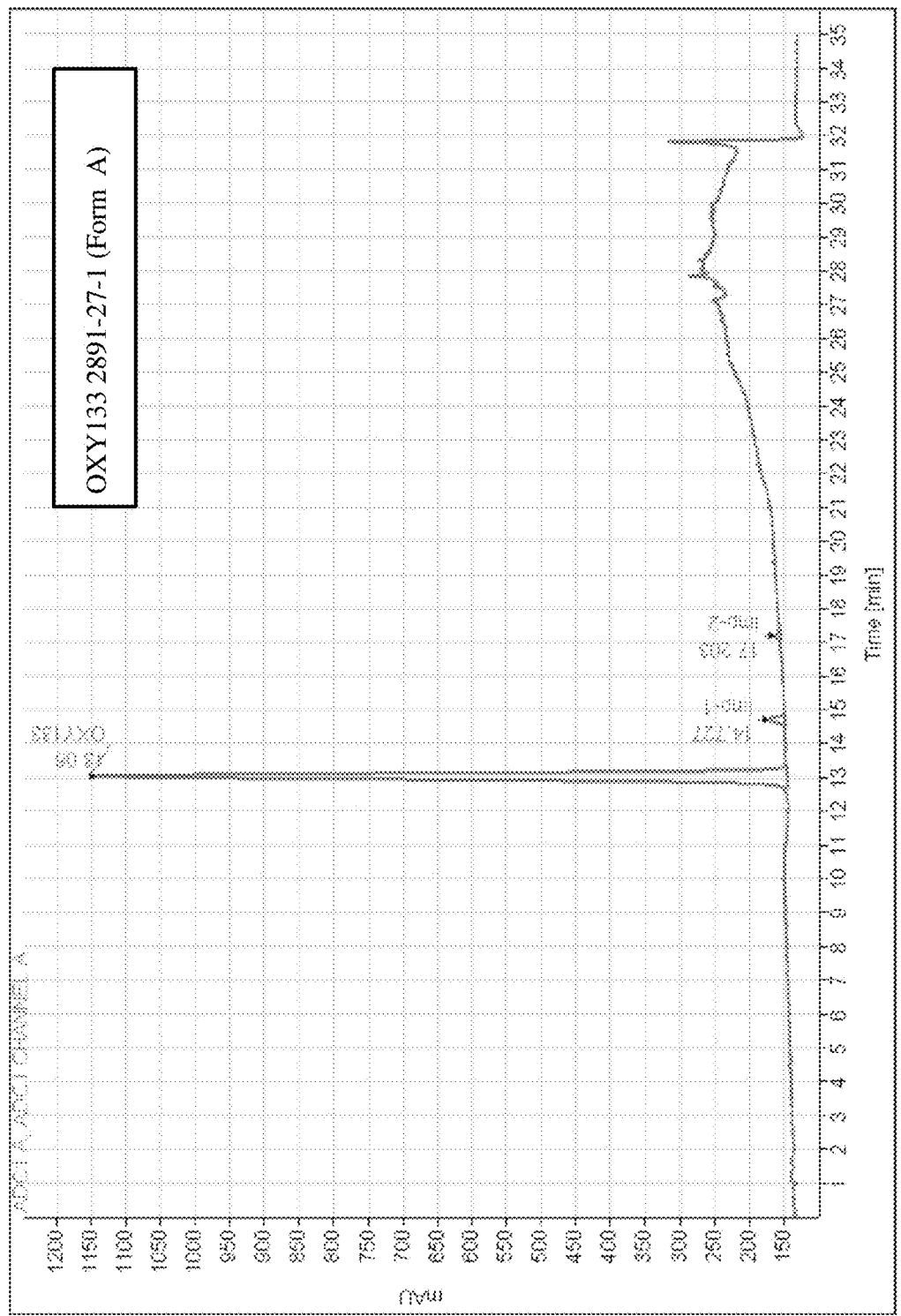
Figure 15I:
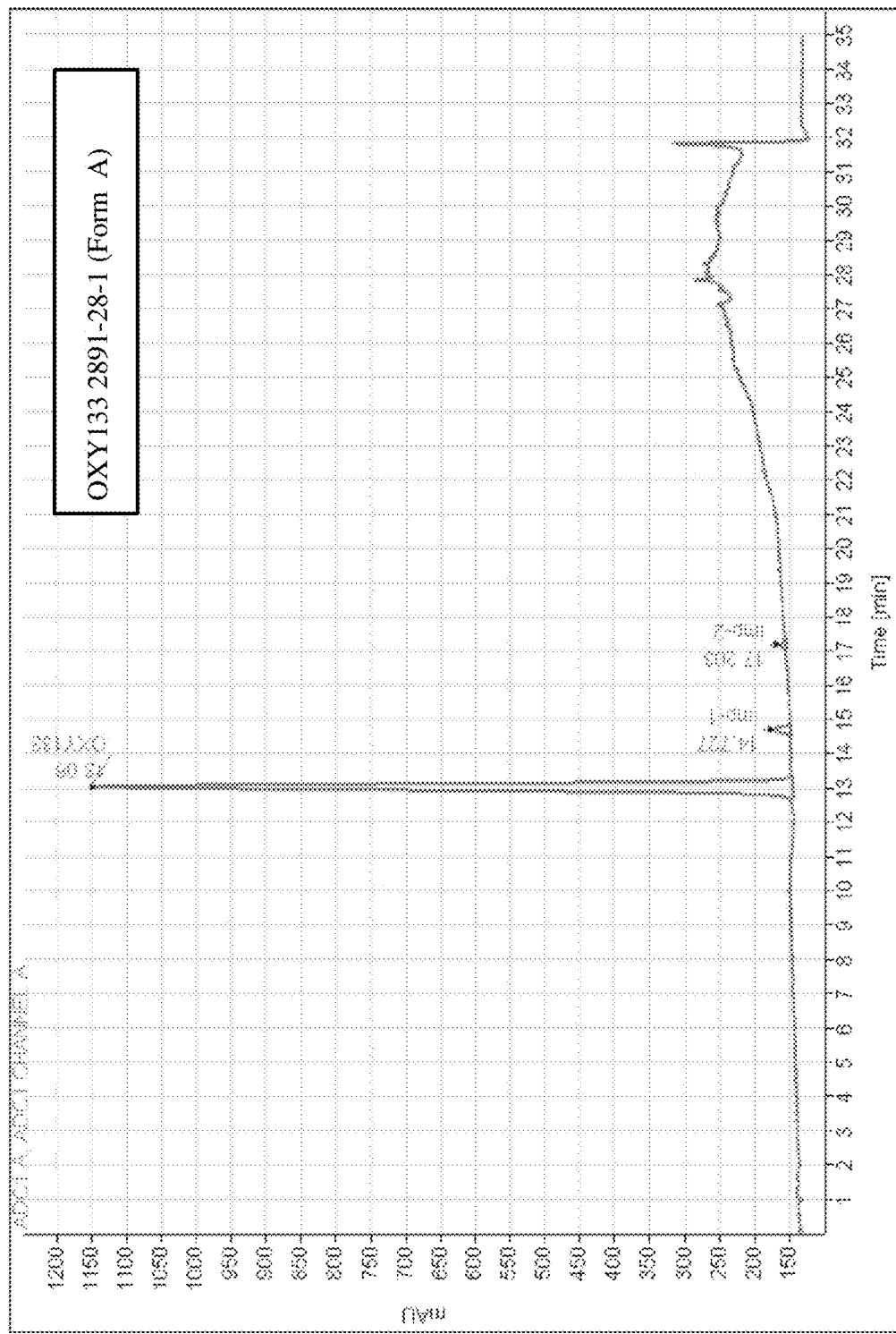
Figure 16:
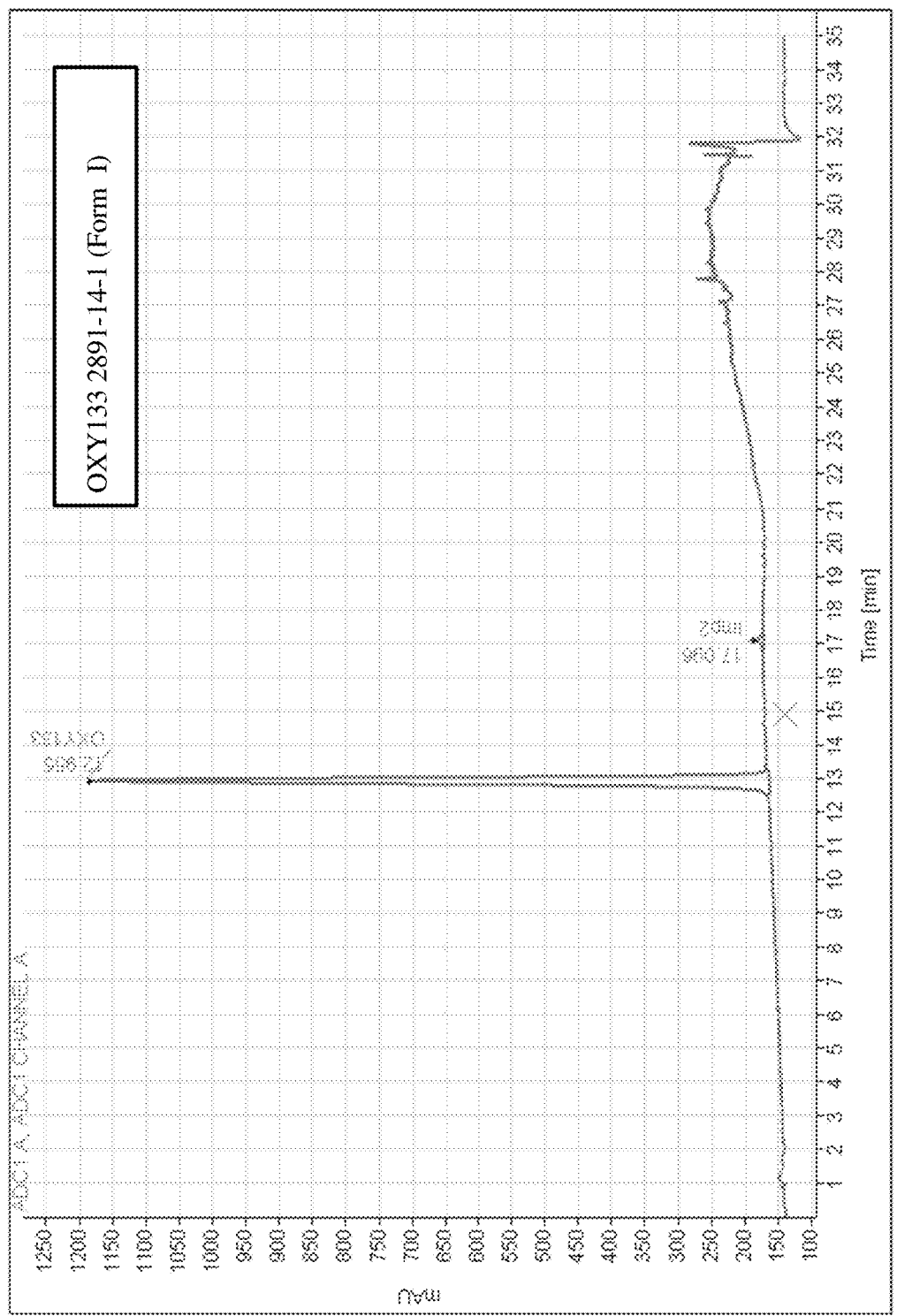
FIG. 16 is a HPLC/CAD single injection report of OXY133 polymorph Form I.
Figure 17:
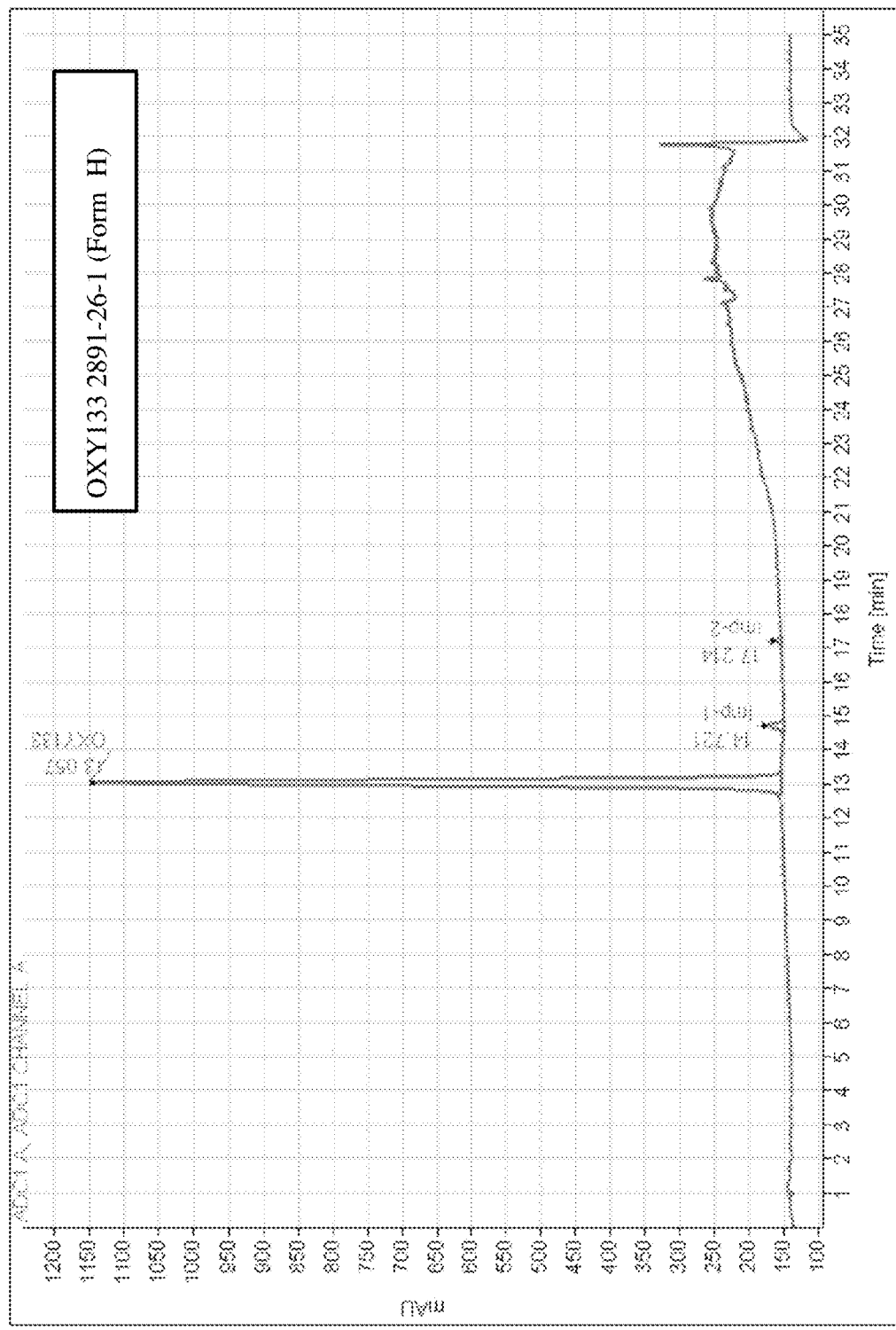
FIG. 17 is a HPLC/CAD single injection report of OXY133 polymorph Form H.
Figure 18:
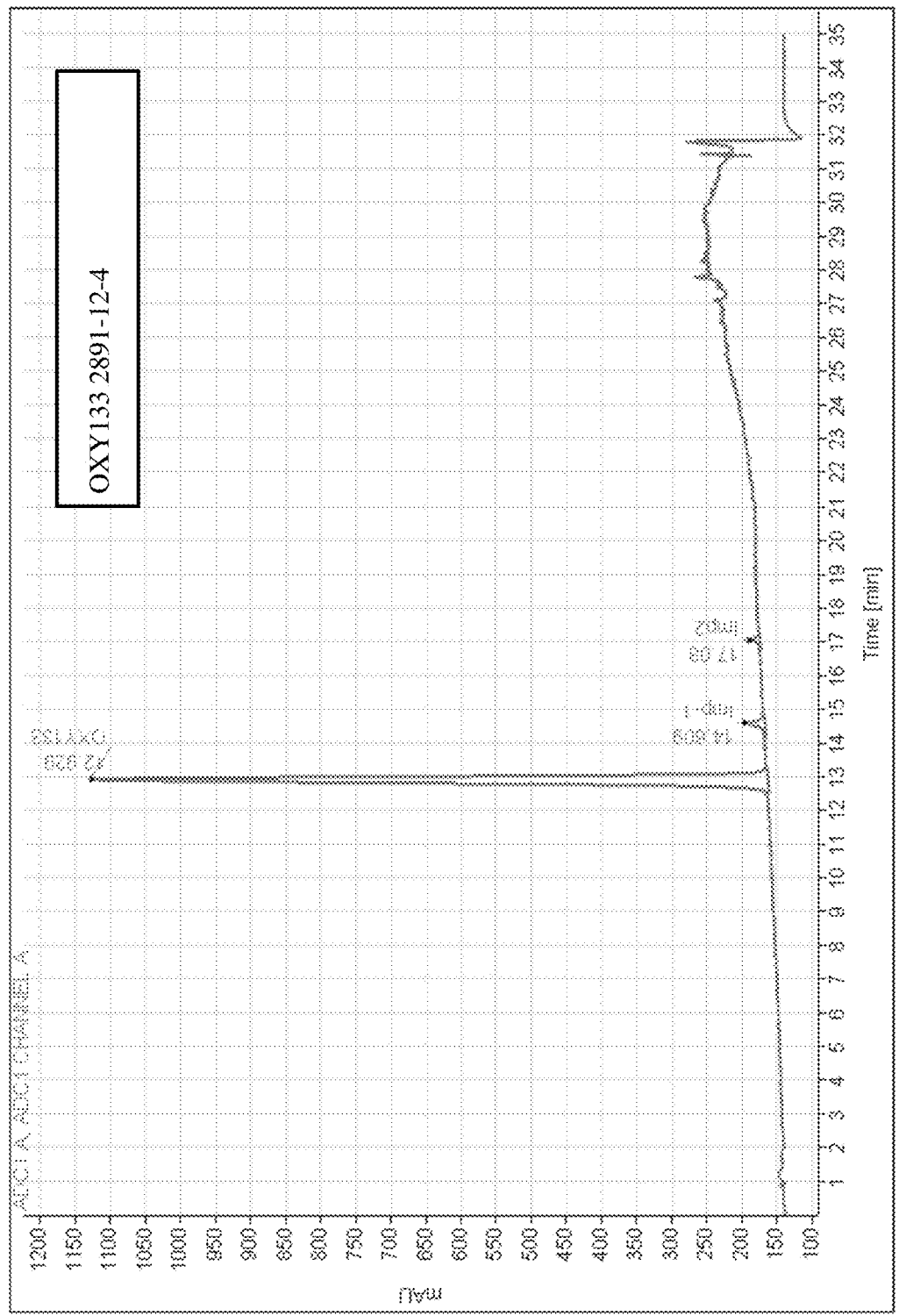
FIG. 18 is a HPLC/CAD single injection report of OXY133 sample 2891-12-4.
Figure 19:
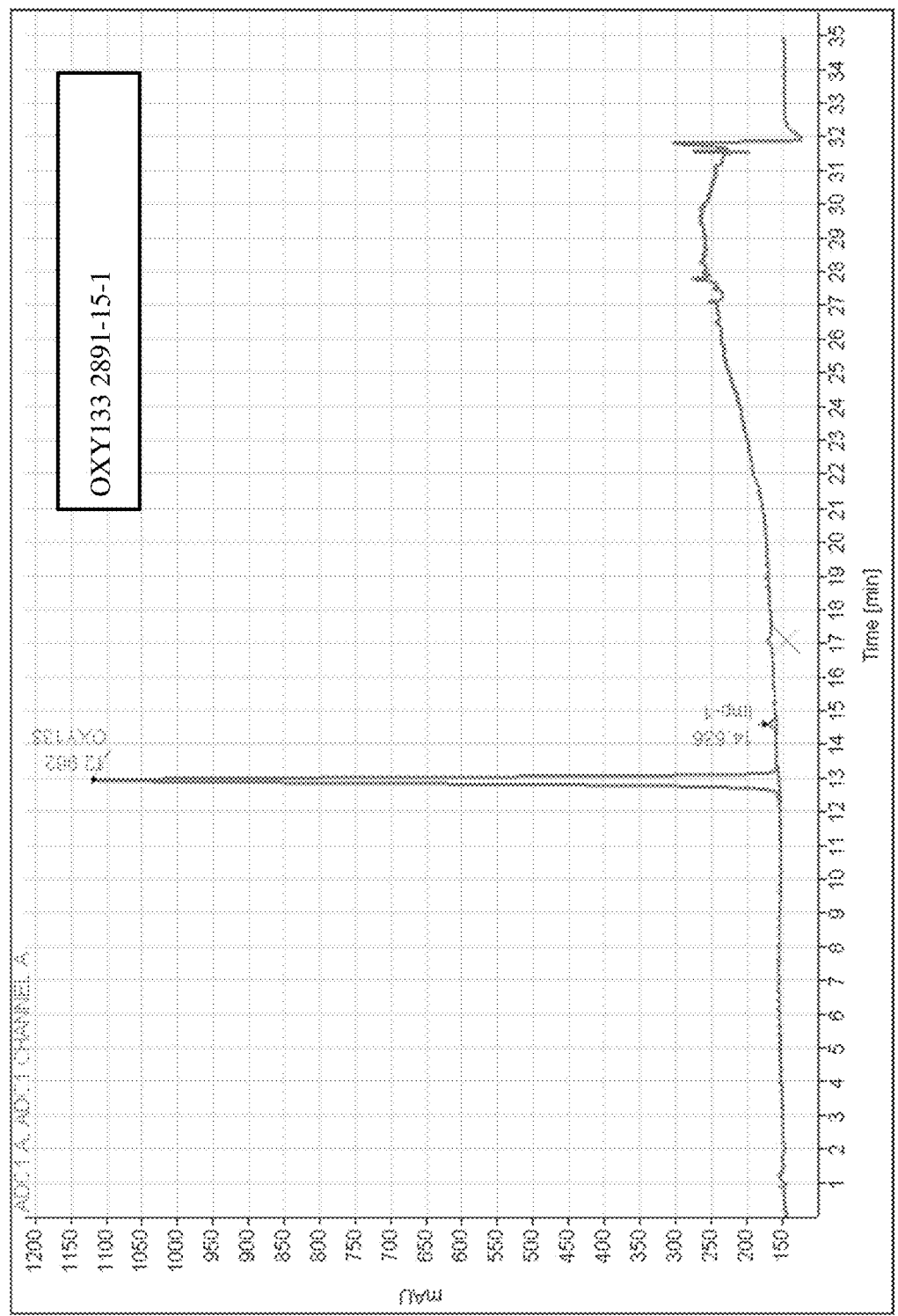
FIG. 19 is a HPLC/CAD single injection report of OXY133 sample 2891-15-1.
Figure 33:
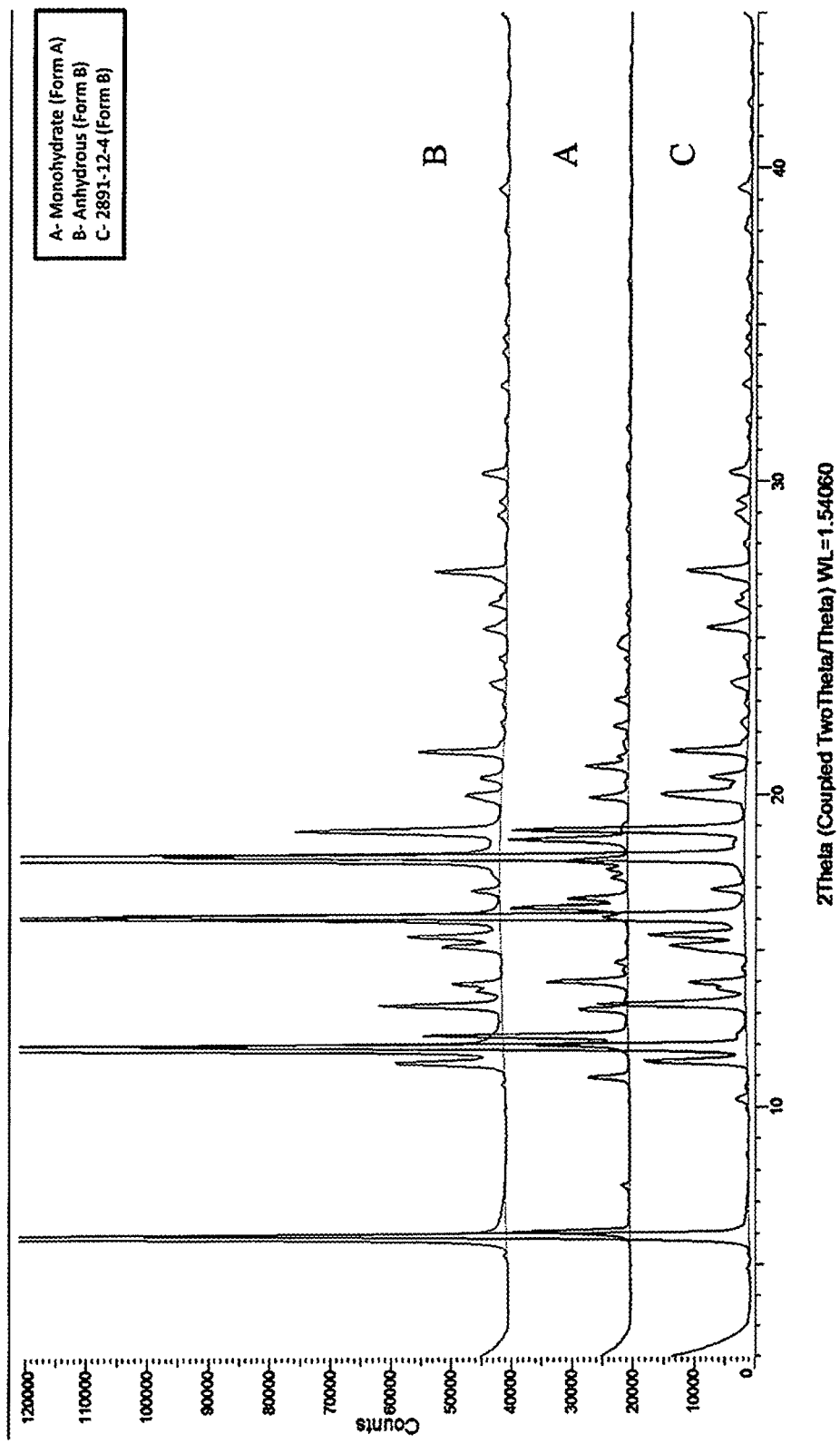
FIG. 33 is an XRPD of OXY133 polymorph Form B.
Figure 34:
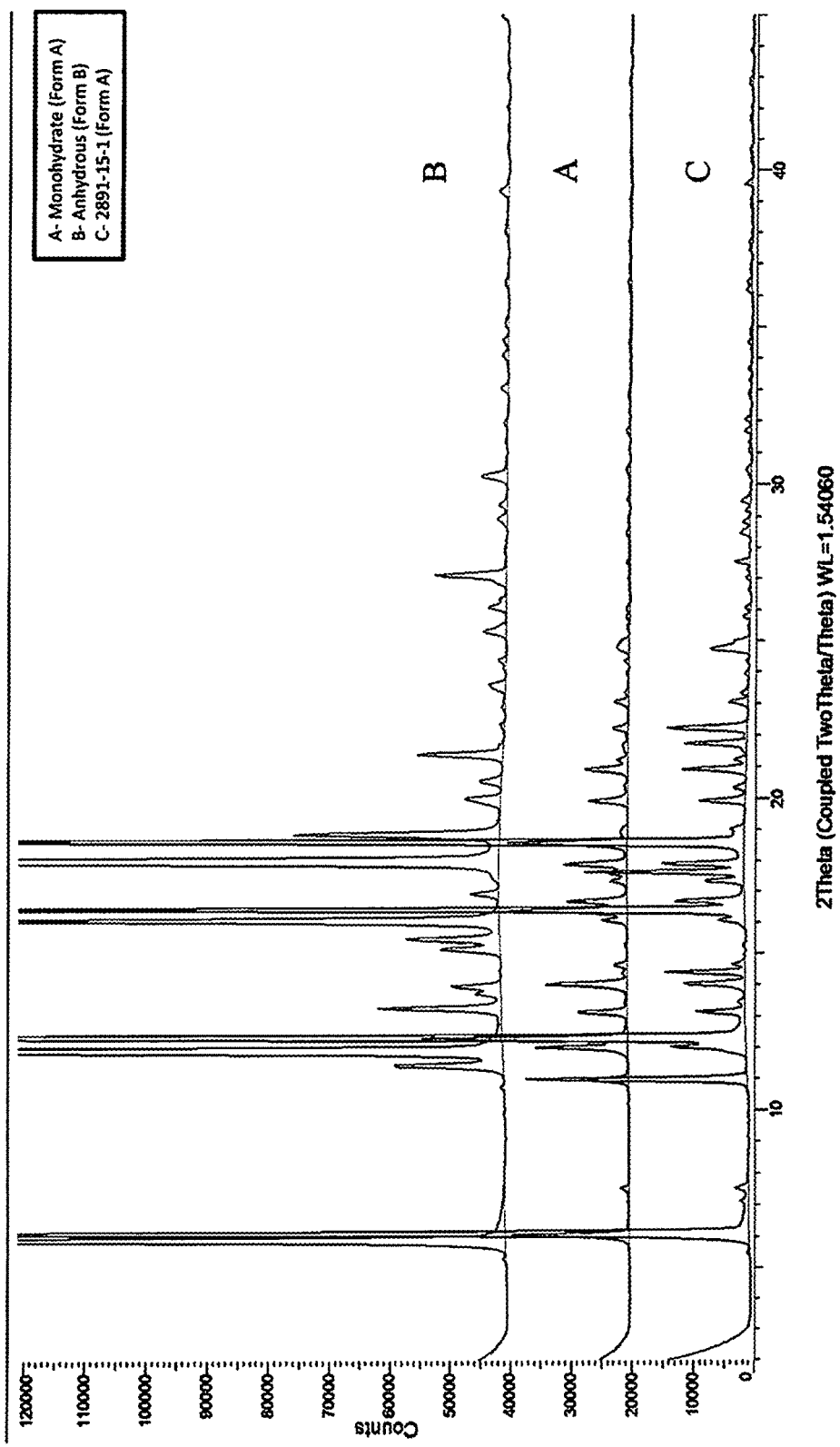
FIG. 34 is an XRPD of OXY133 polymorph Form A.

In various embodiments, some of the HPLC-CAD single injection results are illustrated in FIGS. 14-19. The data collected from these single injection results and associated with each signal is summarized in Table 17. HPLC-CAD data identifying OXY133 polymorph B is found at FIG. 14. HPLC-CAD data identifying OXY133 polymorph A is illustrated in FIGS. 15A, 15B, 15C, 15D, 15E, 15F, 15G, 15H and 15I. HPLC-CAD data identifying OXY133 polymorphs H and I is depicted in FIGS. 16 and 17. FIGS. 18 and 19 illustrate HPLC-CAD data for OXY133 samples of polymorph Form B (2891-12-4) and polymorph Form A (2891-15-1). In other embodiments, FIGS. 33 and 34 are XRPDs of polymorph Form B and polymorph Form A, respectively.

TABLE 17

Signal: ADC1 A, ADC1 Channel A

| FIG./Polymorph Form | RT (min) | Peak Height | Area | Area Percent | Resolution S/N | Tailing | Compound Name |
|---|---|---|---|---|---|---|---|
| FIG. 14 | 13.12 | 977.8 | 12035.04 | 96.88 | NA | 0.9 | OXY133 |
| Form B | 14.81 | 26.1 | 292.059 | 2.351 | 5.9 | 1.2 | Imp-1 |
| | 17.31 | 10.1 | 95.554 | 0.769 | 14.1 | 0.8 | Imp-2 |
| FIG. 15A | 12.96 | 1004.9 | 12862.927 | 96.79 | NA | 0.9 | OXY133 |
| Form A | 14.64 | 27.4 | 323.718 | 2.436 | 5.9 | 0.8 | Imp-1 |
| | 17.12 | 9.9 | 102.861 | 0.774 | 12.0 | 0.9 | Imp-2 |
| FIG. 15B | 12.91 | 971.9 | 12469.852 | 96.747 | NA | 0.9 | OXY133 |
| Form A | 14.58 | 26.4 | 300.637 | 2.332 | 5.9 | 1.1 | Imp-1 |
| | 17.06 | 9.9 | 118.685 | 0.921 | 11.1 | 0.9 | Imp-2 |
| FIG. 15C | 12.97 | 992.3 | 12903.733 | 96.972 | NA | 0.9 | OXY133 |
| Form A | 14.64 | 25.5 | 299.795 | 2.253 | 5.8 | 1.0 | Imp-1 |
| | 17.12 | 8.6 | 103.15 | 0.775 | 14.6 | 0.9 | Imp-2 |
| FIG. 18 | 12.93 | 958.6 | 12543.434 | 96.705 | NA | 0.9 | OXY133 |
| Form B (2891-12-4) | 14.61 | 23.6 | 308.917 | 2.382 | 5.8 | 0.8 | Imp-1 |
| | 17.08 | 10.1 | 118.415 | 0.913 | 13.2 | 0.9 | Imp-2 |
| FIG. 16 | 12.95 | 1012.6 | 13252.109 | 98.872 | NA | 0.9 | OXY133 |
| Form I | 17.10 | 10.5 | 151.170 | 1.128 | 14.8 | 0.8 | Imp-2 |
| FIG. 19 | 12.96 | 961.1 | 12444.046 | 98.778 | NA | 0.9 | OXY133 |
| Form A (2891-15-1) | 14.64 | 12.4 | 153.953 | 1.222 | 6.5 | 0.9 | Imp-1 |

TABLE 17-continued

| | Signal: ADC1 A, ADC1 Channel A | | | | | | |
|---|---|---|---|---|---|---|---|
| FIG./Polymorph Form | RT (min) | Peak Height | Area | Area Percent | Resolution S/N | Tailing | Compound Name |
| FIG. 15D Form A | 12.96 | 995.2 | 12999.925 | 99.314 | NA | 0.9 | OXY133 |
| | 17.14 | 9.3 | 89.849 | 0.686 | 17.9 | 0.9 | Imp-2 |
| FIG. 15E Form A | 12.92 | 991.0 | 12673.089 | 96.569 | NA | 0.9 | OXY133 |
| | 14.58 | 24.0 | 286.633 | 2.184 | 5.8 | 0.9 | Imp-1 |
| | 17.07 | 9.0 | 100.206 | 0.764 | 11.4 | 0.9 | Imp-2 |
| | 17.3 | 8.0 | 63.488 | 0.484 | 1.5 | 1.6 | NA |
| FIG. 15F Form A | 13.14 | 962.4 | 11702.109 | 97.937 | NA | 0.9 | OXY133 |
| | 14.82 | 11.2 | 137.895 | 1.154 | 5.8 | 1.0 | Imp-1 |
| | 17.28 | 9.7 | 108.565 | 0.909 | 11.3 | 1.3 | Imp-2 |
| FIG. 15G Form A | 13.10 | 980.6 | 12547.018 | 97.083 | NA | 0.9 | OXY133 |
| | 14.78 | 23.2 | 274.022 | 2.120 | 6.1 | 0.9 | Imp-1 |
| | 17.26 | 8.9 | 102.958 | 0.797 | 9.4 | 1.0 | Imp-2 |
| FIG. 17 Form H | 13.06 | 989.6 | 12586.536 | 97.265 | NA | 0.9 | OXY133 |
| | 14.72 | 23.2 | 261.195 | 2.018 | 6.1 | 1.0 | Imp-1 |
| | 17.21 | 8.5 | 92.714 | 0.716 | 10.6 | 1.0 | Imp-2 |
| FIG. 15H Form A | 13.07 | 992.6 | 12749.081 | 97.029 | NA | 0.9 | OXY133 |
| | 14.74 | 26.7 | 305.567 | 2.326 | 5.9 | 0.8 | Imp-1 |
| | 17.25 | 10.0 | 84.825 | 0.646 | 16.6 | 1.4 | Imp-2 |
| FIG. 15I Form A | 13.06 | 999.4 | 12778.192 | 97.158 | NA | 0.9 | OXY133 |
| | 14.73 | 24.5 | 278.862 | 2.120 | 5.6 | 1.1 | Imp-1 |
| | 17.20 | 9.4 | 94.863 | 0.721 | 10.3 | 1.2 | Imp-2 |

Differential scanning calorimetry (DSC) and thermo-gravimetric analysis (TGA) were also collected for some of the OXY133 polymorphs. The equipment utilized to collect the DSC/TGA data was a Mettler Toledo DSC 2 equipped with an aluminum 40 μL crimped pan with a pin hole and the ramp rate was 10° C./min. DSC/TGA thermograms identifying several OXY133 polymorphs are illustrated in FIGS. 20-25.

Figure 20:
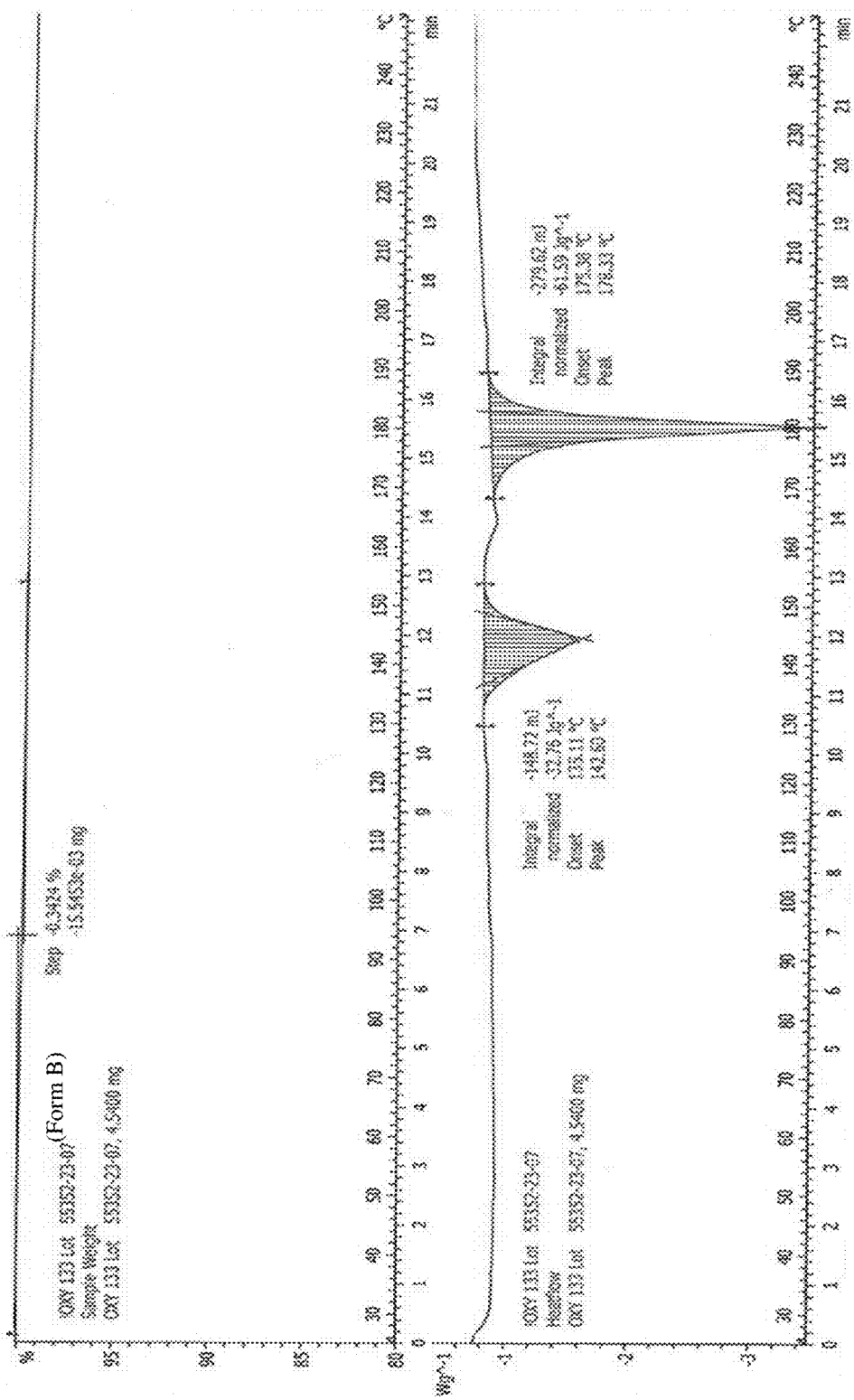
FIG. 20 is a Differential Scanning Calorimetry-Thermogravimetric Analysis (DSC-TGA) thermogram of OXY133 polymorph Form B.
Figure 21A:
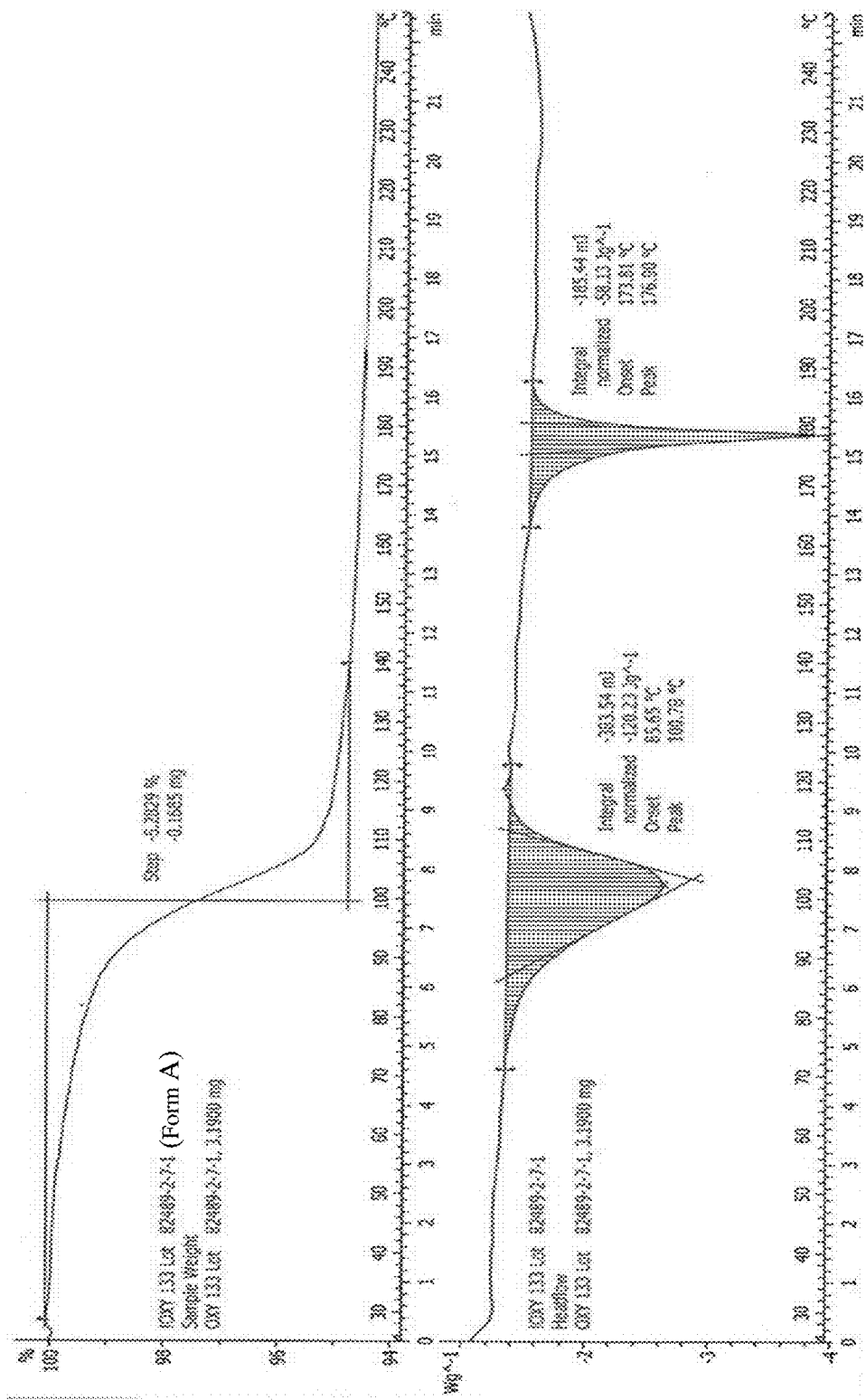
FIGS. 21A, 21B, 21C, 21D, 21E, 21F, 21G, 21H, and 21I are DSC-TGA thermograms of OXY133 polymorph Form A.
Figure 21B:
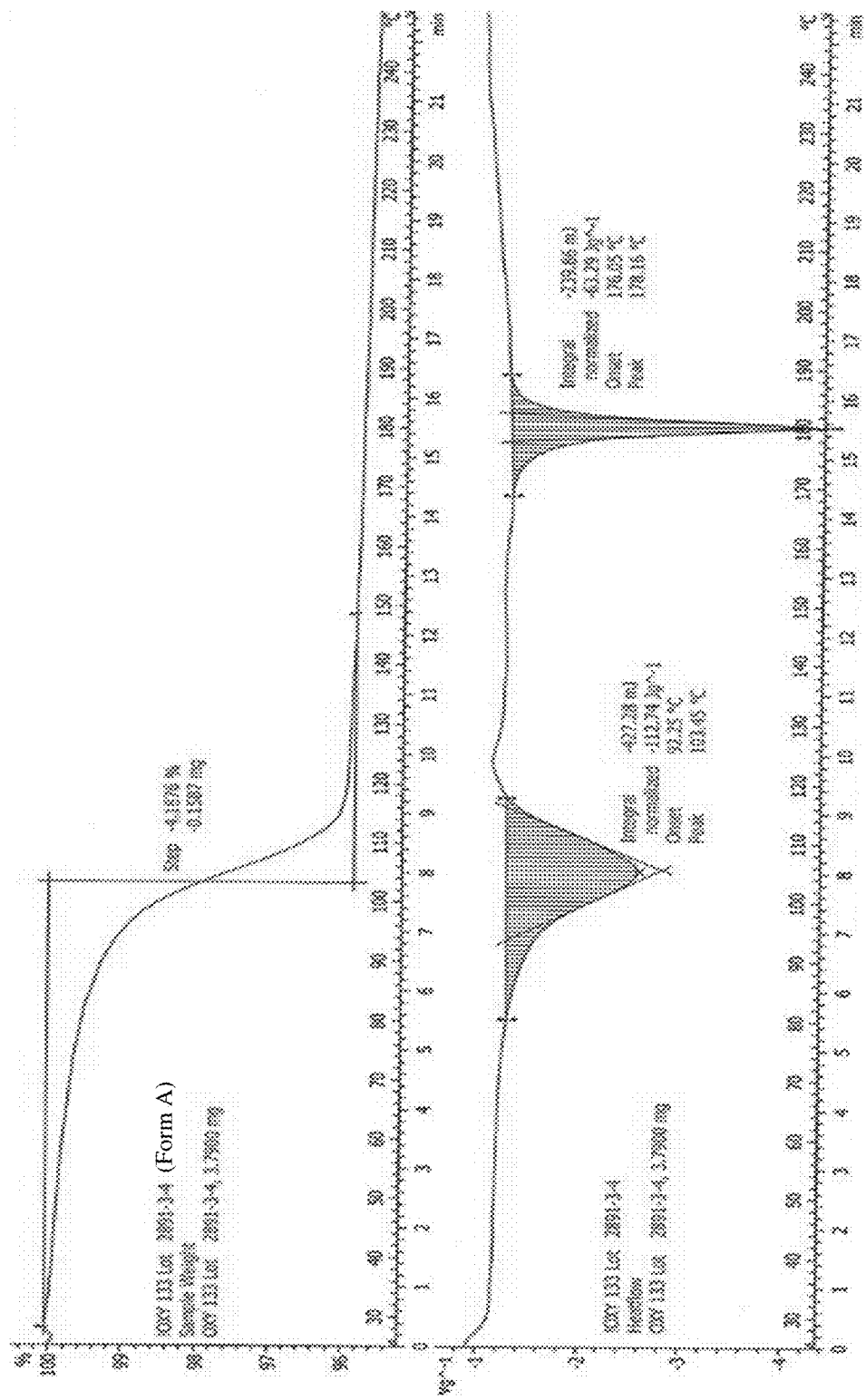
Figure 21C:
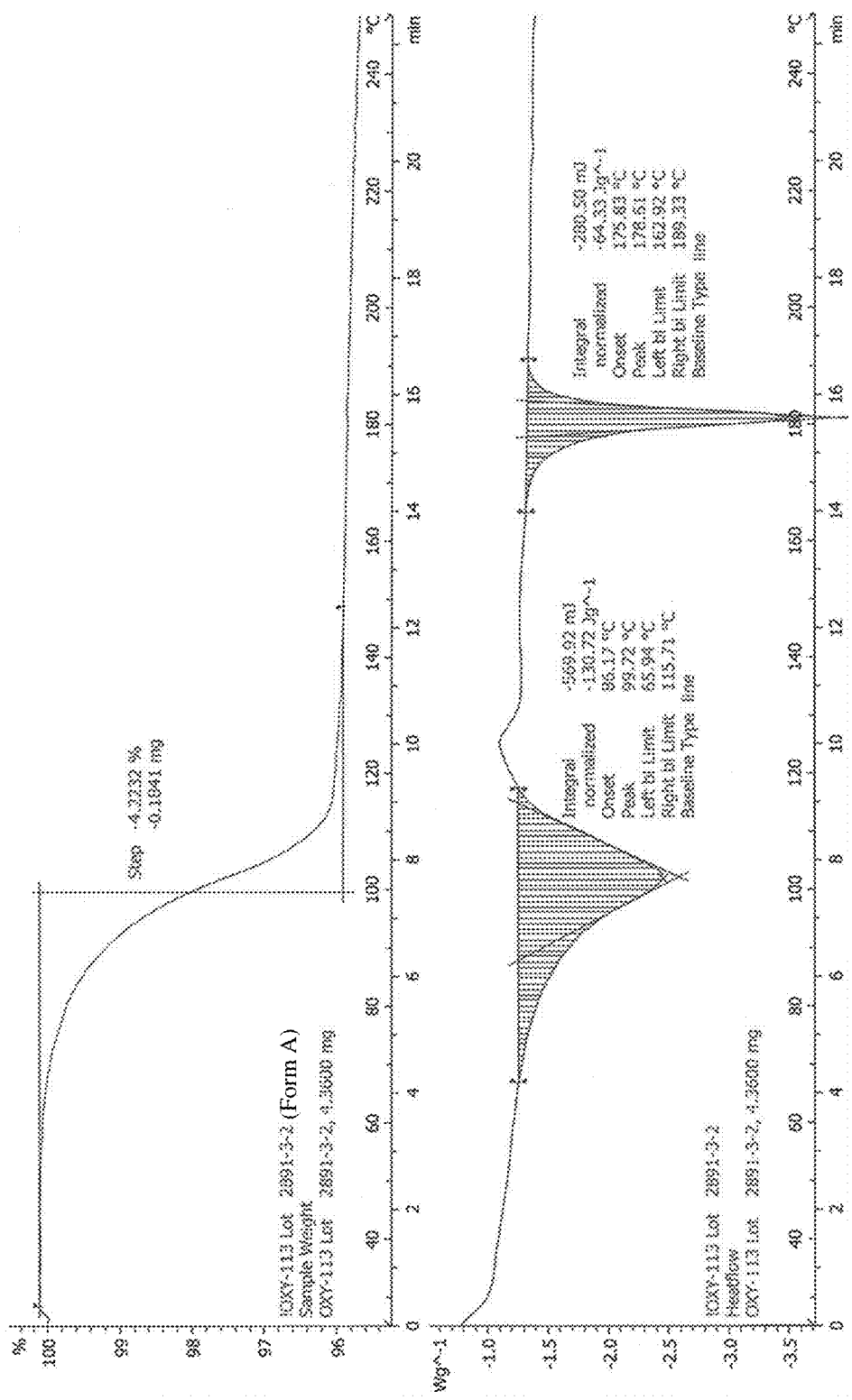
Figure 21D:
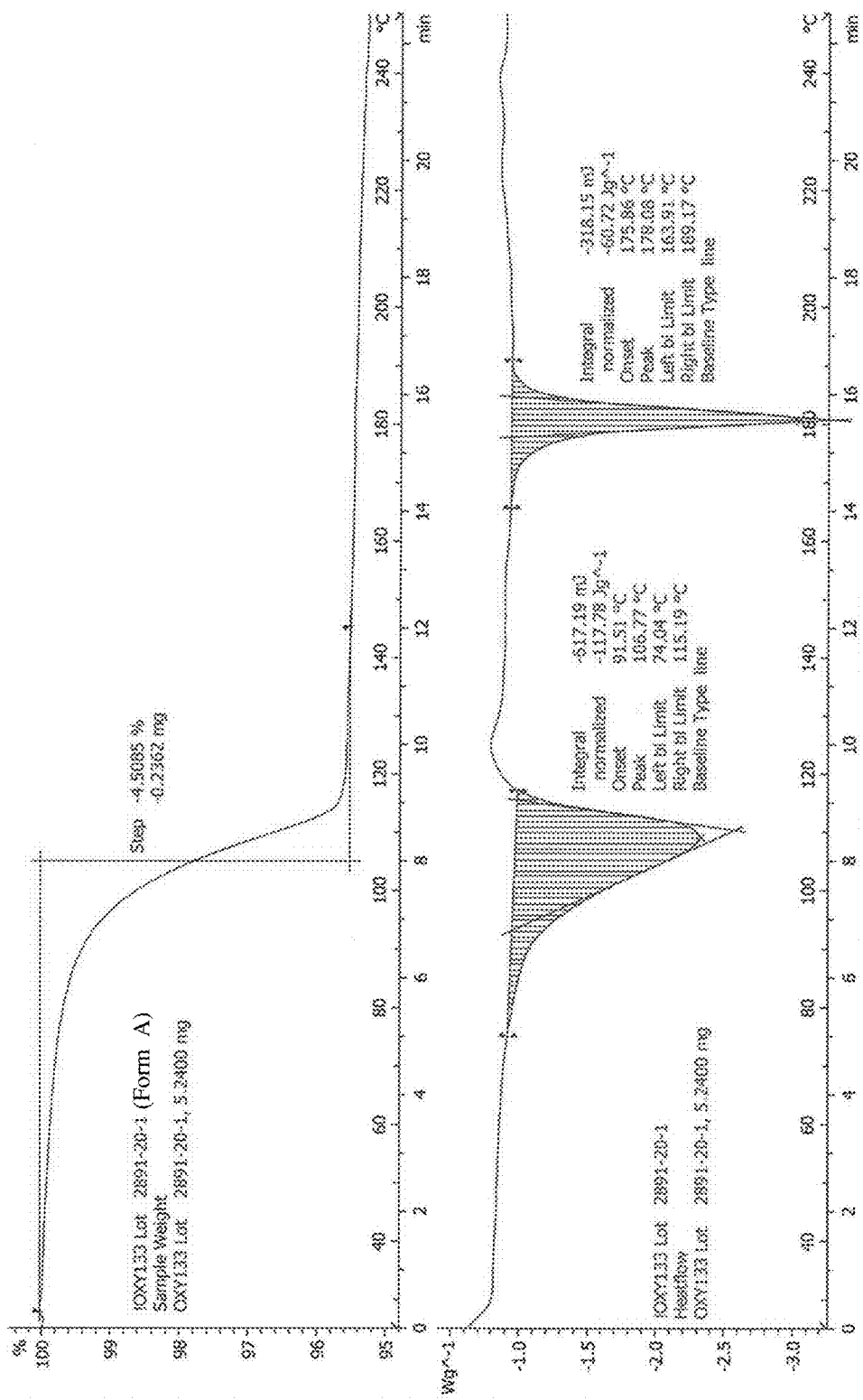
Figure 21E:
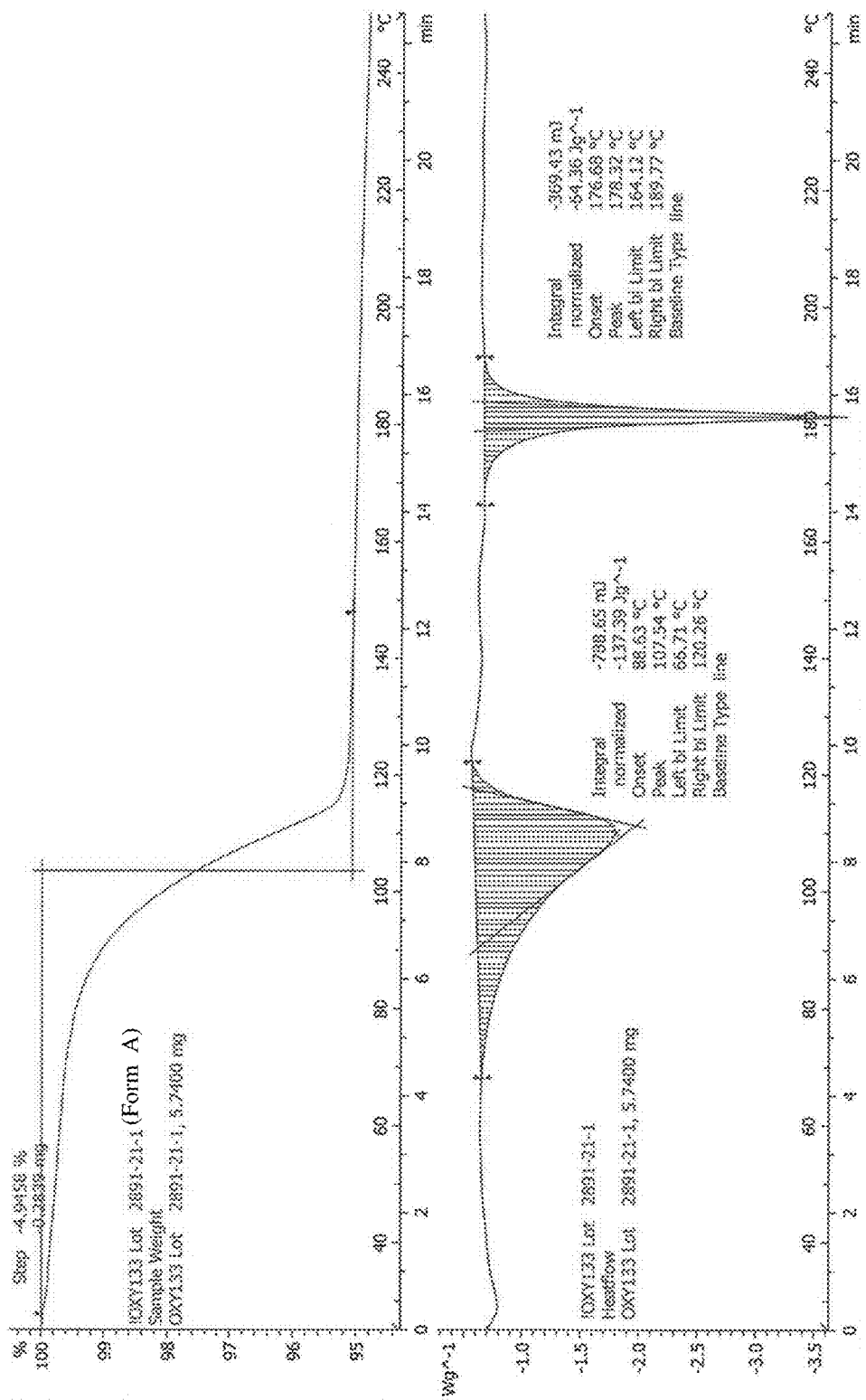
Figure 21F:
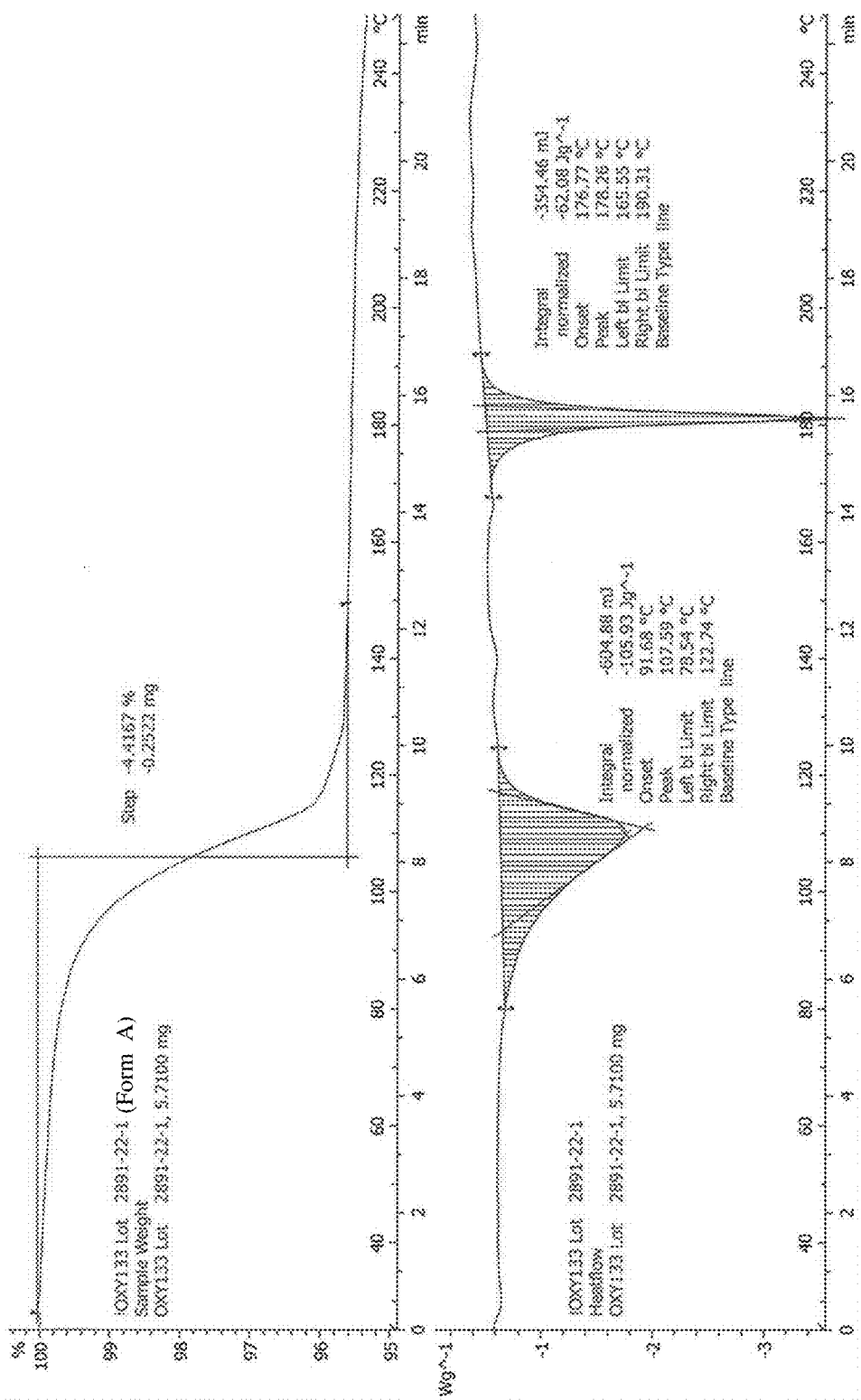
Figure 21G:
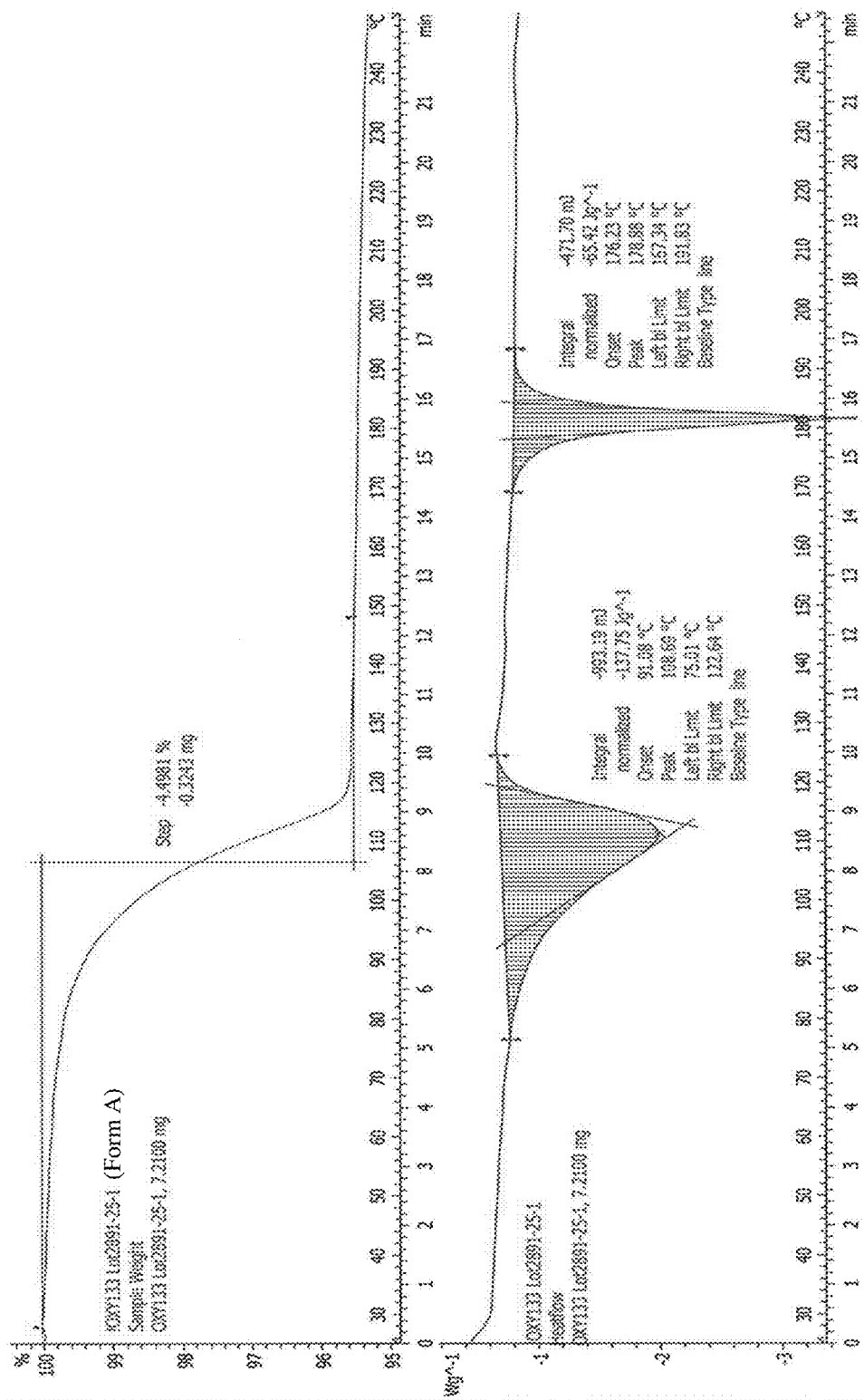
Figure 21H:
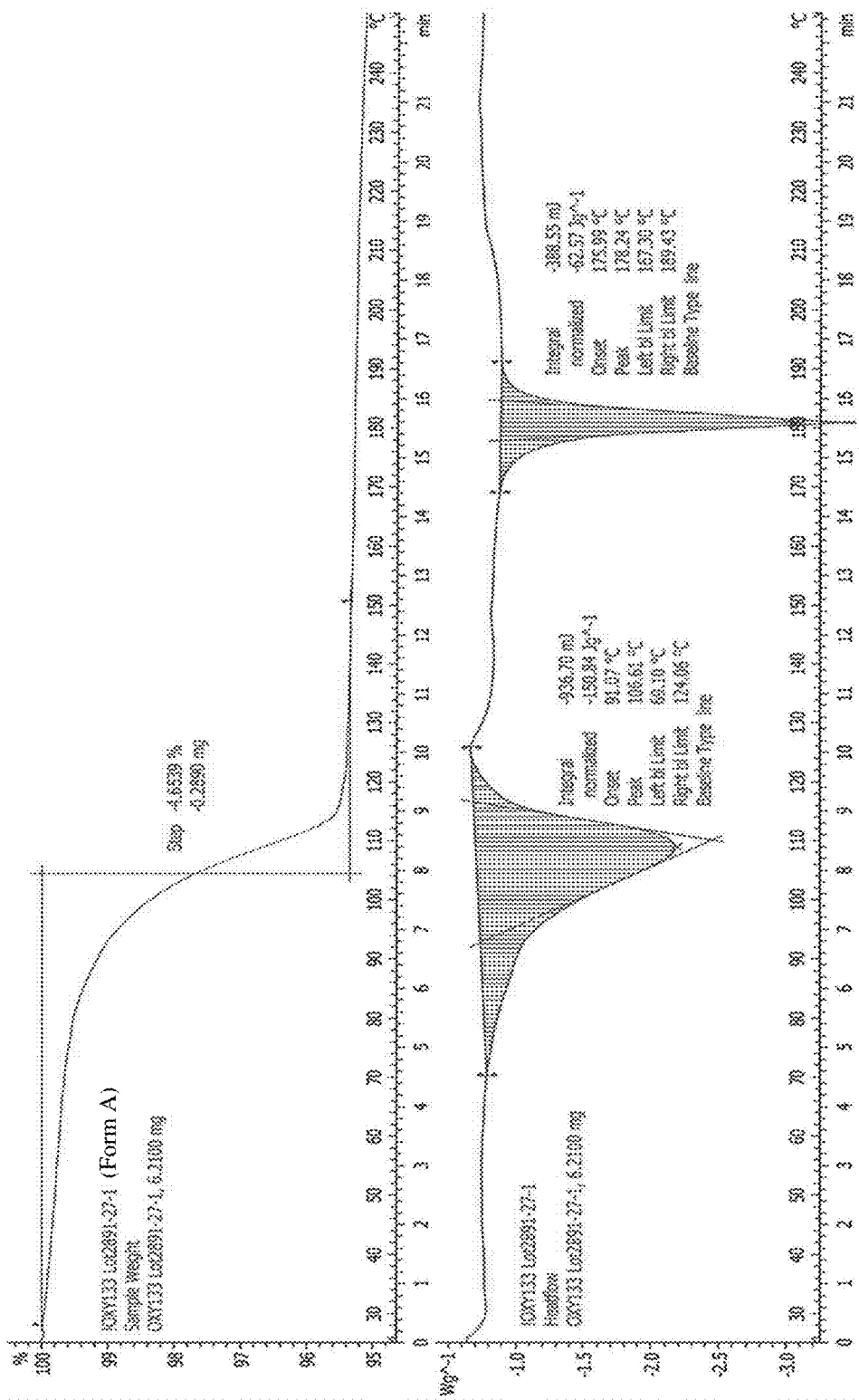
Figure 21I:
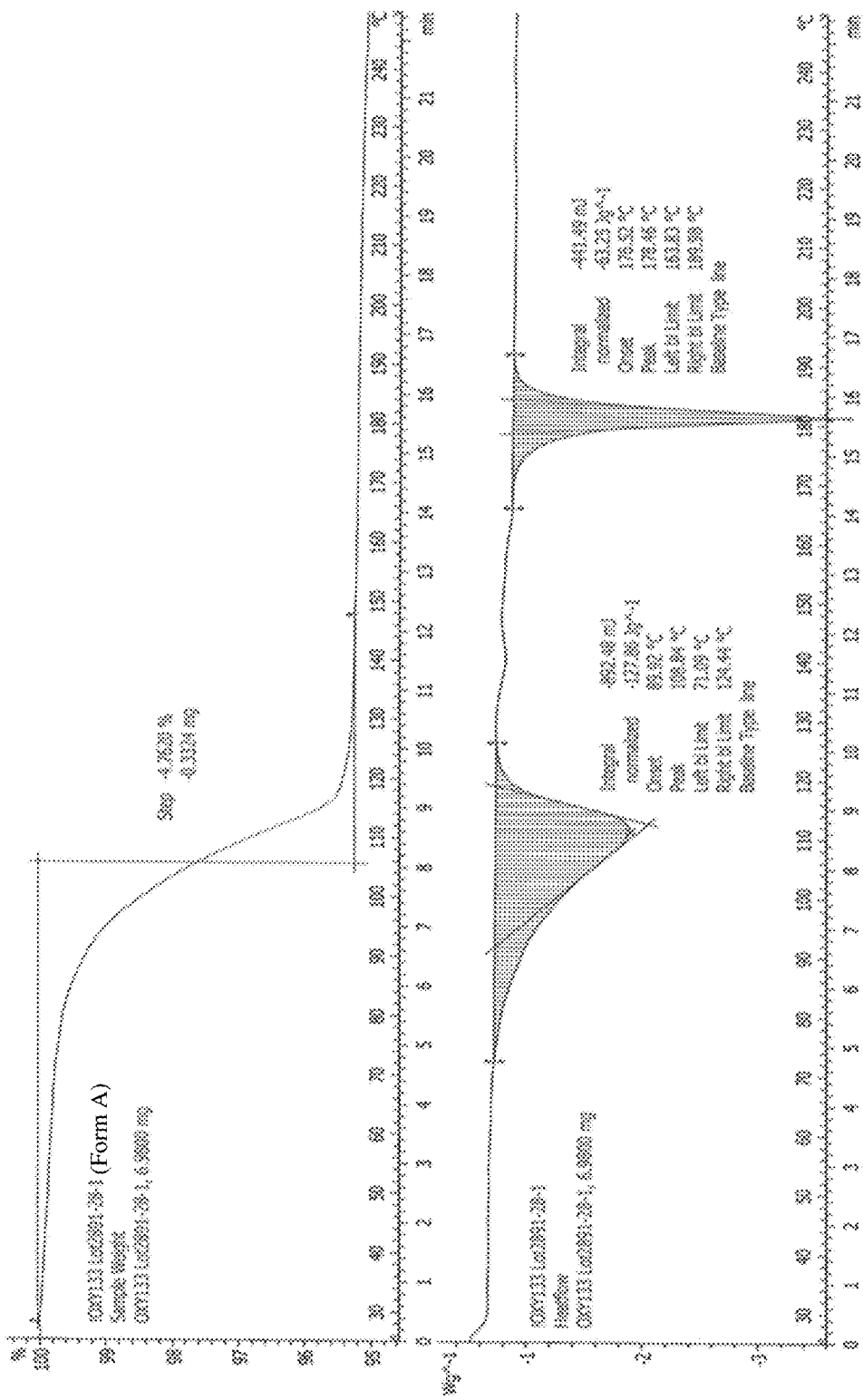
Figure 22:
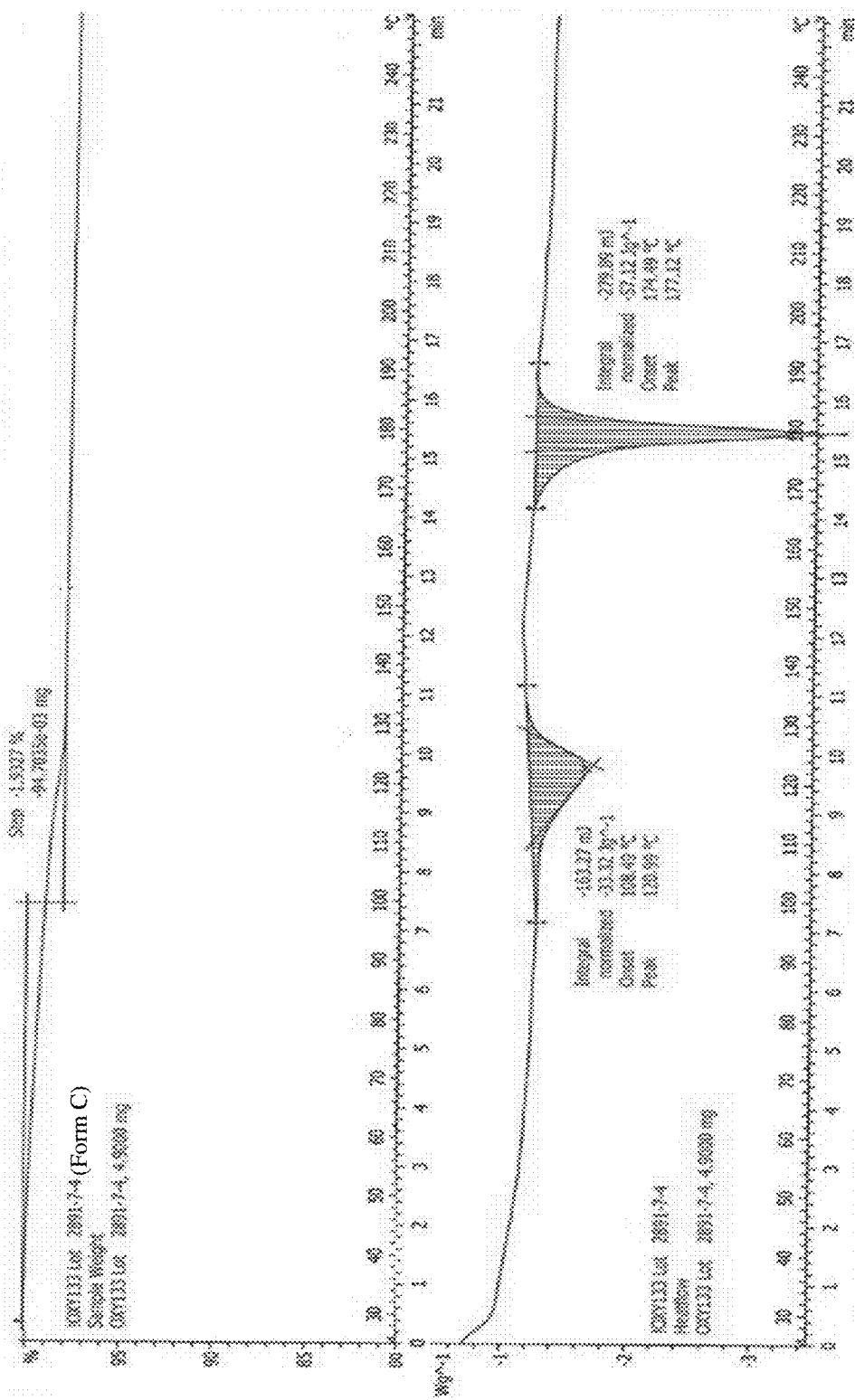
FIG. 22 is a DSC-TGA thermogram of OXY133 polymorph Form C.
Figure 23:
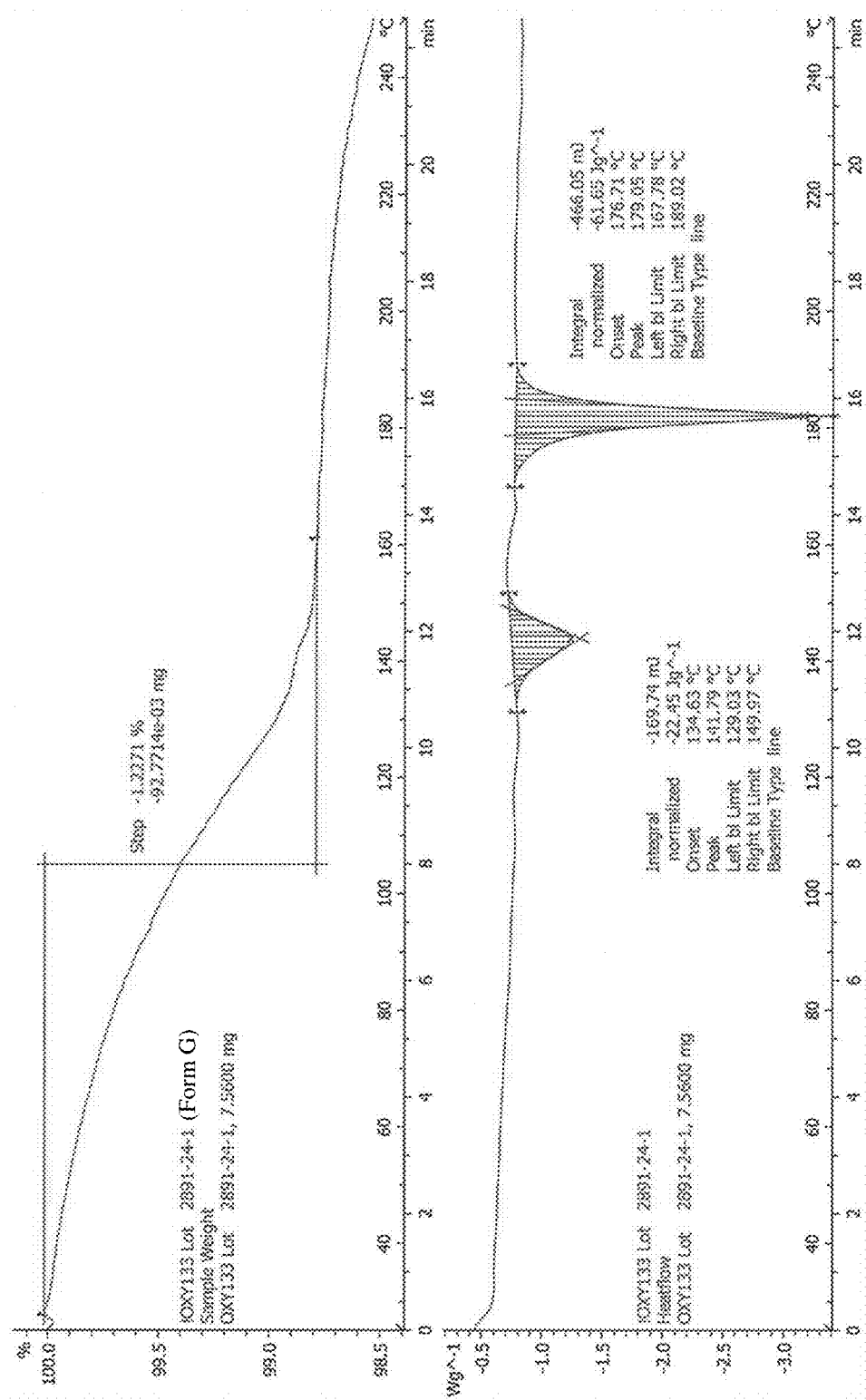
FIG. 23 is a DSC-TGA thermogram of OXY133 polymorph Form G.
Figure 24:
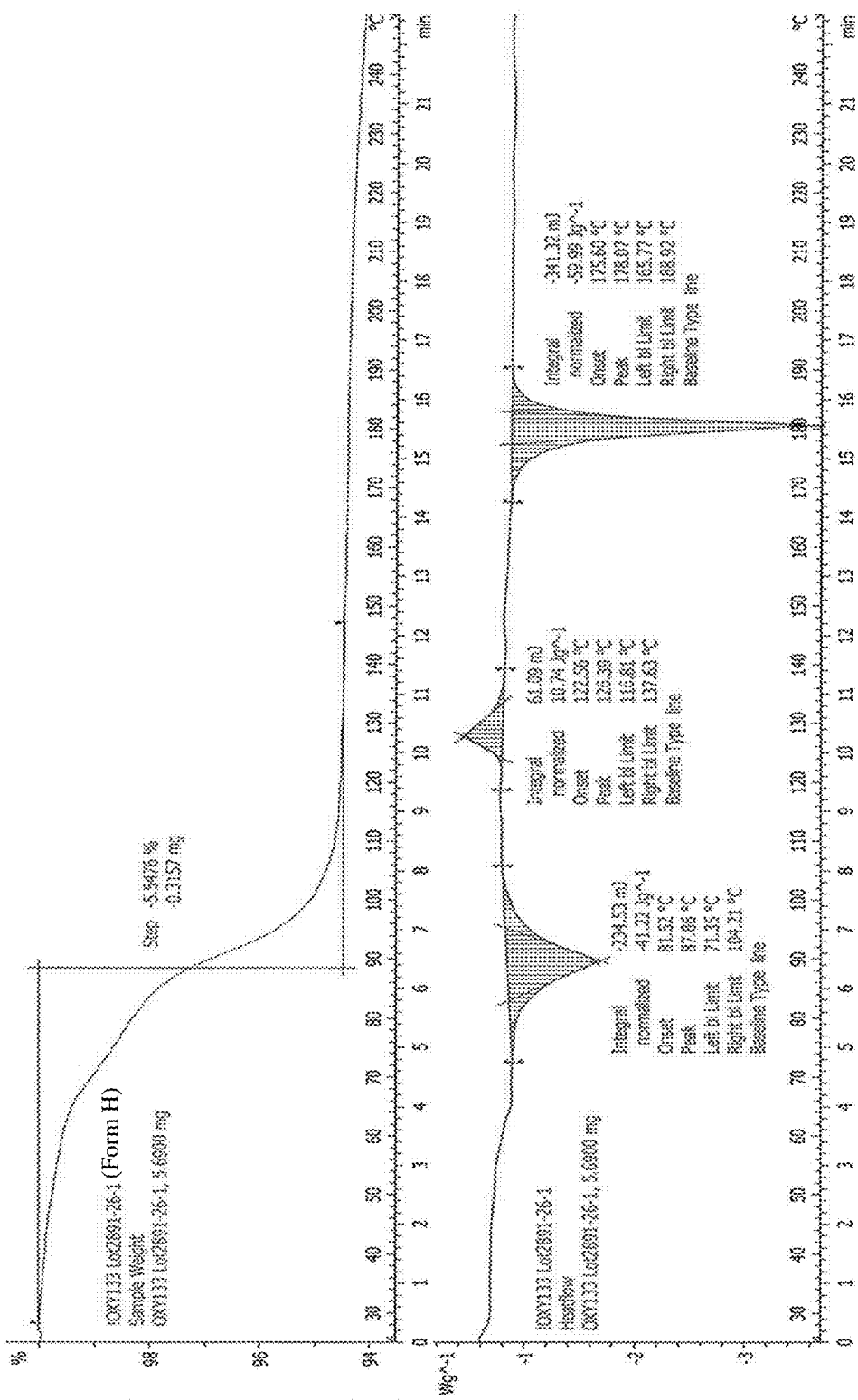
FIG. 24 is a DSC-TGA thermogram of OXY133 polymorph Form H.
Figure 25:
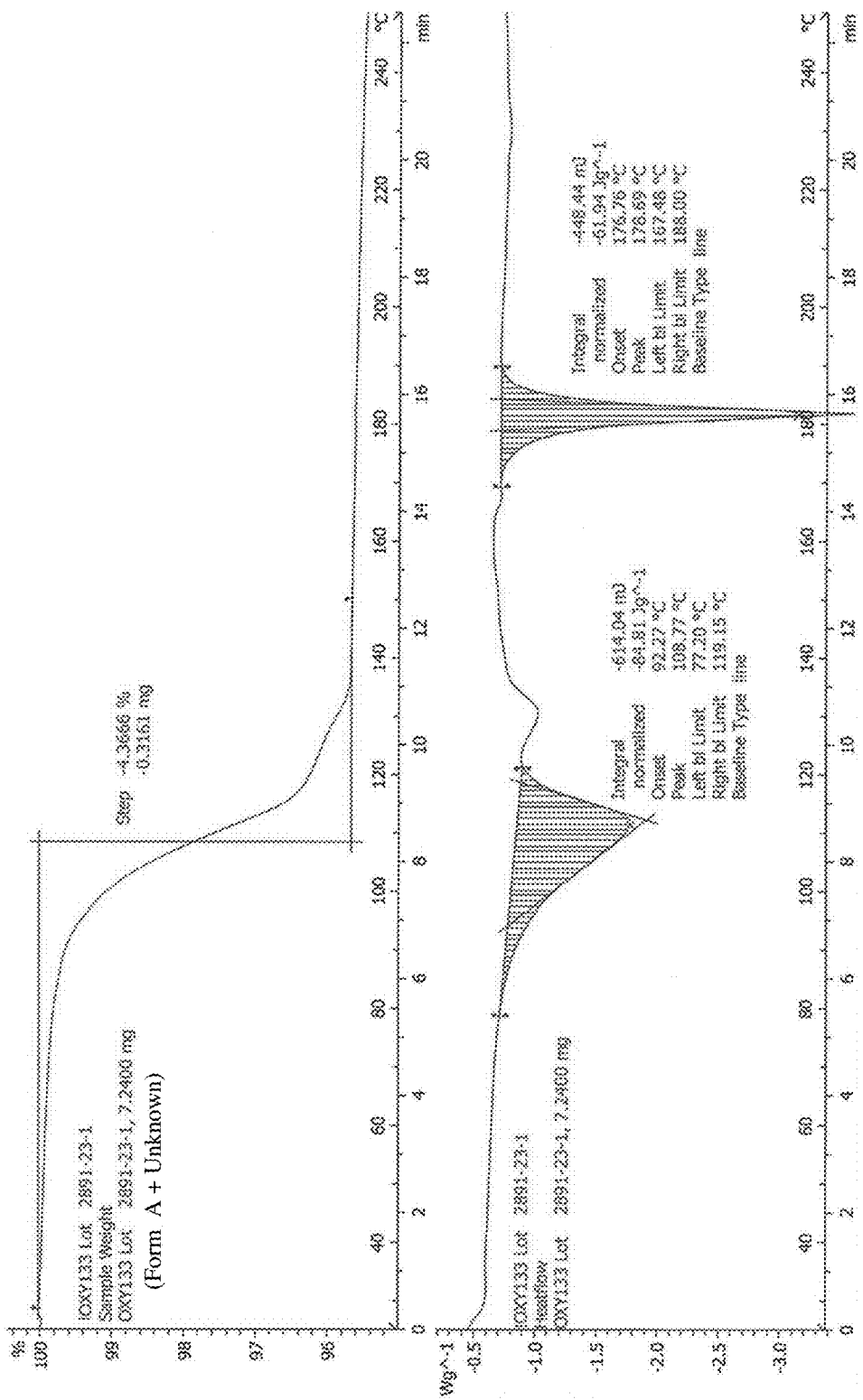
FIG. 25 is a DSC-TGA thermogram of OXY133 polymorph Form A and unknown.

More particularly, FIG. 20 is a DSC-TGA thermogram of OXY133 polymorph Form B; FIGS. 21A, 21B, 21C, 21D, 21E, 21F, 21G, 21H, and 21I are DSC-TGA thermograms of OXY133 polymorph Form A; FIG. 22 is a DSC-TGA thermogram of OXY133 polymorph Form C; FIG. 23 is a DSC-TGA thermogram of OXY133 polymorph Form G; FIG. 24 is a DSC-TGA thermogram of OXY133 polymorph Form H; and FIG. 25 is a DSC-TGA thermogram of OXY133 polymorph Form A and unknown.

In various other embodiments, a method is provided for preparing an OXY133 polymorph, the method including subjecting a slurry of anhydrous OXY133 to conditions sufficient to convert anhydrous OXY133 to the OXY133 polymorph selected from polymorph Form A, polymorph Form B, polymorph Form C, polymorph Form D, polymorph Form E, polymorph Form F, polymorph Form G, polymorph Form H, polymorph Form I or a mixture thereof, wherein OXY133 is prepared by reacting a diol having the formula:

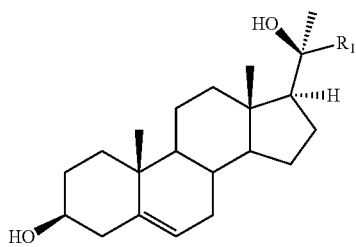

with borane, hydrogen peroxide and tetrahydrofuran to form the oxysterol or a pharmaceutically acceptable salt, hydrate or solvate thereof having the formula:

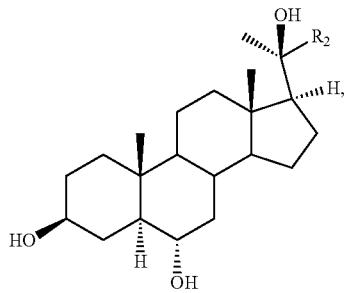

wherein $R_1$ and $R_2$ comprise a hexyl group and the diol comprises (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol (OXY133).

These and other aspects of the present application will be further appreciated upon consideration of the following Examples, which are intended to illustrate certain particular embodiments of the application but are not intended to limit its scope, as defined by the claims.

EXAMPLES

Example 1

Preparation from Pregnenolone Acetate 8.25 mL n-hexylmagnesium chloride (2 M, 16.5 mmol) was added to a solution of pregnenolone acetate in tetrahydrofuran under vigorous electromagnetic stirring and ice bath cooling. The pregnenolone acetate solution contained 1.79 g of compound 1, pregnenolone acetate, (5 mmol) in 4.5 mL tetrahydrofuran. The addition took place over 2 minutes. After addition was completed, the mixture was stirred at room temperature for 3.5 hours, at which point the mixture had turned to a gel. The gel was then digested with a mixture of saturated aqueous $NH_4Cl$ and MTBE (methyl tertiary-butyl ether). The organic layer was separated, washed with water three times and evaporated. The residue was separated by silica gel column chromatography using an EtOAc (ethyl acetate)/petroleum ether mixture (ratio 70/30) to give compound 2, a diol, as a white solid. 1.29 g (3.21 mmol) of the solid diol was extracted for a 64% isolated yield. The reaction is shown below in Scheme A:

Scheme A

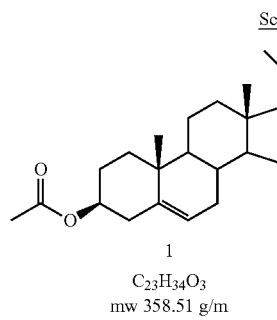

1
$C_{23}H_{34}O_3$
mw 358.51 g/m n-Hexylmagnesiumchloride, THF →

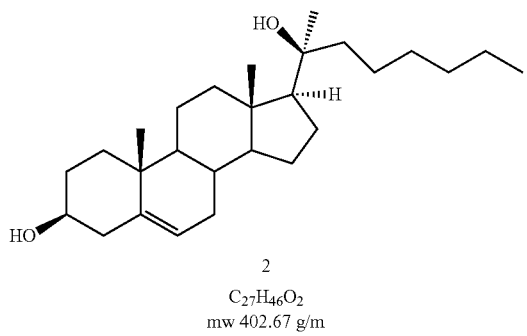

2
$C_{27}H_{46}O_2$
mw 402.67 g/m

The $^1$H NMR data of the diol in CDCl$_3$ at 400 MHz illustrated the following: δ: 0.8-1.9 (40H), 1.98 (m, 1H), 2.09 (m, 1H), 2.23 (m, 1H), 2.29 (m, 1H), 3.52 (m, 1H), 5.35 (m, 1H) in FIG. 6. The $^{13}$C NMR data of the diol in CDCl$_3$ at 100 MHz illustrated the following: d: 13.6, 14.1, 19.4, 20.9, 22.4, 22.6, 23.8, 24.2, 26.4, 30.0, 31.3, 31.6, 31.8, 31.9, 36.5, 37.3, 40.1, 42.3, 42.6, 44.0, 50.1, 56.9, 57.6, 71.7, 75.2, 121.6, 140.8.

The diol created has an IUPAC name of (3S,8S,9S,10R, 13R,14S,17R)-10,13-dimethyl-17-[(S)-2-hydroxyoctan-yl]-2,3,4,7,8,9,11,12,14,15,16,17-dodecahydro-1H-cyclopenta [a]phenanthren-3-ol.

Example 2

Preparation from Pregnenolone

Alternatively to Example 1, compound 2 of reaction scheme A above can be prepared from pregnenolone shown below in B utilizing the same procedure as utilized for the conversion of compound 1 to compound 2. In this procedure 10 g of pregnenolone was converted to 7.05 g of compound 2, which accounted for a 55% yield.

Reaction Scheme B

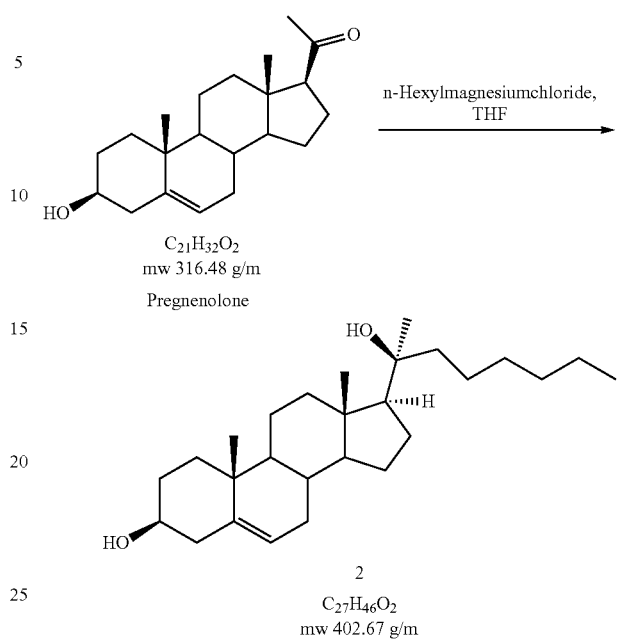

2500 mL of n-hexylmagnesium chloride (2 M, 5 mol) was charged to a reactor and the solution was cooled to −5° C. A solution of pregnenolone in tetrahydrofuran was charged to the reactor at a rate which maintained the internal reaction temperature below 1° C. The pregnenolone solution contained 500 g pregnenolone (1.4 mol) in 8 liters tetrahydrofuran. After the addition was complete, the mixture was held at 0° C. for 1 hour then allowed to warm to room temperature overnight. The reaction mixture had become a solid, gelatinous mass. 2 liters of additional tetrahydrofuran was added followed by 10 ml of glacial acetic acid. The reaction mixture was cooled to 5° C. and quenched by the addition of 350 ml of glacial acetic acid which gave a solution. The reaction mixture was concentrated under reduced pressure to a thick syrup. The compound was dissolved in dichloromethane, washed with water and finally washed with saturated sodium bicarbonate. The organic layer was concentrated under reduced pressure to an amber oil. Mass recovery was about 800 grams. The crude material was utilized as is in the next step.

The diol created has an IUPAC name of (3S,8S,9S,10R, 13R,14S,17R)-10,13-dimethyl-17-[(S)-2-hydroxyoctan-yl]-2,3,4,7,8,9,11,12,14,15,16,17-dodecahydro-1H-cyclopenta [a]phenanthren-3-ol.

Example 3

The crude hexyl diol product (800 grams) was dissolved in 8 liters of tetrahydrofuran, charged to a reactor, and was cooled to −5° C. 6300 mL of borane-tetrahydrofuran complex (1 M, 6.3 moles, 4.5 equivalents) in tetrahydrofuran was charged at a rate which maintained the internal reaction temperature below 1° C. Once the addition was complete, the reaction mixture was stirred at 0° C. for 1.5 hours then allowed to warm to room temperature overnight. The reaction is shown below.

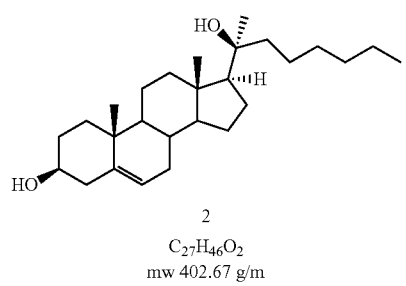

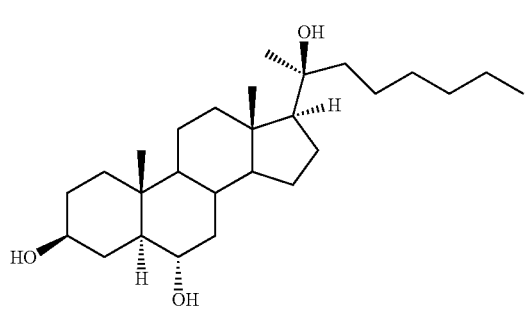

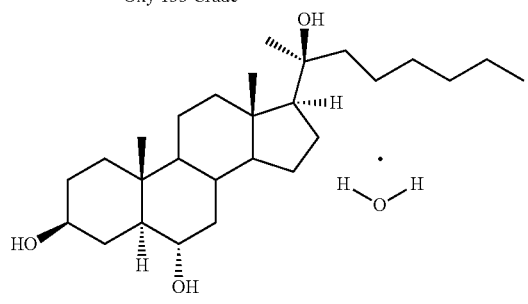

Example 4

The reaction mixture was quenched by addition of a mixture of 10% sodium hydroxide (4750 mL) and 30% hydrogen peroxide (1375 mL). The quench was extremely exothermic and required several hours to complete. The internal temperature was maintained below 10° C. After the addition of the quench volume was complete, the mixture was held cold for 1.5 hours then allowed to warm to room temperature overnight. 8 liters of dichloromethane was then added. The organic layer was isolated and washed with 7 liters of fresh water, and was concentrated under reduced pressure. The product was isolated as a viscous, oily mass which solidified upon standing.

The product was dissolved in 4 liters of dichloromethane and was placed onto a silica gel column prepared in dichloromethane. The column was eluted first with 25% ethyl acetate to elute the 7-methyl-7-tridecyl alcohol by-product. Subsequently, the column was eluted with 10% methanol-ethyl acetate to solvate the OXY133. The collected fractions were combined and concentrated under reduced pressure to a waxy solid. The compound was dissolved in acetone-water mixture (3:1) and concentrated under reduced pressure to remove residual solvents. The resulting crude OXY133 was utilized in the next step.

Alternatively, the viscous product recovered from the hydroboration/oxidation can be solidified by stirring with heptanes, and the product isolated by filtration. The isolated product is suspended in methylene chloride (7.3 mL methylene chloride/g solid). The product was isolated by filtration and used as-is in the next step.

OXY133 was recrystallized by dissolving 630 grams of crude OXY133 into 1500 ml of a 3:1 acetone/water mixture at reflux, then cooling to room temperature. The crystalline solid was recovered by vacuum filtration and dried to afford 336 g, which was a 28% overall yield from compound 1. The OXY133 produced was monohydrous, and has an IUPAC name of (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol, monohydrate.

The $^1$H NMR data of OXY133 in $CDCl_3$ at 400 MHz illustrated the following: δ: 0.66 (m, 1H), 0.85 (m, 10H), 1.23 (m, 18H), 1.47 (m, 9H), 1.68 (m, 4H), 1.81 (m, 1H), 1.99 (m, 1H), 2.06 (m, 1H), 2.18 (m, 1H), 3.42 (m, 1H), 3.58 (m, 1H). The $^{13}$C NMR data of OXY133 in $CDCl_3$ at 400 MHz illustrated the following: d: 13.7, 14.0, 14.3, 21.2, 22.5, 22.8, 23.9, 24.4, 26.6, 30.1, 31.1, 32.1, 32.5, 33.9, 36.5, 37.5, 40.4, 41.7, 43.1, 44.3, 51.9, 53.9, 56.5, 57.9, 69.6, 71.3, 75.4. The infrared spectroscopy data of OXY133 showed peaks at 3342 $cm^{-1}$, 2929 $cm^{-1}$, 2872 $cm^{-1}$, 2849 $cm^{-1}$. The turbo spray mass spectrometry data of the OXY133 showed peaks at 438.4 m/z $[M+NH_4]+$, 420.4 m/z $(M-H_2O+NH_4]+$, 403.4 m/z $[M-H_2O+H]+$, 385.4 m/z $[M-2H_2O+H]+$.

Example 5

Alternative One-Vessel Procedure from Pregnenolone Acetate 100 mL n-hexylmagnesium chloride (2M in tetrahydrofuran, 200 mmol) was charged to a flask and cooled to −10° C. A solution containing 20 g pregnenolone acetate (56 mmol) in 200 ml of anhydrous tetrahydrofuran was added dropwise, while maintaining the internal reaction temperature below −10° C. After the addition was completed, the mixture was stirred for 30 minutes then allowed to warm to room temperature. After 4 hours at room temperature, the mixture had become a gelatinous stirrable mass. The mixture was cooled to 0° C. and 200 mL. Borane-tetrahydrofuran complex (1M in tetrahydrofuran, 200 mmol) was added dropwise, while maintaining the internal temperature below 0° C. Once addition was complete, the resulting solution was allowed to warm to room temperature overnight.

The mixture was cooled to 0° C. and quenched by the slow addition of a mixture of 10% NaOH (190 mL) and 30% $H_2O_2$ (55 mL). Once the quench was complete, the mixture was extracted with MTBE (800 mL total) resulting in an emulsion. Brine was added and the layers were separated. The organic phase was concentrated under reduced pressure to a clear, viscous oil. The oil was further purified utilizing the plug column method previously described.

Example 6

Preparation of OXY133 Monohydrate from Anhydrous OXY133

2.0 g anhydrous OXY133 was added to 10 mL isopropanol in a 100 mL polyblock reactor. The mixture was heated to 30° C. and then stirred at 30° C. for 45 minutes until the solids were dissolved completely. Acceptable heating temperatures ranged from 25° C. to 35° C. A polish filtration step can be added after dissolving the anhydrous OXY133. The mixture of anhydrous OXY133 and isopropanol was then cooled to 5° C. 20 mL of water was then added to the cooled mixture over 120 minutes at 5° C., resulting in the formation of a precipitate approximately one third of the way through the addition of water. The water addition can also be done in temperature ranges from about 0° C. to about 20° C. with no significant effect on the crystal structure. The resulting mixture of OXY133, isopropanol and water was then stirred at 5° C. for 18 hours. However, it is recommended that the resulting mixture could be mixed for at least 2 hours at 5° C. after the water addition was complete to ensure that all solids were precipitated from the solution. A white solid was collected by rapidly filtering the mixture and then washing the solid with 2.0 mL of an isopropanol:water mixture in a ratio of 1:2 v/v. The filtered and washed solids were then dried in a vacuum oven at 20° C. Acceptable temperatures for drying can range from about 20° C. to about 30° C. It is noted that drying at temperatures above this range resulted in the slow conversion of OXY133 monohydrate to a different, unknown crystal form. The reagents utilized and the properties of the resulting OXY133 monohydrate of OXY133 Form A polymorph are summarized in Table 18 below.

Example 7

Preparation of OXY133 Monohydrate from Pregnenolone

Figure 35:
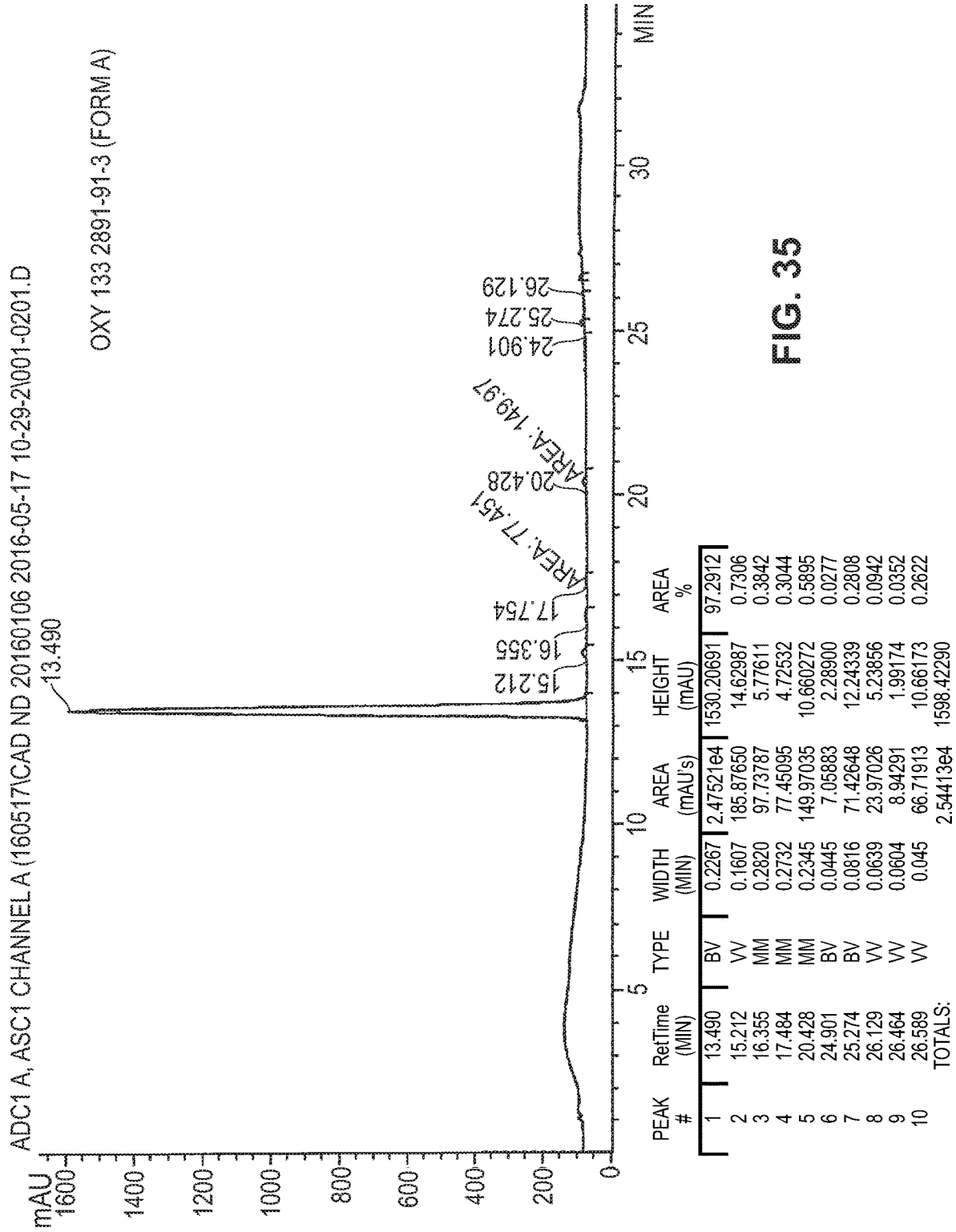
FIG. 35 is a HPLC/CAD single injection report of OXY133 monohydrate sample 2891-91-3.
Figure 36:
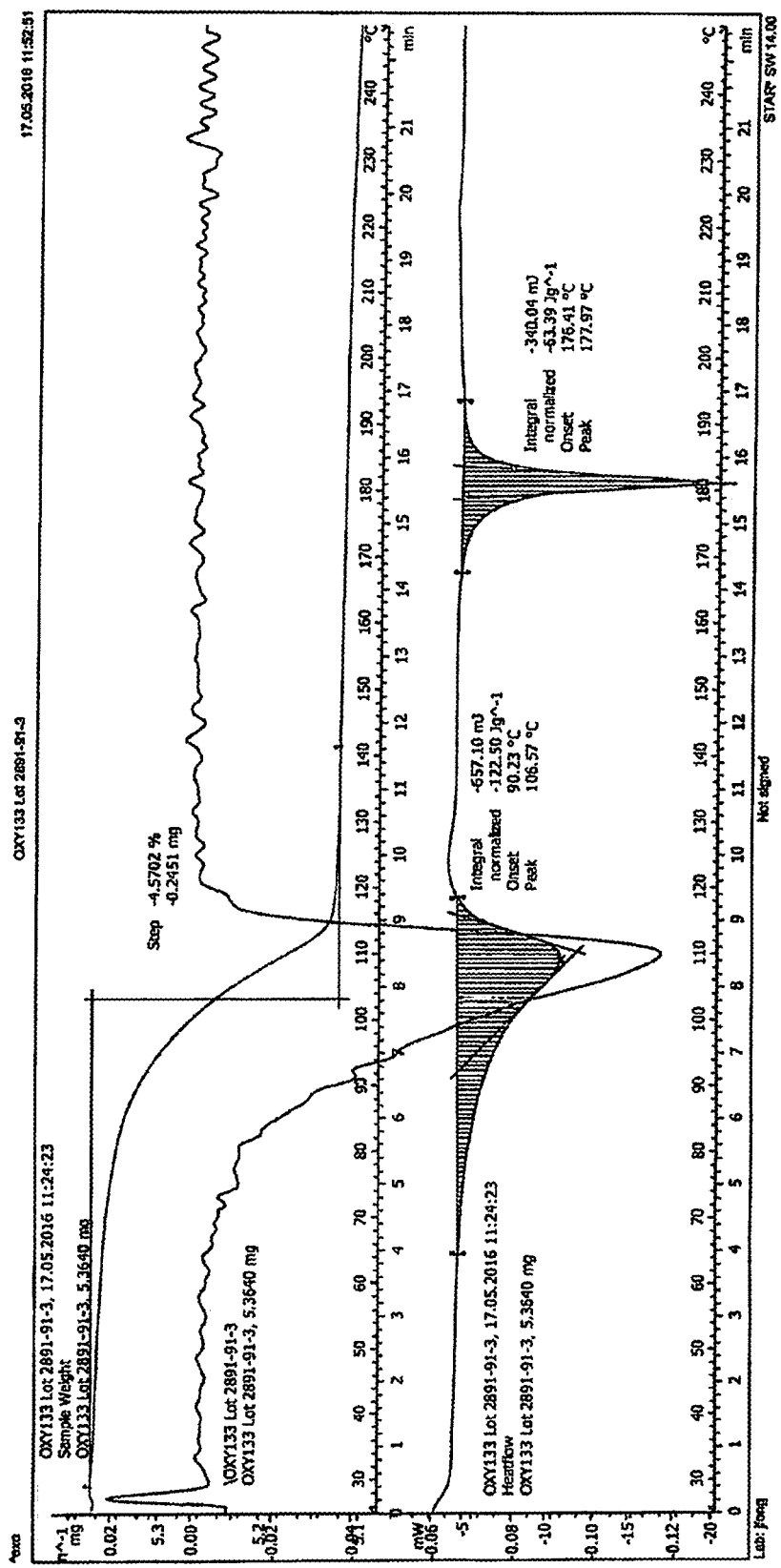
FIG. 36 is a DSC-TGA thermogram of OXY133 polymorph Form A sample 2891-91-3.
Figure 37:
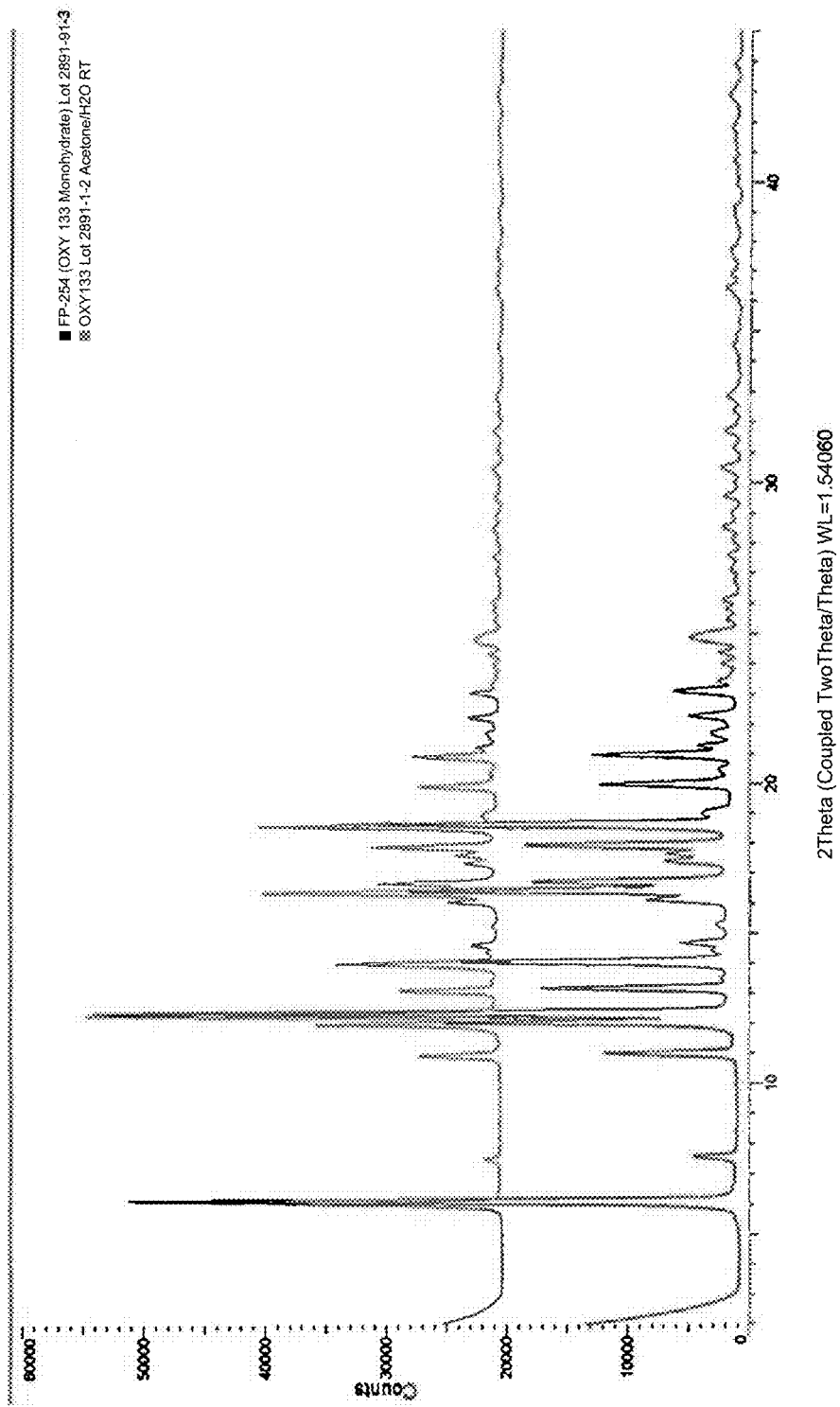
FIG. 37 is an XRPD of OXY133 polymorph Form A of samples 2891-91-3 and 2891-1-2.

In this procedure, 250.0 g pregnenolone was converted to approximately 90 g OXY133 monohydrate having a purity greater than 97%. 250.0 g pregnenolone was charged to a 20 L jacketed reactor. THF was added and the stirred solution was cooled to approximately −25° C. Hexylmagnesium chloride was added slowly, and the reaction mixture was allowed to warm to room temperature. Once the reaction was complete, the reaction mixture was quenched with saturated ammonium chloride, concentrated at reduced pressure, and extracted with MTBE. The diol was precipitated, recrystallized from methanol/water, and dried to afford 162.5 g diol (49% yield) with a purity of 94.1%. The diol was solvated in THF and subjected to azeotropic distillation to remove residual water. Once this was complete, borane/THF complex (2 equivalents) was added slowly while maintaining an internal temperature of approximately −10° C. After addition was complete, the reaction mixture was allowed to warm to room temperature. Once the conversion was complete, the reaction mixture was cooled to approximately 0° C. and $H_2O_2$/NaOH was slowly added. The resulting mixture was diluted with MTBE, the layers were separated, and the organic phase was washed and concentrated. The product was isolated and recrystallized from methanol/water to afford 126 g OXY133 crude with a purity of 97.0%. The crude OXY133 was solvated and precipitated with isopropyl alcohol (IPA)/water, and isolated by filtration. The filter cake was washed once with IPA/water (1:2) and twice with acetone/water (1:1). The yield of OXY133 monohydrate was 89.9 g (53.2% yield from diol) with a purity of 97.2%. DSC/TGA analyses showed a water loss of 4.57% with the onset at 90.2° C. with a final melt at 176.4° C. A monohydrate form of OXY133 was confirmed by XRPD. The results of HPLC-CAD, DSC/TGA and XRPD of OXY133 monohydrate obtained by this procedure are illustrated in FIGS. 35, 36 and 37.

Example 8

Preparation of Scalable OXY133 Monohydrate from Pregnenolone

In this procedure, 4.6 kg of OXY133 monohydrate was synthesized from 15.0 kg of pregnenolone. In step 1 of this process, 15.0 kg pregnenolone was reacted with hexylmagnesium chloride under the conditions described in Example 7 affording 9.0 kg (47% yield) of diol (98% purity by

TABLE 18

| Reacted Compound | Molec. Weight (g/mol) | density (g/mL) | Equivalents | Amount/ moles | Lot Number |
|---|---|---|---|---|---|
| Anhydrous OXY133 | 420.67 | NA | 1.0 | 2.0 g/ .0047 | 55352-23-07 |
| Isopropanol | NA | 0.786 | NA | 10 mL + 0.67 mL | CML-Bulk |
| Water ($H_2O$) | NA | 1.00 | NA | 20 mL + 1.33 mL | CML-Bulk |

| Isolated Solid | Yield | KF | DSC/ TGA | Appearance | Lot Number |
|---|---|---|---|---|---|
| OXY133 Monohydrate | 1.96 g (94% recovery) | 4.07% | 4.76% | white solid | 2891-28-1 |

Figure 38:
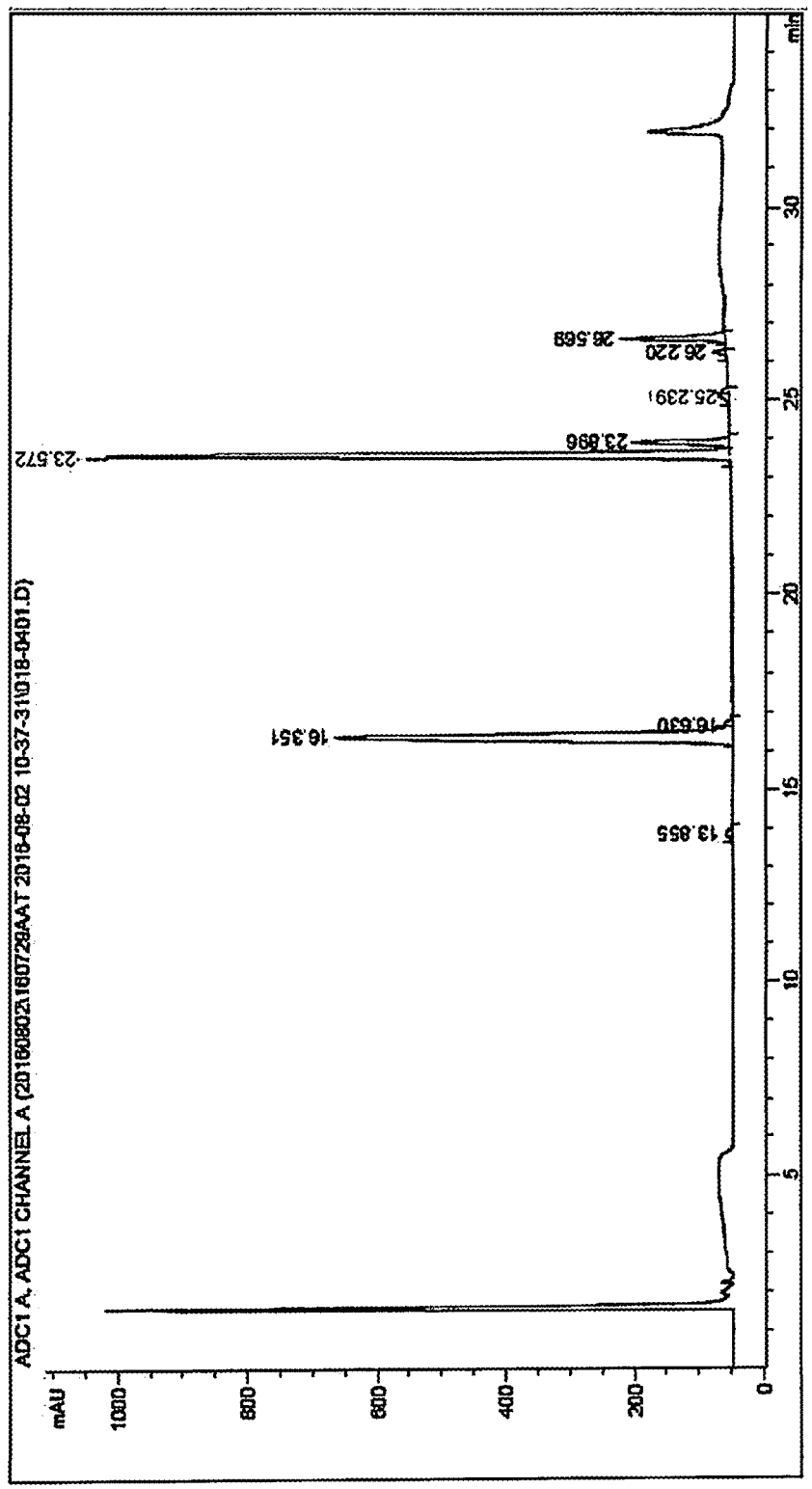
FIG. 38 is an HPLC graph taken at the start of the reaction of pregnenolone with a Grignard reagent.
Figure 39:
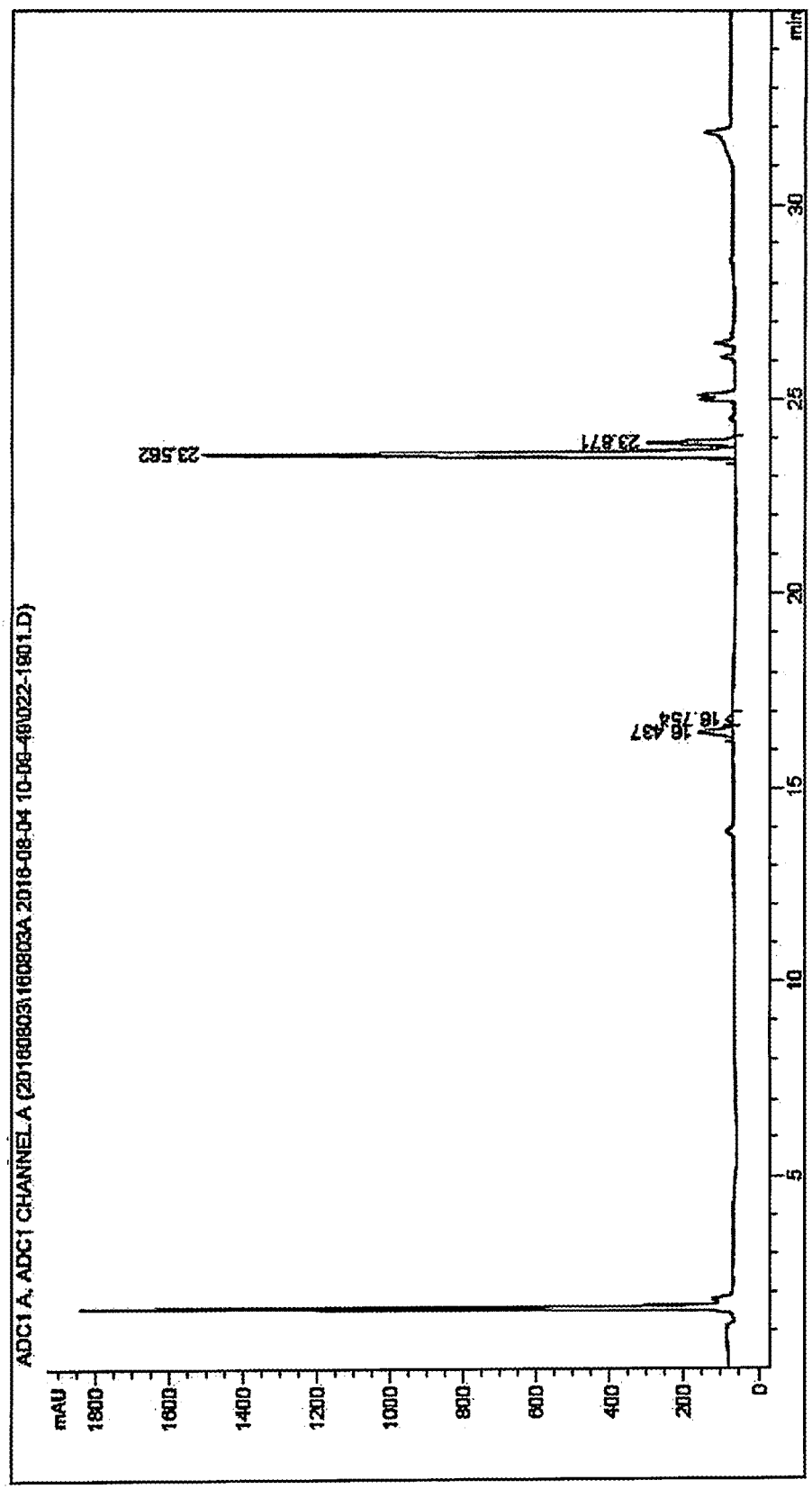
FIG. 39 is an HPLC graph taken at the completion of the reaction of pregnenolone with a Grignard reagent.
Figure 40:
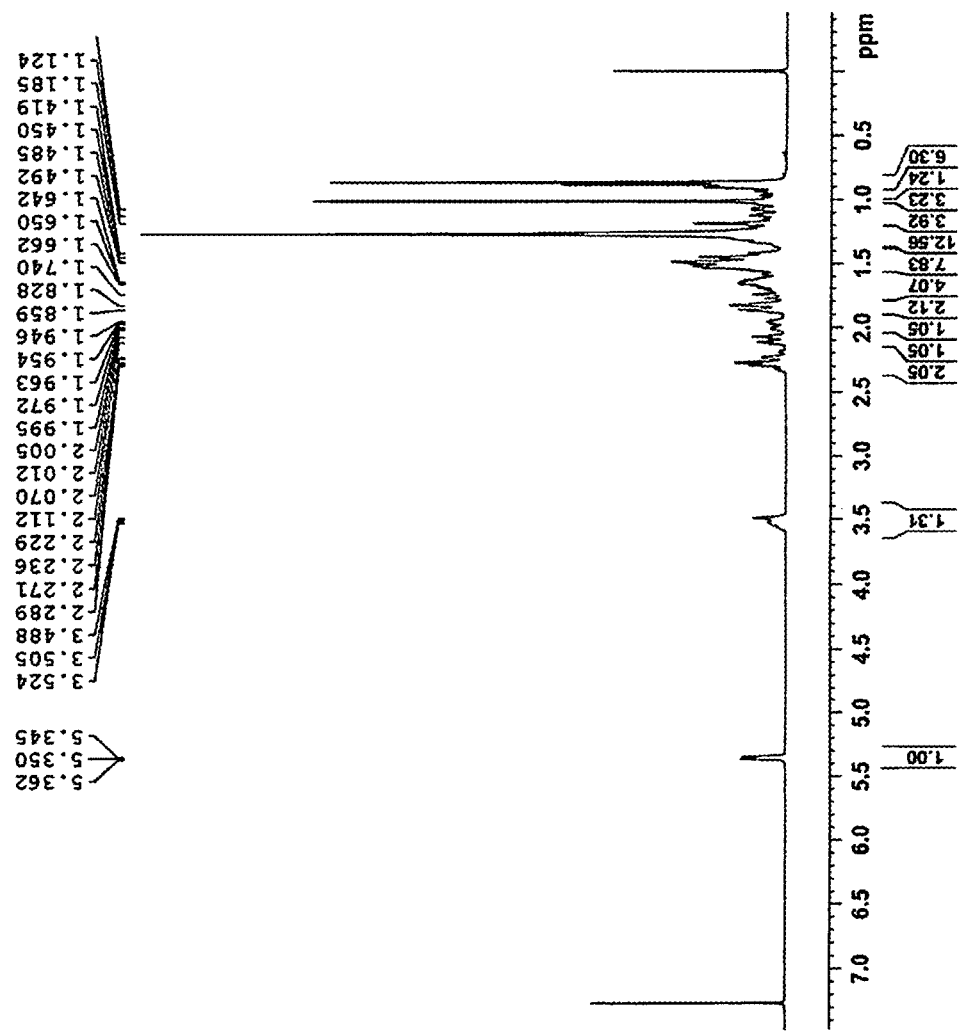
FIG. 40 is an NMR graph of the diol intermediate after purification.

HPLC). FIG. 38 is an HPLC scan taken at the start of the reaction illustrating the formation of the desired diol. FIG. 39 is an HPLC scan showing the reaction at completion. FIG. 40 is an NMR scan of the diol intermediate after purification.

Figure 41:
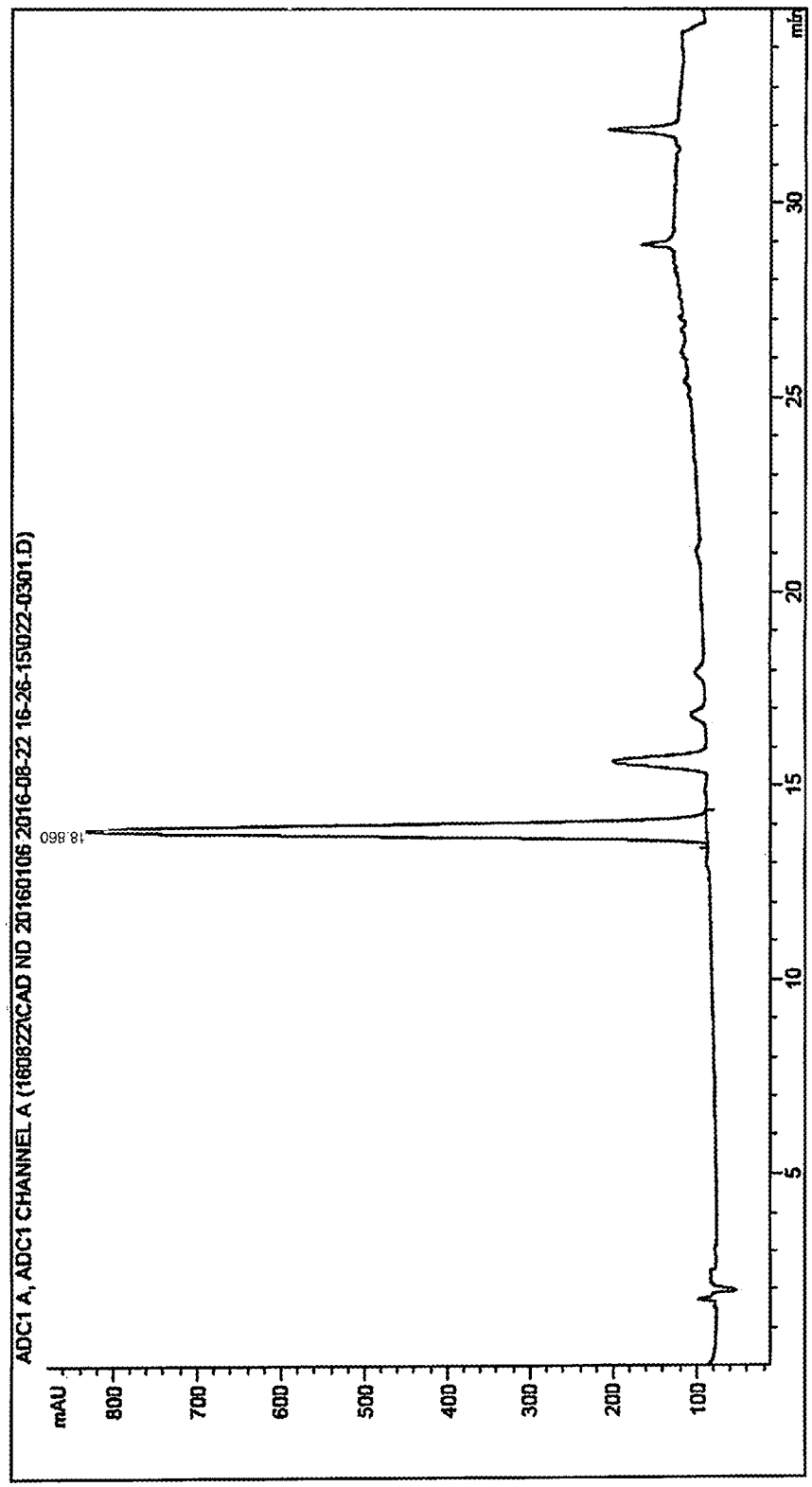
FIG. 41 is an HPLC/CAD graph taken after the completion of the hydroboration reaction.

The diol was solvated in THF and subjected to azeotropic distillation until a water content of NMT 2% was achieved as determined by a Karl-Fisher (KF) analysis. The hydroboration/oxidation was conducted utilizing three equivalents of borane under the processing conditions as previously described in Example 7. FIG. 41 shows the HPLC-CAD taken after the hydroboration reaction. The desired OXY133 monohydrate was isolated, and recrystallized as previously described in Example 7.

Figure 42:
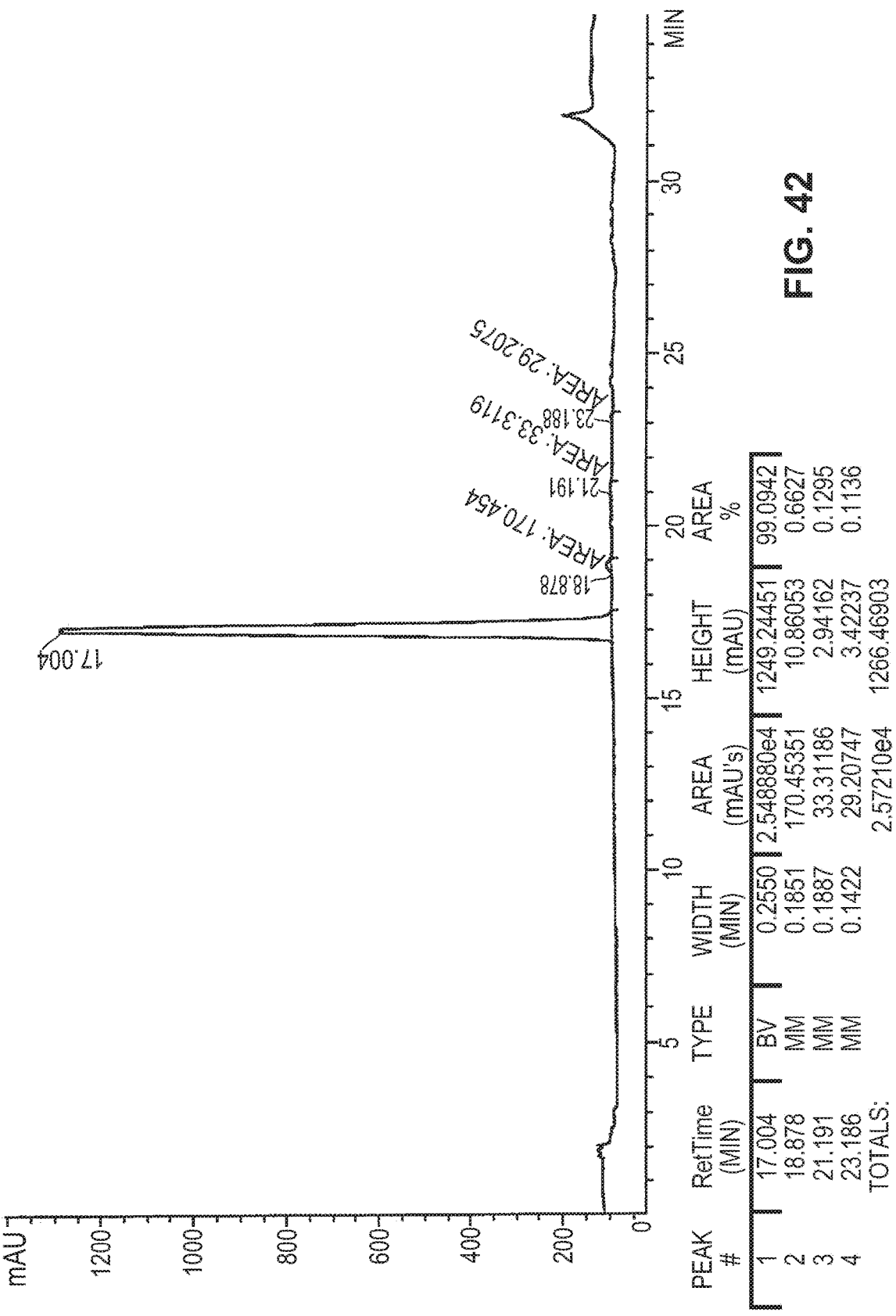
FIG. 42 is an HPLC/CAD graph of the monohydrate form of OXY133 batch FP-000477.

The OXY133 monohydrate product was slowly dried in a tray dryer while maintaining a temperature below 25° C. Once drying was complete, 4.63 kg was isolated (47.8% yield from diol). The resulting OXY133 monohydrate had a purity of 99.1%. The DSC/TGA showed water loss of 4.00% and onset at 73.6° C. with a final melt at 176.4° C. The monohydrate form of OXY133 was confirmed by HPLC-CAD and XRPD as illustrated in FIGS. 42 and 43, respectively.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A solid form of OXY133 polymorph comprising polymorph Form C that produces an X-ray powder diffraction pattern comprising the following reflections: 11.8, 13.2, 13.3, 14.9, 15.96 and 17.9±0.2 degree 2θ having relative intensities of 86.3%, 33.4%, 32.5%, 63.9%, 19.1% and 100%, respectively, wherein the conditions to convert to an OXY133 polymorph comprise mixing OXY133 with an acetone solvent, and a water anti-solvent in a ratio of about 1:1 v/v at a temperature of 70° C. to obtain OXY133 polymorph Form C and the polymorph Form C is configured to be formed from re-slurrying in the acetone solvent and the water anti-solvent in a ratio of 1:1.

2. The polymorph of claim 1, wherein the polymorph Form C produces an X-ray powder diffraction pattern as shown in Table 8.

* * * * *